US008182817B2

(12) United States Patent
Gill et al.

(10) Patent No.: US 8,182,817 B2
(45) Date of Patent: *May 22, 2012

(54) ANTIBODIES TO HUMAN IL-22

(75) Inventors: Davinder S. Gill, Andover, MA (US);
Jing Li, Lexington, MA (US);
Geertruida M. Veldman, Sudbury, MA (US); Lynette A. Fouser, Acton, MA (US); Viia Valge-Archer, Cambridge (GB); David C. Lowe, Cambridge (GB);
Caroline S. Russell, Cambridge (GB);
Suzanne E. Cohen, Cambridge (GB);
Albert G. Thom, Cambridge (GB);
Ralph R. Minter, Cambridge (GB)

(73) Assignees: Wyeth LLC, Madison, NJ (US);
Medimmune Limited, Cambridge (GB)

(*) Notice: Subject to any disclaimer, the term of this patent is extended or adjusted under 35 U.S.C. 154(b) by 233 days.

This patent is subject to a terminal disclaimer.

(21) Appl. No.: 12/696,434

(22) Filed: Jan. 29, 2010

(65) Prior Publication Data
US 2010/0184960 A1 Jul. 22, 2010

Related U.S. Application Data

(63) Continuation of application No. 11/708,061, filed on Feb. 20, 2007, now Pat. No. 7,901,684.

(60) Provisional application No. 60/774,596, filed on Feb. 21, 2006.

(51) Int. Cl.
*C07K 16/24* (2006.01)
*A61K 39/395* (2006.01)

(52) U.S. Cl. ............... 424/145.1; 424/130.1; 424/141.1; 530/388.1; 530/388.15; 530/388.23; 530/389.2

(58) Field of Classification Search .......................... None
See application file for complete search history.

(56) References Cited

U.S. PATENT DOCUMENTS

| | | | |
|---|---|---|---|
| 5,350,836 A | 9/1994 | Kipchick et al. |
| 5,536,637 A | 7/1996 | Jacobs |
| 5,674,487 A | 10/1997 | Smith et al. |
| 5,837,232 A | 11/1998 | De Waal Malefyt et al. |
| 5,863,796 A | 1/1999 | Moore et al. |
| 6,143,867 A | 11/2000 | Akerblom |
| 6,225,117 B1 | 5/2001 | Gately et al. |
| 6,274,710 B1 | 8/2001 | Dumoutier et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,939,545 B2 | 9/2005 | Jacobs et al. |
| 7,279,559 B2 | 10/2007 | Jacobs et al. |
| 7,307,161 B1 | 12/2007 | Jacobs et al. |
| 7,459,533 B2 | 12/2008 | Jacobs et al. |
| 7,811,567 B2 | 10/2010 | Fouser et al. |
| 7,846,444 B2 | 12/2010 | Fouser et al. |
| 7,901,684 B2* | 3/2011 | Gill et al. ............... 424/145.1 |
| 2001/0006637 A1 | 7/2001 | Akahoshi et al. |
| 2001/0023070 A1 | 9/2001 | Ebner et al. |
| 2001/0024652 A1 | 9/2001 | Dumoutier et al. |
| 2002/0012669 A1 | 1/2002 | Presnell et al. |
| 2002/0102723 A1 | 8/2002 | Gurney et al. |
| 2002/0177165 A1 | 11/2002 | Ashkenazi et al. |
| 2002/0187523 A1 | 12/2002 | Tang et al. |
| 2003/0003545 A1 | 1/2003 | Ebner et al. |
| 2003/0012788 A1 | 1/2003 | Renauld et al. |
| 2003/0092133 A1 | 5/2003 | Ebner et al. |
| 2003/0170823 A1 | 9/2003 | Presnell et al. |
| 2004/0023341 A1 | 2/2004 | Xu et al. |
| 2004/0110189 A1 | 6/2004 | Dumoutier et al. |
| 2004/0152125 A1 | 8/2004 | Presnell et al. |
| 2004/0180399 A1 | 9/2004 | Renauld et al. |
| 2005/0042220 A1 | 2/2005 | Li et al. |

FOREIGN PATENT DOCUMENTS

| | | |
|---|---|---|
| WO | WO 94/01548 | 1/1994 |
| WO | 9404678 | 3/1994 |
| WO | 9425591 | 11/1994 |
| WO | 9749805 | 12/1997 |
| WO | WO 99/61617 | 12/1999 |
| WO | WO 00/24758 | 5/2000 |
| WO | WO 00/70049 | 11/2000 |
| WO | WO 00/73457 | 12/2000 |
| WO | WO 00/77037 | 12/2000 |
| WO | WO 01/46422 | 6/2001 |
| WO | WO 02/10393 | 2/2002 |
| WO | WO 02/16611 | 2/2002 |
| WO | WO 02/068476 | 9/2002 |
| WO | WO 2005/000897 | 1/2005 |

OTHER PUBLICATIONS

Sugimoto et al. Gastroenterology: 2006: 130; 4: Suppl. 2: A41.
Sugimoto et al. Gastroenterology: 2005: 128: Suppl. 2: A18.
Van Deventer et al. Reaserach and Clinical Forums. 1998; 20; 11-18.
Andoh et al., "Interleukin-22, a member of the IL-10 subfamily, induces inflammatory responses in colonic subepithelial myofibroblasts", Gastroenterology: 2005 129:969-84.
Brand et al. Am. J. Physiol. Gastrointest. Liver Physiol.: 2006: 290:G827-38.
Sugimoto et al., "IL-22 Ameliorates intestinal inmflammation in a mouse model of ulcerative colitis", The Journal of Clinical Investigation: 2008: 118:534-44.
Mahairas G. et al., Database EST. Accession No. AQ104025. Aug. 1998.

(Continued)

*Primary Examiner* — Prema Mertz
(74) *Attorney, Agent, or Firm* — MH2 Technology Law Group LLP

(57) ABSTRACT

The present application provides human antibodies and antigen binding fragments thereof that specifically bind to the human interleukin-22 (IL-22). The antibodies can act as antagonists of IL-22 activity, thereby modulating immune responses in general, and those mediated by IL-22 in particular. The disclosed compositions and methods may be used for example, in diagnosing, treating or preventing inflammatory disorders, autoimmune diseases, allergies, septic shock, infectious disorders, transplant rejection, cancer, and other immune system disorders.

20 Claims, 84 Drawing Sheets

OTHER PUBLICATIONS

Waterston R. et al., Database GenEmbl. Accession No. AC006734. Feb. 25, 1999.
Wilson R. et. al. J. Mol. Biol. 261:155-172,1996.
Bork et al., Trends in Genetics 12:425-427, 1996.
Vukicevic et al., PNAS USA 93:9021-26, 1996.
Massague, J. Cell 49:437-8, 1987.
Pilbeam et al., Bone 14:717-720, 1993.
Skolnick et al., Trends in Biotech. 18:34-39, 2000.
Dumoutier, L. et al., (2000), J. of Immunol. 164:1814-1819.
Syrbe et al., (1999) Springer Seminars in Immunopathology, 21:263-85.
Dumoutier, L. et al., GenBank Accession NO NM_016971 for Mus musculus interleukin 10-related T cell-derived inducible factor (Iltif). Jun. 8, 2000.
Aoki, I., et al Comparison of the amino acid and nucleotide sequences between human and two guinea pig major basic proteins,: FEBS Lett. 282(1):56-60, 1991.
Dumoutier, L. et al., PNAS 97(18):10144-9,2000.
Dumoutier, L. et al., "IL-TIF/IL-22: genomic organization and mapping of the human and mouse genes," Genes Immun. 1:488-494, 2000.
Ozaki, T. et al. GenBank Accession No. D13973 for Dictyostelium discoideum DNA for Dp87 protein, 1993. Feb. 1, 2000.
Aoki, I., et al. GenBank Accession No. P35709 for Eosinophil granule major basic protein 2 precursor (mbp-2). May 30, 2000.
Xie, M. et al. GenBank Accession No. AF279437 for *Homo sapiens* interleukin 22 (IL22). Oct. 9, 2000.
Dumoutier, L., et al., GenBank Accession No. AJ294727 for Mus musculus ILTIFa gene for IL TIE alpha protein (LI-21), exons la. Dec. 21, 2000.
Dumoutier, L., et al., GenBank Accession No. NP_065386 for Interleukin 22; Interleukin 21; IL-10-related T-cell-derived inducible factor (*Homo sapiens*). Nov. 2, 2000.
Ozaki, T., et al., Developmental regulation of transcription of a novel prespore-specific gene (Dp87) in *Dictyostelium doscoideum*,: Development. 117(4):1299-08, 1993.
Sambrook, J. et al., Molecular Cloning. A Laboratory Manual, 2d ed. Cold Spring Harbor Laboratory Press, 1989, Ch. 17.
Xie, M. et al., J. Biol. Chem. 275(40):31335-9, 2000.
Kotenko, Sergei V. et al., Journal of Biological Chemistry, American Society of Biological Chemists, Baltimore, MD, US, vol. 276, No. 4, Jan. 26, 2001, pp. 2727-2732.
Dumoutier, L. et al., "IL-TIF induces acute phase reactant production by heatocytes through IL-10Rbeta." Immunology Letters, vol. 73, No. 2-3 Sep. 2000, p. 261.
Radaeva, Svetlana, et al., Hepatology, vol. 39, No. 5, May 2004, pp. 1332-1342.
Resmini, C., et al., European Cytokine Network, vol. 14, No. Sup. 3, Sep. 2003, p. 129 and Annual Meeting of Int'l Cytokine Society; Dublin, Sep. 20-24, 2003. ISSN:1448-5493.
Li, J., et al, International Immunopharmacology, Elsevier, Amsterdam, NL, vol. 4, No. 5, May 2004, pp. 693-708.
Amelizad Z et al. Accession No. A60822, Biochem. Pharmacol. 37, 3245-3249, 1988.
International Search Report from PCT/US2007/004692.
International Report on Patentability and Written Opinion of the International Searching Authority for PCT/US2007/004692.
International Search Report from PCT/US2007/004430.
Paul, Fundamental Immunology, 3d Edition, 1993, pp. 292-295.
Lederman et al., Molecular Immuology, 1991. vol. 28, pp. 1171-1181.
Li et al., Proc Natl Aca Sci USA, 1980. vol. 77, pp. 3211-3214.
Daniel at al., Virolgy, 1994. vol. 202, pp. 540-549.
"Anti-Mouse IL-22 Antibody," Internet Citation, Aug. 22, 2002, XP-002307633.
Mikayama et al., Proc. Natl. Acad. Sci. USA (1993) vol. 90, pp. 10056-10060.
Voet et al., Biochemistry, John Wiley and Sons, Inc., (1990) pp. 126-128 and 228-234.
Rudikoff et al., Proc. Natl. Acad. Sci. USA ( Mar. 1982) vol. 79, pp. 1979-1983.
Communication Pursuant to Article 94(3) EPC dated Nov. 10, 2009 from European Patent Application No. 07 751 204.4.
International Preliminary Report on Patentability (1 page) from PCT/US2007/004430.
Written Opinion of the International Searching Authority (9 pages) from PCT/US2007/004430.
"Communication pursuant to Article 94(3) EPC," European Patent Office, European Patent Application No. 07 751 204.4-1222, Nov. 30, 2010, 4 Pages.
Non-Final Office Action dated Mar. 8, 2010 from U.S. Appl. No. 12/474,479.
Nuttall, S. et al., "A naturally occurring NAR variable domain binds the Kgp protease from Porphyromonas gingivalis", FEBS Letters, vol. 516, 2002, pp. 80-86.
Ward, E. et al., "Binding activities of a repertoire of single immunoglobulin variable domains secreted from *Escherichia coli*", Nature, vol. 341, Oct. 12, 1989, pp. 544-546.
Winkler, K. et al., "Changing the antigen binding specificity by single point mutations of an anti-p24 (HIV-1) antibody", The Journal of Immunology, vol. 165, 2000, pp. 4505-4514, XP002579393.
Lambert, A. et al., Toxicologic Pathology, vol. 29, No. 6, Nov. 2001, p. 712.
Bork, P., Genome Research 10:398-400, 2000.
Doerks, et al., Trends in Genetics 14:248-250, 1998.
Smith, et al., Nature Biotechnology 15:1222-1223, 1997.
Brenner, S. E., Trends in Genetics 15:132-133, 1999.
Mahairas, et al., PNAS, USA, 96(17) 739-9744 (1999).
Simon L.S., et al., (Jun. 2000), New and future drug therapies for rheumatoid arthritis, Rheumatology 39: 36-42.
Llorente L., et al. (2000) Arthritis and Rheumatism 43(8): 1790-1800.
Van Den Berg W. (1998), Joint inflammation and cartilage destruction may occur uncoupled, Springer Semin Immunopathol. 20:149-164.
Kotenko, Sergei, Cytokine and Growth Factor Reviews, vol. 13, No. 3, Jun. 2002, pp. 223-240.

\* cited by examiner

SEQ ID NO:1

```
  1 MAALQKSVSS FLMGTLATSC LLLLALLVQG GAAAPISSHC RLDKSNFQQP
 51 YITNRTFMLA KEASLADNNT DVRLIGEKLF HGVSMSERCY LMKQVLNFTL
101 EEVLFPQSDR FQPYMQEWPF LARLSNRLST CHIEGDDLHI QRNVQKLKD
151 TVKKLGESGE IKAIGELDLL FMSLRNACI
```

SEQ ID NO:2

```
   1 GAATTCGGCC AAAGAGGCCT ACAGGTTCTC CTTCCCCAGT CACCAGTTGC
  51 TCGAGTTAGA ATTGTCTGCA ATGGCCGCCC TGCAGAAATC TGTGAGCTCT
 101 TTCCTTATGG GGACCCTGGC CACCAGCTGC CTCCTTCTCT TGGCCCTCTT
 151 GGTACAGGGA GGAGCAGCTG CGCCCATCAG CTCCCACTGC AGGCTTGACA
 201 AGTCCAACTT CCAGCAGCCC TATATCACCA ACCGCACCTT CATGCTGGCT
 251 AAGGAGGCTA GCTTGGCTGA TAACAACACA GACGTTCGTC TCATTGGGGA
 301 GAAACTGTTC CACGGAGTCA GTATGAGTGA GCGCTGCTAT CTGATGAAGC
 351 AGGTGCTGAA CTTCACCCTT GAAGAAGTGC TGTTCCCTCA ATCTGATAGG
 401 TTCCAGCCTT ATATGCAGGA GGTGGTGCCC TTCCTGGCCA GGCTCAGCAA
 451 CAGGCTAAGC ACATGTCATA TTGAAGGTGA TGACCTGCAT ATCCAGAGGA
 501 ATGTGCAAAA GCTGAAGGAC ACAGTGAAAA AGCTTGGAGA GAGTGGAGAG
 551 ATCAAAGCAA TTGGAGAACT GGATTTGCTG TTTATGTCTC TGAGAAATGC
 601 CTGCATTTGA CCAGAGCAAA GCTGAAAAAT GAATAACTAA CCCCCTTTCC
 651 CTGCTAGAAA TAACAATTAG ATGCCCCAAA GCGATTTTTT TAACCAAAA
 701 GGAAGATGGG AAGCCAAACT CCATCATGAT GGGTGGATTC CAAATGAACC
 751 CCTGCGTTAG TTACAAAGGA AACCAATGCC ACTTTTGTTT ATAAGACCAG
 801 AAGGTAGACT TTCTAAGCAT AGATATTTAT TGATAACATT TCATTGTAAC
 851 TGGTGTTCTA TACACAGAAA ACAATTTATT TTTTAAATAA TTGTCTTTTT
 901 CCATAAAAAA GATTACTTTC CATTCCTTTA GGGGAAAAAA CCCCTAAATA
 951 GCTTCATGTT TCCATAATCA GTACTTTATA TTTATAAATG TATTTATTAT
1001 TATTATAAGA CTGCATTTTA TTTATATCAT TTTATTAATA TGGATTTATT
1051 TATAGAAACA TCATTCGATA TTGCTACTTG AGTGTAAGGC TAATATTGAT
1101 ATTTATGACA ATAATTATAG AGCTATAACA TGTTTATTTG ACCTCAATAA
1151 ACACTTGGAT ATCCTAAAAA AAAAAAAAAA AAAGCGGCCG C
```

FIG. 5

SEQ ID NO:3

MAVLQKSMSFSLMGTLAASCLLLIALWAQEANALPVNTRCKLEVSNFQQPYI
VNRTFMLAKEASLADNNTDVRLIGEKLFRGVSAKDQCYLMKQVLNFTLEDVL
LPQSDRFQPYMQEVVPFLTKLSNQLSSCHISGDDQNIQKNVRRLKETVKKLG
ESGEIKAIGELDLLFMSLRNACV

SEQ ID NO:4

ATGGCTGTCCTGCAGAAATCTATGAGTTTTTCCCTTATGGGGACTTTGGC
CGCCAGCTGCCTGCTTCTCATTGCCCTGTGGGCCCAGGAGGCAAATGCGC
TGCCCGTCAACACCCGGTGCAAGCTTGAGGTGTCCAACTTCCAGCAGCCG
TACATCGTCAACCGCACCTTTATGCTGGCCAAGGAGGCCAGCCTTGCAGA
TAACAACACAGACGTCCGGCTCATCGGGGAGAAACTGTTCCGAGGAGTCA
GTGCTAAAGATCAGTGCTACCTGATGAAGCAGGTGCTCAACTTCACCCTG
GAAGACGTTCTGCTCCCCAGTCAGACAGGTTCCAGCCCTACATGCAGGA
GGTGGTACCTTTCCTGACCAAACTCAGCAATCAGCTCAGCTCCTGTCACA
TCAGCGGTGACGACCAGAACATCCAGAAGAATGTCAGAAGGCTGAAGGAG
ACAGTGAAAAAGCTTGGAGAGAGTGGAGAGATCAAGGCGATTGGGGAACT
GGACCTGCTGTTTATGTCTCTGAGAAATGCTTGCGTCTGA

FIG. 6

GIL01

V_H (SEQ ID NO:5) with H1, H2, and H3 underlined (SEQ ID NO:8-10, respectively)

E V Q L V E S G G G L V T P G G S L R L S C A A S G F T F S
D Y Y M S W I R Q A P G R G L E W V S A I S G G G S T Y Y
A D S V K G R I T I S R D N A K N S L Y L Q M S S L R S E D
T A V Y Y C A R G L W V W D P L D Y W G R G T L V T V S S

V_H (SEQ ID NO:14) with H1, H2, and H3 underlined (SEQ ID NO:17-19, respectively)

GAGGTGCAGTTGGTGGAGTCTGGGGGAGGCTTGGTCACCCCTGAGGGTCCAGCCTCTGAGACTCTCCTGTGCAGCCTCTGGATTCACCTTCAGTGACTACTACATGAGCTGGATCCGCCAGGCTCCAGG
GAGGGGGCTGGAGTGGGTCTCAGCTATTAGTGGTGGTGGTAGTACCTATTACTACGCAGACTCCGTGAAGGGCCGGATCACCATCTCCAGAGACAACGCCAAGAACTCACTGTATCTGCAAATGA
GCAGCCTGAGATCTGAGGACACGGCCGTCTATTACTGTGCGAGAGGGCTTTGGGTTTGGGATCCCCTCGACTACTGGGGCCAGGGAACCCTGGTCACCGTCTCCTCA

V_L (SEQ ID NO:6) with L1, L2, and L3 underlined (SEQ ID NO:11-13, respectively)

D I Q M T Q S P S T L S A S I G D R V T I T C R A S E G I Y H
W L A W Y Q Q K P G K A P K L L I Y K A S S L A S G A P S R F
S G S G S G T D F T L T I S S L Q P D D F A T Y Y C Q Q Y S N
Y P L T F G G G T K L E I K R

V_L (SEQ ID NO:15) with L1, L2, and L3 underlined (SEQ ID NO:20-22, respectively)

GACATCCAGATGACCCAGTCTCCTTCCACCCTGTCTGCATCTATTGGAGACAGAGTCACCATCACTTGCCGGGCCAGTGAGGGTATTTATCACTGGTTGGCTTGGTATCAGCAGAAGCCAGG
GAAAGCCCCTAAACTCCTGATCTATAAGGCCTCTAGTTTAGCCAGTGGGGCCCCATCAAGGTTCAGCGGCAGTGGATCTGGGACAGATTTCACTCTCACCATCAGCAGCCTGCAGCCTGATG
ATTTTGCAACTTATTACTGCCAACAATATAGTAATTATCCGCTCACTTTCGGCGGAGGGACCAAGCTGGAGATCAAACGT

FIG. 7

GIL16

V_H (SEQ ID NO:23) with H1, H2, and H3 underlined (SEQ ID NO:26-28, respectively)

Q V Q L V E S G A E V K K P G A S V K V S C K A S G Y T F T S Y G I
S W V R Q A P G Q G L E W M G W I S A Y T G N T N Y A Q K F Q G R V
T M T T D T S T S T A Y M E L R S L R S D D T A V Y Y C A R D R G Y
Y D A F D I W G Q G T L V T V S S

V_H (SEQ ID NO:32) with H1, H2, and H3 underlined (SEQ ID NO:35-37, respectively)

CAGGTGCAGCTGGTGGAGTCTGGAGCTGAGGTGAAGAAGCCTGGGGCCTCAGTGAAGGTCTCCTGCAAGGCTTCTGGTTACACCTTTACCAGTTATGGTATC
AGCTGGGTGCGACAGGCCCCTGGACAAGGGCTTGAGTGGATGGGATGGATCAGCGCTTACACTGGTAACACAAACTATGCACAGAAGTTCCAGGGCAGAGTC
ACCATGACCACAGACACATCCACGAGCACAGCCTACATGGAGCTGAGGAGCCTGAGATCTGAGGACACGGCCGTGTATTACTGTGCGAGAGATCGTGGATAC
TATGATGCTTTTGATATCTGGGGCCAAGGGACCACCCTGGTCACCGTCTCCTCA

V_L (SEQ ID NO:24) with L1, L2, and L3 underlined (SEQ ID NO:29-31, respectively)

D I Q M T Q S P S T L S A S I G D R V T I T C R A S E G I Y H W L A
W Y Q Q K P G K A P K L L I Y K A S S L A S G A P S R F S G S G S G
T D F T L T I S S L Q P D D F A T Y Y C Q Q Y S N Y P L T F G G G T
K L E I K R

V_L (SEQ ID NO:33) with L1, L2, and L3 underlined (SEQ ID NO:38-40, respectively)

GACATCCAGATGACCCAGTCTCCTTCCACCCTGTCTGCATCTATTGGAGACAGAGTCACCATCACCTGCCGGGCCAGTGAGGGTATTTATCACTGGTTGGCC
TGGTATCAGCAGAAGCCAGGAAAGGCCCCTAAACTCCTGATCTATAAGGCCTCCAGTTTAGCCAGTGGGGCCCATCAGTTCAGCGGCAGTGGATCTGGG
ACAGATTTCACTCTCACCATCAGCAGCCTGCAGCCTGATGATTTTGCAACTTATTACTGCCAACAATATAGTAATTATCCGCTCACTTTCGGCGGAGGGACC
AAGCTGGAGATCAAACGT

FIG. 7(cont.)

GIL45

V_H (SEQ ID NO:41) with H1, H2, and H3 underlined (SEQ ID NO:44-46, respectively)

Q M Q L V Q S G G G V V Q P G R S L R L S C A A S G F T F S N Y G M Y W V R Q
A P G K G L E W V A H I W Y D G S N E K Y A D S V K G R M T V S R D N S R N T
L Y L Q M N S L R A E D T A V Y Y C A T E Q H W I T A F D I W G K G T L V T V
S S

V_H (SEQ ID NO:50) with H1, H2, and H3 underlined (SEQ ID NO:53-55, respectively)

CAGATGCAGCTGGTGCAGTCTGGGGGAGGCGTGGTCCAGCCTGGGAGGTCCCTGAGACTCTCCTGTGCAGCCTCTGGATTCACCTTCAGTAACTATGGCATGTACTGGGTCCGCCA
GGCTCCAGGCAAGGGGCTGGAGTGGGTGGCACATATTTGGTATGATGGAAGTAATGAAAAGTATGCAGACTCCGTGAAGGGCCGAATGACCGTCTCCAGAGACAATTCCAGGAACA
CGTTGTATTTGCAAATGAACAGCCTGAGAGCCGAGGACACTGCGGTGTATTACTGTGCGACAGAGCAACTGGATTGCTTTTGATATCTGGGGCAAAGGCACCCTGGTCACCGTCTCCTCA

V_L (SEQ ID NO:42) with L1, L2, and L3 underlined (SEQ ID NO:47-49, respectively)

Q S V L T Q P A S V S G S P G Q S I T I S C T G T S S D V G G Y N Y V S W Y Q
Q H P G K A P K L M I Y E G S K R P S G V S N R F S G S K S G N T A S L T I S
G L Q A E D E A D Y Y C S S Y T T R S T R V F G G G T K L T V L G

V_L (SEQ ID NO:51) with L1, L2, and L3 underlined (SEQ ID NO:56-58, respectively)

CAGTCTGTGCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCA
ACAACACCCAGGCAAAGCCCCCAAACTCATGATTTATGAGGGCAGTAAGCGGCCCTCAGGGGTTTCTAATCGCTTCTCTGGCTCCAAGTCTGGCAACACGGCCTCCCTGACAATCT
CTGGGCTCCAGGCTGAGGACGAGGCTGATTATTACTGCAGCTCATATACAACCAGGAGCACTCGAGTTTTCGGCGGAGGGACCAAGCTGACCGTCCTAGGT

FIG. 7(cont.)

GIL60

V_H (SEQ ID NO:59) with H1, H2, and H3 underlined (SEQ ID NO:62-64, respectively)

E V Q L V E S G G G V V R P G G S L R L S C A A S G F T F D D Y G M N
W V R Q A P G K G L E W V S G V N W N G G T R D Y A A S V K G R F T I
S R D N A K N S L Y L Q M N S L R A E D T A L Y Y C A R G W Y S G S F
Y Y F G Y W G R G T L V T V S S

V_H (SEQ ID NO:68) with H1, H2, and H3 underlined (SEQ ID NO:71-73, respectively)

GAGGTGCAGCTGGTGGAGTCCGGGGGAGGTGTGGTACGGCCTGGGGGGTCCCTGAGACTCTCCTGTGCAGCCTCTGGATTCACCTTTGACGATTATGGCATGAA
CTGGGTCCGCCAAGCTCCAGGGAAGGGGCTGGAGTGGGTCTCTGGTGTTAATTGGAATGGTGGTACCAGAGATTATGCAGCCTCCGTGAAGGGCCGATTCACCA
TCTCCAGAGACAACGCCAAGAACTCCCTGTATCTGCAAATGAACAGTCTGAGAGCCGAGGACACGGCCCTTGTATTACTGTGCGAGAGGATGGTATAGTGGGAGC
TTCTACTACTTTGGCTACTGGGGCCGAGGAACCCTGGTCACCGTCTCCTCA

V_L (SEQ ID NO:60) with L1, L2, and L3 underlined (SEQ ID NO:65-67, respectively)

Q A V L T Q P S S V S G S P G Q S I T I S C T G A S G D V G A Y N E V
S W Y Q Q H P G K T P K L I I Y D V N K R P S G V S N R F S G S K S G
N T A S L T I S G L Q A E D E S D Y Y C S S Y T S T F S V V F G G T
K V T V L G

V_L (SEQ ID NO:69) with L1, L2, and L3 underlined (SEQ ID NO:74-76, respectively)

CAGGCTGTGCTGACTCAGCCGTCCTCCGTGTCTGGGTCTCCTGGACAGTCGATCACCATCTCCTGCACTGGAGCCAGCGGTGACGTTGGTGCTTATAACTTTGT
CTCCTGGTACCAACAACACCCAGGCAAAACCCCCAAACTAATTTATGATGTCAATAAGCGGCCCTCAGGGGTTTCTAATCGCTTCTGGCTCCAAGTCTG
GCAACACGGCCTCCCTGACCATCTCGGGCTCCAGGCGGACGAGTCGATTATTACTGCAGCTCATATACAAGCACCTTCTCTGTGGTATTTGGCGGAGGG
ACCAAGGTCACCGTCCTAGGT

FIG. 7(cont.)

GIL68

V_H (SEQ ID NO:77) with H1, H2, and H3 underlined (SEQ ID NO:80-82, respectively)

E V Q L V Q S G A E V K K P G A S V K V S C Q A S G Y T F S D Y Y I H W V R Q T P G
Q G F E W M G W V N P D T G G T R Y A Q K F Q G W V T M T R D M S N T T A Y M E L P
R L R D D D T A V Y Y C A R D L T G F D P F E D I W G Q G T L V T V S S

V_H (SEQ ID NO:86) with H1, H2, and H3 underlined (SEQ ID NO:89-91, respectively)

GAGGTGCAGCTGGTGCAGTCTGGGGCTGAGGTGAAGAAGCCTGGGGCCTCAGTGAAGGTCTCCTGTCAGGCTTCTGGATACACCTTCAGCGATTACTACTATATTCACTGGGTGCGACAGACCCCTGGA
CAAGGGTTTGAGTGGATGGGATGGGTCAACCCTGACACTGGTGGCCACAAGATACGCGCAGAAGTTTCAGGGCTGGGTCACAATGACCAGGGACATGTCCAACACCACAGCCTACATGGAGCTGCCC
AGGCTGAGAGACGACGACACGGCCGTATATTACTGTGCGAGAGATCTAACTGGATTTGATCCTTTTGATATCTGGGGCCAGGGAACCCTGGTCACCGTCTCCTCA

V_L (SEQ ID NO:78) with L1, L2, and L3 underlined (SEQ ID NO:83-85, respectively)

Q S V L T Q P P S V S V A P G K T A T I T C G G N N F R N K R V H W Y Q Q R P G Q A
P V L V I Y Y D S D R P S G I P E R F S G S R S G N T A T L T I S R V E A G D E A D
F Y C Q V W D S S T D R P L F G G G T K L T V L G

V_L (SEQ ID NO:87) with L1, L2, and L3 underlined (SEQ ID NO:92-94, respectively)

CAGTCTGTGCTGACTCAGCCACCCTCAGTGTCAGTGGCCCCAGGAAAGACGGCCACGATTACCTGTGGGGGAAACAACTTCAGAATAAAGAGTACACTGGTATCAGCAGAGGCCAGGCCAGG
CCCCTGTCCTGGTCATCTATTATGATTCAGACCGGCCCTCAGGGATCCCTGAGCGATTCTCTGGCTCCCGCTCTGGGAACACGGCCACCCTGACCATCAGCAGGGTCGAGGCCGGGGATGAGGC
CGACTTTTACTGTCAGGTGTGGGATAGTAGTACTGATCGTCCCCTGTTCGGCGGAGGGACCAAGCTGACCGTCCTAGGT

FIG. 7(cont.)

GIL92

V_H (SEQ ID NO:95) with H1, H2, and H3 underlined (SEQ ID NO:98-100, respectively)

Q V Q L V Q S G A E V K K P G A S V K V S C K A S G Y T F T D Y Y
M H W V R Q A P G Q G L E W V G W I N P Y T G G A F Y A Q K F R G
R V T M T R D T S I N T A Y M E L S R L G S D D T A V Y Y C A R E
P E K F D F W G G D N W G R G T M V T V S S

V_H (SEQ ID NO:104) with H1, H2, and H3 underlined (SEQ ID NO:107-109, respectively)

CAGGTCCAGCTGGTGCAGTCTGGGGCTGAGGTGAAGAAGCCTGGGGCCTCAGTGAAGGTCTCCTGCAAGGCTTCTGGATACACCTTCACCGACTACTA
TATGCACTGGGTGCGACAGGCCCCTGGACAAGGGCTTGAGTGGGTGGGATGGATCAACCCTTATACTGGTGGCGCATTCTATGCACAGAAGTTTCGGG
GCAGGGTCACAATGACCAGGGACACGTCCATCAACACAGCCTACATGGAGCTGAGCAGACTGGGATCTGAGGACACGGCCGTGTATTATTGTGCGAGA
GAACCTGAAAAATTCGATTTTTGGGGGGGTGACAACTGGGGCCGGGGAACCATGGTCACCGTCTCCTCA

V_L (SEQ ID NO:96) with L1, L2, and L3 underlined (SEQ ID NO:101-103, respectively)

Q A V L T Q P S S V S G A P G Q R V T I S C T G S S S N I G A G Y
G V H W Y Q Q L P G T A P K L L I Y G N S N R P S G V P D R F S G
S K S G T S A S L A I T G L Q A E D E A D Y Y C Q S Y D S S L S G
Y V F G T G T Q L T V L G

V_L (SEQ ID NO:105) with L1, L2, and L3 underlined (SEQ ID NO:110-112, respectively)

CAGGCTGTGCTGACTCAGCCGTCCTCAGTGTCTGGGGCCCCAGGGCAGAGGGTCACCATCTCCTGCACTGGGAGCAGCTCCAACATCGGGGCAGGTTA
TGGTGTACACTGGTACCAACAGCTTCCAGGAACAGCCCCCAAACTCCTCATCTATGTAACAGCAATCGCCCTCAGGGGTCCCTGACCGATTCTCTG
GCTCCAAGTCTGGCACCTCAGCCTCCCTGGCCATCACTGGGCTCCAGGCTGAGGATGAGGCTGATTATTACTGCCAGTCCTATGACAGCAGCCTGAGT
GGTTATGTCTTCGGAACTGGGACCCAGCTCACCGTCCTAGGT

V_H (SEQ ID NO:113) with H1, H2, and H3 underlined (SEQ ID NO:116-118, respectively)

E V Q L V E S G G G L V T P G G S L R L S C A A S G F T F S D Y Y M
S W V R Q A P G R G L E W V S A I S G G S T Y Y A D S V K G R I
T I S R D N A K N S L Y L Q M S S L R S E D T A V Y Y C A R G L W V
W D P L D Y W G R G T L V T V S S

V_H (SEQ ID NO:122) with H1, H2, and H3 underlined (SEQ ID NO:125-127, respectively)

GAGGTCCAGCTGGTGGAGTCTGGGGGAGGCTTGGTCACGCCTGGAGGGTCCCTGAGACTCTCCTGTGCAGCCTCTGGATTCACCTTCAGTGACTACTACATG
AGCTGGGTCCGCCAGGCTCCAGGGAAGGGGCTGGAGTGGGTCTCAGCTATTAGTGGTAGTGGTAGTACATACTACGCAGACTCCGTGAAGGGCCGGATC
ACCATCTCCAGAGACAACGCCAAGAACTCACTGTATCTGCAAATGAACAGCCTGAGATCTGAGGACACGGCCGTGTATTACTGTGCGAGAGGGCTTTGGGTT
TGGGATCCTCTTGACTACTGGGGCCAGGGAACCCTGGTCACCGTCTCCTCA

V_L (SEQ ID NO:114) with L1, L2, and L3 underlined (SEQ ID NO:119-121, respectively)

D I Q M T Q S P S T L S A S I G D R V T I T C R A S E G I Y H W L A
W Y Q Q K P G K A P K L L I Y K A S S L A S G A P S R F S G S G F G
T D F T L T I S S L Q P D D F A T Y Y C Q Q Y S E F A W T F G G G T
K L E I K R

V_L (SEQ ID NO:123) with L1, L2, and L3 underlined (SEQ ID NO:128-130, respectively)

GACATCCAGATGACCCAGTCTCCTTCCACCCTGTCTGCATCTATTGGAGACAGAGTCACCATCACCTGCCGGGCCAGTGAGGGTATTTATCACTGGTTGGCC
TGGTATCAGCAGAAGCCAGGGAAAGCCCCTAAACTCCTGATCTATAAGGCCTCTAGTTTAGCCAGTGGGGCCCCATCAAGGTTCAGCGGCAGTGGATTGGG
ACCGATTTCACTCTCACCATCAGCAGCCTGCAGCCTGATGATTTTGCAACTTATTACTGCCAACATACAGCAGTTCGCCTGGACCTTCGGCGGAGGGACC
AAGCTGGAGATCAAACGT

V_H (SEQ ID NO:131) with H1, H2, and H3 underlined (SEQ ID NO:134-136, respectively)

Q V Q L V E S G A E V K K P G A S V K V S C K A S G Y T F T S Y G I
S W V R Q A P G Q G L E W M G W M V S A Y T G N T N Y A Q K F Q G R V
T M T T D T S T A Y M E L R G L R S D D T A V Y Y C A R D R G Y
Y D A F D I W G Q G T L V T V S S

V_H (SEQ ID NO:84) with H1, H2, and H3 underlined (SEQ ID NO:143-145, respectively)

AGGTCAGCTGGTGGAGTCTGGGGCTGAGGTGAAGAAGCCTGGGGCCTCAGTGAAGGTCTCCTGCAAGGCTTCTGGTTACACCTTTACCAGTTATGGTATCA
GCTGGGTGCGACAGGCCCCTGGACAAGGGCTTGAGTGGATGGAATGGAACTGGAACTGAGTTCCAGGGCAGAGTCA
CCATGACCACAGACACATCCACGAGCCTACAGCCTACATGGAACTGAGGGGCCTACATCGAGATCTGACGACACGGCCGTGTATTACTGTGCGAGAGATCGTGGATACT
ATGATGCTTTTGATATCTGGGGCCAAGGCACCCTGGTCACCGTCTCCTCA

L (SEQ ID NO:132) with L1, L2, and L3 underlined (SEQ ID NO:137-139, respectively)

I Q M T Q S P S T L S A S I G D R V T I T C R A S E G I Y H W L A W
Y Q Q K P G K A P K L L I Y K A S S L A S G A P S R F S G S G F G T
D F T L T I S S L Q P D D F A T Y Y C Q Q M G E Y N A T I G G G T K
L E I K R

L (SEQ ID NO:141) with L1, L2, and L3 underlined (SEQ ID NO:146-148, respectively)

ACATCCAGATGACCCAGTCTCCTTCCACCCTGTCTGCATCTATTGGAGACAGAGTCACCATCACCTGCCGGGCCAGTGAGGGTATTTATCACTGGTTGGCCT
GGTATCAGCAGAAGCCAGGGAAAGCCCCTAAACTCCTGATCTATAAGGCCTCAGTTTAGCCAGTGGGGCCCCATCAAGGTTCAGCGGCAGTGGGATTTGGGA
CAGATTTCACTCTCACCATCAGCAGCCTGCAGCCTGATGATTTCGCAACTTATTACTGCCAACAAATGGGCGAGTACAACGCCACCATCGGCGGAGGGACCA
AGCTGGAGATCAAACGT

V_H (SEQ ID NO:149) with H1, H2, and H3 underlined (SEQ ID NO:152-154, respectively)

Q V Q L V E S G A E V K K P G A S V K V S C K A S G Y T F T S Y G I S
W V R Q A P G Q G L E W M G W I S A Y T G N T N Y A Q K F Q G R V T M
T T D T S T A Y M E L R S L R S D D T A V Y Y C A R D R G Y Y D A
F D I W G Q G T L V T V S S

V_H (SEQ ID NO:158) with H1, H2, and H3 underlined (SEQ ID NO:161-163, respectively)

CAGGTGCAGCTGGTGGAGTCTGGAGCTGAGGTGAAGAAGCCTGGGGCCTCAGTGAAGGTCTCCTGCAAGGCTTCTGGTTACACCTTTACCAGTTATGGTATCAGC
TGGGTGCGACAGGCCCCTGGACAAGGGCTTGAGTGGATGGGATGGATCAGCGCTTACACAGAAGTTCACAGAAGTTCAGGCAGAGTCACCATG
ACCACAGACACATCCACGAGCACAGCCTACATGGAACTGAGGAGCCTGAGATCTGAGGACACTGCAGTGTATTACTGTGCGAGAGATCGTGGATACTATGATGCT
TTCGATATCTGGGGCCAAGGCACCCTGGTCACCGTCTCCTCA

V_L (SEQ ID NO:150) with L1, L2, and L3 underlined (SEQ ID NO:155-157, respectively)

D I Q M T Q S P S T L S A S I G D R V T I T C R A S E G I Y H W L A W
Y Q Q K P G K A P K L L I Y K A S S L A S G A P S R F S G S G F G T D
F T L T I S S L Q P D D F A T Y Y C Q Q M G E W K A A F G G G T K L E
I K R

V_L (SEQ ID NO:159) with L1, L2, and L3 underlined (SEQ ID NO:164-166, respectively)

GACATCCAGATGACCCAGTCTCCTTCCACCCTGTCTGCATCTATTGGAGACAGAGTCACCATCACCTGCCGGGCCAGTGAGGGTATTTATCACTGGTTGGCCTGG
TATCAGCAGAAAGCCAGGAAAGCCCCTAAACTCCTGATCTATAAGGCCTCTAGTTTAGCCAGTGGGGCCCCATCAAGGTTCAGCGGCAGTGGATTTGGGACAGAT
TTCACTCTCACCATCAGCAGCCTGCAGCCTGATGATTTTGCAACTTATTACTGCCAACAATGGGGAGTGGAAGGCGGCTTCGGCGGAGGGACCAAGCTGGAGATCAAACGT

V_H (SEQ ID NO:167) with H1, H2, and H3 underlined (SEQ ID NO:170-172, respectively)

E V Q L V E S G G G V V R P G G S L R L S C A A S G F T F D D Y G M N
W V R Q A P G K G L E W V S G V N W N G G T R D Y A A S V K G R F T I
S R D N A K N S L Y L Q M N S L R A E D T A L Y Y C A R G W Y S G A A
W N M G Y W G R G T L V T V S S

V_H (SEQ ID NO:176) with H1, H2, and H3 underlined (SEQ ID NO:179-181, respectively)

GAGGTGCAGCTGGTGGAGTCCGGGGGAGGTGTGGTACGGCCTGGGGGGTCCCTGAGACTCTCCTGTGCAGCCTCTGGATTCACCTTTGACGATTATGGCATGAAC
TGGGTCCGCCAAGCTCCAGGGAAGGGCTGGAGTGGGTCTCTGGTGTTAATTGGAATGGTGGTACCAGAGATTATGCAGCCTCCGTGAAGGGCCGATTCACCATC
TCCAGAGACAACGCCAAGAACTCCCTGTATCTGCAAATGAACAGTCTGAGACCGGAGGACACGGCCTTGTATTACTGTGCGAGAGGATGGTATAGTGGGGCCGCG
TGGAACATGGGCTACTGGGGCCGAGGAACCCTGGTCACCGTCTCCTCA

V_L (SEQ ID NO:168) with L1, L2, and L3 underlined (SEQ ID NO:173-175, respectively)

Q A V L T Q P S S V S G S P G Q S I T I S C T G A S G D V G A Y N F V
S W Y Q Q H P G K T P K L I I Y D V N K R P S G V S N R F S G S K S S
N T A S L T I S G L Q A E D E S D Y Y C S S Y T S T F S V V F G G G T
K V T V L G

V_L (SEQ ID NO:177) with L1, L2, and L3 underlined (SEQ ID NO:182-184, respectively)

CAGGCTGTGCTGACTCAGCCGTCCTCCGTGTCTGGGTCTCCTGGACAGTCGATCACCATCTCCTGCACTGGAGCCAGTGGTGACGTTGGTGCTTATAACTTTGTC
TCCTGGTACCAACAACCCCAGGCCAAAACCCCCAAACTCATAATTTATGATGTCAATAAGCGGCCCTCAGGGGTTTCTAATCGCTTCTCTGGCTCCAAGTCTAGC
AACACGGCCTCCCTGACCATCTCTGGGCTCCAGGCTGAGGACGAGAGTGATTACTGCAGCTCATATACAAGCACCTTCTCTGTGGTATTTGGCGGAGGGACC
AAGGTCACCGTCCTAGGT

V_H (SEQ ID NO:185) with H1, H2, and H3 underlined (SEQ ID NO:188-190, respectively)

E V Q L V E S G G G V V R P G G S L R L S C A A S G F T F D D Y G M N W V
R Q A P G K G L E W V S G V N W N G G T R D Y A A S V K G R F T I S R D N
A K N S L Y L Q M N S L R A E D T A L Y Y C A R G W Y S G S P W S L G H W
G R G T L V T V S S

V_H (SEQ ID NO:194) with H1, H2, and H3 underlined (SEQ ID NO:197-199, respectively)

GAGGTGCAGCTGGTGGAGTCCGGGGGAGGTGTGGTACGGCCTGGGGGGTCCCTGAGACTCTCCTGTGCAGCCTCTGGATTCACCTTTGACGATTATGGCATGAACTGGGT
CCGCCAAGCTCCAGGGAAGGGCTGGAGTGGGTCTCTGGTGTTAATTGGAATGGTGGTACCAGAGATTACGCCGCTTCCGTGAAGGGCCGATTCACCATCTCCAGAGACA
ACGCCAAGAACTCCCTGTATCTGCAAATGAACAGTCTGAGAGCTGAGGACACGGCCCTTGTATTACTGTGCGAGAGGATGGTATAGTGGCAGCCCGTGGTCGCTGGGCCAC
TGGGGCCGAGGAACCCTGGTCACCGTCTCCTCA

V_L (SEQ ID NO:186) with L1, L2, and L3 underlined (SEQ ID NO:191-193, respectively)

Q A V L T Q P S S V S G S P G Q S V T I S C T G A S G D V G A Y N F V S W
Y Q Q H P G K T P K L I I Y D V N K R P S G V S N R F S G S K S G N T A S
L T I S R L Q A E D E S D Y Y C S S Y T S R Y T T F G G G T K V T V L G

V_L (SEQ ID NO:195) with L1, L2, and L3 underlined (SEQ ID NO:200-202, respectively)

CAGGCTGTGCTGACTCAGCCGTCAGCCCGTCTCCGTGTCTGGATCTCCTGGACAGTCGGTCACCATCTCCTGCACTGGAGCCAGCGGTGACGTTGGTGCTTATAACTTTGTCTCCTG
GTACCAACAACACCCAGGCAAAAACCCCAAACTCATAATTTATGATGTCAATAAGCGGCCCTCAGGGGTTTCTAATCGCTTCTCTGGCTCCAAGTCTGGCAACACGGCCT
CCCTGACCATCTCTAGGCTCCAGGCTGAGGATGAGTCGGATTATTACTGCAGCTCATATACATCGAGGTACGACCGAGTTTGGCGGAGGGACCAAGGTCACCGTCCTAGGT

V_H (SEQ ID NO:203) with H1, H2, and H3 underlined (SEQ ID NO:206-208, respectively)

E V Q L V E S G G G V V R P G G S L R L S C A A S G F T F D D Y G M N W
V R Q A P G K G L E W V S G V N W N G G T R D Y A A S V K G R F T I S R
D N A K N S L Y L Q M N S L R A E D T A L Y Y C A R G W Y S G A A W N M
G Y W G R G T L V T V S S

V_H (SEQ ID NO:212) with H1, H2, and H3 underlined (SEQ ID NO:215-217, respectively)

GAGGTCCAGCTGGTGGAGTCCGGGGGAGGTGTGGTACGGCCTGGGGGGTCCCTGAGACTCTCCTGTGCAGCCTCTGGATTCACCTTTGACGATTATGGCATGAACTG
GGTCCGGCCAAGCTCCAGGGAAGGGCTGGAGTGGGTCTCTGGTGTGTTAATTGGAATGGTGGTACCAGAGATTATGCAGCCTCCGTGAAGGGCCGATTCACCATCTCCA
GAGACAACGCCAAGAACTCCCTGTATCTGCAAATGAACAGTCTGAGAGCCGAGGACACGGCCTTGTATTACTGTGCGAGAGGATGGTATAGTGGGGCCGCCTGGAAC
ATGGGCTACTGGGGCCGAGGAACCCTGGTCACCGTCTCCTCA

V_L (SEQ ID NO:204) with L1, L2, and L3 underlined (SEQ ID NO:209-211, respectively)

Q A V L T Q P S S V S G S P G Q S I T I S C T G A S G D V G A Y N F V S
W Y Q Q H P G K T P K L I I Y D V N K R P S G V S N R F S G S K S G N T
A S L T I S G L Q A E D E S D Y Y C A S L V S D F S V V F G G G T K V T
V L G

V_L (SEQ ID NO:213) with L1, L2, and L3 underlined (SEQ ID NO:218-220, respectively)

CAGGCTGTGCTGACTCAGCCGTCCTCCGTGTCTGGGTCCCCTGGACAGTCGATCACCATCTCCTGCACTGGAGCCAGCGGTGACGTTGGTGCTTATAACTTTGTCTC
CTGGTACCAACAACACCCAGGCAAACCCCAAACTCATAATTTATGATGTCAATAAGCGGCCCTCAGGGGTTTCTAATCGCTTCTCTGGCTCCAAGTCTGGCAACA
CGGCCTCCCTGACCATCTCTGGGCTCCAGGCTGAGGACGAGTCTGATTATTACTGCGCTTCGCTTGTGTGTATTTGGCGGAGGACCAAGGTCACCGTCCTAGGT

V_H (SEQ ID NO:221) with H1, H2, and H3 underlined (SEQ ID NO:224-226, respectively)

E V Q L V Q S G A E V K K P G A S V K V S C Q A S G Y T F S D Y Y I H W
V R Q T P G Q G F E W M G W V N P D T G G T R Y A Q K F Q G W V T M T R
D M S N T T A Y M E L P R L R D D D T A V Y Y C A R D L T G F D P F D I
W G Q G T L V T V S S

V_H (SEQ ID NO:230) with H1, H2, and H3 underlined (SEQ ID NO:233-235, respectively)

GAGGTGCAGCTGGTGCAGTCTGGGGCTGAGGTGAAGAAGCCTGGGGCCTCAGTGAAGGTCTCCTGCCAGGCTTCTGGATACACCTTCAGC<u>GATTACTATATTCACTG</u>
GGTGCGACAGACCCCTGGACAAGGGTTTGAGTGGATGGGA<u>TGGGTCAACCCTGACACTGGTGGCACAAGATACGCGCAGAAGTTTCAGGGC</u>TGGGTCACAATGACCA
GGGACATGTCCAACACCACAGCCTACATGGAGCTGCCCAGCTGAGAGACGACGACACGGCCGTATATTACTGTGCGAGA<u>GATCTAACTGGATTTGATCCTTTTGAT</u>
<u>ATCTGG</u>GGCCAGGGAACCCTGGTCACCGTCTCCTCA

V_L (SEQ ID NO:222) with L1, L2, and L3 underlined (SEQ ID NO:227-229, respectively)

Q S V L T Q P P S V S V A P G K T A T I T C G G N F R N K R V H W Y Q
Q R P G Q A P V L V I Y Y D S D R P S G I P E R F S G S R S G N T A T L
T I S R V E A G D E A D F Y C Q V W D L F N D N G V F G G G T K L T V L
G

V_L (SEQ ID NO:231) with L1, L2, and L3 underlined (SEQ ID NO:236-238, respectively)

CAGTCTGTGCTGACTCAGCCACCCTCAGTGTCCGTGGCCCCAGGAAAGACGGCCACGATTACCTGT<u>GGGGGAAACAACTTTCGAAATAAAGAGTACACTGGTATCA</u>
GCAGAGGCCAGGCCAGGCCAGGCCCCTGTCCTGGTCATCTATTAT<u>GACTCAGACCGGCCCTCA</u>GGGATCCCTGAGCGATTCTCTGGCTCCCGCTCTGGGAACACGGCCACCC
TGACCATCAGCAGGGTCGAGGCCGGGGATGAGGCCGACTTTTACTGT<u>CAGGTGTGGGATCTCTTCAACGACAACGGCGTGTTC</u>GGCGGAGGGACCAAGCTGACCGTCCTAGGT

V_H (SEQ ID NO:239) with H1, H2, and H3 underlined (SEQ ID NO:242-244, respectively)

E V Q L V Q S G A E V K K P G A S V K V S C Q A S G Y T F S D Y Y I H W V
R Q T P G Q G F E W M G W V N P D T G G T R Y A Q K F Q G W V T M T R D M
S N T T A Y M E L P R L R D D D T A V Y Y C A R D L T G F D P F D I W G Q
G T L V T V S S

V_H (SEQ ID NO:248) with H1, H2, and H3 underlined (SEQ ID NO:251-253, respectively)

GAGGTGCAGCTGGTGCAGTCTGGGGCTGAGGTGAAGAAGCCTGGGGCCTCAGTGAAGGTCTCCTGCAGGCTTCTGGATACACCTTCAGTGATTACTATATTCACTGGGT
GCGACAGACCCCTGGACAAGGGTTTGAGTGGATGGGATGGGTCAACCCTGACACTGGTGGCACAAGATACGGCAGAAGTTTCAGGGCTGGTCACAATGACCAGGGACA
TGTCCAACACCACAGCCTACATGGAGCTGCCCAGGCTGAGAGACGACGACACGGCCGTATATTACTGTGCGAGAGATCTAACTGGATTTGATCCTTTTGATATCTGGGGC
CAGGGAACCCTGGTCACCGTCTCCTCA

V_L (SEQ ID NO:240) with L1, L2, and L3 underlined (SEQ ID NO:245-247, respectively)

Q S V L T Q P P S V S V A P G K T A T I T C G G N N F R N K R V E W Y Q Q
R P G Q A P V L V I Y Y D S D R P S G I P E R F S G S R S G N T A T L T I
S R V E A G D E A D F Y C Q V W D F L T D S G S F G G G T K L T V L G

V_L (SEQ ID NO:249) with L1, L2, and L3 underlined (SEQ ID NO:254-256, respectively)

CAGTCTGTGCTGACTCAGCCACCCTCAGTGTCAGTGGCCCCAGGAAAGACGGCCACCATTACCTGTGGGGGAAACAACTTTCGAAATAAAAGAGTACACTGGTATCAGCA
GAGGCCAGGCCAGGCCCGTCCTGGTCATCTATTATGATTCAGACCGGCCCTCAGGGATCCCTGAGCGATTCTCTGGCTCCCGCTCTGGGAACACGGCCACCCTGACCA
TCAGCAGGGTCGAGGCCGGGGATGAGGCTGACTTTTACTGTCAGGTGTGGGATTTCCTCACCGACTCGGGGTCGTTCGGCGGAGGGACCAAGCTGACCGTCCTAGGT

V_H (SEQ ID NO:257) with H1, H2, and H3 underlined (SEQ ID NO:260-262, respectively)

E V Q L V Q S G A E V K K P G A S V K V S C Q A S G Y T F S D Y Y I H W
V R Q T P G Q G F E W M G W V N P D T G G T R Y A Q K F Q G W V T M T R
D M S T N T A Y M E L P R L R D D D T A V Y Y C A R D L T G Y D Y Y D R
W G Q G T L V T V S S

V_H (SEQ ID NO:266) with H1, H2, and H3 underlined (SEQ ID NO:269-271, respectively)

GAGGTGCAGCTGGTGCAGTCTGGGGCTGAGGTGAAGAAGCCTGGGGCCTCAGTGAAGGTCTCCTGTCAGGCTTCTGGATACACCTTCAGCGATTACTATATTCACTG
GGTGCGACAGACCCCTGGACAAGGGTTGAGTGGATGGGATGGGTCAACCCTGACACTGGTGGCACAAGATACGGCAGAAGTTTCAGGGCTGGTCACAATGACCA
GGGACATGTCCAACACCACAGCCTACATGGAGCTGCCCAGGCTGAGAGACGACGACACGGCCGTATATTACTGTGCGAGAGATCTAACTGGATACGACTACTACGAC
CGGTGGGGCCAGGGAACCCTGGTCACCGTCTCCTCA

V_L (SEQ ID NO:258) with L1, L2, and L3 underlined (SEQ ID NO:263-265, respectively)

Q S V L T Q P P S M S V A P G K T A T I T C G G N F R N K R V H W Y Q
Q R P G Q A P V L V I Y Y D S D R P S G I P E R F S G S R S G N T A T L
T I S R V E A G D E A D F Y C Q V W D F L A D E A M F G G G T K L T V L

V_L (SEQ ID NO:267) with L1, L2, and L3 underlined (SEQ ID NO:272-274, respectively)

CAGTCTGTGCTGACTCAGCCGCCCTCAGTGTCAGTGGCCCCAGGAAAGACGGCCACGATTACCTGTGGGGGAAACAACTTTCGAATAAAAGAGTACACTGGTATCA
GCAGAGGCCAGGCCAGGCCCCTGTCCTGGTCATCTATTATGATTCAGACCGGCCATTCTCTGGCTCCCGCTCTGAGCGATTCCTCAGGATCCTCAGGGAACACGGCCACCC
TGACCATCAGCAGGGTCGAGGCCGGGGATGAGGCCGACTTTTACTGTCAGGTGTGGGATTTCCTCGCCGACGAGGCGATGTTCGGCGGAGGGACCAAGCTGACCGTCCTAGGT

V$_H$ (SEQ ID NO:275) with H1, H2, and H3 underlined (SEQ ID NO:278-280, respectively)

E V Q L V Q S G A E V K K P G A S V K V S C Q A S G Y T F S D Y Y I H
W V R Q T P G Q G F E W M G W V N P D T G G T R Y A Q K F Q G W V T M
T R D M S N T T A Y M E L P G L R D D D T A V Y Y C A R D L T G Y D Q
Y T A W G Q G T L V T V S S

V$_H$ (SEQ ID NO:284) with H1, H2, and H3 underlined (SEQ ID NO:287-289, respectively)

GAGGTGCAGCTGGTGCAGTCTGGGGCTGAGGTGAAGAAGCCTGGGGCCTCAGTGAAGGTCTCCTGTCAGGCTTCTGGATACACCTTCAGCGATTACTATATTCA
CTGGGTGCGACAGACCCCAGGACAAGGGTTTGAGTGGATGGGATGGGTCAACCCTGACACTGGTGGCACTGGCACCCCAGAAGTTTCAGGGCTGGGTCACAA
TGACCAGGGACATGTCCAACACACAGCCTACATGGAGCTGCCCGGGCTGAGAGACGACGACGCCGTATATTACTGTGCGAGAGATCTAACTGGGTACGAC
CAGTACACGGCCTGGGGCCAGGGAACCCTGGTCACCGTCTCCTCA

V$_L$ (SEQ ID NO:276) with L1, L2, and L3 underlined (SEQ ID NO:281-283, respectively)

Q S V L T Q P P S V S V A P G K T A T I T C G G N F R N K R V H W Y
Q Q R P G Q A P V L V I Y Y D S D R P S G I P E R F S G S R S G N T A
T L T I S R V E A G D E A D F Y C S T F D P F T D R P L F G G G T K L
T V L G

V$_L$ (SEQ ID NO:285) with L1, L2, and L3 underlined (SEQ ID NO:290-292, respectively)

CAGTCTGTGCTGACTCAGCCACCCTCAGTGTCAGTGGCCCCAGGAAAGACGGCCACGATTACCTGTGGGGAAACAACTTTCGAAATAAAAGAGTACACTGGTA
TCAGCAGAGGCCAGGCCAGGCCCCTGTCCTGGTCATCTATTATGATCAGACCGCCCTCAGGGATCCCGAGCGATTCTCTGGCTCCCGCTCTGGGAACACGG
CCACCCTGACCATCAGCAGGGTCGAGGCTGGGGATGAGGCCGACTTTTACTGTAGCACCTTTGACCCCTTCACTGATCGTCCGCTGTTCGGCGGAGGGACCAAG
CTGACCGTCCTAGGT

V$_H$ (SEQ ID NO:293) with H1, H2, and H3 underlined (SEQ ID NO:296-298, respectively)

QVQLVQSGAEKKPGASVKVSCKASGYTFT<u>DYYMH</u>WVRQAPGQGLEWVG<u>WINPYTGAFYAQKERGRVTMTRDTSINTAYMELSRLGSDDTAVYYCARE<u>PERFGGSTG</u>
QVWGRGTMVTVSS</u>

V$_H$ (SEQ ID NO:302) with H1, H2, and H3 underlined (SEQ ID NO:305-307, respectively)

CAGGTCCAGTTGGTGCAGTCTGGGGCTGAGGTGAAGAAGCCTGGGGCCTCAGTGAAGGTCTCCTGCAAGGCTTCTGGATACACCTTCACC<u>GACTACTATATGCACTG</u>
GGTGCGACAGGCCCCTGGACAAGGGCTTGAGTGGGTGGGA<u>TGGATCAACCCTTATACTGGTGCGCATTCTATGCACAGAAGTTTCGGGG</u>CAGGGTCACAATGACCA
GGGACACGTCCATCAACACAGCCTACATGGAGCTAAGCAGACTGGGATCTGACGACACGGCCGTGTATTATTGTGCGAGA<u>GAACCTGAAAGATTCGGCGACTCCACG</u>
<u>GGGCAGGTCTGGGGCCGGGGACAATGGTCACCGTCTCGAGT</u>

V$_L$ (SEQ ID NO:294) with L1, L2, and L3 underlined (SEQ ID NO:299-301, respectively)

QAVLTQPSSVSGAPRQRVTISCTGS<u>SSNIGAGYGVH</u>WYQQLPGTAPKLLIY<u>GNSNRPS</u>GVPDRFSGSKSGTSASLAITGLQAEDEADYYC<u>YHWDKEQSGYV</u>FGTGTQLTVLSA

V$_L$ (SEQ ID NO:303) with L1, L2, and L3 underlined (SEQ ID NO:308-310, respectively)

CAGGCTGTGCTGACTCAGCCGTCCTCAGTGTCTGGGGCCCCAAGGCAGAGGGTCACCATCTCCTGC<u>ACTGGGAGCAGTCCAACATGGGGCAGGTTATGGTGTACA</u>
<u>CT</u>GGTACCAACAGCTTCCAGGAACACAGCCCCCAAACTCCTCATCTATG<u>GTAACAGCAATCGGCCCTCA</u>GGGGTCCCTGACCGATTCTCTGGCTCCAAGTCTGGCACCT
CAGCCCTCCCTGGCCATCACTGGGCTCCAGGCTGAGGATGAGGCTGATTATTACTGC<u>TACCACTGGGACAAGGAGCAGAGTGGTTAGTGTCTT</u>CGGAACTGGGACCCAG
CTCACCGTTTTAAGTGCG

V<sub>H</sub> (SEQ ID NO:311) with H1, H2, and H3 underlined (SEQ ID NO:314-316, respectively)

EVQLVQSGAEVKKPGASVKVSCQASGYTFTDYYMHWVRQAPGQGLEWVGWINPYTGSAFYAQKFRGRATMTRNTSINTAYMELSRLGSDDTAVYYCAREPEKFGES
SGQLWGRGTMVTISS

V<sub>H</sub> (SEQ ID NO:320) with H1, H2, and H3 underlined (SEQ ID NO:323-325, respectively)

GAAGTGCAGCTGGTGCAGTCTGGGGCTGAGGTGAAGAAGCCTGGGGCCTCAGTGAAGGTCTCCTGTCAGGCTTCTGGATACACCTTCACCGACTACTATATGCACT
GGGTGCGACAGGCCCCTGGACAAGGGCTTGAGTGGGTGGGATGGATCAACCCTTATACTGGTAGCGCATTCTATGCACAGAAGTTTCGGGGCCAGGGCCACAATGAC
CAGGAACACGTCCATCAACACAGCCTACATGGAGCTGAGCAGACTGGGATCTGACGACACGGCCGTGTATTATTGTGCGAGAGAACCTGAAAAATTCGGCGAGTCC
AGCGGCCAGTTGTGGGGCCGGGGACAATGGTCACCGTCTCGAGT

V<sub>L</sub> (SEQ ID NO:312) with L1, L2, and L3 underlined (SEQ ID NO:317-319, respectively)

QAVLTQPSSVSGAPGQRVTISCTGSSSNIGPGYGVHWYQQLPGTAPKLLIYGDSNRPSGVPDRFSGSKSGTSASLAITGLQAEDEADYCQSYDSGLSGYVFGTGTQLTVLSA

V<sub>L</sub> (SEQ ID NO:321) with L1, L2, and L3 underlined (SEQ ID NO:326-328, respectively)

CAGGCTGTGCTGACTCAGCCGTCCTCAGTGTCTGGGGCCCCAGGGCAGAGGGTCACCATCTCCTGCACTGGGAGCAGCAGTTCCAACATCGGGGCAGTTATGGTAC
ACTGGTACCAACAGCTTCCAGGAACAGCCCCCAAACTCCTCATCTATGGTGACAGCAATAGCGCCCTCTGACCGATTCTCTGGCTCCAAGTCTGGCAC
CTCAGCCTCCCTGGCCATCACTGGGCTCCAGGCTGAGGATGAGGCTGATTATTACTGCCAGTCCTATGACAGCGGCCTGAGTGGTTATGTCTTCGGAACTGGGACC
CAGCTCACCGTTTAAGTGCG

V_H (SEQ ID NO:329) with H1, H2, and H3 underlined (SEQ ID NO:332-334, respectively)

QVQLVQSGAEVKKPGASVKVSCKASGYTFTHYMHWVRQAPGQGLEWGWINPYTGGAFYAQKFQGRVTMTRDTSINTAYMELSRLGSDDTAVYYCAREPEKFDSPN
AEIWGRGTMVTISS

V_H (SEQ ID NO:338) with H1, H2, and H3 underlined (SEQ ID NO:341-343, respectively)

CAGGTCCAGCTGGTGCAGTCTGGGGCTGAGGTGAAAAAGCCTGGGGCCTCAGTGAAGGTCTCCTGCAAGGCTTCTGATACACCTTCACCCACTACTATATGCACTG
GGTGCGACAGGCCCCTGGACAAGGGCTTGAGTGGGTGGGATGGATCAACCCTTATACTGGTGGGGCCATTCTATGCACAGAAGTTTCAGGGCAGGGTCACAATGACCA
GGGACACGTCCATCAACACAGCCTACATGGAGCTGAGCAGACTGGGATCTGACGACACGGCCGTGTATTATTGTGCGAGAGAACCTGAAAAATTCGACTCGCCGAAC
GCCGAGATCTGGGGCCGGGGCACAATGGTCACCATCTCGAGT

V_L (SEQ ID NO:330) with L1, L2, and L3 underlined (SEQ ID NO:335-337, respectively)

QAVLTQPSSVSGAPGQRVTISCTGSSSNIGAGYGVHWYQQLPGTAPKLLIYGNSNRPSGVPDRFSGSKSGTSASLAITGLQAEDEADYCQSYDSSLSGYVFGTGTQLTVLSA

V_L (SEQ ID NO:339) with L1, L2, and L3 underlined (SEQ ID NO:344-346, respectively)

CAGGCTGTGCTGACTCAGCCGTCCTCAGTGTCTGGGGCCCCAGGGCAGAGGGTCACCATCTCCTGCACTGGGAGCAGCTCCAACATCGGGGCAGGTTATGGTGTACA
CTGGTACCAACAGCTTCCAGGAACAGCCCCCAAACTCCTACTCATCTATGGTAACAGCAATCGGCCCTCAGGGGTCCCTGACCGATTCTCTGGCTCCAAGTCTGGCACCT
CAGCCTCCCTGGCCATCACTGGGCTCCAGGCTGAGGATGAGGCTGATTATTACTGCCAGTCCTATGACAGCAGCAGCCTGAGTGGTTATGTCTTCGGAACCGGGACCCAG
CTCACCGTTTTAAGTGCG

V_H (SEQ ID NO:347) with H1, H2, and H3 underlined (SEQ ID NO:350-352, respectively)

QVQLVQSGAEVKKPGASVKVSCKASGYTF<u>TNYYMH</u>WVRQAPGQGLEWVG<u>WINPYTGSAFYAQKFRG</u>RVTMTRDTSINTAYMELSRLGSDDTAVYYCAR<u>EPE
KFDSDDSDV</u>WGRGTMVTVSG

V_H (SEQ ID NO:356) with H1, H2, and H3 underlined (SEQ ID NO:359-361, respectively)

CAGGTTCAGCTGGTGCAGTCTGGGGCTGAGGTGAAGAAGCCTGGGGCCTCAGTGAAGGTCTCCTGCAAGGCTTCTGGATACACCTTC<u>ACCAACTACTATAT
GCAC</u>TGGGTGCGACAGGCCCCTGGACAGGGGCTTGAGTGGGTTGGA<u>TGGATCAACCCTTATACTGGTAGCGCATTCTATGCACAGAAGTTTCGGGGCAGG</u>
GTTACAATGACCAGGACGGACACGTCCATCAACACAGCCTACATGGAGCTGAGCAGGCTGGGATCTGACGACACGGCCGTGTATTATTGTGCGAGAGAACTGAA
AATTCGACTCCGACGACTCCGAC</u>GTCTGGGGCCGCGGGACAATGGTCACCGTCTCGGGT

V_L (SEQ ID NO:348) with L1, L2, and L3 underlined (SEQ ID NO:353-355, respectively)

QAVLTPPSVSGAPGQRVTISC<u>TGSSNIGAGYGVH</u>WYQQLPGTAPKLIIY<u>GDSSRPSG</u>VPDRFSGSKSGTSASLAITGLQAEDEADYYC<u>QSYDNSLSGYV</u>FGTGTQLIVLSA

V_L (SEQ ID NO:357) with L1, L2, and L3 underlined (SEQ ID NO:362-364, respectively)

CAGGCTGTGCTGACTCAGCCGCCCTCAGTGTCTGGGGCCCCAGGGCAGAGGGTCACCATCTCCTGC<u>ACTGGGAGCAGCTCCAACATCGGGGCAGGTTATGG
TGTACAC</u>TGGTACCAACAGCTTCCAGGAACAGCCCCCAAACTCATCATCTAT<u>GGTGACAGCAGTCGGCCCTCAGG</u>GGTCCCTGACCGATTCTCTGGCTCCA
AGTCTGGCACCTCAGCCTCCCTGGCCATCACTGGGCTCCAGGCTGAGGATGAGGCTGATTATTACTGC<u>CAGTCCTATGACAACAGCCTGAGCGGTTATGTC
</u>TTCGGAACTGGGACCCAGCTCACCGTTTTAAGTGCG

FIG. 7(cont.)

GIL01

V_H (SEQ ID NO:365) with H1, H2, and H3 underlined (SEQ ID NO:368-370, respectively)

QVQLVESGGGLVKPGGSLRLSCAASGFTFSDYYMSWIRQ
APGKGLEWVSAISGSGGSTYYADSVKGRITISRDNAKNS
LYLQMNSLRAEDTAVYYCARGLWVWDPLDYWGRGTLVTV
SS

V_H (SEQ ID NO:374) with H1, H2, and H3 underlined (SEQ ID NO:377-379, respectively)

CAAGTGCAGCTGGTGGAGTCTGGGGGAGGCTTGGTCAAGCCTGGAGGGTCCCTGAGACTCTCCTGTGCAGCCTCTGGATTCACCTTCAGTGACTACTACATGAGCTGGATCCGCCA
GGCTCCAGGGAAGGGGCTGGAGTGGGTCTCAGCTATTAGTGGTAGTGGTGGTAGCACATACTACGCAGACTCCGTGAAGGGCCGGATCACCATCTCCAGAGACAACGCCAAGAACT
CACTGTATCTGCAAATGAACAGCCTGAGAGCTGAGGACACGGCCGTGTATTACTGTGCGAGAGGGCTTTGGGTTTGGGATCCTCTTGACTACTGGGGCCAGAGAACCCTGGTCACCGTCTCTTCA

V_L (SEQ ID NO:366) with L1, L2, and L3 underlined (SEQ ID NO:371-373, respectively)

DIQMTQSPSTLSASVGDRVTITCRASEGIYHWLAWYQQK
PGKAPKLLIYKASSLASGVPSRFSGSGSGTEFTLTISSL
QPDDFATYYCQQYSNYPLTFGGGTKVEIKR

V_L (SEQ ID NO:375) with L1, L2, and L3 underlined (SEQ ID NO:380-382, respectively)

GACATCCAGATGACCCAGTCTCCTTCCACCCTGTCTGCATCTGTTGGAGACAGAGTCACCATCACCTGCCGGGCCAGTGAGGGTATTTATCACTGGTTGGCCTGGTATCAGCAGAA
GCCAGGGAAAGCCCCTAAACTCCTGATCTATAAGGCCTCTAGTTTAGCCAGTGGGGTCCCATCAAGGTTCAGCGGCAGTGGATCTGGGACAGAGTTCACTCTCACCATCAGCAGCC
TGCAGCCTGATGATTTTGCAACTTATTACTGCCAACAATATAGTAATTATCCGCTCACTTTCGGCGGAGGGACCAAGGTGGAGATCAAACGT

FIG. 8

GIL16

$V_H$ (SEQ ID NO:383) with H1, H2, and H3 underlined (SEQ ID NO:386-388, respectively)

Q V Q L V Q S G A E V K K P G A S V K V S C K A S G Y T F T S Y G I S W V
R Q A P G Q G L E W M G W I S A Y T G N T N Y A Q K F Q G R V T M T T D T
S T S T A Y M E L R S L R S D D T A V Y Y C A R D R G Y Y D A F D I W G Q
G T L V T V S S $V_H$ (SEQ ID NO:392) with H1, H2, and H3 underlined (SEQ ID NO:395-397, respectively)

CAGGTGCAGCTGGTGCAGTCTGGAGCTGAGGTGAAGAAGCCTGGGGCCTCAGTGAAGGTTTCCTGCAAGGCTTCTGGTTACACCTTTACCAGTTATGGTATCAGCTGGGT
GCGACAGGCCCCTGGACAAGGGCTTGAGTGGATGGGATGGATCAGCGCTTACACTGGTAACACAAACTATGCGCAGAAGTTCCAGGGCAGAGTCACCATGACCACAGACA
CATCCACGACAGCCTACATGGAACTGAGGAGCCTGAGATCTGAGGACACGGCCGTGTATTACTGTGCGAGAGATCGTGGATACTATGATGCTTTTGATATCTGGGGC
CAAGGCACCCTGGTCACCGTCTCCTCA $V_L$ (SEQ ID NO:384) with L1, L2, and L3 underlined (SEQ ID NO:389-391, respectively)

D I Q M T Q S P S T L S A S V G D R V T I T C R A S E G I Y H W L A W Y Q
Q K P G K A P K L L I Y K A S S L A S G V P S R F S G S G S G T E F T L T
I S S L Q P D D F A T Y Y C Q Q Y S N Y P L T F G G G T K V E I K R $V_L$ (SEQ ID NO:393) with L1, L2, and L3 underlined (SEQ ID NO:398-400, respectively)

GACATCCAGATGACCCAGTCTCCTTCCACCCTGTCTGCATCTGTTGGAGACAGAGTCACCATCACCTGCGGGGCCAGTGAGGGTATTTATCACTGGTTGGCCTGGTATCA
GCAGAAGCCAGGGAAAGCCCCTAAACTCCTGATCTATAAGGCCTCTAGTTTAGCCAGTGGGGTCCCATCAAGGTTCAGCGGCAGTGGATCTGGGACAGAGTTCACTCTCA
CCATCAGCAGCCTGCAGCCTGATGATTTTGCAACTTATTACTGCCAACAATATAGTAATTATCCGCTCACTTTCGGCGGAGGGACCAAGGTGGAGATCAAACGT

*FIG. 8(cont.)*

GIL45

V_H (SEQ ID NO:401) with H1, H2, and H3 underlined (SEQ ID NO:404-406, respectively)

Q M Q L V E S G G G V V Q P G R S L R L S C A A S G F T F S N Y G M
Y W V R Q A P G K G L E W V A H I W Y D G S N E K Y A D S V K G R M
T V S R D N S K N T L Y L Q M N S L R A E D T A V Y Y C A T E Q H W
I T A F D I W G K G T L V T V S S

V_H (SEQ ID NO:410) with H1, H2, and H3 underlined (SEQ ID NO:413-415, respectively)

CAGATGCAGCTGGTGGAGTCTGGGGGAGGCGTGGTCCAGCCTGGGAGGTCCCTGAGACTCTCCTGTGCAGCCTCTGGATTCACCTTCAGTAACTATGGCAT
GTACTGGGTCCGCCAGGCTCCAGGCAAGGGGCTGGAGTGGGTGGCACATTGGTATGATGGAAGTAATGAAAAGTATGCAGACTCCGTGAAGGGCCGAA
TGACCGTCTCCAGAGACAATTCCAAGAACACGTTGTATTTGCAAATGAACAGCCTGAGAGCCGAGGACACGGCTGTGTATTACTGTGCGACAGAGCAACAC
TGGATTACTGCTTTTGATATCTGGGGCAAAGGAACCCTGGTCACCGTCTCCTCA

V_L (SEQ ID NO:402) with L1, L2, and L3 underlined (SEQ ID NO:407-409, respectively)

Q S A L T Q P A S V S G S P G Q S I T I S C T G T S S D V G G Y N Y
V S W Y Q Q H P G K A P K L M I Y E G S K R P S G V S N R F S G S K
S G N T A S L T I S G L Q A E D E A D Y Y C S S Y T T R S T R V F G
G G T K L T V L G

V_L (SEQ ID NO:411) with L1, L2, and L3 underlined (SEQ ID NO:416-418, respectively)

CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTA
TGTCTCCTGGTACCAACAGCACCCAGGCAAAGCCCCCAAACTCATGATTTATGAGGGCAGTAAGCGGCCCTCAGGGGTTTCTAATCGCTTCTCTGGCTCCA
AGTCTGGCAACACGGCCTCCCTGACAATCTCTGGGCTCCAGGCTGAGGACGAGGCTGATTACTACTGCAGCTCATATACAACCAGGAGCACTCGAGTTTTC
GGCGGAGGGACCAAGCTGACCGTCCTAGGT

FIG. 8(cont.)

GIL60

V_H (SEQ ID NO:419) with H1, H2, and H3 underlined (SEQ ID NO:422-424, respectively)

```
E V Q L V E S G G G V V R P G G S L R L S C A A S G F T F D D Y G M N W V
R Q A P G K G L E W V S G V N W N G G T R D Y A A S V K G R F T I S R D N
A K N S L Y L Q M N S L R A E D T A L Y H C A R G W Y S G S F Y Y F G Y W
G R G T L V T V S S
```

V_H (SEQ ID NO:428) with H1, H2, and H3 underlined (SEQ ID NO:431-433, respectively)

GAGGTGCAGCTGGTGGAGAGCGGGGGAGGTGTGGTACGGCCTGGGGGTCTGTGTACGGGCTGGGGAGGTGTGGTACGGGCCTGGGGGTC
CGCCAAGTCCAGGGAAGGGCTGGAGTGGGTCTCTGGTGTTAATTGGAATGGTGGTACCAGAGATTATGCAGCCTCGAAGGCCGATTCAGCCTCCAGAGACAAC
GCCAAGAACTCCCTGTATCTGCAAATGAACAGTCTGAGAGCCGAGGACACGGCCTTGTATCACTGTGCGAGAGATGTAGAGTGCGAGCTTCTACTACTTTGGCTACTGG
GGCCGAGGAACCCTGGTCACCGTCTCCTCA

V_L (SEQ ID NO:420) with L1, L2, and L3 underlined (SEQ ID NO:425-427, respectively)

```
Q A A L T Q P A S V S G S P G Q S I T I S C T G A S G D V G A Y N F V S W
Y Q Q H P G K A P K L I I Y D V N K R P S G V S N R F S G S K S G N T A S
L T I S G L Q A E D E A D Y Y C S S Y T S S T F S V V F G G G T K L T V L G
```

V_L (SEQ ID NO:429) with L1, L2, and L3 underlined (SEQ ID NO:434-436, respectively)

CAGGCTGCGCTGACTCAGCCGGCCTCCGTCTCGGGTCTCCTGGACAGTCGATCACCATCTCCTGCACTGGAGCCAGCGGTGACGTTGGTGCTTATAACTTTGTCTCCTGG
TACCAACAACACCCAGGCAAAGCCCCAAACCTCATAATTTATGATGTCAATAAGCGGCCCTCAGGGGTTCTAATGCTTCTCTGGCTCCAAGTCTGGCAACACGGCCTCC
CTGACCATCTCTGGGCTCCAGGCTGAGGACGAGGCTGATTATTACTGCAGCTCATATACAAGCAGCACCTTCTCTGTGGTATTTGGCGGAGGGACCAAGCTGACCGTCCTAGGT

*FIG. 8(cont.)*

GIL68

V_H (SEQ ID NO:437) with H1, H2, and H3 underlined

QVQLVQSGAEVKKPGASVKVSCKASGYTFSDYYIHWVRQ
APGQGLEWMGWVNPDTGGTRYAQKFQGRVTMTRDMSIT
AYMELSRLRSDDTAVYYCARDLTGFDPFDIWGQGTLVTV
SS

V_H (SEQ ID NO:446) with H1, H2, and H3 underlined

CAGGTCCAGCTGGTGCAGTCTGGGGCTGAGGTGAAGAAGCCTGGGGCCTCAGTGAAGGTCTCCTGTAAGGCTTCTGGATACACCTTCAG<u>CGATTACTATATTCAC</u>TGGGTGCGACA
GGCCCCTGGACAAGGGTTGGAGTGGATGGGA<u>TGGGTCAACCCTGACACTGGTGGTACACGCGCTACAAGATACGCGCAGAAGTTTCAGG</u>GCCGGGTCACAATGACCAGGGACATGTCCATCTCA
GCCTACATGGAGCTGTCCAGGCTGAGGAGCGACGACACGGCCGTATATTACTGTGCGAGAGA<u>TCTAACTGGATTTGATCCTTTTGATATCTG</u>GGGCCAGGGAACCCTGGTCACCGTCTCCTCA

V_L (SEQ ID NO:438) with L1, L2, and L3 underlined

SSVLTQPPSVSVAPGKTARITCGGNFRNKRVHWYQQKP
GQAPVLVIYYDSDRPSGIPERFSGSRSGNTATLTISRVE
AGDEADYYCQVWDSSTDRPLFGGGTKLTVLG

V_L (SEQ ID NO:447) with L1, L2, and L3 underlined

TCGTCTGTGCTGACTCAGCCACCCTCAGTGTCAGTGGCCCCAGGAAAGACGGCCCGCATTACCTGTGGGGGAAACAACTTTCGAAATAAAAGAGTACACTGGTATCAGCAGAAGCC
AGGCCAGGCCCCTGTCCTGGTCATCTATTATGATTCAGACAGGCCCTCAGGGATCCCTGAGCGATTCCTGGCTCTCCGCTCTGGGAACACGGCCACCCTGACCATCAGCAGGGTCG
AGGCCGGGGATGAGGCCGACTATTACTGTCAGGTGTGGGATAGTAGTACTGATCGTCCGCTGTTCGGCGGAGGGACCAAGCTGACCGTCCTAGGT

*FIG. 8(cont.)*

GIL92

V_H (SEQ ID NO:455) with H1, H2, and H3 underlined (SEQ ID NO:458-460, respectively)

Q V Q L V Q S G A E V K K P G A S V K V S C K A S G Y T F T D Y Y M H W V R
Q A P G Q G L E W V G W I N P Y T G A E Y A Q K F R G R V T M T R D T S I
S T A Y M E L S R L R S D D T A V Y Y C A R E P E K F D F W G G D N W G R G
T L V T V S S

V_H (SEQ ID NO:464) with H1, H2, and H3 underlined (SEQ ID NO:467-469, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCGACTACTATATGCACTGGGTGCG
ACAGGCCCCTGGACAAGGGCTTGAGTGGATGGGATGGATCAACCCTTATACTGGTGCCATTCTATGCCCAGAAGTTTCGGGGCAGGGTCACAATGACCAGGGACACGTCCA
TCAGCACAGCCTACATGGAGCTGAGCAGGCTGAGATCTGAGGACACGGCCGTGTATTATTGTGCGAGAGAACCTGAAAAATTCGATTTTTGGGGGGTGACAACTGGGGCCGG
GGGACATTGGTCACCGTCTCCTCA

V_L (SEQ ID NO:456) with L1, L2, and L3 underlined (SEQ ID NO:461-463, respectively)

Q A V L T Q P P S V S G A P G Q R V T I S C T G S S S N I G A G Y G V H W Y
Q Q L P G T A P K L L I Y G N S N R P S G V P D R F S G S K S G T S A S L A
I T G L Q A E D E A D Y Y C Q S Y D S S L S G Y V F G G G T Q L T V L G

V_L (SEQ ID NO:465) with L1, L2, and L3 underlined (SEQ ID NO:470-472, respectively)

CAGGCTGTGCTGACTCAGCCGCCGTCAGTGTCTGGGGCCCCAGGGCAGAGGGTCACCATCTCCTGCACTGGGAGCAGCAGCTCCAACATCGGGGCAGGTTATGGTGTACACTGGTA
CCAACAGCTTCCAGGAACAGCCCCCAAACTCCTCATCTATGGTAACAGCAATCGGCCCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGTCCTATGACAGCAGCCTGAGTGGTTATGTCTTCGGAGGTGGGACCCAGCTCACCGTCCTAGGT

V_H (SEQ ID NO:473) with H1, H2, and H3 underlined (SEQ ID NO:476-478, respectively)

Q V Q L V Q S G A E V K K P G A S V K V S C K A S G Y T F T S Y G I S W
V R Q A P G Q G L E W M G W V S A Y T G N T N Y A Q K F Q G R V T M T T
D T S T A Y M E L R S L R S D D T A V Y Y C A R D R G Y Y D A F D I
W G Q G T L V T V S S

V_H (SEQ ID NO:482) with H1, H2, and H3 underlined (SEQ ID NO:485-487, respectively)

CAGGTGCAGCTGGTGCAGTCTGGAGCTGAGGTGAAGAAGCCTGGGGCCTCAGTGAAGGTCTCCTGCAAGGCTTCTGGTTACACCTTTACCAGTTATGGTATCAGCTG
GGTGCGACAGGCCCCTGGACAAGGGCTTGAGTGGATGGGATGGGTCAGCGCTTACACTGGTAACACAAACTATGCACAGAAGTTCCAGGGCAGAGTCACCATGACCA
CAGACACATCCACGGCCTACATGGAACTGAGGAGCCTGAGATCTGACGACACGGCCGTGTATTACTGTGCGAGAGATCGTGGATACTATGCTTTTGAT
ATCTGGGGCCAAGGGACCACCCTGGTCACCGTCTCCTCA

V_L (SEQ ID NO:474) with L1, L2, and L3 underlined (SEQ ID NO:479-481, respectively)

D I Q M T Q S P S T L S A S V G D R V T I T C R A S E G I Y H W L A W Y
Q Q K P G K A P K L L I Y K A S S L A S G V P S R F S G S G S G T E F T
L T I S S L Q P D D F A T Y Y C Q Q M G E Y N A T F G G G T K V E I K R

V_L (SEQ ID NO:483) with L1, L2, and L3 underlined (SEQ ID NO:488-490, respectively)

GACATCCAGATGACCCAGTCTCCTTCCACCCTGTCTGCATCTGTTGGAGACAGAGTCACCATCACCTGCCGGGCCAGTGAGGTATTTATCACTGGTTGGCTGGTA
TCAGCAGAAGCCAGGGAAAGCCCCTAAACTCCTGATCTATAAGGCCTCTAGTTTAGCCAGTGGGGTCCCATCAAGGTTCAGCGGCAGTGGATCTGGGACAGAGTTCA
CTCTCACCATCAGCAGCCTGCAGCCTGATGATTTTGCAACTTATTACTGCCAACAAATGGGCGAGTACAACGCCACCTTCGGCGGAGGGACCAAGGTGGAGATCAAACGT

V_H (SEQ ID NO:491) with H1, H2, and H3 underlined (SEQ ID NO:494-496, respectively)

E V Q L V E S G G G V V R P G G S L R L S C A A S G F T F D D Y G M N W V
R Q A P G K G L E W V S G V N W N G G T R D Y A A S V K G R F T I S R D N
A K N S L Y L Q M N S L R A E D T A L Y H C A R G W Y S G A A W N M G Y W
G R G T L V T V S S

V_H (SEQ ID NO:500) with H1, H2, and H3 underlined (SEQ ID NO:503-505, respectively)

GAGGTGCAGCTGGTGGAGTCTGGGGGAGGCGTGGTGCAGCCTGGGGGGTCCCTGAGACTCTCCTGTGCAGCCTCTGGATTCACCTTTGACGATTATGGCATGAACTGGGTC
CGCCAAGCTCCAGGGAAGGGGCTGGAGTGGGTCTCTGGTGTTAATTGGAATGGTGGTACCAGAGATTATGCAGCCTCCGTGAAGGGCCGATTCACCATCTCCAGAGACAAC
GCCAAGAACTCCCTGTATCTGCAAATGAACAGTCTGAGAGCCGAGGACACGGCCTTGTATCACTGTGCCAGAGGATGGTATAGTGGGGCCGTGGAACATGGGCTACTGG
GGCCGAGGAACCCTGGTCACCGTCTCCTCA

V_L (SEQ ID NO:492) with L1, L2, and L3 underlined (SEQ ID NO:497-499, respectively)

Q A A L T Q P A S V S G S P G Q S I T I S C T G A S G D V G A Y N F V S W
Y Q Q H P G K A P K L I I Y D V N K R P S G V S N R F S G S K S G N T A S
L T I S G L Q A E D E A D Y Y C S S Y T S V V F G G G T K L T V L G

V_L (SEQ ID NO:501) with L1, L2, and L3 underlined (SEQ ID NO:506-508, respectively)

CAGGCTGCGCTGACTCAGCCGGCCTCCGTGTCTGGGTCTCCTGGACAGTCGATCACCATCTCCTGCACTGGAGCCAGCGGTGGTGCTTATAACTTTGTCTCCTGG
TACCAACAACACCCAGGCAAAGCCCCCAAACTCATAATTTATGATGTCAATAAGGCCCTCAGGGGTTTCTAATCGCTTCTCTGGCTCCAAGTCTGGCAACACGGCCTCC
CTGACCATCTCTGGGCTCCAGGCCGAGGACGAGGCTGATTATTACTGCAGCTCATATACAAGCACCTTCTCGTGGTATTTGGCGGAGGACCAAGCTGACCGTCCTAGGT

V_H (SEQ ID NO:509) with H1, H2, and H3 underlined (SEQ ID NO:512-514, respectively)

```
Q V Q L V Q S G A E V K K P G A S V K V S C K A S G Y T F S D Y Y I H W V
R Q A P G Q G L E W M G W V N P D T G G T R Y A Q K F Q G R V T M T R D M
S I S T A Y M E L R S D D T A V Y Y C A R D L T G F D P F D I W G Q
G T L V T V S S
```

V_H (SEQ ID NO:518) with H1, H2, and H3 underlined (SEQ ID NO:521-523, respectively)

CAGGTCCAGCTGGTGCAGTCTGGGGCTGAGGTGAAGAAGCCTGGGGCCTCAGTGAAGGTCTCCTGTAAGGCTTCTGGATACACCTTCAGCGATTACTATATTCACTGGGT
GCGACAGGCCCCTGGACAAGGGTTGGAGTGGATGGGATGGGTCAACCCTGACACTGGTGGCACAGATACGCAGAAGTTTCAGGGCAGAGTCACAATGACCAGGACA
TGTCCATCTCCACAGCCTACATGGAGCTGAGGAGCGACGACACGGCCGTATATTACTGTGCGAGAGATCTAACTGGATTTGATCCTTTTGATATCTGGGGC
CAGGGAACCCTGGTCACCGTCTCCTCA

V_L (SEQ ID NO:510) with L1, L2, and L3 underlined (SEQ ID NO:515-517, respectively)

```
S S V L T Q P P S V S V A P G K T A R I T C G G N F R N K V H W Y Q Q K
P G Q A P V L V I Y Y D S D R P S G I P E R F S G S R S G N T A T L T I S
R V E A G D E A D Y Y C Q V W D L F N D N G V F G G G T K L T V L G
```

V_L (SEQ ID NO:519) with L1, L2, and L3 underlined (SEQ ID NO:524-526, respectively)

TCGTCTGTGCTGACTCAGCCACCCTCAGTGTCAGTGGCCCCAGGAAAGACGGCCCGCATTACTGTGGGGGAAATAAAAGAGTACACTGGTATCAGCA
GAAGCCAGGCCAGGCCCCTGTCCTGGTCATCTATTATGATTCAGACCGGCCATCCCTGAGCGATTCTTCTGGCTCCCGCTCTGGGAACACGGCCACCCTGACCA
TCAGCAGGGTCGAGGCCGGGGATGAGGCCGACTATTACTGTCAGGTGTGGGATCTCTTCAACGACAACGGGGTGTTCGGCGGAGGGACCAAGCTGACCGTCCTAGGT

V_H (SEQ ID NO:527) with H1, H2, and H3 underlined (SEQ ID NO:530-532, respectively)

Q V Q L V Q S G A E V K K P G A S V K V S C K A S G Y T F S <u>D Y Y I H</u> W V R
Q A P G Q G L E W M G <u>W V N P D T G G T R Y A Q K F Q</u> G R V T M T R D M S I
S T A Y M E L S R L R S D D T A V Y Y C A R <u>D L T G F D P F D I</u> W G Q G T L
V T V S S

V_H (SEQ ID NO:536) with H1, H2, and H3 underlined (SEQ ID NO:539-541, respectively)

CAGGTCCAGCTGGTGCAGTCTGGGGCTGAGGTGAAGAAGCCTGGGGCCTCAGTGAAGGTCTCCTGTAAGGCTTCTGGATACACCTTCAGCGAT<u>TACTATATTCAC</u>TGGGTGCG
ACAGGCCCCTGGACAAGGGTTGGAGTGGATGGGA<u>TGGGTCAACCCTGACACTGGTGGCACAAGATACGCCAGAAGTTTCAG</u>GGCCGGGTCACAATGACCAGGGACATGTCCA
TCTCCACAGCCTACATGGAGCTGTCCAGGCTGAGAAGCTGACGACGCCGTATATTACTGTGCGAGA<u>GATCTAACTGATTTGATCCTTTTGATATC</u>TGGGGCCAGGGAACC
CTGGTCACCGTCTCCTCA

V_L (SEQ ID NO:528) with L1, L2, and L3 underlined (SEQ ID NO:533-535, respectively)

S S V L T Q P P S V S V A P G K T A R I T C G G <u>N N F R N K R V H</u> W Y Q Q K
P G Q A P V L V I Y <u>Y D S D R P S G</u> I P E R F S G S R S G N T A T L T I S R
V E A G D E A D Y Y C <u>Q V W D F L T D S G S</u> F G G G T K L T V L G

V_L (SEQ ID NO:537) with L1, L2, and L3 underlined (SEQ ID NO:542-544, respectively)

TCGTCTGTGCTGACTCAGCCACCCTCAGTGTCAGTGGCCCCAGGAAAGACGGCCCGCATTACCTGTGGGGAAACAACTTTCGAAATAAAGAGTACACTGGTATCAGCAGAA
GCCAGGCCAGGCCCCTGTCCTGGTCATCTATTATGATTCAGACGGCCCTCAGGGATCCTGAGCGATTCTCTGGCTCTGGAACACGGCCACCCTGACCATCAGCA
GGGTCGAGGCCGGGGATGAGGCCGACTATTACTGTCAGGTGTGGGATTTCCTCACCGACTCGGGGTCGTTCGGCGGAGGGACCAAGCTGACCGTCCTAGGT

V$_H$ (SEQ ID NO:545) with H1, H2, and H3 underlined (SEQ ID NO:548-550, respectively)

Q V Q L V Q S G A E V K K P G A S V K V S C K A S G Y T F T D Y Y M H W V R
Q A P G Q G L E W V G W I N P Y T G G A E Y A Q K F R G R V T M T R D T S I
S T A Y M E L R S D D T A V Y Y C A R E P E R F G D S T G Q V W G R G
T L V T V S S

V$_H$ (SEQ ID NO:554) with H1, H2, and H3 underlined (SEQ ID NO:557-559, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCGACTACTATATGCACTGGGTGCG
ACAGGCCCCTGGACAAGGGCTTGAGTGGGTGGGATGGATCAACCCTTATACTGGTGGCGCATTCTATGCACAGAAGTTTCGGGGCAGGGTCACAATGACCAGGGACACGTCCA
TCAGCACAGCCTACATGGAGCTGAGGAGCGACGACACGGCCGTGTATTATTGTGCGAGAGAACCTGAAAGATTCGGGGACTCCACGGGGCAGGTCTGGGGCCGG
GGGACATTGGTCACCGTCTCCTCA

V$_L$ (SEQ ID NO:546) with L1, L2, and L3 underlined (SEQ ID NO:551-553, respectively)

Q A V L T Q P P S V S G A P G Q R V T I S C T G S S N I G A G Y G V H W Y
Q Q L P G T A P K L L I Y G N S N R P S G V P D R F S G S K S G T S A S L A
I T G L Q A E D E A D Y Y C Y H W D K E Q S G Y V F G G G T Q L T V L G

V$_L$ (SEQ ID NO:555) with L1, L2, and L3 underlined (SEQ ID NO:560-562, respectively)

CAGGCTGTGCTGACTCAGCCGCCGTCAGTGTCTGGGGCCCCAGGACAGAGGGTCACCATCTCCTGCACTGGGAGCAGCAACATCGGGGCAGGTTATGGTGTACACTGGTA
CCAACAGCTTCCAGGAACAGCCCCCAAACTCCTCATCTATGGTAACAGCAATCGGCCCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCTACCACTGGGACAAGGAGCAGAGTGGTTATGTCTTCGGAGGTGGGACCCAGCTGACCGTCCTAGGT

V_H (SEQ ID NO:563) with H1, H2, and H3 underlined (SEQ ID NO:566-568, respectively)

Q V Q L V Q S G A E V K K P G A S V K V S C K A S G Y T F T D Y Y M H W V
R Q A P G Q G L E W V G W I N P Y T G S A F Y A Q K F R G R V T M T R D T
S I S T A Y M E L R S D D T A V Y Y C A R E P E K F G E S S G Q L W
G R G T L V T V S S

V_H (SEQ ID NO:572) with H1, H2, and H3 underlined (SEQ ID NO:575-577, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCGACTACTATATGCACTGGGTG
CGACAGGCCCCTGGACAAGGGCTTGAGTGGATGGGATGGATCAACCCTTATACTGGTAGCGCTTTCTATGCACAGAAGTTTCGGGGCCAGGGTCACAATGACCAGGGACACG
TCCATCAGCACAGCCTACATGGAGCTGAGACTGAGCGACGACACGGCCGTGTATTATTGTGCGAGAGAACCTGAAAAATTCGGCGAGTCCAGCGGCCAGTTGTGG
GGCCGGGGACATTGGTCACCGTCTCCTCA

V_L (SEQ ID NO:564) with L1, L2, and L3 underlined (SEQ ID NO:569-571, respectively)

Q A V L T Q P P S V S G A P G Q R V T I S C T G S S N I G A G Y G V H W
Y Q Q L P G T A P K L L I Y G D S N R P S G V P D R F S G S K S G T S A S
L A I T G L Q A E D E A D Y Y C Q S Y D S G L S G Y V F G G G T Q L T V L
G

V_L (SEQ ID NO:573) with L1, L2, and L3 underlined (SEQ ID NO:578-580, respectively)

CAGGCTGTGCTGACTCAGCCGCCCTCAGTGTCTGGGGCCCCAGGGCAGAGGGTCACCATCTCCTGCACTGGGAGCAGCAACATCGGGGCAGTTATGTGTACACTGG
TACCAACAGCTTCCAGGAACAGCCCCCAAACTCCCTCATCTATGGTGACAGCAATCGGCCCTCAGGGGTCCCTGACCGATTCTCTGGCTCTGGCACCTCAGCCTCC
CTGGCCATCACTGGGCTCCAGGCTGAGGATGAGGCTGATTATTACTGCCAGTCCTATGACAGCGGCCTGAGTGGTTATGTCTTCGGAGGTGGGACCCAGCTCACCGTCCTAGGT

V_H (SEQ ID NO:581) with H1, H2, and H3 underlined (SEQ ID NO:584-586, respectively)

Q V Q L V Q S G A E V K K P G A S V K V S C K A S G Y T F T H Y Y
M H W V R Q A P G Q G L E W V G W I N P Y T G G A E Y A Q K F Q G
R V T M T R D T S I S T A Y M E L S R L R S D D T A V Y Y C A R E
P E K F D S P N A E I W G R G T L V T V S S

V_H (SEQ ID NO:590) with H1, H2, and H3 underlined (SEQ ID NO:593-595, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCCACTACTAT
ATGCACTGGGTGCGACAGGCCCCTGGACAAGGGCTTGAGTGGGTGGGATGGATCAACCCTTATACTGGTGGCGCATTCTATGCACAGAAGTTTCAGGGC
AGGGTCACAATGACCAGGGACACGTCCATCAGCACAGCCTACATGGAGCTGAGCAGACTGAGATCTGACGACACGGCCGTGTATTATTGTGCGAGAGAA
CCTGAAAAATTCGACTCGCCGAACGCCGAGATCTGGGGCCGGGGGACATTGGTGACCGTCTCCTCA

V_L (SEQ ID NO:582) with L1, L2, and L3 underlined (SEQ ID NO:587-589, respectively)

Q A V L T Q P P S V S G A P G Q R V T I S C T G S S S N I G A G Y
G V H W Y Q Q L P G T A P K L L I Y G N S N R P S G V P D R F S G
S K S G T S A S L A I T G L Q A E D E A D Y Y C Q S Y D S S L S G
Y V F G G G T Q L T V L G

V_L (SEQ ID NO:591) with L1, L2, and L3 underlined (SEQ ID NO:596-598, respectively)

CAGGCTGTGCTGACTCAGCCGCCCTCAGTGTCTGGGGCCCCAGGGCAGAGGGTCACCATCTCCTGCACTGGGAGCAGCTCCAACATCGGGGCAGGTTAT
GGTGTACACTGGTACCAACAGCTTCCAGGAACAGCCCCCAAACTCCTCATCTATGGTAACAGCAATCGGCCCTCAGGGGTCCCTGACCGATTCTCTGGC
TCCAAGTCTGGCACCTCAGCCTCCCTGGCCATCACTGGGCTCCAGGCTGAGGATGAGGCTGATTATTACTGCCAGTCCTATGACAGCAGCCTGAGTGGT
TATGTCTTCGGAGGTGGGACCCAGCTCACCGTCCTAGGT

V$_H$ (SEQ ID NO:599) with H1, H2, and H3 underlined (SEQ ID NO:602-604, respectively)

```
Q V Q L V Q S G A E V K K P G A S V K V S C K A S G Y T F T N Y Y M H W
V R Q A P G Q G L E W V G W I N P Y T G S A F Y A Q K F R G R V T M T R
D T S I S T A Y M E L S R L R S D D T A V Y Y C A R E P E K F D S D D S
D V W G R G T L V T V S S
```

V$_H$ (SEQ ID NO:608) with H1, H2, and H3 underlined (SEQ ID NO:611-613, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCAACTACTATATGCACTGG
GTGCGACAGGCCCCTGGACAAGGGCTTGAGTGGGTGGGATGGATCAACCCTTATACTGGTAGCGCATTCTATGCACAGAAGTTTCGGGGCAGGGTCACAATGACCAGG
GACACGTCCATCAGCACAGCCTACATGGAGCTGAGCAGACTGAGATCTGACGACACGGCCGTGTATTATTGTGCGAGAGAACCTGAAAAATTCGACTCCGACGACTCC
GACGTCTGGGGCCGCGGGACATTGGTCACCGTCTCCTCA

V$_L$ (SEQ ID NO:600) with L1, L2, and L3 underlined (SEQ ID NO:605-607, respectively)

```
Q A V L T Q P P S V S G A P G Q R V T I S C T G S S S N I G A G Y G V H
W Y Q Q L P G T A P K L L I Y G D S N R P S G V P D R F S G S K S G T S
A S L A I T G L Q A E D E A D Y Y C Q S Y D N S L S G Y V F G G G T Q L
T V L G
```

V$_L$ (SEQ ID NO:609) with L1, L2, and L3 underlined (SEQ ID NO:614-616, respectively)

CAGGCTGTGCTGACTCAGCCGCCCTCAGTGTCTGGGGCCCCAGGGCAGAGGGTCACCATCTCCTGCACTGGGAGCAGCTCCAACATCGGGGCAGGTTATGGTGTACAC
TGGTACCAACAGCTTCCAGGAACAGCCCCCAAACTCCTCATCTATGGTGACAGCAATCGGCCCTCAGGGGTCCCTGACGATTCTCTGGCTCCAAGTCTGGCACCTCA
GCCTCCCTGGCCATCACTGGGCTCCAGGCTGAGGATGAGGCTGATTATTACTGCCAGTCCTATGACAACAGCCTGAGCGGTTATGTCTTCGGAGGTGGGACCCAGCTCACCGTCCTAGGT
```

V_H (SEQ ID NO:617) with H1, H2, and H3 underlined (SEQ ID NO:620-622, respectively)

EVQLVESGGG VVRPGGSLRL SCAASGFTFD DYGMNWVRQA PGKGLEWVSG

VNWNGGTRDY AASVKGRFTI SRDNAKNSLY LQMNSLRAED TALYHCARGW

YSGAAWNMGY WGRGTLVTVS S

V_H (SEQ ID NO:626) with H1, H2, and H3 underlined (SEQ ID NO:629-631, respectively)

GAGGTGCAGCTGGTGGAGAGCGGCGGAGGCGTGGTGAGACCAGGCGGCAGCCTGAGACTGAGCTGCGCCGCCAGGGCTTCACCTTCGACGACTACGGCATGAA
CTGGGTGAGGCAGGCCCCAGGAAGGGCCTGAGTGGGTGTCCGGCGTGAACTGGAACGGCGGCACCAGAGACTACGCCGCCTCTGTGAAGGCAGATTCACCA
TCAGCCGGGACAACGCCAAGAACAGCCTGTACCTGCAGATGAACAGCCTGAGAGCCGAGGACACCGCCCTGTACCACTGCGCCAGAGGCTGGTACAGCGGAGCC
GCCTGGAACATGGGCTACTGGGGCAGAGGCACCCTGGTCACCGTGTCCAGC

V_L (SEQ ID NO:618) with L1, L2, and L3 underlined (SEQ ID NO:623-625, respectively)

QAALTQPASV SGSPGQSITI SCTGASGDVG AYNFVSWYQQ HPGKAPKLII

YDVNKRPSGV SNRFSGSKSG NTASLTISGL QAEDEADYYC ASLVSDFSVV

FGGGTKLTVL

V_L (SEQ ID NO:627) with L1, L2, and L3 underlined (SEQ ID NO:632-634, respectively)

CAGGCCGCCCTGACCCAGCCCGCCAGCGTGTCTGGCAGCCCAGGCCAGAGCATCACCATCAGCTGCACCGGCGCCAGCGGCGATGTGGGCGCCTACAACTTCGT
GTCCTGGTATCAGCAGCACCCCGGCAAGGCCCCCAAGCTGATCATCTACGACGTGAACAAGAGACCCAGCGGCGTGTCCAACAGATTCAGCGGCAGCAAGAGCG
GCAACACCGCCAGCCTGACCATCAGCGGCCTGCAGGCCGAGGACGAGGCCGACTACTGCGCCAGCCTGGTGTCCGACTTCAGCGTGGTGTTCGGCGGAGGC
ACCAAGCTGACCGTGCTG

*FIG. 8(cont.)*

GIL01

SEQ ID NO:7

E V Q L V E S G G G L V T P G G S L R L S C A A S G F T F
S D Y Y M S W V R Q A P H R G L E W V S Y I S S S G S T I Y
Y A D S V K G R F T I S R D N A K N P L Y L Q M T A S G R F
S E D T A V Y Y C A R G T H W V G G S E G I H W L A W S Y P
S S A S G D R L I S T F Y L D A S E H A S G Q W Y S N Y P L F
V S K A P L I H L L K Q P P D F A T Y Y C Q Q - - - - - -
G K D F L T L E I K R A A A
D G G T K

SEQ ID NO:16

GAAGTGCAGCTGGTGGAGTCTGGGGGAGGCTTGGTCACGCCTGGAGGGT
CCCTGAGACTCTCCTGTGCAGCCTCTGGATTCACCTTCAGTGACTACTA
CATGAGCTGGGTCCGCCAGGCTCCAGGGAAGGGGCTGGAGTGGGTCTCA
GCTATTAGTAGTAGTGGTAGTACATACTACGCAGACTCCGTGAAGG
GCCGGATCACCATCTCCAGAGACAACGCCAAGAACTCACTGTATCTGCA
AATGAGCAGCCTGAGATCTGAGGACACGGCCGTGTATTACTGTGCGAGA
GGGCTTTGGGTTTGGGATCCTCTTGAGGCGGTTCAGGCGGGTGGCAGCGCGG
TCACCGTCTCTTCAGGTGGAGGCGGTTCAGGCGGAGGTGGCAGCGGCGG
TGGCGGATCGGACATCCAGATGACCCAGTCTCCTTCCACCCTGTCTGCA
TCTATTGGAGACAGAGTCACCATCAGCAGAAGCCAGGGAAGCCCCTAAACT
ATCACTGGTTGCCTGGTATCAGCAGAAAGCCAGGGAAGCCCCTAAACT
CCTGATCATATAAGGCCTCTAGTTTAGCCAGTGGGGTCCCATCAAGGTTC
AGCGGCAGTGGATCTGGGACAGATTTCACTCTCACCATCAGCAGCCTGC
AGCCTGATGATTTTGCAACTTATTACTGCCAACAATATAGTAATTATCC
GCTCACTTTCGGCGGAGGGACCAAGCTGGAGATCAAACGTGCGGCCGCA

FIG. 9

GIL16

SEQ ID NO:25

Q V Q L V E S G A E V K K P G A S V K V S C K A S G Y T F
T S Y G I S W V R Q A P G Q G L E W M G W I S A Y M G T N
N Y A Q K F Q G R V T M T R D T S T A Y M E L R S L R S D
S D D T A V Y Y C A R D R G Y D G S D I Q W L A Y W G Q G T
V S S A S T K G P S V F P L A P S S K S T S G G T A A L G
C L V K D Y F P E P V T V S W N S G A L T S G V H T F P A
V L Q S S G L Y S L S S V V T V P S S S L G T Q T Y I C N
V N H K P S N T K V D K R V E P K S C

SEQ ID NO:34

CAGGTGCAGCTGGTGGAGTCTGGGGCTGAGGTGAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
ATCAGCGCTTACATGGGTAACACAAACTATGCACAGAAGTTCCAGGGCAG
AGTCACCATGACCAGAGACACATCCACGGCCTACATGGAGCTGAGGAGCC
TGAGATCTGACGACACGGCCGTGTATTACTGTGCGAGAGATCGT
GGATACTATGATGCTTTTGATATCTGGGGCCAAGGGACCACCGTCACCGT
CTCCTCAGGTGAGGCGGTTCAGGCCCAGTCTCCTCCACCCTCCTCTGCCA
CGGACATCCAGATGACCCAGTCTCCATCCTCCCTGTCTGCATCTATTGGA
GACAGAGTCACCATCACTTGCCGGGCAAGTCAGAGCATTAGCAGCTATTT
AGCCTGGTATCAGCAGAAACCAGGGAAAGCCCCTAAGGTCCTGATCTATG
CTGCATCCAGTTTGCAATCAGGGGTCCCATCAAGGTTCAGCGGCAGTGGA
TCTGGGACAGATTTCACTCTCACCATCAGCAGCCTGCAGCCTGATGATTT
TGCAACTTATTACTGCCAACAATATAGTAATTATCCGCTCACTTTCGGCG
GAGGGACCAAGCTGGAGATCAAACGTGCGGCCGCA

*FIG. 9(cont.)*

GIL45

SEQ ID NO:43

Q M Q L V Q S G G G V V Q P G R S L R L S C A A S G F T F S S Y D
N Y G M Y W Y R Q A P G K G L E W V A H I W Y D G S N E K Y A E D S
A D S V K G R M T V S R D N S R N T L Y L Q M N S L R A E D S G Q P
T A V Y Y C A T G Q H W I T A F D I W G K P A S V Q G T L V T V S S
G G G S I T G S G T S S D V G G Y N Y V S W Y Q Q H P G K A P
S K L M I Y E G S K R P S G V S N R F S G S K S G N T G T
I S G L Q A E D E A D Y Y C S S Y T R S T R V L F G G G T K
L T V L G A A A H

SEQ ID NO:52

CAGATGCAGCTGGTGCAGTCTGGGGGAGGCGTGGTCCAGCCTGGGAGGT
CCCTGAGACTCTCCTGTGCAGCCTCTGGATTCACCTTCAGTAACTATGG
CATGTACTGGGTCCGCCAGGCTCCAGGCAAGGGGCTGGAGTGGGTGGCA
CATATTTGGTATGATGGAAGTAATGAAAAGTATGCAGACTCCGTGAAGG
GCCGAATGACCGTCTCCAGAGACAATTCCAGGAACACGTTGTATTTGCA
AATGAACAGCCTGAGAGCCGAGGACACGGCTGTGTATTACTGTGCGACA
GAGCAACACTGGATTACTGCTTTTGATATCTGGGGCAAAGGCACCCTGG
TCACCGTCTCCTCAGGTGGAGGCGGTTCAGGCGGAGGTGGCAGCGGCGG
TGGCGGATCGAGTCTGTGCTGACTCAGCCACCCTCCCTGTCTGCGGTCT
CCTGGACAGTCGATCACCATCTCCTGCACTGGAACCAGCAGCAGTGACGTTG
GTGGTTATAACTATGTCTCCTGGTACCAACAACACCCCAGGCAAAGCCCC
CAAACTCATGATTTATGAGGGCAGTAAGCGGCCCTCAGGGGTTTCTAAT
CGCTTCTCTGGCTCCAAGTCTGGCAACACGGCCTCCCTGACAATCTCTG
GGCTCCAGGCTGAGGACGAGGCTGATTATTACTGCAGCTCATATACAAC
CAGGAGCACTCGAGTTTTCGGCGGAGGGACCAAGCTGACCGTCCTAGGT
GCGGCCGCA

*FIG. 9(cont.)*

GIL60

SEQ ID NO:61

E V Q L V E S G G G V V R P G G S L R L S C A A S G F T F D D Y
D Y G M N W V R Q A P G K G L E W V S G V N W L Q M G R T L R A E D Y
A A S V K G R F T I S R D N A K N S L Y L Q M N S L R A E D T V S
T A L Y Y C A R G W Y S G S F Y G G S A V G A N R F V S W Y Q S V F G G
S G P D Q T H I Y D V N K R P S G V S T F S K S G V F G G
K T P K L I Y D A E D E S D Y Y C S S Y T S T F S V F G G
S L T I S G L Q A E D A A
G T K V T V L G

SEQ ID NO:70

GAGGTGCAGCTGGTGGAGTCCGGGGAGGTGTGGTACGGCCTGGGGGT
CCCTGAGACTCTCCTGTGCCAGCCTCTGGATTCACCTTTGACGATTATGG
CATGAACTGGGTCCGCCAAGCTCCAGGGAAGGGGCTGGAGTGGGTCTCT
GGTGTTAATGGGAATGGTGTACCAGAGATTATGCAGAGACTCCCGTGAAGG
GCCGATTCACCATCTCCAGAGACAACGCCAAGAACTCCCTGTATCTGCA
AATGAACAGTCTGAGAGCCGAGGACACGGCCTTGTATTACTGTGCGAGA
GGATGGTATAGTGGGAGCTTCTACTACTTTGGCTCAGGGGAGGTGGCTC
CCCTGGTCACCGTCTCGAGTGGAGGCGGCGGTTCAGGCGGAGGTGGCTC
TGGCGGTGGCGGAAGTGCACAGTCTGATCACCATCTCCTGACTGGAGACGCG
TCTGGGTCTCCTGGACAGTCGTTATAACTTTGTCTCCTGGTACCAACACACCCAGG
GTGACGTTGGTGTGCTTATAACTCATAATTATGATGTCAATAAGCGGCCCTCAGGG
CAAAACCCCCAAACTCATAATTTATGATGTCAATAAGCGGCCCTCAGGG
GTTTCTAATCGCTTCTCTGGCTCCAAGTCTGGCAACACGGCCTCCCTGA
CCATCTCTGGGCTCCAGGCCGAGGCGAGTGATTATTACTGCAGCTC
ATATACAAGCACCTTCTCTGTGGTATTTGGCGGAGGGACCAAGGTCACC
GTCCTAGGTGCGGGCC

*FIG. 9(cont.)*

GIL68

SEQ ID NO:79

```
E V Q L V Q S G A E V K K P G E T V K V S C Q A S G Y T F T Y A D Q V
V Y I H W V R Q T P G Q M T R D M S N T I W T A Y G K D G T R Y T F S
K F Q G W R D L T G G F D D P F D L T Q P R L V A P L R D D G K T A V S
Y Y C A R S G G S A Q S V H W Y Q Q R S G K V I Y E A G D A
G G G T G G G N F R N K R V H W Y Q Q R S G K V I Y E A G D A
T C G G N I P E R F S G S R P L I S R V L G A A
D R P S G C Q V W D S T D R P L F G N T K L T V L G A A
A D F Y
```

SEQ ID NO:88

GAAGTGCAGCTGGTGCAGTCTGGGGCTGAGGTGAAGAAGCCTGGGGCCTC
AGTGAAGGTCTCCTGTCAGGCTTCTGGATACACCTTCAGCGATTACTATA
TTCACTGGGTGCGACAGGACCCCTGGACAAGGGTTTGAGTGGATGGGATGG
GTCAACCCTGACACTGGTGGCACAGATACGCCAGAAGTTTCAGGGCTG
GGTCACCATGACCAGGGACACTGTCCAACACCACAGCCTACATGGAGCTGC
CCAGGCTGAGAGACGACGACACGGCCGTATATTACTGTGCGAGAGATCTA
ACTGGATTTGATCCTTTGATATCTGGGGCCAGGGAGCTGGCTCTGGCGAA
CTCGGTGGAGGCGGCGGTTCAGGCGGGCGGACTGACTCAGCCACCCTCA
GTGCACAGTCTGTGCTGCAGATTACCTGTGGGGAAACAACTTTCGAAATAAAGAGT
AAGACGGCCACGATTCAGCAGGCCAGGCCAGGATCCCTGAGCGATTCTGGCTCCCGC
ACACTGGTATCAGACACCGGCCGCCACCCTGACCATCAGCAGGGTGGATGA
ATGATTCAGAAATTTACTGTCAGGTGTGGATAGTAGTACTGATCGTCCGCTGT
TCGGCGGAGGGACCAAGCTGACCGTCCTAGGTGCGGCCGCA
```

*FIG. 9(cont.)*

GIL92

SEQ ID NO:97

| Q | V | Q | L | V | Q | S | G | A | E | V | K | K | P | G | A | S | V | K | V | S | C | K | A | S | G | Y | T | F | T | D | Y |
|---|---|---|---|---|---|---|---|---|---|---|---|---|---|---|---|---|---|---|---|---|---|---|---|---|---|---|---|---|---|---|---|
| M | H | W | V | R | Q | A | P | G | Q | G | L | E | W | M | G | W | I | N | P | Y | T | G | D | D | T | A | V | Y | A | Q | K |
| F | Q | G | R | V | T | M | T | R | D | T | S | I | N | T | A | Y | M | E | L | S | R | L | G | S | D | D | T | A | V | Y | Y |
| C | A | R | E | P | E | K | F | D | F | W | G | D | D | T | W | Y | M | R | G | V | S | G | A | F | Y | A | Q | K | F | R | G |
| G | G | S | A | Q | A | V | L | T | Q | P | P | S | V | S | G | A | P | G | Q | R | V | T | I | S | C | G | G | S | S | S | G |
| I | G | A | G | Y | G | V | H | W | Y | Q | Q | L | P | G | T | A | P | K | L | L | I | Y | G | N | S | N | R | P | S | G | V |
| P | D | R | F | S | G | S | K | S | V | F | G | T | G | T | Q | L | T | V | L | S |   |   |   |   |   |   |   |   |   |   |   |
| S | S | L | S | G | Y | V |   |   |   |   |   |   |   |   |   |   |   |   |   |   |   |   |   |   |   |   |   |   |   |   |   |

SEQ ID NO:106

```
CAGGTCCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGGCGACACGTCCATCAACACAGCCTACATGGAG
GGTCACCATGACCAGGGACACGTCCATCAACACAGCCTACATGGAGCTGA
GCAGACTGGGATCTGACGACACGGCCGTGTATTATTGTGCGAGAGAACCT
GAAAAATTCGATTTTTGGGGGGTGACAACTGGGGCCGGGGACAATGGT
CACCGTCTCGAGTGGAGGCGGTTCAGGCGGAGGTGGCTCTGGCGGTG
GCGGAAGTGCACAGGCTGTGCTGACTCAGCCTCCCTCACTGGGAGCCCCA
CCAGGGCAGAGGGTCACCATCTCTGCAGCTCCAGGAGCAGCTCCAACATCGG
GGCAGGTTATGGTGTACACTGGTACCAGCAGCTTCCAGGAACAGCCCCCA
AACTCCTCATCTATGGTAACAGCAATCGGCCCTCAGGGGTCCCTGACCGA
TTCTCTGGCTCCAAGTCTGGCACCTCAGCCTCCCTGGCCATCACTGGGCT
CCAGGCTGAGGATGAGGCTGATTATTACTGCCAGTCCTATGACAGCAGCC
TGAGTGGTTATGTCTTCGGAACTGGGACCCAGCTCACCGTTTAAGTGCG
GCCGCA
```

SEQ ID NO:115

EVQLVESGGGLVTPGGSLRLSCAASGFTFSDYYMSWVRQAPGRGLEWVSAIS
GSGGSTYYADSVKGRITISRDNAKNSLYLQMSSLRSEDTAVYYCARGLWVWD
PLDYWGRGTLVTVSSGGGGSGGGGSGGGGSDIQMTQSPSTLSASIGDRVTIT
CRASEGIYHWLAWYQQKPGKAPKLLIYKASSLASGAPSRFSGSGFGTDFTLT
ISSLQPDDFATYCQQYSEFAWTFGGGTKLEIKRAAAH

SEQ ID NO:124

GAGGTGCAGCTGGTGGAGTCTGGGGGAGGCTTGGTCACGCCTGGAGGGT
CCCTGAGACTCTCCTGTGCAGCCTCTGGATTCACCTTCAGTGACTACTA
CATGAGCTGGGTCCGCCAGGCTCCAGGGAAGGGGCTGGAGTGGGTCTCA
GCTATTAGTGGTAGTGGTGTAGCACATACTACGCAGACTCCGTGAAGG
GCCGGATCACCATCTCCAGAGACAACGCCAAGAACTCACTGTATCTGCA
AATGAGCAGCCTGAGATCTGAGGACACAGCCGTGTATTACTGTGCGAGA
GGGCTTTGGGTTTGGGATCCTCTTGACTACTGGGGCCAGAGGAACCCTGG
TCACCGTCTCTTCAGGTGGCGGCGGTTCAGGCGGAGGTGGCAGCGGCGG
TGGCGGATCGGACATCCAGATGACCCAGTCCCCTTCCACCCTGTCTGCA
TCTATTGGAGACAGAGTCACCATCACCTGCCGGGCCAGTGAGGGTATTT
ATCACTGGTTGGCCTGGTATCAGCAGAAGCCAGGGAAAGCCCCTAAACT
CCTGATCTATAAGGCCTCTAGTTTAGCCAGTGGGGCCCCATCAAGGTTC
AGCGGCAGTGGATTTGGGACAGATTTCACTCTCACCATCAGCAGCCTGC
AGCCTGATGATTTTGCAACTTATTACTGCCAACAATACAGCGAGTTCGC
CTGGACCTTCGGCGGAGGGACCAAGCTGGAGATCAAACGTGCGGCCGCA
CAT

062A09

SEQ ID NO:133

QVQLVESGAEVKKPGASVKVSCKASGYTFTSYGISWVRQAPGQGLEWMGWV
SAYTGNTNYAQKFQGRVTMTTDTSTSTAYMELRGLRSDDTAVYYCARDRGY
YDAYDIWGQGTLVTVSSGGGGSGGGGSGGGGSDIQMTQSPSTLSASIGDRV
TITCRASEGIYHWLAWYQQKPGKAPKLLIYKASSLASGAPSRFSGSGFGTD
FTLTISSLQPDDFATYYCQQMGEYNATIGGGTKLEIKRAAAH

SEQ ID NO:142

CAGGTGCAGCTGGTGGAGTCTGGGGCTGAGGTGAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
GTCAGCGCTTACACTGGTAACACAAACTATGCACAGAAGTTCCAGGGCAG
AGTCACCATGACCACAGACACATCCACGAGCACAGCCTACATGGAACTGA
GGGGCCTGAGATCGACGACAGGCCGTGTATTACTGTGCGAGAGATCGT
GGATACTATGATGCTTATGATATCTGGGGCCAAGGGACCACCCTGGTCACCGT
CTCCTCAGGTGGAGGCGGTTCAGGCGGAGGTGGCAGCGGCGGTGGCGGAT
CGGACATCCAGATGACCCAGTCTCCTTCCACCCTGTCTGCATCTATTGGA
GACAGAGTCACCATCACCTGCCGGGCCAGTGAGGGTATTTATCACTGGTT
GGCCTGGTATCAGCAGAAGCCAGGGAAAGCCCCTAAACTCCTGATCTATA
AGGCCTCTAGTTTAGCCAGTGGGGTCCCATCAAGGTTCAGCGGCAGTGGA
TTTGGGACAGATTTCACTCTCACCATCAGCAGCCTGCAGCCTGATGATTT
TGCAACTTATTACTGCCAACAAATGGGCGAGTACAACGCCACCATCGGCG
GAGGGACCAAGCTGGAGATCAAACGTGCGGCCGCACAT

SEQ ID NO:151

QVQLVESGAEVKKPGASVKVSCKASGYTFTSYGISWVRQAPGQGLEWMGWI
SAYTGNTNYAQKFQGRVTMTDTSTSTAYMELRSLRSDDTAVYYCARDRGY
YDAFDIWGQGTLVTVSSGGGGSGGGGSGGGGSDIQMTQSPSTLSASIGDRV
TITCRASEGIYHWLAWYQQKPGKAPKLLIYKASSLASGAPSRFSGSGFGTD
FTLTISSLQPDDFATYYCQQMGEWKAAFGGGTKLEIKRAAAH

SEQ ID NO:160

CAGGTGCAGCTGGTGGAGTCTGGAGCTGAGGTGAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
ATCAGCGCTTACACTGGTAACACAAACTATGCACAGAAGTTCCAGGGCAG
AGTCACCATGACCACAGACACATCCACGAGCACAGCCTACATGGAACTGA
GGAGCCTGAGATCTGACGACACGGCCGTGTATTACTGTGCGAGAGATCGT
GGATACTATGATGCTTTTGATATCTGGGGCCAAGGCACCCTGGTCACCGT
CTCCTCAGGTGGGGGCGGTTCAGGCGGAGGTGGCAGCGGCGGTGGCGGAT
CGGACATCCAGATGACCCAGTCTCCTTCCACCCTGTCTGCATCTATTGGA
GACAGAGTCACCATCACCTGCCGGGCCAGTGAGGGTATTTATCACTGGTT
GGCCTGGTATCAGCAGAAGCCAGGGAAAGCCCCTAAACTCCTGATCTATA
AGGCCTCTAGTTTAGCCAGTGGGGCCCCATCAAGGTTCAGCGGCAGTGGA
TTTGGGACAGATTTCACTCTCACCATCAGCAGCCTGCAGCCTGATGATTT
TGCAACTTATTACTGCCAACAAATGGGGGAGTGGAAGGCGGCCTTCGGCG
GAGGGACCAAGCTGGAGATCAAACGTGCGGCCGCACAT

SEQ ID NO:169

EVQLVESGGGVVRPGGSLRLSCAASGFTFDDYGMNWVRQAPGKGLEWVSGV
NWNGGTRDYAASVKGRFTISRDNAKNSLYLQMNSLRAEDTALYYCARGWYS
GAAWNMGYWGRGTLVTVSSGGGGSGGGGSGGGGSAQAVLTQPSSVSGSPGQ
SITISCTGASGDVGAYNFVSWYQQHPGKTPKLIIYDVNKRPSGVSNRFSGS
KSSNTASLTISGLQAEDESDYCSSYTSTFSVVFGGGTKVTVLGAAAH

SEQ ID NO:178

CGAGGTGCAGCTGGTGGAGTCCGGGGGAGGTGTGTACGGCCTGGGGGTCCCTG
AGACTCTCCTGTGCAGCCTCTGATTCACCTTTGACGATTATGGCATGAACTGGG
TCCGCCAAGCTCCAGGGAAGGGGCTGGAGTGGGTCTCTGGTGTTAATTGGAATGG
TGGTACCAGAGATTATGCAGCCTCCGTGAAGGGCCGATTCACCATCTCCAGAGAC
AACGCCAAGAACTCCCTGTATCTGCAAATGAACAGTCTGAGAGCCGAGGACACGG
CCTTGTATTACTGTGCGAGAGGATGGTATAGTGGGGCCGCGTGAACATGGGCTA
CTGGGGCCCAGGAACCCTGGTCACCGTCTCGAGTGCAGCCTGTGCTGCACAGGCT
GGTGGCTCTGGCGGTGGCGGATCAGGTGGAAGTCGACAGTCGATCACCATCTCCTGCACAGGCT
TGTCTGGGGCTCCTGGACAGTCGATCACCATCTCCTGCACTGGAGCCAGCGGTGA
CGTTGGTGCTTATAACTTTGTCTCCTGGTACCAACAACACCAGGCAAAACCCCC
AAACTCATAATTTATGATGTCAATAAGCGGCCCTCAGGGGTTTCTAATCGCTTCT
CTGGCTCCAAGTCTAGCAACACGGCCTCCCTGACCATCTCTGGGCTCCAGGCCGA
GGACGAGTCTGATTATTACTGCAGCTCATATACAAGCACCTTCTCTGTGTATTT
GGCGGAGGGACCAAGGTCACCGTCCTAGGTGCGGCCGCACAT

SEQ ID NO:187

EVQLVESGGGVVRPGGSLRLSCAASGFTFDDYGMNWVRQAPGKGLEWVSG
VNWNGGTRDYAASVKGRFTISRDNAKNSLYLQMNSLRAEDTALYYCARGW
YSGSPWSLGHWGRGTLVTVSSGGGGSGGGGSGGGGSGGGGSGGGGSGGGS
GGGGSAQAVLTQPSSVSGSPGQSVTISCTGASGDVGAYNFVSWYQQHPGK
TPKLIIYDVNKRPSGVSNRFSGSKSGNTASLTISRLQAEDESDYCSSYT
SRYTEFGGGTKVTVLGAAAH

SEQ ID NO:196

GAGGTGCAGCTGGTGGAGTCCGGGGGAGGTGTGGTACGGCCTGGGGGGT
CCCTGAGACTCTCCTGTGCAGCCTCTGGATTCACCTTTGACGATTATGG
CATGAACTGGGTCCGCCAAGCTCCAGGGAAGGGGCTGGAGTGGGTCTCT
GGTGTTAATTGGAATGGTGGTACCAGAGATTATGCAGCCTCCGTGAAGG
GCCGATTCACCATCTCCAGAGACAACGCCAAGAACTCCCTGTATCTGCA
AATGAACAGTCTGAGAGCCGAGGACACGGCCTTGTATTACTGTGCGAGA
GGATGGTATAGTGGGAGCCCGTGGTCGCTGGGCCACTGGGGCCGAGGAA
CCCTGGTCACCGTCTCGAGTGGAGGCGGCGGTTCAGGCGAGGTGGCTC
TGGCGGTAGCGAGGTGGCTCTGGCGGTAGCGGAGGTGGCTCCTAGCGGA
GGTGGCTCTGGCGGTCTGGGTCTCGGACCAGTCGGTGCTGCTCAGCCGT
CCTCCGTCTGGGTCTGCGGTGACGTTGGTGCTTATAACTTTGTCTCTGG
AGCCAGCGGTGACGTTGGTGCTTATAACTTTGTCTCTGGTACCAACAA
CACCCAGGCAAAACCCCCAAACTCATAATTTATGATGTCAATAAGCGGC
CCTCAGGGGTTTCTAATCGCTTCTCTGGCTCCAAGTCTGGCAACACGGC
CTCCCTGACCATCTCTAGGCTCCAGGCCGAGGACGAGTCTGATTATTAC
TGCAGCTCATATACATCGAGTACACGACCGAGTTTGGCGGAGGGACCA
AGGTCACCGTCCTAGGTGCGGCCGCACAT

SEQ ID NO:205

EVQLVESGGGVVRPGGSLRLSCAASGFTFDDYGMNWVRQAPGKGLEWVSG
VNWNGGTRDYAASVKGRFTISRDNAKNSLYLQMNSLRAEDTALYYCARGW
YSGAAWNMGYWGRGTLVTVSSGGGGSGGGGSGGGGSGGGGSGGGGSGGGS
AQAVLTQPSSVSGSPGQSITISCTGASGDVGAYNFVSWYQQHPGKTPKLI
IYDVNKRPSGVSNRFSGSKSGNTASLTISGLQAEDESDYYCASLVSDFSV
VFGGGTKVTVLGAAAH

SEQ ID NO:214

GAGGTGCAGCTGGTGGAGTCCGGGGGAGGTGTGGTACGGCCTGGGGGGT
CCCTGAGACTCTCCTGTGCAGCCTCTGGATTCACCTTTGACGATTATGG
CATGAACTGGGTCCGCCAAGCTCCAGGGAAGGGGCTGGAGTGGTCTCT
GGTGTTAATTGGAATGGTGGTACCAGAGATTATGCAGCCTCCGTGAAGG
GCCGATTCACCATCTCCAGAGACAACGCCAAGAACTCCCTGTATCTGCA
AATGAACAGTCTGAGAGCCGAGGACACGGCCTTGTATTACTGTGCCGAGA
GGATGGTATAGTGGGGCCGCGTGAACATGGGCTACTGGGGCCGAGGAA
CCCTGGTCACCGTCTCGAGTGGAGGCGGCGGTTCAGGCGGAGGTGGCTC
TGGCGGTAGCGGAGGTGGCTCTGGCGGTGCTGACTCAGCCGTCTCCGTGTCTGGGT
GCCGAAGTGCACAGGCTGTGCTGACTCAGCCGTCTCCGTGTCTGGGT
CCCCTGGACAGTCGATCACCATCTCCTGCACTGGAGCCAGCGGTGACGT
TGGTGCTTATAACTTTGTCTCCTGGTACCAACAACACCCAGGCAAAACC
CCCAAACTCATAATTTATGATGTCAATAAGCGGCCCTCAGGGGTTTCTA
ATCGCTTCTCTGGCTCCAAGTCTGGCAACACGGCCTCCCTGACCATCTC
TGGGCTCCAGGCCGAGGACGAGTCTGATTATTACTGCGCCTCCCTGTC
TCCGACTTCTCTGTGGTATTTGGCGGAGGACCAAGGTCACCGTCCTAG
GTGCGGCCGCACAT

SEQ ID NO:223

EVQLVQSGAEVKKPGASVKVSCQASGYTFSDYYIHWVRQTPGQGFEWMGWV
NPDTGGTRYAQKFQGWVTMTRDMSNTTAYMELPRLRDDDTAVYYCARDLTG
FDPFDIWGQGTLVTVSSGGGSSGGGSGGGSAQSVLTQPPSVSVAPGKTA
TITCGGNNFRNKRVHWYQQRPGQAPVLVIYYDSDRPSGIPERFSGSRSGNT
ATLTISRVEAGDEADFYCQVWDLFNDNGVFGGGTKLTVLGAAAH

SEQ ID NO:232

GAAGTGCAGCTGGTGCAGTCTGGGGCTGAGGTGAAGAAGCCTGGGGCCTC
AGTGAAGGTCTCCTGTGCAGTTTCAGGCTTCTGGATACACCTTCAGCGATTACTACATA
TTCACTGGGTGCGACAGACCCCTGGACAAGGGTTTGAGTGGATGGGATGG
GTCAACCCTGACAATGACCAGGAGACACTGGTGCACAAGATACGGCAGAAGTTTCAGGGCTG
GGTCACAATGACCAGGAGAGACACGAGCCTACACAGCCTACATGGAGCTGC
CCAGGCTGAGAGAGACGACGACAGGCCGTATATTACTGTGCGAGAGATCTA
ACTGGATTTGATCCTTTTGATATCTGGGGCCAGGGAACCCTGGTCACCGT
CTCGAGTGGAGGCGGCAGTTCAGGTTCAGGTGGAGGTGGCTCTGGCGGTGGCGGAA
GTGCACAGTCTGTGCTGACTCAGCCACCCTCAGTGTCAGTGGCCCCAGGA
AAGACGGGCCACGATTACCTGTGGGGAAACAACTTTCGAAATAAAGAGT
ACACTGGTATCAGCAGAGGCCAGGCCAGGATCCCTGAGCGATTCTCTGGCTCCCGC
ATGATTCAGACCGGCCCCTCAGGGATCCATCAGCAGGGTCGAGGCCGGGATGA
TCTGGGAACACGGCCACCCTGACCATCAGCAGGGTCGAGGCCGGGATGA
GGCCGACTTTTACTGTCAGGTGTGGGATCTCTTCAACGACAACGGCGTGT
TCGGCGGAGGGACCAAGCTGACCGTCCTAGGTGCGGCCGCACAT

166G05

SEQ ID NO:241

EVQLVQSGAEVKKPGASVKVSCQASGYTFSDYYIHWVRQTPGQGFEWMGWV
NPDTGGTRYAQKFQGWVTMTRDMSNTTAYMELPRLRDDDTAVYYCARDLTG
FDPFDIWGQGTLVTVSSGGGGSGGGGSGGGGSAQSVLTQPPSVSVAPGKTA
TITCGGNNFRNKRVHWYQQRPGQAPVLVIYDSDRPSGIPERFSGSRSGNT
ATLTISRVEAGDEADFYCQVWDFLTDSGSFGGGTKLTVLGAAAH

SEQ ID NO:250

GAAGTGCAGCTGGTGCAGTCTGGGGCTGAGGTGAAGAAGCCTGGGGCCTC
AGTGAAGGTCTCCTGCAAGGCTTCTCAGGCTTCTGGATACACCTTCAGCGATTACTATA
TTCACTGGGTGCGACAGACCCCTGGACAAGGGTTTGAGTGGATGGGATGG
GTCAACCCTGACACTGGTGGCACAAGATACGCAGAAGTTTCAGGGCTG
GGTCACAATGACCAGGGACACAGTCCAACACCACAGCCTACATGGAGCTGC
CCAGGCTGAGAGACGACGACACGGCCGTATATTACTGTGCGAGAGATCTA
ACTGGATTTGATCCTTTTGATATCTGGGGCCAGGGAACCCTGGTCACCGT
CTCGAGTGGAGGCGGCGGTTCAGGCGGAGGTGGCTCTGGCGGTGGCGGAA
GTGCACAGTCTGTGCTGACTCAGCCACCCTCAGTGTCAGTGGCCCCAGGA
AAGACGGCCACAATTACCTGTGGGGAAACAACTTTCGAAATAAAGAGT
ACACTGGTATCAGCAGAGGCCAGGCCAGGCCCTGTCCTGTCATCTATT
ATGATTCAGACCGGCCCTCAGGGATCCCTGAGCGATTCTCTGGCTCCCGC
TCTGGGAACACGGCCACCCTGACCATCAGCAGGGTCGAGGCCGGGATGA
GGCCGACTTTTACTGTCAGGTGTGGGATTTCCTCACCGACTCGGGTCGT
TCGGCGGAGGGACCAAGCTGACCGTCCTAGGTGCGGGGCGCCCACAT

SEQ ID NO:259

EVQLVQSGAEVKKPGASVKVSCQASGYTFSDYYIHWVRQTPGQGFEWMGW
VNPDTGTRYAQKFQGWVTMTRDMSNTTAYMELPRLRDDDTAVYYCARDL
TGYDYYDRWGQGTLVTVSSGGGGSGGGGSGGGGSGGGGSGGGGSAQ
SVLTQPPSMSVAPGKTATITCGGNNFRNKRVHWYQQRPGQAPVLVIYDS
DRPSGIPERFSGSRSGNTATLTISRVEAGDEADFYCQVWDFLADEAMFGG
GTKLTVLGAAAH

SEQ ID NO:268

GAAGTGCAGCTGGTGCAGTCTGGGGCTGAGGTGAAGAAGCCTGGGGCCTC
AGTGAAGGTCTCCTGTGACAGCTTCAGGCTTCTGGATACACCTTCAGCGATTACTATA
TTCACTGGGTGCGACAGACCCCTGGACAAGGGTTTGAGTGCTGATGGGATGG
GTCAACCCTGACAATGACCAGGGACATGTCCAACACCACAGCCTACATGGAGCTGC
CCAGGCTGAGAGACGACGACACGGCCGTATATTACTGTGCGAGAGATCTA
ACTGGATACGACTACTACGACCGGTTCAGGCGGAGGTGGCTCTGGCGGTGGCGGAG
TGGCTCTGGCGGTGGCGGAGTGGCTCTGGCGGTGGCGGAAGTGCACAG
TCTGTGCTGACTCAGCCGCCCTCAAGTCAGTGGCCCCAGGAAAGACGGC
CACGATTACCTGTGGGGGAAACAACTTTCGAAATAAAGAGTACACTGGT
ACCAGAGGCCAGGCCAGGCTCCCTGAGCGATTCTCTGGCTCCCGGCTCA
GACGGCCACCCTGACCCTGACCATCAGCAGGGTCGAGGCCGGGATGAGGCCGACT
TTTACTGTCAGGTGTGGGATTTCCTGCCGACAGAGGCGATGTTCGGCGGA
GGGACCAAGCTGACCGTCCTAGGTGCGGCCGCACAT

SEQ ID NO:277

EVQLVQSGAEVKKPGASVKVSCQASGYTFSDYYIHWVRQTPGQGFEWMGW
VNPDTGGTRYAQKFQGWVTMTRDMSNTTAYMELPGLRDDDTAVYYCARDL
TGYDQYTAWGQGTLVTVSSGGGGSGGGGSGGGGSAQSVLTQPPSVSVAPG
KTATITCGGNNFRNKRVHWYQQRPGQAPVLVIYDSDRPSGIPERFSGSR
SGNTATLTISRVEAGDEADFYCSTFDPFTDRPLFGGGTKLTVLGAAAH

SEQ ID NO:286

GAAGTGCAGCTGGTGCAGTCTGGGGCTGAGGTGAAGAAGCCTGGGGCCTC
AGTGAAGGTCTCCTGTCAGGCTTCTGGATACACCTTCAGCGATTACTATA
TTCACTGGGTGCGACAGAGACCCCAGGACAAGGGTTTGAGTGGATGGGAT GG
GTCAACCCTGACACTGGTGGCACAGACGACACCAGCTACACACAGCTAC
GGTCACAATGACCAGGACACTGTCCAACACCAGCTACATGGAGCTGC
CCGGGCTGAGAGACGACGACACGGCCGTATATTACTGTGCGAGAGATCTA
ACTGGGTACGACCAGTACACGGCCTGGGGCCAGGGAACCCTGGTCACCGT
CTCGAGTGGAGGCGGCGGTTCAGGCGGAGGTGGCTCTGGCGGTGGCGGAA
GTGCACAGTCTGTGCTGACTCAGCCACCCTCAGTGTCAGTGGCCCCAGGA
AAGACGGCCACGATTACCTGTGGGGGAAACAACTTTCGAAATAAAAGAGT
ACACTGGTATCAGCAGAGGCCAGGCCAGGCCCCTGTCCTGGTCATCTATT
ATGATTCAGACCGGCCCTCAGGGATCCCTGAGCGATTCTCTGGCTCCCGC
TCTGGGAACACGGCCACCCTGACCATCAGCAGGGTCGAGGCCGGGATGA
GGCCGACTTTTACTGTAGCACCTTCGACCCCTTCACTGATCGTCCGTGT
TCGGGCGGAGGGACCAAGCTGACCGTCCTAGGTGGCGCCGCCCACAT

SEQ ID NO:295

QVQLVQSGAEKKPGASVKVSCKASGYTFTDYYMHWRQAPGQGLEWVGWIN
PYTGGAFYAQKFRGRVTMTRDTSINTAYMELSRLGSDDTAVYYCAREPERF
GDSTGQVWGRGTMVTVSSGGGGSGGGGSGGGGSRSAQAVLTQPSSVSGAPRQR
VTISCTGSSSNIGAGYGVHWYQQLPGTAPKLLIYGNSNRPSGVPDRFSGSK
SGTSASLAITGLQAEDEADYCYHWDKEQSGYVFGTGTQLTVLSA

SEQ ID NO:304

CAGGTCCAGTTGGTGCAGTCTGGGGCTGAGGTGAAGAAGCCTGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGGCGCATTCTATGCACAGAAGTTCCGGGGCAG
GGTCACAATGACCAGGGACACGTCCATCAACACAGCCTACATGGAGCTAA
GCAGACTGGGATCTGACGACACGGCCGTGTATTATTGTGCGAGAGAACCT
GAAAGATTCGGCGACTCCACGGGCCAGGTCTGGGGCCGGAGGTGGCTCTGGCGGTA
CACCGTCTCGAGTGGGGCGGCGGTTCAGGCGGAGGTGGCTCTGGCGGCC
GCAGAAGTGCACAGGCTGTGCTGACTCAGCCGTCCTCAGTGTCTGGGGCC
CCAAGGCAGAGGGTCACCATCTCCTGCACTGGGAGCAGCTCCAACATCGG
GGCAGGTTATGGTGTATACACTGGTACCAACAGCTTCCAGGAACAGCCCCA
AACTCCTCATCTATGGTAACAGCAATCGGCCCTCAGGGGTCCCTGACCGA
TTCTCTGGCTCCAAGTCTGGCACCTCAGCTCTCCTGGCCATCACTGGGCT
CCAGGCTGAGGATGAGGCTGATTATTACTGCTACCACTGGGACAAGGAGC
AGAGTGGTTATGTCTTCGGAACTGGGACCCAGCTCACCGTTTTAAGTGCG

SEQ ID NO:313

EVQLVQSGAEVKKPGASVKVSCQASGYTFTDYYMHWVRQAPGQGLEWVGWI
NPYTGSAFYAQKFRGRATMTRNTSINTAYMELSRLGSDDTAVYYCAREPEK
FGESSGQLWGRGTMVTISSGGGGSGGGGSGGGGSAQAVLTQPSSVSGAPGQ
RVTISCTGSSSNIGPGYGVHWYQQLPGTAPKLLIYGDSNRPSGVPDRFSGS
KSGTSASLAITGLQAEDEADYCQSYDSGLSGYVFGTGTQLTVLSA

SEQ ID NO:322

GAAGTGCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGGTGGGGTGG
ATCAACCCTTATACTGGTAGCGCATTCTATGCACAGAAGTTTCGGGGCAG
GGCCACAATGACCAGGAACACGTCCATCAACACAGCCTACATGGAGCTGA
GCAGACTGGGATCTGACGACACGGCCGTGTATTATTGTGCGAGAGAACCT
GAAAAATTCGGCGAGTCCAGCGGCCAGTTGTGGGGCCGAGGTGGCTCTGGCGGTA
CACCATCTCGAGTGGAGGCGGCGGTTCAGGCGGAGGTGGCTCTGGCGGTG
GCGGAAGTGCACAGGCTGTGCTGACTCAGCCGTCCTCAGTGTCTGGGGCC
CCAGGGCAGAGGGTCACCATCTCCTGCACTGGGAGCAGCTCCAACATCGG
GGCAGGTTATGGTGTACACTGGTACCAACAGCTTCCAGGAACAGCCCCCA
AACTCCTCATCTATGGTGACAGCAATCGGCCCTCAGGGGTCCCTGACCGA
TTCTCTGGCTCCAAGTCTGGCACCTCAGCCTCCCTGGCCATCACTGGGCT
CCAGGCCGAGGATGAGGCTGATTATTACTGCCAGTCCTATGACAGCGGCC
TGAGTGGTTATGTCTTCGGAACTGGGACCCAGCTCACCGTTTTAAGTGCG

355E04

SEQ ID NO:331

QVQLVQSGAEVKKPGASVKVSCKASGYTFTHYYMHWVRQAPGQGLEWVGWI
NPYTGGAFYAQKFQGRVTMTRDTSINTAYMELSRLGSDDTAVYYCAREPEK
EDSPNAEIWGRGTMVTISSEGGSGGSGGSGGSAQAVLTQPSSVSGAPGQ
RVTISCTGSSNIGAGYGVHWYQQLPGTAPKLLIYGNSNRPSGVPDRFSGS
KSGTSASLAITGLQAEDEADYCQSYDSSLSGYVFGTGTQLTVLSA

SEQ ID NO:340

CAGGTCCAGCTGGTGCAGTCTGGGGCTGAGGTGAAAAAGCCTGGGGCCTC
AGTGAAGGTCTCCTGCAAGGCTTCTGGATACACCTTCACCCACTACTATA
TGCACTGGGTGCGACAGGCCCCTGGACAAGGGCTTGAGTGGGTGGGATGG
ATCAACCCTTATACTGGTGGCGCATTCTATGCACAGAAGTTTCAGGGCAG
GGTCACAATGACCAGGGACACGTCCATCAACACAGCCTACATGGAGCTGA
GCAGACTGGGATCTGACGACACGGCCGTGTATTATTGTGCGAGAGAACCT
GAAAAATTCGACTCGCCAACGCCCGAGATCTGGGGCCGGGGACAATGGT
CACCATCTCGAGTGAAGGCGGCGGTTCTGCTGACTCAGCCGTCCTCAGTG
GCGAAGTGCACAGGCTGTGCTGACTCAGCCGTCCTCAGTGTCTGGGGCC
CCAGGCCAGAGAGGTCACCATCTCCTGCACTGGGAGCAGCAGCTCCAACATCGG
GGCAGGTTATGGTGTACACTGGTACCAACAGCTTCCAGGAACAGCCCCCA
AACTCCTCATCTATGGTAACAGCAATCGGCCCTCAGGGGTCCCTGACCGA
TTCTCTGGCTCCAAGTCTGGCACCTCAGCCTCCCTGGCCATCACTGGGCT
CCAGGCTGAGGATGAGGCTGATTATTACTGCCAGTCCTATGACAGCAGCC
TGAGTGGTTATGTCTTCGGAACCGGGACCCAGCTCACCGTTTTAAGTGCG

SEQ ID NO:349

QVQLVQSGAEVKKPGASVKVSCKASGYTFTNYYMHWVRQAPGQGLEWVGWI
NPYTGSAFYAQKFRGRVTMTRDTSINTAYMELSRLGSDDTAVYYCAREPEK
FDSDDSDVWGRGTMVTVSGGGGSGGGGSGGGGSAQVLTPPSVSGAPGQR
VTISCTGSSSNIGAGYGVHWYQQLPGTAPKLIIYGDSSRPSGVPDRFSGSK
SGTSASLAITGLQAEDEADYYCQSYDNSLSGYVFGTGTQLTVLSA

SEQ ID NO:358

CAGGTTCAGCTTGGTGCAGTCTGGGGCTGAGGTGAAGAAGCCTGGGCCTC
AGTGAAGGTCTCCTGCAAGGCTTCTGGATACACCTTCACCAACTACTATA
TGCACTGGGTGCGACAGGCCCCTGGACAGGGGCTTGAGTGGTGGGATGG
ATCAACCCTTATACTGGTAGCGCATTCTATGCACAGAAGTTTCGGGGCAG
GGTTACAATGACCAGGACAGTCCATCAACACAGCCTACATGGAGCTGA
GCAGACTGGGATCTGACGACACGGCCGTGTATTATTGTGCAGAGAACCT
GAAAAATTCGACTCCGACGACTCCGACGTCTGGGGCCGGGAGGTCTGGCGGTA
CACCGTCTCCGGGTCGGAGGCGCAGTTCAGGCGGAGGTGGCTCTGGCGGTA
GCGGAAGTGCACAGGCTGTGTCGACTCAGCCCCCTCAGTGTCTGGGGCC
CCAGGGCAGAGAGGGTCACCATCTCCTGCACTGGGAGCAGCTCCAACATCGG
GGCAGGTTATGGTGTACACTGGTACCAACAGCTTCCAGGAACAGCCCCCA
AACTCATCATCTATGGTGACAGCAGTCGGCCCTCAGGGGTCCCTGACCGA
TTCTCTGGCTCCAAGTCTGGCACCTCAGCTCCCTGGCCATCACTGGGCT
CCAGGCTGAGGATGAGGCTGATTATTACTGCCAGTCCTATGACAACAGCC
TGAGCGGTTATGTCTTCGGAACTGGGACCCAGCTCACCGTTTTAAGTGCG

*FIG. 9(cont.)*

GIL01

SEQ ID NO:367

QVQLVESGGGLVKPGGSLRLSCAASGFTFSDYYMSWIRQAPGKGLEWVSAIS
GSGGSTYYADSVKGRITISRDNAKNSLYLQMNSLRAEDTAVYYCARGLWVWD
PLDYWGRGTLVTVSSGGGGSGGGGSGGGGSDIQMTQSPSTLSASVGDRVTIT
CRASEGIYHWLAWYQQKPGKAPKLLIYKASSLASGVPSRFSGSGSGTDFTLT
ISSLQPDDFATYYCQQYSNYPLTFGGGTKVEIKRA

SEQ ID NO:376

CAAGTGCAGCTGGTGGAGTCTGGGGGAGGCTTGGTCAAGCCTGGAGGGTC
CCTGAGACTCTCCTGTGCAGCCTCTGGATTCACCTTCAGTGACTACTACA
TGAGCTGGATCCGCCAGGCTCCAGGGAAGGGGCTGGAGTGGGTCTCAGCT
ATTAGTGGTAGTGGTGGTAGCACATACTACGCAGACTCCGTGAAGGGCCG
GATCACCATCTCTCCAGAGACAACGCCAAGAACTCACTGTATCTGCAAATGA
ACAGCCTGAGAGCTGAGGACACGGCCGTGTATTACTGTGCGAGAGGGCTT
TGGGTTTGGGATCCTCTTGACTACTGGGGCCAGGGAACCCTGGTCACCGT
CTCTTCAGGTGGAGGCGGTTCAGGCGGAGGTGGCAGCGGCGGTGGCGGAT
CGGACATCCAGATGACCCAGTCTCCTTCCACCCTGTCTGCATCTGTTGGA
GACAGAGTCACCATCACTTGCCGGGCCAGTGAGGGTATTATCACTGGTT
GGCCTGGTATCAGCAGAAGCCAGGGAAAGCCCCTAAACTCCTGATCTATA
AGGCCTCTAGTTTAGCCAGTGGGGTCCCATCAAGGTTCAGCGGCAGTGGA
TCTGGGACAGATTTCACTCTCACCATCAGCAGCCTGCAGCCTGATGATTT
TGCAACTTATTACTGCCAACAATATAGTAATTATCCGCTCACTTTCGGCG
GAGGGACCAAGGTGGAGATCAAACGTGCG

GIL16

SEQ ID NO:385

QVQLVQSGAEVKKPGASVKVSCKASGYTFTSYGISWVRQAPGQGLEWMGWI
SAYTGNTNYAQKFQGRVTMTTDTSTSTAYMELRSLRSDDTAVYYCARDRGY
YDAFDIWGQGTLVTVSSGGGGSGGGGSGGGGSDIQMTQSPSTLSASVGDRV
TITCRASEGIYHWLAWYQQKPGKAPKLLIYKASSLASGVPSRFSGSGSGTE
FTLTISSLQPDDFATYYCQQYSNYPLTFGGGTKVEIKRA

SEQ ID NO:394

CAGGTCAGCTGGTGCAGTCTGGAGCTGAGGTGAAGAAGCCTGGGCCTC
AGTGAAGGTCTCCTGCAAGGCTTCTGGTTACACCTTTACCAGTTATGTA
TCAGCTGGGTGCGACAGGCCCCTGGACAAGGGCTTGAGTGGATGGGATGG
ATCAGCGCTTACACTGGTAACACAAACTATGCACAGAAGTTCCAGGCCAG
AGTCACCATGACCACAGACACATCCACGAGCACAGCCTACATGGAACTGA
GGAGCCTGAGATCTGAGGACACGGCCGTGTATTACTGTGCGAGAGATCGT
GGATACTATGATGCTTTTGATATCTGGGGCCAAGGGACACCCTGGTCACCGT
CTCCTCAGGTGGCGGTTCAGGCGGAGGTGGCAGCGGCGGTGGCGGGGAT
CGGACATCCAGATGACCCAGTCTCCTTCCACCCTGTCTGCATCTGTTGGA
GACAGAGTCACCATCACCTGCCGGGCCAGTGAGGGTATTTATCACTGGTT
GGCCTGGTATCAGCAGAAGCCAGGGAAAGCCCCTAAACTCCTGATCTATA
AGGCCTCTAGTTTAGCCAGTGGGGTCCCATCAAGGTTCAGCGGCAGTGGA
TCTGGGACAGAGTTCACTCTCACCATCAGCAGCCTGCAGCCTGATGATTT
TGCAACTTATTACTGCCAACAATATAGTAATTATCCGCTCACTTTCGGCG
GAGGGACCAAGGTGGAGATCAAACGTGCG

GIL45

SEQ ID NO:403

QMQLVESGGGVVQPGRSLRLSCAASGFTFSNYGMYWVRQAPGKGLEWVAHI
WYDGSNEKYADSVKGRMTVSRDNSKNTLYLQMNSLRAEDTAVYYCATEQHW
ITAFDIWGKGTLVTVSSGGGGSGAGGSGGGGSGGGGSQSALTQPASVSGSPGQSIT
ISCTGTSSDVGGYNYVSWYQQHPGKAPKLMIYEGSKRPSGVSNRFSGSKSG
NTASLTISGLQAEDEADYCSSYTTRSTRVFGGGTKLTVLGA

SEQ ID NO:412

CAGATGCAGCTGGTGGAGTCTGGGGGAGGCGTGGTCCAGCCTGGGAGGT
CCCTGAGACTCTCCTGTGCAGCCTCTGGATTCACCTTCAGTAACTATGG
CATGTACTGGGTCCGCCAGGCTCCAGGCAAGGGGCTGGAGTGGGTGGCA
CATATTTGGTATGATGGAAGTAATGAAAAGTATGCAGACTCCGTGAAGG
GCCGAATGACCGTCTCCAGAGACAATTCCAAGAACACGTTGTATTTGCA
AATGAACAGCCTGAGAGCCGAGGACACGGCTGTGTATTACTGTGCGACA
GAGCAACACTGGATTACTGCTTTTGATATCTGGGGCAAAGGCACCCTGG
TCACCGTCTCCTCAGGTGGAGGCGGTTCAGGCGGAGGTGGCAGCGGCGG
TGGCGGATCACAGTCTGCGCTGACTCAGCCTGCCTCCGTGTCTGGGTCT
CCTGGACAGTCGATCACCATCTCCTGCACTGGAACCAGCAGTGACGTTG
GTGGTTATAACTATGTCTCCTGGTACCAACAACACCCCAGGCAAAGCCCC
CAAACTCATGATTTATGAGGGCAGTAAGCGGCCCTCAGGGGTTTCTAAT
CGCTTCTCTGGCTCCAAGTCTGGCAACACGGCCTCCCTGACAATCTCTG
GGCTCCAGGCTGAGGACGAGGCTGATTATTACTGCAGCTCATATACAAC
CAGGAGCACTCGAGTTTTCGGCGGAGGGACCAAGCTGACCGTCCTAGGT
GCG

FIG. 10(cont.)

GIL60

SEQ ID NO:421

EVQLVESGGGVVRPGGSLRLSCAASGFTFDDYGMNWVRQAPGKGLEWVSG
VNWNGGTRDYAASVKGRFTISRDNAKNSLYLQMNSLRAEDTALYHCARGW
YSGSFYYFGYWGRGTLVTVSSGGGSGGGGSGGGGSAQAALTQPASVSGS
PGQSITISCTGASGDVGAYNFVSWYQQHPGKAPKLIIYDVNKRPSGVSNR
FSGSKSGNTASLTISGLQAEDEADYCCSSYTSTFSVVFGGGTKLTVLGA

SEQ ID NO:430

GAGGTGCAGCTGGTGGAGTCCGGGGGAGGAGTGTGGTACGGCCTGGGGGTC
CCTGAGACTCTCCTGTGCAGCCTCCTGGATTCACCTTTGACGATTATGGCA
TGAACTGGGTCCGCCAAGCTCCAGGGAAGGGGCTGGAGTGGGTCTCTGGT
GTTAATTGGAATGGTGGTACCAGAGATTATGCAGCCTCCGTGAAGGGCCG
ATTCACCATCTCCAGAGACAACGCCAAGAACTCCCTGTATCTGCAAATGA
ACAGTCTGAGAGCCGAGGACACGGCCTTGTATCACTGTGCGAGAGGATGG
TATAGTGGGAGCTTCTACTACTTTGGCTACTGGGGCCGAGGAACCCTGGT
CACCGTCTCGAGTGGAGGCGGCGGTTCAGGCGGAGGTGGCTCTGGCGGTG
GCGGAAGTGCACAGGCTGCCCTGACTCAGCCTGCCTCCGTGTCTGGGTCT
CCTGGACAGTCGATCACCATCTCCTGCACTGGAGCCAGCGGTGACGTTGG
TGCTTATAACTTTGTCTCTGTGTACCAACAACACCCAGGCAAAGCCCCA
AACTCATAATTATGATGTCAATGTCAAATCGGCCCTCAGGGTTTCTAATCGC
TTCTCTGGCTCCAAGTCTGGCAACACGGCCCTCCCTGACCATCTCTGGGCT
CCAGGCCGAGGACGAGGCTGATTATTACTGCAGCTCATATACAAGCACCT
TCTCTGTGGTATTTGGCGGAGGGACCAAGCTCACCGTCCTAGGTGCG

*FIG. 10(cont.)*

GIL68

SEQ ID NO: 439

QVQLVQSGAEVKKPGASVKVSCKASGYTFSDYYIHWVRQAPGQGLEWMGWV
NPDTGGTRYAQKFQGRVTMTRDMSISTAYMELSRLRSDDTAVYYCARDLTG
FDPEDIWGQGTLVTVSSGGGGSGGGGSGGGGSASSVLTQPPSVSVAPGKTA
RITCGGNNFRNKRVHWYQQKPGQAPVLVIYYDSDRPSGIPERFSGSRSGNT
ATLTISRVEAGDEADYYCQVWDSSTDRPLFGGGTKLTVLGA

SEQ ID NO:448

CAAGTGCAGCTGGTGCAGTCTGGGGCTGAGGTGAAGAAGCCTGGGGCCTC
AGTGAAGGTCTCCTGTAAGGCTTCTGGATACACCTTCAGCGATTACTATA
TTCACTGGGTGCGACAGGCCCCTGGACAAGGGTTGGAGTGGATGGGATGG
GTCAACCCTGACAATGACCAGGGACAGTGTCCATCTCCACAGCCTACAGCCTGTGT
GGTCACAATGACCAGGGACACATGTCCATCTCCACAGCCTACATGGAGCTGT
CCAGGCTGAGAAGCGACACAGCCCGTATATTACTGTGCGAGAGATCTA
ACTGGATTTGATCCTTTGATATCTGGGGCCAGGGAACCCTGGTCACCGT
CTCGAGTGGAGGCGGCGGTTCAGGCGGCGGTGGCTCTGGCGGTGGCGGAA
GTGCATCGTCTGTGCTGACTCAGCCACCCTCAGTGTCAGTGGCCCCAGGA
AAGACGGCCCGCATTACCTGTGGGGAACAACTTTCGAAATAAAGACT
ACACTGGTATCAGCACCGGCCCTCAGGATCCCTGACCATCAGCAGGGTCAGGGGTC
ATGATTCAGACCCCTCAGGATCCCTGAGCGATTCTCTGGCTCCCGC
TCTGGGAACACGGCCACCCTGACCATCAGCAGGGTCGAGGCGGGATGA
GGCCGACTATTACTGTCAGGTGTGGGATAGTAGTACTGATCGTCCGCTGT
TCGGCCGAGGGACCAAGCTGACCGTCCTAGGTGCG

*FIG. 10(cont.)*

GIL92

SEQ ID NO:457

QVQLVQSGAEVKKPGASVKVSCKASGYTFTDYYMHWVRQAPGQGLEWVGWI
NPYTGGAFYAQKFRGRVTMTRDTSISTAYMELSRLRSDDTAVYYCAREPEK
FDFWGGDNWGRGTLVTVSSGGGGSGGGGSGGGGSAQAVLTQPPSVSGAPGQ
RVTISCTGSSSNIGAGYGVHWYQQLPGTAPKLLIYGNSNRPSGVPDRFSGS
KSGTSASLAITGLQAEDEADYYCQSYDSSLSGYVFGGGTQLTVLSA

SEQ ID NO:466

CAGGTCCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGGCCATTCTATGCACAGAAGTTCGGGGCAG
GGTCACAATGACCAGGACACGTCCATCAGCACAGCCTACATGGAGCTGA
GCAGACTGAGATCTGACGACACGGCCGTGTATTATTGTGCGAGAGAACCT
GAAAAATTCGATTTTTGGGGTGACAACTGGGGCCGGGGCACATTGGT
CACCGTCTCGAGTGGAGGCGGCGGTTCAGGCGGAGGTGGCTCTGGCGGTG
GCGGAAGTGCACAGGCTGTGCTGACTCAGCCGCCCTCAGTGTCTGGGGCC
CCAGGGCAGAGGGTCACCATCTCTGCACTGGGAGCAGCTCCAACATCGG
GGCAGGTTATGGTGTACACTGGTACCAACAGCTTCCAGAACAGCCCCA
AACTCCTCATCTATGGTAACAGCAATCGGCCCTCAGGGGTCCCTGACCGA
TTCTCTGGCTCCAAGTCTGGCACCTCAGCTCCCTGGCCATCACTGGGCT
CCAGGCTGAGGATGAGGCTGATTATTACTGCCAGTCCTATGACAGCAGCC
TGAGTGGTTATGTCTTCGGAGGTGGGACCCAGCTCACCGTTTTAAGTGCG

SEQ ID NO:475

```
Q V Q L V Q S G A E V K K P G A S V K V S C K A S G Y T
F T S Y G W F Q V R Q A P G Q R V T M E W M G Y I N P
N T N Y A Q K F Q G R V T I T A D K S T S T A Y M E L R
S L R S D D T A V Y Y C A R D G G T I T D A E G S D I Q H M G Q G
T L V T V S S G G G G S V G G S G G G G S L A S L G I Y H L A
S P S T L A S V K P G K A P K L L I Y K A S D D F A T Y Y C
W Y Q Q K P G T E F T L T I S S L Q P V P Y Y C
S G S G Y N A T F G G G T K V E I K R
```

SEQ ID NO:484

```
CAGGTGCAGCTGGTGCAGTCTGGAGCTGAGGTGAAGAAGCCTGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
GTCAGCGCTTACACTGGTAACACAGAACTATGCAGAGCAAGCCTACATGGAACTGA
AGTCACCATGACCAGACAGAATCTGAGACGAGACACGGCCGTGTATTACTGTGCGAGAGATCGT
GGAGCCTGAGATCTGAGACGAGACACGGCCGTGTATTACTGTGCGAGAGATCGT
GGATACTATGATGCTTTTGATATCTGGGGCCAAGGGACCACGGTCACCGT
CTCCTCAGGTGGAGGCGGTTCAGGCGGAGGTGGCAGCGGCGGTGGCGGAT
CGGACATCCAGATGACCCAGTCTCCTTCCACCCTGTCTGCATCTGTTGGA
GACAGAGTCACCATCACTTGCCGGGCAAGTCAGGGCATTAGCAGTTACTTAGCC
GGCCTGGTATCAGCAGAAGCCAGGGAAAGCCCCTAAACTCCTGATCTATA
AGGCCTCTAGTTTAGCCAGTGGGGTCCCATCAGCAGCCTGAGTGGA
TCTGGGACAGATTCACTCTCACCATCAGCAGCCTGCAGCCTGATGATTT
TGCAACTTATTACTGCCAACAAATGGGCGAGTACAACGCCACCTTCGGCG
GAGGGACCAAGGTGGAGATCAAACGT
```

SEQ ID NO:493

EVQLVESGGGVVRPGGSLRLSCAASGFTFD D
DYGMNWVRQAPGKGLEWVSLYWNSLYAE D
AASVKGRFTISRDNAKNMGAAWNMSCAAS Y
TAYLHCAGSYSGGGSAGSNMRQLVASGLV S
SGGSIHIYGASGDVGAWYAPASYQHG G
PGQQPKLIYDVNKRPSGVSNRFSGWYKGP T
KAPKLIHYLQAEDEADYYCSSYTSTFGA G
SLTVLG
GTKLTVLG

SEQ ID NO:502

GAGGTGCAGCTGGTGGAGAGCGGGGGAGGTGTGGTACGGCCTGGGGGGTC
CCTGAGACTCTCCTGTGCAGCCTCTGGATTCACCTTTGACGATTATGGCA
TGAACTGGGTCCGCCAAGCTCCAGGGAAGGGGCTGGAGTGGGTCTCTGGT
GTTAATTGGAATGTGTGGTACCAGAGATTATGCAGCCTCCGTGAAGGGCCG
ATTCACCATCTCCAGAGACAACGCCAAGAACTCCCTGTATCTGCAAATGA
ACAGTCTGAGAGCCGAGGACACGGCCGTGTATCACTGTGCGAGAGGATGG
TATAGTGGGCCGCGTCAGGAGGCCGGTTGACTCAGCCGACTCGGCCGGTG
GCGGAAGTGCACAGCTGCCTGCCATCTCCTGCACTGGGAGCAGCTCTGGTCT
CCTGGACAGTCGATCACCATCTCCTGTGCTACCACAACAACGGCCCTCCA
TGCTTATAACTTTGTCTCATAAGTCAATAAGGCCCTCAGGGGTTTCTAATCGC
AACTCATAATTTATGATGTCAAGTCTGGCAACACGCCCTCCCTGACCATCTCTGGGCT
TTCTCTGGCTCCAAGTCTGGCAACACGGCCCTCCCTGACCATCTCTGGGCT
CCAGGCCGAGGACGAGGCTGATTATTACTGCAGCTCATATACAAGCACCT
TCTCTGTGGTATTTGGCGGAGGGACCAAGCTGACCGTCCTAGGT

SEQ ID NO:511

```
Q V Q L V Q S G A E V K K P G A S V K V S C K A S G Y T
F S D Y Y I H W V R Q A P G Q G L E W M G W V N P D T G
G T R Y A Q K F Q G R V T M T R D M S T A Y M E L S G L
R L R S D D T A V Y Y C A R D L G S G S A S N P D W G Q
T L V T V S S V G G G A P G A R I T Y D R P S G I P E R F
Q P P Q K P Q A P V L T I S R V E A G D E A D Y Y C Q V
W Y Q Q K P G N T A T L T I H G T K L T V L G
S G S G N T A T L T I S R V E A G D E A D Y Y C Q V
W D L F N D G V F G G G T K L T V L G
```

SEQ ID NO:520

```
CAGGTCCAGCTGGTGCAGTCTGGGGCTGAGGTGAAGAAGCCTGGGGCCTC
AGTGAAGGTCTCCTGTAAGGCTTCTGGATACACCTTCAGCGATTACTATA
TTCACTGGGTGCGACAGGCCCCTGGACAAGGGTTGGAGTGGATGGGATGG
GTCAACCCTGACACTGGTGGCACAGGGATACGCGCAGAAGTTTCAGGGCCG
GGTCACAATGACCAGGGACATGTCCATCTCCACAGCCTACATGGAGCTGT
CCAGGCTGAGAAGCGACGACACGGCCGTCTATTATTACTGTGCGAGATCTA
ACTGGGATTTGATCCTTTGATATCTGGGCAGGTGAGGTGGCTCTGGTCACCGT
CTCCTCAGGAGGCGGCAGTTGACTCAGCCACCCTCAGTGTCAGTGGCCCCAGGA
GTGCATCGTCTGTGCTGACTCAGCCACCCTCAGTGTCAGTGGCCCCAGGA
AAGACGGCCCGCATTACAGCAGAAGCCAGGCCAGCCCCTGAAACAACTTTGAAATAAAGAGT
ACACTGGTATCAGCAGACCGGCCCTCAGGGATCCCTGAGCGATTCTCGGCTCCCGC
ATGATTCAGACCGGCCCTCACCCTGACCATCAGCAGGCTCGAGGCCGGGATGA
TCTGGGAACACGGCCTATTACTGTCAGGTGTGGGATCTCTTCAACGACGGGATGA
GGCCGACTATTACTGTCAGGTGTGGGATCTCTTCAACGACGGGCGTGT
TCGGCGGAGGGACCAAGCTGACCGTCCTAGGT
```

SEQ ID NO:529

Q V Q L V Q S G A E V K K P G A S V K V S C K A S G Y T
F S D Y Y I H W F Q G W F R Q A P G Q T M R D M S I A Y M E L S
G T R Y A Q K F Q D T A V G G Y C A R G S T F D P F D I W G Q G
R L R S D D T A S S V A P G K T A P V L T I S R V H P E R F
T L T V S S V A P G Q A T L T G G T K L T V L G
Q P P S Q K P G N S F G G S
W Y Q Q L T D S G
W D F L T D S G

SEQ ID NO:538

CAGGTCCAGCTGGTGCAGTCTGGGGCTGAGGTGAAGAAGCCTGGGGCCTC
AGTGAAGGTCTCCTGTAAGGCTTCTGGATACACCTTCAGCGATTACTATA
TTCACTGGGTGCGACAGGCCCCTGGACAAGGGTTGGAGTGGATGGATGG
GTCAACCCTGACACTGTGGCAGGACATGTCCATCTCCACAGCCTACATGGAGCTGT
GGTCACAATGACCAGGACGACGACGCCGTATATTACTGTGCGAGAGATCTA
CCAGGCTGAGAAGCCCTCAGTCCTCAGTCCAGGAACCCTGGTCACCGT
ACTGGATTTGATCCTTTTGATATCTGGGCGGAGTGGCTCTGGCGGCCCAGGA
CTCCCTCAGGAGGCGGTTCTGACTCAGCCACCCTCAGTGTCAGTGCCCCAGGA
GTGCATCGTCTGTGCTGCGACATTACCTGTGGGGGAAACAACTTTCGAAATAAAGAGT
AAGACGGCCCGCATTACCTGTGGGGGAAACAACTTTCGAAATAAAGAGT
ACACTGGTATCAGCAGAAGCCAGGCCCTCAGGGTCGAGCCATCAGCAGGT
ATGATTCAGAACACGGCCCACCCTGACCATCAGCAGGTCGCCGGGATGA
TCTGGGAACACGGCCCACCCTGACCATCAGCAGGTCCTGGCTCCCGC
GGCCGACTATTACTGTCAGGTGTGGGATTCCTCACCGACTCGGGGTCGT
TCGGGCGGAGGGACCAAGCTGACCGTCCTAGGT

SEQ ID NO:547

Q V Q L V Q S G A E V K K P G A S V K V S C K A S G Y T F T
D Y Y M H W V R Q A Q M T R D T F G G S L E W M G W I N P Y T G A F Y
A Q K F R G R V T R F G S R S A Q A V Y M E L R S L R S D D
T A V Y Y C A R G G S S N I G A G Y H W G Q P T V
S G Q R V L I Y S T G V P D R F S G S K S G Y V
P G T A P K L L I Y Q L A E D E A D Y Y C G T P V F
S L A I T Q L T V L G
G G T Q L T V L G

SEQ ID NO:556

CAGGTGCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGCGCATTCTATGCGACAGAGCCTACATGGGCAG
GGTCACAACAATGACCAGGACACGTCCATCAGCACCGCGTGTATTATTGTGCGAGAACCT
GCAGACTGAGATCTGACGACGACTCCACGGGGCAGGTCTGGGGCGAGGTGGCTCTGGCGGTA
GAAAGATTCGGCGACTCCTCAGGGCGCGGCCGTTGCTGACTCCAGTGTCTGGGGCC
CACCGTCTCCTCAGGGGCGCGGCCGTTGCTGACTCCAGTGTCTGGGGCC
GCAGAAGTGCACAGAGGCCTGTCACCATCTCCTGCACCAACAGCCTCGG
CCAGGGCAGAGAGGTGTACACTGGTGTACAACAGCTTCCAGAACAGCCCCCA
GGCAGGTTATGGTGTACACTGGTAACAGCAATCGGGCCCTCAGGGGTCCCCTGACCGA
AACTCCCTACATCTATGGTAACAGCAATCGGGCCCTCAGGGGTCCCCTGACCGA
TTCTCTGGCCTCCAAGTCTGGCACCTCAGCCTCCCTGGCCATCACTGGGCT
CCAGGCTGAGGATGAGGCTGATTATTACTGTGCTACCACTGGGACAAGGAGC
AGAGTGGTTATGTCTTCGGAGGTTGGGACCCCAGTCACCGTCCTAGT

SEQ ID NO:565

| Q | V | Q | L | V | Q | S | G | A | E | V | K | K | P | G | A | S | V | K | V | S | C | K | A | S | G | Y | T |
| F | T | D | Y | Y | M | H | W | V | R | Q | A | P | G | Q | G | L | E | W | V | G | W | I | N | P | Y | T | G |
| S | A | F | Y | A | Q | K | F | R | G | Y | V | C | A | R | E | P | T | R | D | T | A | Y | M | E | L | S | S |
| R | L | R | S | D | D | T | A | V | Y | S | G | A | P | G | Q | G | T | M | T | R | D | P | E | K | W | A | V |
| R | G | T | L | V | T | V | S | S | G | Q | L | P | G | S | S | G | G | Q | T | S | L | A | I | P | S | G | A |
| L | T | Q | P | P | S | V | Y | Q | K | S | G | T | S | G | Q | R | V | A | P | K | L | L | I | Y | G | N | R |
| G | Y | G | V | H | W | Y | Q | Q | L | P | G | T | A | S | G | V | C | Y | F | D | S | N | R | P | S | E | D |
| V | P | D | R | F | S | G | S | Y | D | S | G | L | S | G | T | D | F | T | L | T | I | S | L | Q | A | E | D |
| Y | Y | C | Q | S | Y | D | S | G | L | S | G | Y | V | F | G | T | G | T | Q | L | T | V | L | G |  |  |  |

SEQ ID NO:574

CAGGTGCAGCTGGTGCAGTCTGGGGCTGAGGTGAAGAAGCCTGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGGTGGGATGG
ATCAACCCTTATACTGGTAGCGCTTTCTATGCACAGAAGTTTCGGGGCAG
GGTCACAATGACCAGGGACACGTCCATCAGCACAGCCTACATGGAGCTGA
GCAGACTGAGATCTGACGACACGGCCGTGTATTATTGTGCGAGAGAACCT
GAAAAATTCGGCGAGTCCAGGAGCGGCGGTTCAGGCGGAGTGGCTCTGGCGGTA
CACCGTCTCCTCAGGAGGCGTGTCCTCAGGAGGCGTGTCAGTGTCTGGGCC
GCGGAAGTGCACAGAGGGTCACCATCTCCTGCACTGGAGCAGCTCCAACATCGG
CCAGGGCAGAGGGTCACCATCTCCTGCACTGGTACCAACAGCTTCCAGGAACAGCCCCCA
GGCAGGTTATGGTGGTACACTGGTACCAACAGCTTCCAGGAACAGCCCCCA
AACTCCTCATCTATGGTGACAGCAATCGGCCCTCAGGGGTCCCTGACCGA
TTCTCTGGCTCCAAGTCTGGCACCTCAGCCTCCCTGGCCATCACTGGGCT
CCAGGCTGAGGATGAGGCTGATTATTACTGCCAGTCCTATGACAGCAGCGCC
TGAGTGGTTATGTCTTCCGGAGCTGGGACCCAGCTCACCGTCCTAGGT

SEQ ID NO:583

Q V Q L V Q S G A E V K K P G A S V K V S C K A S G Y T
F T H Y M H W V R Q A P G Q G L E W M I N P Y T G
G A F Y A Q K F Q G R V T M T R D T S T A Y M E L S
R L R S D D T A V Y Y C A R E P G G S P N A E I G A V G
R G T L V T V S S A S T K G P S V F P L A P S S K S T S G
L T Q P P S V S Q A P G T A P K L L I Y G N S N R P S G
G Y G V H W Y Q Q L P G T A P K L L I Y G N S N R P S G
V P D R F S G S K S G T S A S L A I T G L Q A E D E A D
Y Y C Q S Y D S S L S G Y V F G G G T Q L T V L G

SEQ ID NO:592

CAGGTGCAGCTGGTGCAGTCTGGGGCTGAGGTGAAGAAGCCTGGGGCCTC
AGTGAAGGTCTCCTGCAAGGCTTCTGGATACACCTTCACCCACTACTATA
TGCACTGGGTGCGACAGGCCCCTGGACAAGGGCTTGAGTGGATGGGATGG
ATCAACCCTTATACTGGTGGCGACACAGTCCATGCACAGAAGTTCAGGGCAG
GGTCACACAATGACCAGGGACACGTCCATCACAGCCTACATGGAGCTGA
GCAGACTGAGATCGACGACGCCGTGTATTATTGTGCGAGAGAACCT
GAAAAATTCGACTCGCCGACGCCGAGATCTGGGCCGGAGTGGCTCTGGCGTA
CACCGTCTCCTCAGAAGGCGGGCTGCTGCTGAGCCCCTCAGTGTCTGGGCC
GCGGAAGTGCACAGAGGTCACCATCTCCTGCACTGGGAGCAGCTCCAACATCGG
CCAGGGCAGAGGGTCACCATCTCCTGCACTGGGAGCAGCTCCAACATCGG
GGCAGGTTATGGTGTACACTGGTACCAACAGCAATGGCCCTCAGGGGTCCCTGACCGA
AACTCCTCATCTATGTGTAACAGCAATCGGCCCTCAGGGGTCCCTGACCGA
TTCTCTGGCTCCAAGTCTGGCACCTCAGCTCTGCCAGTCCATCACTGGGCT
CCAGGCTGAGGATGAGGCTGATTATTACTGCCAGTCCTATGACAGCAGCC
TGAGTGGTTATGTCTTCGGAGGTGGGACCCAGCTCACCGTCCTAGGT

SEQ ID NO:601

Q V Q L V Q S G A E V K K P G A S V K V S C K A S G Y T
F T N Y Y M H W V R Q A P G Q G L E W M G I I N P Y T G
S A F Y A Q K F Q G R V T M T R D T S T S T A Y M E L S
R L R S D D T A V Y Y C A R E P G G S D D S S G S A V A G
R G T L V T V S S G A P G S Q R V T I S C L L H G D
L T Q P P S V S Q L P G T A P K L L I Y G Q L T V L G
G Y G V H W Y Q Q K S G T S A S L A I T G T Q L T V L G
V P D R F S G S K S G T S A S L A I T G T Q L T V L G
Y Y C Q S Y D N S L S G Y V F G G G T Q L T V L G

SEQ ID NO:610

CAGGTGCAGCTGGTGCAGTCTGGGGCTGAGGTGAAGAAGCCTGGGGCCTC
AGTGAAGGTCTCCTGCAAGGCTTCTGGATACACCTTCACCAACTACTATA
TGCACTGGGTGCGACAGGCCCCTGGACAAGGGCTTGAGTGGATGGGGATGG
ATCAACCCTTATACTGGTAGCGCACACGTCCATCAGCAAGCCACATGGAGCTGAG
GGTCACACAATGACCAGGGACACGAGTCTGACACAGCCTGTATTATTGTGCGAGACTGA
GCAGACTGAGATCTGACGACACGGCCGTGTATTATTGTGCGAGAGAACCT
GAAAATTCGACTCCTCCTCAGGAGGCGGCAGTTCAGCGCAGGCTCTGGCCGTA
GCGGAAGTCACAGAGGCTGTGCTCACTCAGCCCGTCTCAGTGTCTGGGCC
CCAGGGCAGAGGGTCACCATCTCCTGCACTGGGTACCAACAGCTTCCAGGAACATCGG
GGCAGGTTATGGTGTATGTGACAGCAATCGGCCCTCAGCCTCCTGGCCATCTGGGCT
AACTCCTCATCTATGGTGACAAGTCTGGCCACCTCAGGTCCAGTCCTATGCAACAGCC
TTCTCTGGCTCCAAGTCTGGCAACTCGGCCACCCTGACCATCACTGGACTCCAGACT
CCAGGGCTGAGGATGAGGCTGATTATTACTGCCAGTCCTATGACAACAGCC
TGAGCGGTTATGTCTTCGGAGGTGGGACCCAGCTCACCGTCCTAGGT

SEQ ID NO: 619

EVQLVESGGGVVRPGGSLRLSCAASGFTFDDYGMNWVRQAPGKGLEWVSGV
NWNGGTRDYAASVKGRFTISRDNAKNSLYLQMNSLRAEDTALYHCARGWYS
GAAWNMGYWGRGTLVTVSSGGGGSGGGGSGGGGSGGGGSGGGGSAQA
ALTQPASVSGSPGQSITISCTGASGDVGAYNFVSWYQQHPGKAPKLIIYDV
NKRPSGVSNRFSGSKSGNTASLTISGLQAEDEADYYCASLVSDFSVVFGGG
TKLTVL

SEQ ID NO: 628

GAGGTGCAGCTGGTGGAGAGCGGCGGCGGAGGCCGTGGTGAGACCAGGCGGCA
GCCTGAGACTGAGCTGCGCCGCCAGCGGCTTCACCTTCGACGACTACGG
CATGAACTGGGTGAGGCAGGCCCCAGGCAAGGGCCTGGAGTGGGTGTCC
GGCGTGAACTGGAACGGCGGCACCAGAGACTACGCCGCCTCTGTGAAGG
GCAGATTCACCATCAGCCGGGACAACGCCAAGAACAGCCTGTACCTGCA
GATGAACAGCCTGAGAGCCGAGGACACCGCCCTGTACCACTGCGCCAGA
GGCTGGTACAGCGGAGCCGCCTGGAACATGGGCTACTGGGGCAGAGGCA
CCCTGGTGACCGTGTCCAGCGGAGGCGGCGGTTCAGCGGAGGTGGCTC
TGGTGGTAGCGGAGGTGGCTCTGGCGGTGGCGGCTCTGCCCAGGCCGGT
GGCGGAAGTGCACAGGCCCGCCCTGACCCAGCCCGCCAGCGTGTCTGGCA
GCCCAGGCCAGAGCATCACCATCAGCTGCACCGGCGCCAGCGGCGATGT
GGGCGCCTACAACTTCGTGTCCTGGTATCAGCAGCACCCCGGCAAGGCC
CCCAAGCTGATCATCTACGACGTGAACAAGAGACCCAGCGGCGTGTCCA
ACAGATTCAGCGGCAGCAAGAGCGGCAACACCGCCAGCCTGACCATCAG
CGGACTGCAGGCCGAGGACGAGGCCGACTACTACTGCGCCAGCCTGGTG
TCCGACTTCAGCGTGGTGTTCGGCGGAGGCACCAAGCTGACCGTGCTG

ANTIBODIES TO HUMAN IL-22

CROSS REFERENCE TO RELATED APPLICATIONS

The present application is a continuation application of U.S. application Ser. No. 11/708,061, filed 20 Feb. 2007 (pending), which claims the benefit of U.S. provisional application No. 60/774,596, filed Feb. 21, 2006, the entire disclosure of which is relied upon and incorporated by reference.

SEQUENCE LISTING

The instant application contains a Sequence Listing which has been submitted in ASCII format via EFS-Web and is hereby incorporated by reference in its entirety. Said ASCII copy, created on Feb. 8, 2012, is named WYT10402.txt and is 294,192 bytes in size.

TECHNICAL FIELD

This invention relates to antibodies, e.g., human antibodies, and antigen-binding fragments thereof that bind interleukin-22 (IL-22), in particular, human IL-22, and their use in regulating IL-22-associated activities. The antibodies disclosed herein are useful in diagnosing, preventing, and/or treating IL-22 associated disorders, e.g., autoimmune disorders, including arthritis.

BACKGROUND OF THE INVENTION

Antigens initiate immune responses and activate the two largest populations of lymphocytes: T cells and B cells. After encountering antigen, T cells proliferate and differentiate into effector cells, while B cells proliferate and differentiate into antibody-secreting plasma cells. These effector cells secrete and/or respond to cytokines, which are small proteins (<about 30 kDa) secreted by lymphocytes and other cell types.

Interleukin-22 (IL-22) is a class II cytokine that shows sequence homology to IL-10. Its expression is up-regulated in T cells by IL-9 or ConA (Dumoutier L. et al. (2000) *Proc Natl Acad Sci USA* 97(18):10144-9). Further studies have shown that expression of IL-22 mRNA is induced in vivo in response to LPS administration, and that IL-22 modulates parameters indicative of an acute phase response (Dumoutier L. et al. (2000); Pittman D. et al. (2001) *Genes and Immunity*, 2:172). In addition, IL-22 enhances the expression of antimicrobial peptides associated with host defense, including β-defensin, S100A7, S100A8, and S100A. Wolk et al., *Immunity*, 21:241-54 (2004); Boniface et al., *J. Immunol.* 174:3695-3702 (2005); Liang et al., *J. Exp. Med.,* 203(10):2271-79 (2006). Taken together, these observations indicate that IL-22 plays a role in inflammation (Kotenko S. V. (2002) *Cytokine & Growth Factor Reviews* 13(3):223-40).

IL-22 is believed to bind to a receptor complex consisting of IL-22R and IL-10R2, two members of the type II cytokine receptor family (CRF2) (Xie M. H. et al. (2000) *J Biol Chem* 275(40):31335-9; Kotenko S. V. et al. (2001) *J Biol Chem* 276(4):2725-32). Both chains of the IL-22 receptor are expressed constitutively in a number of organs. Epithelial cell lines derived form these organs are responsive to IL-22 in vitro (Kotenko S. V. (2002) *Cytokine & Growth Factor Reviews* 13(3):223-40). IL-22 induces activation of the JAK/STAT3 and ERK pathways, as well as intermediates of other MAPK pathways (Dumoutier L. et al. (2000) supra; Xie M. H. et al. (2000) supra; Dumoutier L. et al. (2000) *J Immunol* 164(4):1814-9; Kotenko S. V. et al. (2001) *J Biol Chem* 276(4):2725-32; Lejeune, D. et al. (2002) *J Biol Chem* 277(37): 33676-82).

CRF2 members are receptors for IFNα/β, IFNγ, coagulation factor VIIa, IL-10 and the IL-10 related proteins IL-19, IL-20, IL-22, IL-24, IL-26, as well as the recently identified IFN-like cytokines, IL-28 and IL-29 (Kotenko S. V. (2002) *Cytokine & Growth Factor Reviews* 13(3):223-40; Kotenko, S. V. et al. (2000) *Oncogene* 19(21):2557-65; Sheppard, P. et al. (2003) *Nature Immunology* 4(1):63-8; Kotenko, S. V. et al. (2003) *Nature Immunology* 4(1):69-77). In addition to these membrane receptors, the CRF2 family also includes a soluble protein, IL-22 binding protein (IL-22BP), which is specific for IL-22 and blocks its activity (Dumoutier, L. et al. (2001) *J Immuno/*166(12):7090-5; Kotenko, S. V. et al. (2001) *J Immunol* 166(12):7096-103; Xu, W. et al. (2001) *Proc Natl Acad Sci USA* 98(17):9511-6; Gruenberg, B. H. et al. (2001) *Genes & Immunity* 2(6):329-34; Wei C-C et al. (2003) *Genes & Immunity* 4:204-211). While the IL-22 receptor complex is unique for IL-22, each chain (i.e., IL-22R and IL-10R2) is shared with other CRF2 members to define functional receptors for other cytokines, including IL-20, IL-24 (IL-22R/IL-20R2), IL-28, IL-29 (IFN-λR1/IL-10R2) and IL-10 (IL-10R1/IL-10R2) (Dumoutier, L. et al. (2001) *J. Immunol.* 167(7):3545-9; Wang, M. et al. (2002) *J Biol Chem* 277(9):7341-7; Parrish-Novak, J. et al. (2002) *J Biol Chem* 277(49):47517-23; Kotenko, S. V. et al. (1997) *EMBO J.* 16(19):5894-903; Spencer, S. D. et al. (1998) *J Exp Med* 187(4):571-8).

Both chains of the CRF2-composed receptor are necessary for signal transduction. One chain of the composed receptor has been historically defined as a ligand binding chain (e.g., IFNγR1) based on its high affinity for the cytokine. The other chain (e.g., IFNγR2) has been characterized as a helper or accessory chain, and shows minimal affinity for the cytokine alone (Kotenko, S. V. et al. (2000) *Oncogene* 19(21):2557-65). For IL-22, IL-22R is the high affinity receptor subunit with IL-10R2 subsequently binding to the IL-22/IL-22R complex (Li, J. et al. (2004) *Int. Immunopharmacol.* 4(5): 673-708; Logsdon, N. J. et al. (2002) *J. Interferon Cytokine Res* 22(11):1099-1112).

SUMMARY OF THE INVENTION

The present application provides, at least in part, IL-22 binding agents such as antibodies and antigen-binding fragments thereof that bind to interleukin-22 ("IL-22"), in particular, human IL-22, with high affinity and specificity. The antibodies and antigen-binding fragments thereof of the present invention are also referred to herein as "anti-IL-22 antibodies" and "fragments thereof," respectively. In one embodiment, the antibody or fragment thereof reduces, inhibits, or antagonizes IL-22 activity. Such antibodies can be used to regulate immune responses or IL-22-associated disorders by antagonizing IL-22 activity. In other embodiments, the anti-IL-22 antibody can be used diagnostically, or as a targeting antibody to deliver a therapeutic or a cytotoxic agent to an IL-22-expressing cell. Thus, the anti-IL-22 antibodies of the invention are useful in diagnosing, treating, and/or preventing IL-22-associated disorders, e.g., autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD.

Accordingly, in one aspect, the invention features an isolated antibody that binds to IL-22, in particular, human IL-22. In certain embodiments, the anti-IL-22 antibody may have at least one of the following characteristics: (1) it is a monoclonal or single specificity antibody; (2) it is a human antibody; (3) it is an in vitro generated antibody; (4) it is an in vivo generated antibody (e.g., transgenic mouse system); (5) it binds to IL-22 with an association constant of at least $10^{12}$ $M^{-1}$; (6) it binds to IL-22 with an association constant of at least $10^{11}$ $M^{-1}$; (7) it binds to IL-22 with an association constant of at least $10^{10}$ $M^{-1}$; (8) it binds to IL-22 with an association constant of at least $10^{9}$ $M^{-1}$; (9) it binds to IL-22 with an association constant of at least $10^{6}$ $M^{-1}$; (10) it binds to IL-22 with a dissociation constant of 500 nM or less; (11) it binds to IL-22 with a dissociation constant of 10 nM or less; (12) it binds to IL-22 with a dissociation constant of 150 pM or less; (13) it binds to IL-22 with a dissociation constant of 60 pM or less; (14) it inhibits binding of IL-22 to IL-22R or a receptor complex of IL-22R and IL-10R2 with an $IC_{50}$ of 10 nM or less; (15) it blocks IL-22 mediated proliferation of IL-22 receptor engineered BaF3 cells with an $IC_{50}$ of 1 nM or less in one embodiment, with an $IC_{50}$ of 150 pM or less in another embodiment, with an $IC_{50}$ of 100 pM or less in another embodiment, and with an $IC_{50}$ of 10 pM or less in another embodiment; and (16) it blocks IL-22 mediated GROa secretion from HT29 cells with an $IC_{50}$ of 1 nM or less in one embodiment, with an $IC_{50}$ of 150 pM or less in another embodiment, and with an $IC_{50}$ of 10 pM or less in another embodiment. IL-22 mediated BaF3 cell proliferation and IL-22 mediated GROa secretion from HT29 cells can be measured as described in the examples.

Nonlimiting illustrative embodiments of the antibodies of the invention are referred to herein as "GIL01," "GIL16," "GIL45," "GIL60," "GIL68," "GIL92," "097D09," "062A09," "062G05," "087B03," "367D04," "368D04," "166B06," "166G05," "375G06," "376B10," "354A08," "355B06," "355E04," and "356A11." These antibodies can be germlined or non-germlined. In another embodiment, the antibody is chosen from 356A11, 354A08, 087B03, and 368D04. The antibodies of the invention may specifically bind to the same IL-22 epitope or a similar epitope (e.g., an overlapping epitope) that GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 binds to. In other embodiments, the antibodies specifically bind to a fragment of an IL-22, e.g., a fragment of at least 10, 20, 50, 75, 100, 150, or 200 amino acids contiguous to the amino acid sequence set forth in SEQ ID NO:1, or a sequence that is at least 85%, 90%, 95%, 96%, 97%, 98%, 99% or more identical thereto. In other embodiments, the antibody competitively inhibits the binding of at least one of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 to its target epitope.

In one embodiment, the antibody of the present invention includes a $V_H$ domain, $V_L$ domain, or combination thereof, of the $F_v$ fragment of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11. For example, the antibody includes a $V_H$ and/or a $V_L$ domain having amino acid sequence as set forth in Tables 1 and 7 (SEQ ID NO:5, 23, 41, 59, 77, 95, 113, 131, 149, 167, 185, 203, 221, 239, 257, 275, 293, 311, 329, 347, 365, 383, 401, 419, 437, 455, 473, 491, 509, 527, 545, 563, 581, 599, or 617 for $V_H$ and SEQ ID NO:6, 24, 42, 60, 78, 96, 114, 132, 150, 168, 186, 204, 222, 240, 258, 276, 294, 312, 330, 348, 366, 384, 402, 420, 438, 456, 474, 492, 510, 528, 546, 564, 582, 600, or 618 for $V_L$), or a sequence substantially identical thereto (e.g., a sequence at least about 85%, 90%, 95%, 96%, 97%, 98%, 99% or more identical thereto, or which differs by no more than 1, 2, 5, 10 or 15 amino acid residues from SEQ ID NO:5, 6, 23, 24, 41, 42, 59, 60, 77, 78, 95, 96, 113, 114, 131, 132, 149, 150, 167, 168, 185, 186, 203, 204, 221, 222, 239, 240, 257, 258, 275, 276, 293, 294, 311, 312, 329, 330, 347, 348, 365, 366, 383, 384, 401, 402, 419, 420, 437, 438, 455, 456, 473, 474, 491, 492, 509, 510, 527, 528, 545, 546, 563, 564, 581, 582, 599, 600, 617, or 618).

In another embodiment, the antibody of the present invention includes a $V_H$ domain, $V_L$ domain, or combination thereof, of the $F_v$ fragment of an antibody chosen from 356A11, 354A08, 087B03, and 368D04. In this embodiment, the antibody, or antigen-binding fragment thereof, comprises:

a $V_H$ domain comprising the amino acid sequence set out in SEQ ID NO:167 or 491 and/or a $V_L$ domain comprising the amino acid sequence set out in SEQ ID NO:168 or 492 (087B03);

a $V_H$ domain comprising the amino acid sequence set out in SEQ ID NO:293 or 545 and/or a $V_L$ domain having the amino acid sequence set out in SEQ ID NO:294 or 546 (354A08);

a $V_H$ domain comprising the amino acid sequence set out in SEQ ID NO:203 or 617 and/or a $V_L$ domain comprising the amino acid sequence set out in SEQ ID NO:204 or 618 (368D04); or a $V_H$ domain comprising the amino acid sequence set out in SEQ ID NO:347 or 599 and/or a $V_L$ domain comprising the amino acid sequence set out in SEQ ID NO:348 or 600 (356A11).

In another embodiment, the antibody includes a $V_H$ and/or $V_L$ domain encoded by a nucleic acid having a nucleotide sequence as set forth in Tables 1 and 7 (SEQ ID NO:14, 32, 50, 68, 86, 104, 122, 140, 158, 176, 194, 212, 230, 248, 266, 284, 302, 320, 338, 356, 374, 392, 410, 428, 446, 464, 482, 500, 518, 536, 554, 572, 590, 608, or 626 for $V_H$ and SEQ ID NO:15, 33, 51, 69, 87, 105, 123, 141, 159, 177, 195, 213, 231, 249, 267, 285, 303, 321, 339, 357, 375, 393, 411, 429, 447, 465, 483, 501, 519, 537, 555, 573, 591, 609, or 627 for $V_L$), or a sequence substantially identical thereto (e.g., a sequence at least about 85%, 90%, 95%, 96%, 97%, 98%, 99% or more identical thereto, or which differs by no more than 1, 2, 3, 6, 15, 30 or 45 nucleotides from SEQ ID NO: 14, 15, 32, 33, 50, 51, 68, 69, 86, 87, 104, 105, 122, 123, 140, 141, 158, 159, 176, 177, 194, 195, 212, 213, 230, 231, 248, 249, 266, 267, 284, 285, 302, 303, 320, 321, 338, 339, 356, 357, 374, 375, 392, 393, 410, 411, 428, 429, 446, 447, 464, 465, 482, 483, 500, 501, 518, 519, 536, 537, 554, 555, 572, 573, 590, 591, 608, 609, 626, or 627).

In other embodiments, the antibody includes an Fv domain having an amino acid sequence as set forth in Tables 1 and 7 (SEQ ID NO:7, 25, 43, 61, 79, 97, 115, 133, 151, 169, 187, 205, 223, 241, 259, 277, 295, 313, 331, 349, 367, 385, 403, 421, 439, 457, 475, 493, 511, 529, 547, 565, 583, 601, or 619), or a sequence substantially identical thereto (e.g., a sequence at least about 85%, 90%, 95%, 96%, 97%, 98%, 99% or more identical thereto, or which differs by no more than 1, 2, 5, 10, 15, 20, 30 or 35 amino acid residues from SEQ ID NO:7, 25, 43, 61, 79, 97, 115, 133, 151, 169, 187, 205, 223, 241, 259, 277, 295, 313, 331, 349, 367, 385, 403, 421, 439, 457, 475, 493, 511, 529, 547, 565, 583, 601, or 619). In another embodiment, the antibody of the present invention includes an Fv domain of an antibody chosen from 356A11 (SEQ ID NO:349 or 601), 354A08 (SEQ ID NO:295 or 547), 087B03 (SEQ ID NO:169 or 493), and 368D04 (SEQ ID NO:205 or 619). In another embodiment, the antibody includes an Fv domain encoded by a nucleic acid having a nucleotide sequence as set forth in Tables 1 and 7 (SEQ ID NO:16, 34, 52, 70, 88, 106, 124, 142, 160, 178, 196, 214, 232, 250, 268, 286, 304, 322, 340, 358, 376, 394, 412, 430, 448, 466, 484, 502, 520, 538, 556, 574, 592, 610, or 628), or a sequence substantially identical thereto (e.g., a sequence at least about 85%, 90%, 95%, 96%, 97%, 98%, 99% or more identical thereto, or which differs by no more than 1, 2, 3, 6, 15, 30, 45, 60, 90 or 105 nucleotides from SEQ ID NO: 16, 34, 52, 70, 88, 106, 124, 142, 160, 178, 196, 214, 232, 250, 268, 286, 304, 322, 340, 358, 376, 394, 412, 430, 448, 466, 484, 502, 520, 538, 556, 574, 592, 610, or 628). In yet other embodiments, the antibody comprises at least one complementarity determining region (CDR) of these $V_H$ and $V_L$ domains. For example, the antibody can include one, two, or three CDR's of the $V_H$ domain having an amino acid sequence as set forth in or included within the sequences in Tables 1 and 7 (SEQ ID NO:5, 7, 8, 9, 10, 23, 25, 26, 27, 28, 41, 43, 44, 45, 46, 59, 61, 62, 63, 64, 77, 79, 80, 81, 82, 95, 97, 98, 99, 100, 113, 115, 116, 117, 118, 131, 133, 134, 135, 136, 149, 151, 152, 153, 154, 167, 169, 170, 171, 172, 185, 187, 188, 189, 190, 203, 205, 206, 207, 208, 221, 223, 224, 225, 226, 239, 241, 242, 243, 244, 257, 259, 260, 261, 262, 275, 277, 278, 279, 280, 293, 295, 296, 297, 298, 311, 313, 314, 315, 316, 329, 331, 332, 333, 334, 347, 349, 350, 351, 352, 365, 367, 368, 369, 370, 383, 385, 386, 387, 388, 401, 403, 404, 405, 406, 419, 421, 422, 423, 424, 437, 439, 440, 441, 442, 455, 457, 458, 459, 460, 473, 475, 476, 477, 478, 491, 493, 494, 495, 496, 509, 511, 512, 513, 514, 527, 529, 530, 531, 532, 545, 547, 548, 549, 550, 563, 565, 566, 567, 568, 581, 583, 584, 585, 586, 599, 601, 602, 603, 604, 617, 619, 620, 621, or 622), or a sequence substantially homologous thereto (e.g., a sequence at least about 85%, 90%, 95%, 96%, 97%, 98%, 99% or more identical thereto). In another embodiment, the antibody of the present invention includes one, two, or three CDR's of the $V_H$ domain of an antibody chosen from 356A11, 354A08, 087B03, and 368D04. In this embodiment, the antibody, or antigen-binding fragment thereof, comprises a heavy chain variable region comprising:

a) SEQ ID NO:170 or 494; b) SEQ ID NO: 171 or 495; and/or c) SEQ ID NO: 172 or 496 (087B03);

a) SEQ ID NO:296 or 548; b) SEQ ID NO:297 or 549; and/or c) SEQ ID NO:298 or 550 (354A08);

a) SEQ ID NO:206 or 620; b) SEQ ID NO:207 or 621; and/or c) SEQ ID NO:208 or 622 (368D04); or a) SEQ ID NO:350 or 602; b) SEQ ID NO:351 or 603; and/or c) SEQ ID NO:352 or 604 (356A11).

In another embodiment, the antibody can include one, two, or three CDR's of the $V_L$ domain having an amino acid sequence as set forth in or included within the sequences in Tables 1 and 7 (SEQ ID NO:6, 7, 11, 12, 13, 24, 25, 29, 30, 31, 42, 43, 47, 48, 49, 60, 61, 65, 66, 67, 78, 79, 83, 84, 85, 96, 97, 101, 102, 103, 114, 115, 119, 120, 121, 132, 133, 137, 138, 139, 150, 151, 155, 156, 157, 168, 169, 173, 174, 175, 186, 187, 191, 192, 193, 204, 205, 209, 210, 211, 222, 223, 227, 228, 229, 240, 241, 245, 246, 247, 258, 259, 263, 264, 265, 276, 277, 281, 282, 283, 294, 295, 299, 300, 301, 312, 313, 317, 318, 319, 330, 331, 335, 336, 337, 348, 349, 353, 354, 355, 366, 367, 371, 372, 373, 384, 385, 389, 390, 391, 402, 403, 407, 408, 409, 420, 421, 425, 426, 427, 438, 439, 443, 444, 445, 456, 457, 461, 462, 463, 474, 475, 479, 480, 481, 492, 493, 497, 498, 499, 510, 511, 515, 516, 517, 528, 529, 533, 534, 535, 546, 547, 551, 552, 553, 564, 565, 569, 570, 571, 582, 583, 587, 588, 589, 600, 601, 605, 606, 607, 618, 619, 623, 624, or 625), or a sequence substantially identical thereto (e.g., a sequence at least about 85%, 90%, 95%, 96%, 97%, 98%, 99% or more identical thereto). In another embodiment, the antibody of the present invention includes one, two, or three CDR's of the $V_L$ domain of an antibody chosen from 356A11, 354A08, 087B03, and 368D04. In this embodiment, the antibody, or antigen-binding fragment thereof, comprises a light chain variable region comprising:

a) SEQ ID NO:173 or 497; b) SEQ ID NO: 174 or 498; and/or c) SEQ ID NO:175 or 499 (087B03);

a) SEQ ID NO:299 or 551; b) SEQ ID NO:300 or 552; and/or c) SEQ ID NO:301 or 553 (354A08);

a) SEQ ID NO:209 or 623; b) SEQ ID NO:210 or 624; and/or c) SEQ ID NO:211 or 625 (368D04); or a) SEQ ID NO:353 or 605; b) SEQ ID NO:354 or 606; and/or c) SEQ ID NO:355 or 607 (356A11).

In a still further embodiment, the antibody comprises an H3 fragment of the $V_H$ domain of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11, e.g., an H3 fragment having the amino acid sequence as set forth in Tables 1 and 7 (SEQ ID NO:10, 28, 46, 64, 82, 100, 118, 136, 154, 172, 190, 208, 226, 244, 262, 280, 298, 316, 334, 352, 370, 388, 406, 424, 442, 460, 478, 496, 514, 532, 550, 568, 586, 604, or 622), or a sequence substantially identical thereto (e.g., a sequence at least about 85%, 90%, 95%, 96%, 97%, 98%, 99% or more identical thereto).

The antibody of the invention can be full-length (e.g., include at least one complete heavy chain and at least one complete light chain) or can include only an antigen-binding fragment (e.g., a Fab, F(ab')$_2$, Fv, a single chain Fv fragment, a Fd fragment, or a dAb fragment). The antibody can include a constant region, or a portion thereof, chosen from any of: the kappa, lambda, alpha, gamma, delta, epsilon and mu constant region genes. For example, heavy chain constant regions of the various isotypes can be used, including: IgG$_1$, IgG$_2$, IgG$_3$, IgG$_4$, IgM, IgA$_1$, IgA$_2$, IgD, and IgE. The light chain constant region can be chosen from kappa or lambda. The antibody may be an IgG, or it may also be IgG$_{1\kappa}$ or IgG$_{1\gamma}$.

The anti-IL-22 antibody described herein can be derivatized or linked to another functional molecule (such as another peptide or protein (e.g., a Fab fragment)). For example, an antibody of the invention can be functionally linked (e.g., by chemical coupling, genetic fusion, non-covalent association or otherwise) to at least one other molecular entity, such as another antibody (e.g., a bispecific or a multispecific antibody), toxin, radioisotope, cytotoxic or cytostatic agent, among others.

In another aspect, the invention features a pharmaceutical composition containing at least one anti-IL-22 antibody and a pharmaceutically acceptable carrier. The pharmaceutical composition can further include a combination of at least one anti-IL-22 antibody and at least one therapeutic agent (e.g., cytokine and growth factor inhibitors, immunosuppressants, anti-inflammatory agents, metabolic inhibitors, enzyme inhibitors, cytotoxic agents, cytostatic agents, or combinations thereof, as described in more detail herein). Combinations of the anti-IL-22 antibody and a therapeutic agent are also within the scope of the invention. The compositions and combinations of the invention can be used to regulate IL-22-associated inflammatory conditions, e.g., by modulating IL-22 signaling through its receptors located on epithelial cells of a variety of tissues, including, but not limited to, those of the pancreas, skin, lung, gut, liver, kidney, salivary gland, and vascular endothelia, in addition to potentially activated and tissue localized immune cells.

In another aspect, the invention features a method of treating a subject with an IL-22-associated disorder. The method includes administering to the subject an anti-IL-22 antibody in an amount sufficient to inhibit at least one IL-22 activity of immune cells, thereby treating the IL-22-associated disorder.

The anti-IL-22 antibody can be administered to the subject, alone or in combination, with other therapeutic agents as described herein. The subject may be a mammal, e.g. human. For example, the method can be used to treat a subject with an IL-22-associated disorder such as autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD.

In another aspect, the invention features a method of decreasing, inhibiting or reducing an acute phase response in a subject. The method includes administering to the subject an IL-22 binding agent, e.g., an IL-22 antagonist, (e.g., an anti-IL-22 antibody or fragment thereof as described herein), in an amount sufficient to decrease, inhibit or reduce the acute phase response in the subject. In one embodiment, the subject is a mammal, e.g., a human suffering from an IL-22-associated disorder, including, e.g., respiratory disorders, inflammatory disorders and autoimmune disorders. In one embodiment, the IL-22 binding agent is administered locally, e.g., topically, subcutaneously, or other administrations that are not in the general circulation.

In another aspect, an IL-22 binding agent can be used to alter the type of immune response and/or increase the efficacy of a vaccine formulation used to immunize a subject. For example, an anti-IL-22 antibody of the present invention can be administered before, during and/or after an immunization to increase vaccine efficacy. In one embodiment, the vaccine formulation contains one or more IL-22 antagonists and an antigen, i.e., an immunogen, including, for example, viral, bacterial, or tumor antigens. In another embodiment, the IL-22 antagonist and the immunogen are administered separately, e.g., within one hour, three hours, one day or two days of each other.

In another aspect, the invention provides a method for detecting the presence of IL-22 in a sample in vitro. Samples may include biological samples such as serum, plasma, tissue and biopsy. The subject method can be used to diagnose a disorder, such as an IL-22-associated disorder as described herein. The method includes: (1) contacting the sample or a control sample with an anti-IL-22 antibody, and (2) detecting formation of a complex between the anti-IL-22 antibody and the sample or the control sample, wherein a statistically significant change in the formation of the complex in the sample relative to a control sample, is indicative of the presence of the IL-22 in the sample.

In another aspect, the invention provides a method for detecting the presence of IL-22 in vivo (e.g., in vivo imaging in a subject). The method can be used to diagnose a disorder, e.g., an IL-22-associated disorder as described herein. The method includes: (1) administering an anti-IL-22 antibody to a subject or a control subject under conditions that allow binding of the antibody to IL-22, and (2) detecting formation of a complex between the antibody and IL-22, wherein a statistically significant change in the formation of the complex in the subject relative to a control, e.g., a control subject, is indicative of the presence of IL-22.

The antibody may be directly or indirectly labeled with a detectable substance to facilitate detection of the bound or unbound antibody. Suitable detectable substances include various enzymes, prosthetic groups, fluorescent materials, luminescent materials and radioactive materials.

In another aspect, the invention provides a method for delivering or targeting an agent, e.g., a therapeutic or a cytotoxic agent, to an IL-22-expressing cell in vivo. The method includes administering an anti-IL-22 antibody to a subject under conditions that allow binding of the antibody to IL-22. The antibody may be coupled to a second therapeutic moiety, such as a toxin.

The disclosure provides nucleic acid sequences from the $V_H$ and $V_L$ domains of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11. Also provided are nucleic acid sequences that comprise at least one CDR from GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11. The disclosure also provides vectors and host cells comprising such nucleic acids.

The disclosure further provides methods of producing new $V_H$ and $V_L$ domains and functional antibodies comprising all or a portion of such domains derived from the $V_H$ or $V_L$ domains of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11.

Additional aspects of the disclosure will be set forth in part in the description, and in part will be obvious from the description, or may be learned by practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve only to illustrate embodiments and not limit the invention.

BRIEF DESCRIPTION OF THE FIGURES

FIG. 5. Amino acid and nucleotide sequences of human IL-22. The nucleotide sequence of human IL-22 is SEQ ID NO:2 and includes a poly (A) tail. The disclosed nucleotide sequence includes an open reading frame and the amino acid sequence of full-length IL-22 protein corresponding to the foregoing nucleotide sequence is reported in SEQ ID NO:1. The amino acid sequence of mature IL-22 corresponds to about amino acids 34-179 of SEQ ID NO:1.

FIG. 6. Amino acid and nucleotide sequences of mouse IL-22.

FIG. 7. Amino acid and nucleotide sequences of non-germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11, including $V_H$ and $V_L$ domains, and CDRs (H1, H2, H3, L1, L2, and L3).

FIG. 8. Amino acid and nucleotide sequences of germlined GIL01, GIL16, GIL45, GIL60, GIL68, GIL92, 062A09, 087B03, 166B06, 166G05, 354A08, 355B06, 355E04, 356A11, and 368D04, including $V_H$ and $V_L$ domains, and CDRs (H1, H2, H3, L1, L2, and L3).

FIG. 9. Amino acid and nucleotide sequences of scFv's for non-germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11, with CDRs underlined (H1, H2, H3, L1, L2, and L3).

FIG. 10. Amino acid and nucleotide sequences of scFv's for germlined GIL01, GIL16, GIL45, GIL60, GIL68, GIL92, 062A09, 087B03, 166B06, 166G05, 354A08, 355B06, 355E04, 356A11, and 368D04 with CDRs underlined (H1, H2, H3, L1, L2, and L3).

DETAILED DESCRIPTION

I. Definitions

Figure 1:
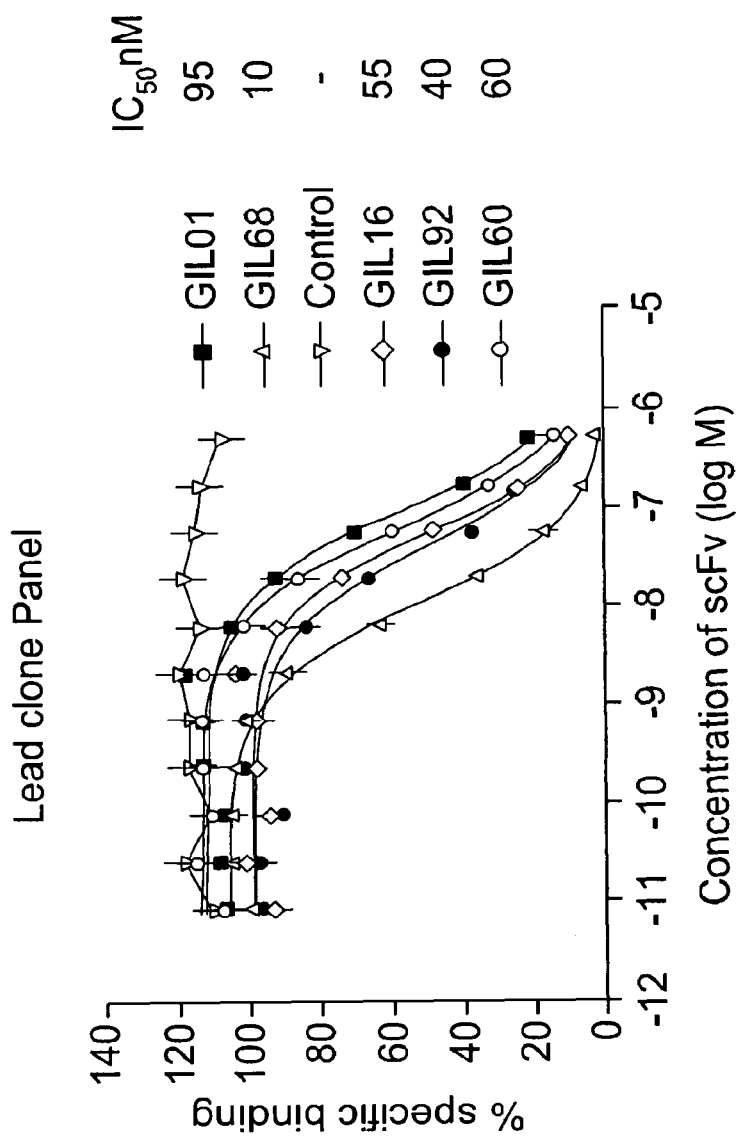
FIG. 1. Potency of parent anti-IL-22 scFv clones in the IL-22 receptor complex assay: bio.IL-22 binding IL-22 receptor complex DELFIA competition assay.
Figure 2A:
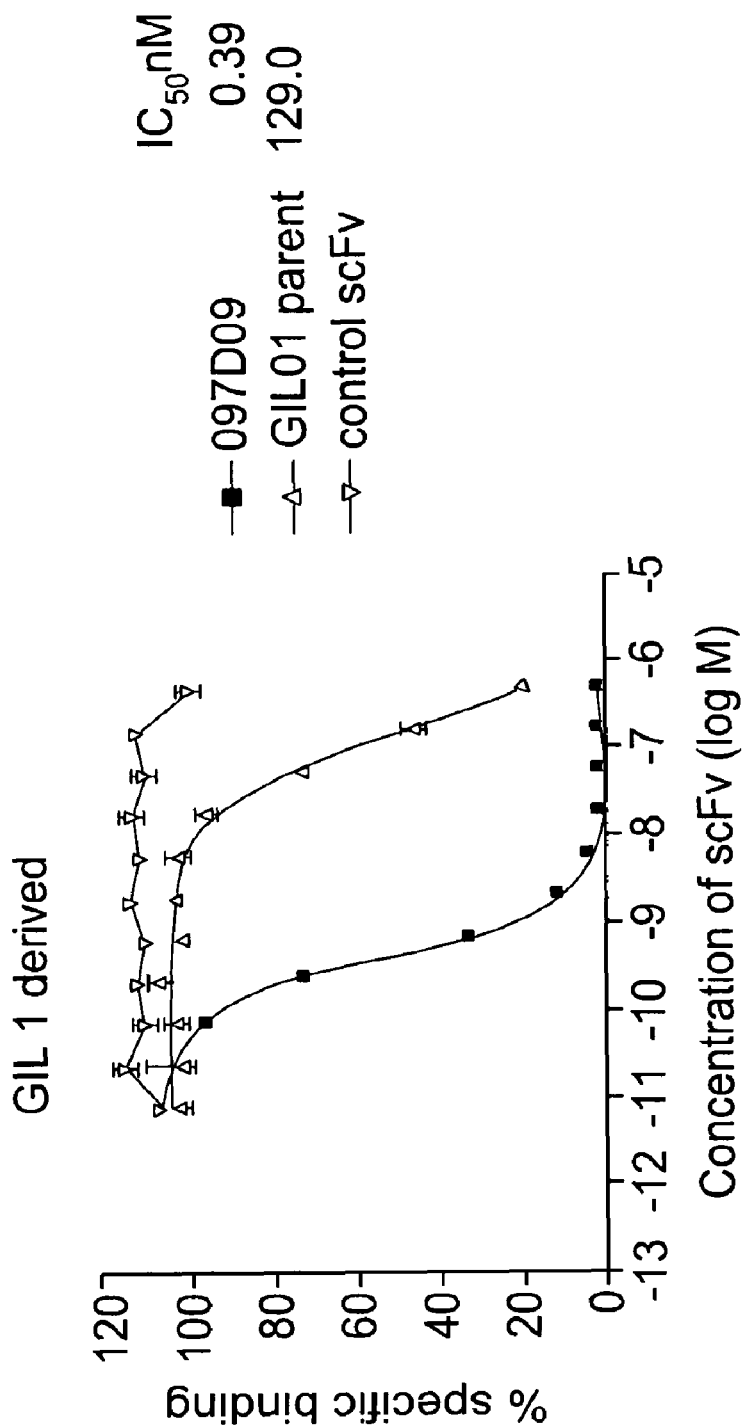
FIG. 2. Profiling of lead scFv clones in IL-22 receptor complex assay: bio.IL-22 binding IL-22 receptor complex DELFIA competition assay. (A) GIL 1 derived. (B) GIL 16 derived. (C) GIL 16, GIL 60, and GIL 68 derived. (D) GIL 60 derived. (E) GIL 68 derived. (F) GIL 68 derived. (G) GIL 92 derived.
Figure 2B:
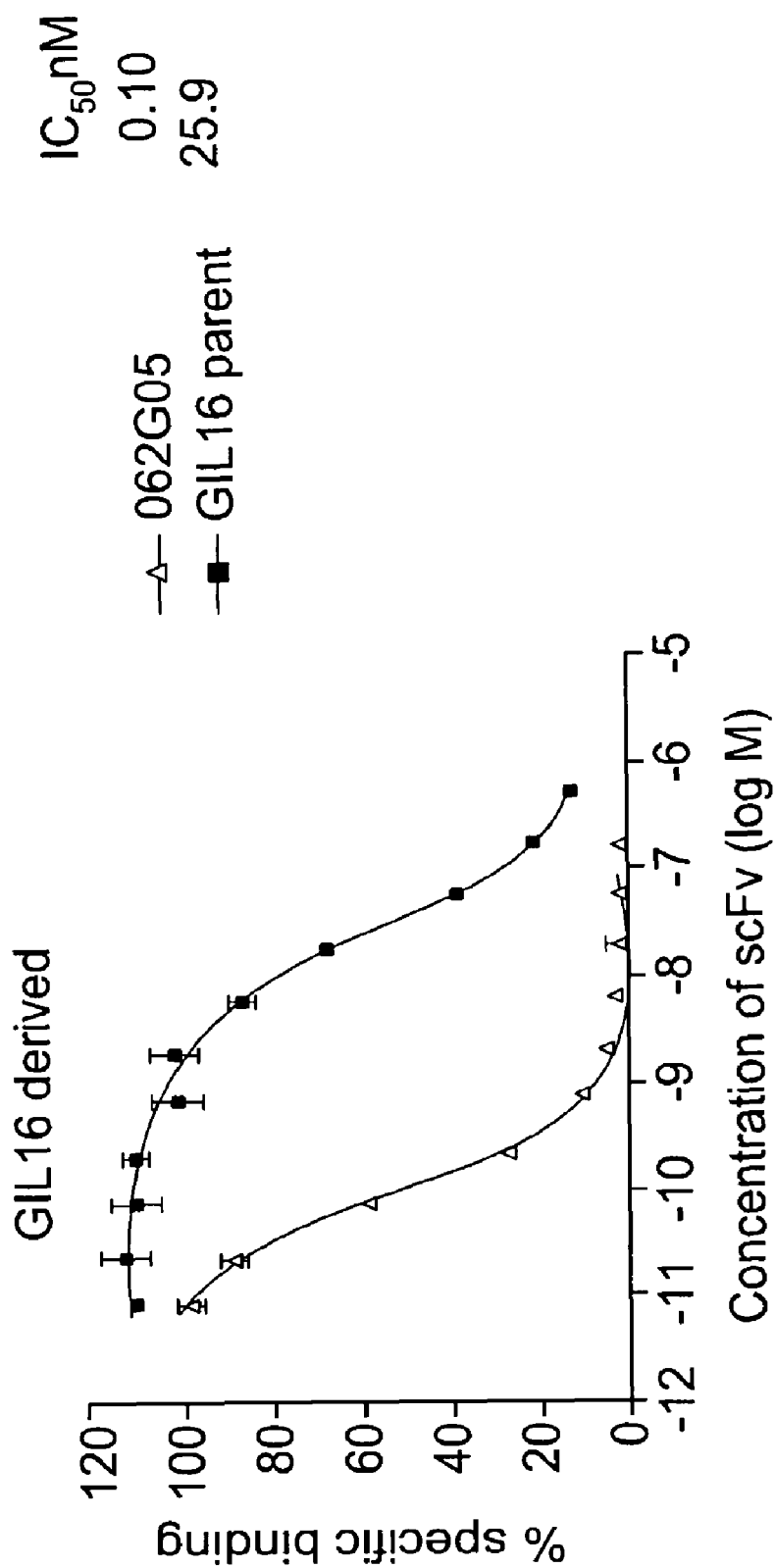
Figure 2C:
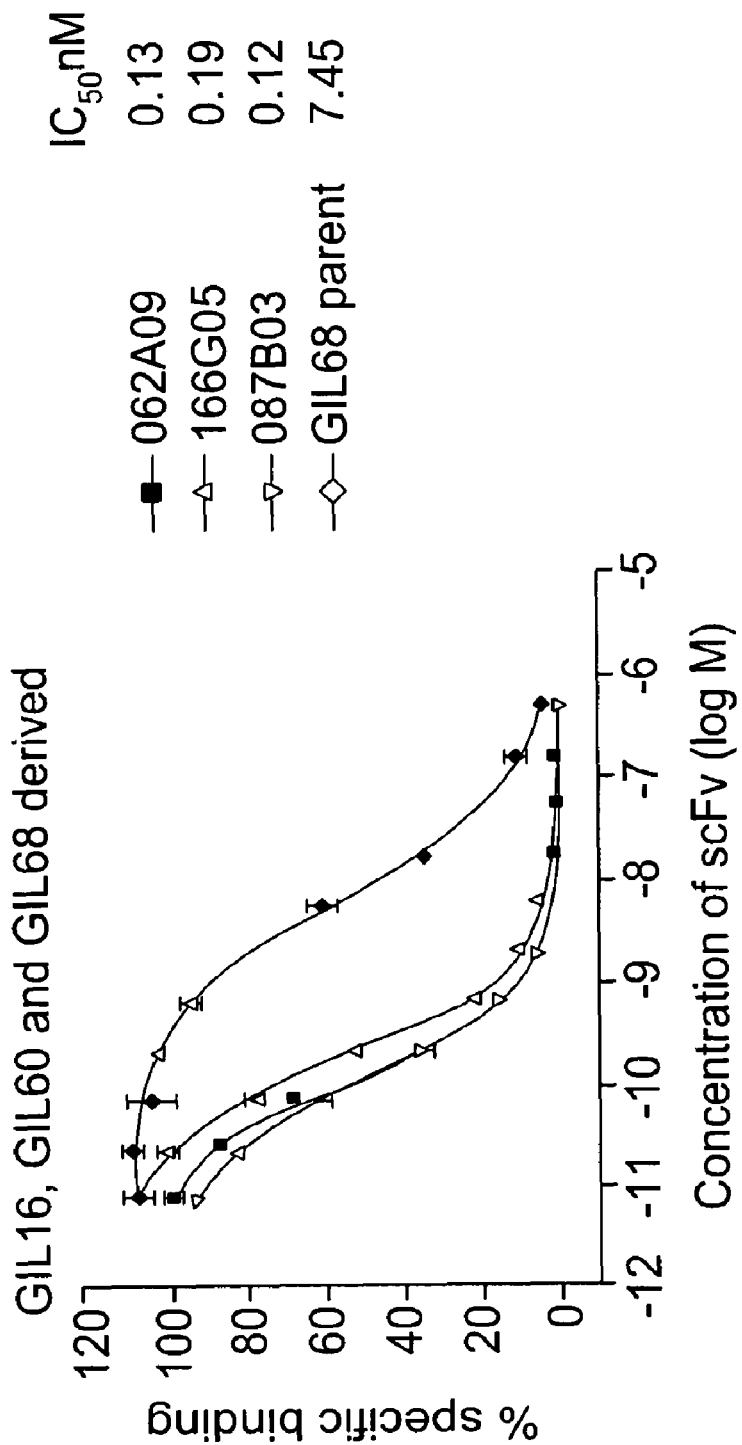
Figure 2D:
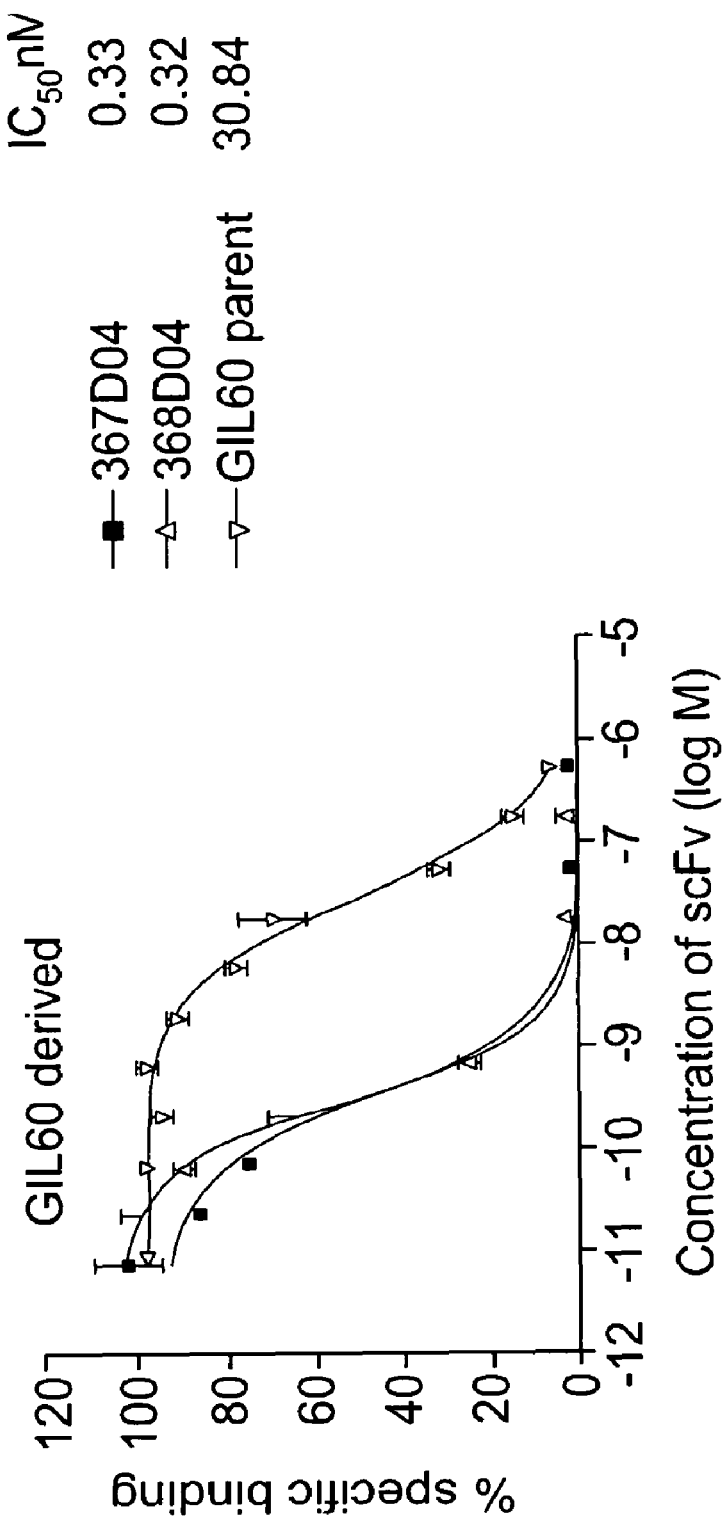
Figure 2E:
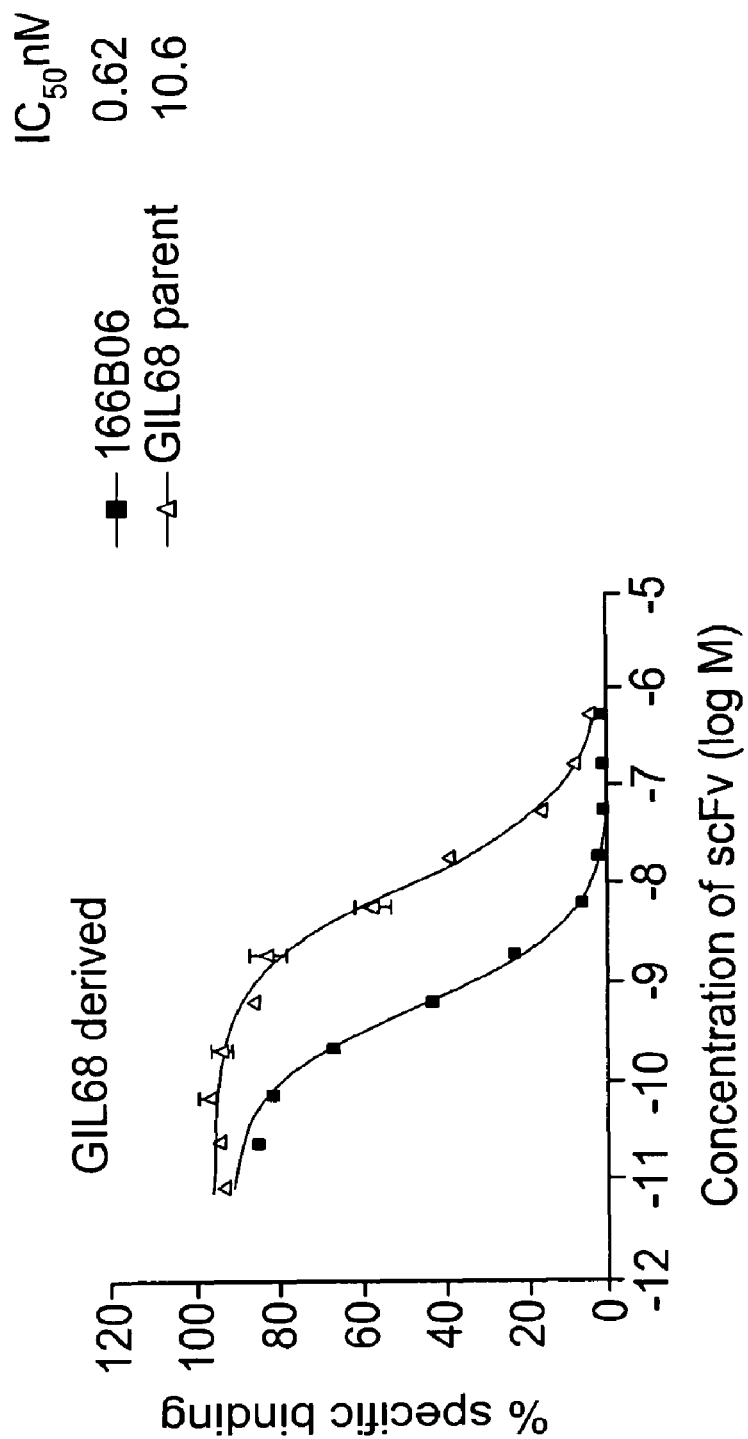
Figure 2F:
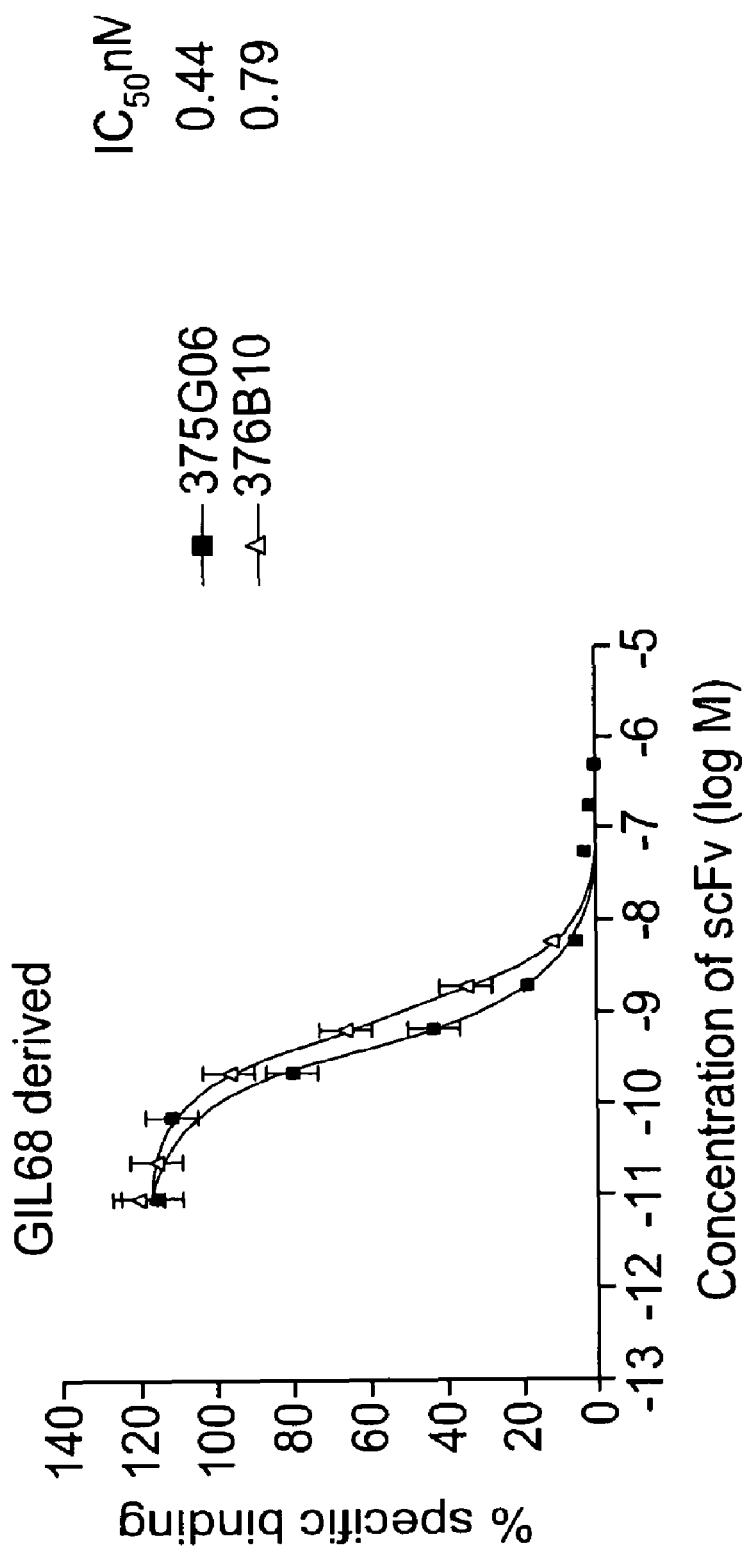
Figure 2G:
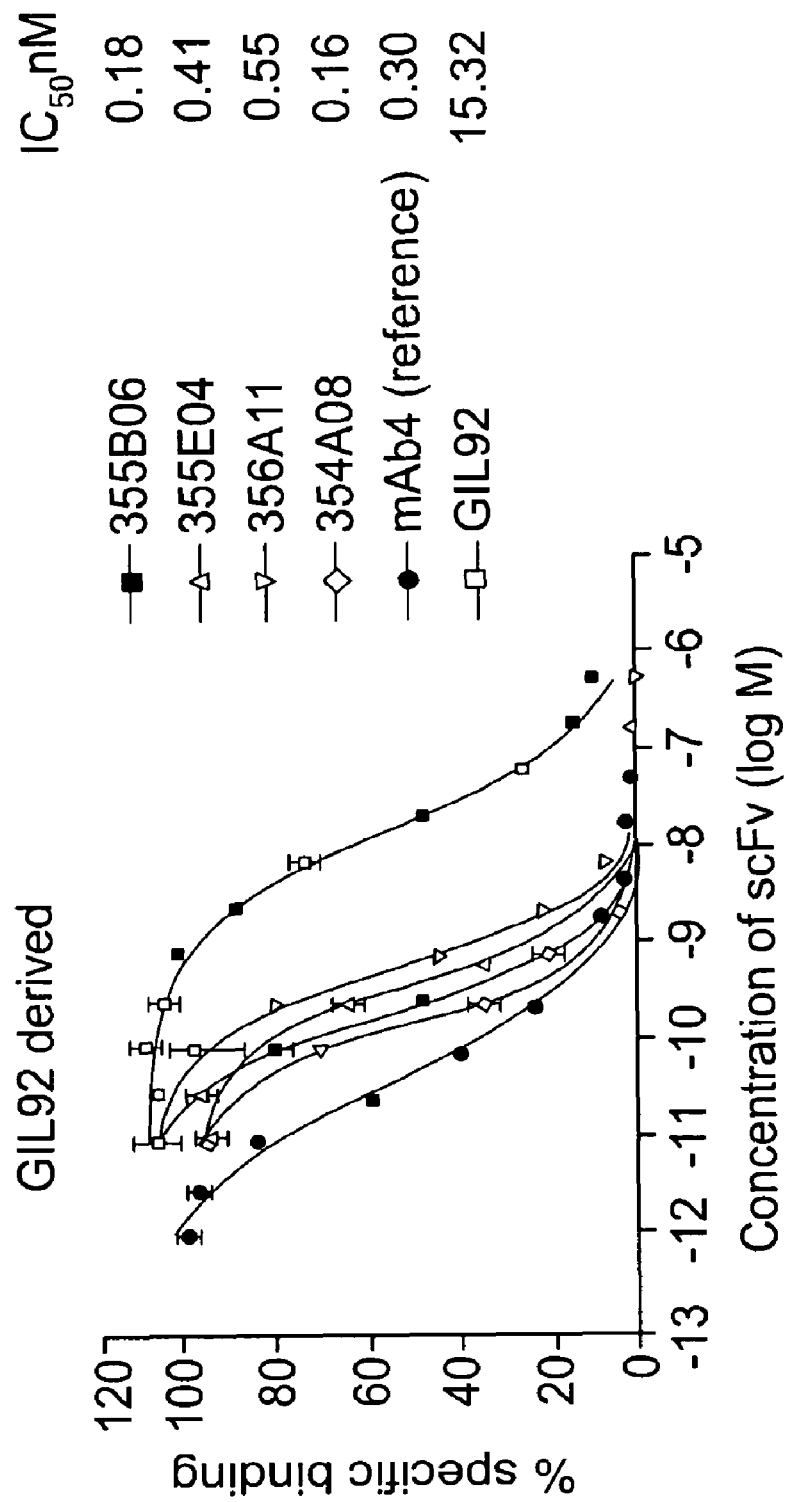

In order that the present invention may be more readily understood, certain terms are first defined. Additional definitions are set forth throughout the detailed description.

The term "antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Typically, such fragments would comprise an antigen-binding domain.

The terms "antigen-binding domain" and "antigen-binding fragment" refer to a part of an antibody molecule that comprises amino acids responsible for the specific binding between antibody and antigen. The part of the antigen that is specifically recognized and bound by the antibody is referred to as the "epitope." An antigen-binding domain may comprise an antibody light chain variable region ($V_L$) and an antibody heavy chain variable region ($V_H$); however, it does not have to comprise both. Fd fragments, for example, have two $V_H$ regions and often retain some antigen-binding function of the intact antigen-binding domain. Examples of antigen-binding fragments of an antibody include (1) a Fab fragment, a monovalent fragment having the $V_L$, $V_H$, $C_L$ and $C_H1$ domains; (2) a F(ab')$_2$ fragment, a bivalent fragment having two Fab fragments linked by a disulfide bridge at the hinge region; (3) a Fd fragment having the two $V_H$ and $C_H1$ domains; (4) a Fv fragment having the $V_L$ and $V_H$ domains of a single arm of an antibody, (5) a dAb fragment (Ward et al., (1989) Nature 341:544-546), which has a $V_H$ domain; (6) an isolated complementarity determining region (CDR), and (7) a single chain Fv (scFv). Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). These antibody fragments are obtained using conventional techniques known to those with skill in the art, and the fragments are evaluated for function in the same manner as are intact antibodies.

The term "effective amount" refers to a dosage or amount that is sufficient to regulate IL-22 activity to ameliorate clinical symptoms or achieve a desired biological outcome, e.g., decreased T cell and/or B cell activity, suppression of autoimmunity, suppression of transplant rejection, etc.

The term "human antibody" includes antibodies having variable and constant regions corresponding substantially to human germline immunoglobulin sequences known in the art, including, for example, those described by Kabat et al. (See Kabat, et al. (1991) Sequences of Proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The phrase "inhibit" or "antagonize" IL-22 activity and its cognates refer to a reduction, inhibition, or otherwise diminution of at least one activity of IL-22 due to binding an anti-IL-22 antibody, wherein the reduction is relative to the activity of IL-22 in the absence of the same antibody. The activity can be measured using any technique known in the art, including, for example, as described in Examples 7 and 9. Inhibition or antagonism does not necessarily indicate a total elimination of the IL-22 polypeptide biological activity. A reduction in activity may be about 10%, 20%, 30%, 40%, 50%, 60%, 70%, 80%, 90%, or more.

The term "interleukin-22" or "IL-22" refers to a class II cytokine (which may be mammalian) capable of binding to IL-22R and/or a receptor complex of IL-22R and IL-10R2, and has at least one of the following features: (1) an amino acid sequence of a naturally occurring mammalian IL-22 polypeptide (full length or mature form) or a fragment thereof, e.g., an amino acid sequence shown as SEQ ID NO:1 (human) or SEQ ID NO:3 (murine) or a fragment thereof; (2) an amino acid sequence substantially identical to, e.g., at least 85%, 90%, 95%, 96%, 97%, 98%, 99% identical to, an amino acid sequence shown as SEQ ID NO:1 or amino acids 34-179 thereof (human) or SEQ ID NO:3 (murine) or a fragment thereof; (3) an amino acid sequence which is encoded by a naturally occurring mammalian IL-22 nucleotide sequence or a fragment thereof (e.g., SEQ ID NO:2 or nucleotides 71 to 610 (human) or SEQ ID NO:4 (murine) or a fragment thereof); (4) an amino acid sequence encoded by a nucleotide sequence which is substantially identical to, e.g., at least 85%, 90%, 95%, 96%, 97%, 98%, 99% identical to, a nucleotide sequence shown as SEQ ID NO:2 or nucleotides 71 to 610 thereof (human) or SEQ ID NO:4 (murine) or a fragment thereof; (5) an amino acid sequence encoded by a nucleotide sequence degenerate to a naturally occurring IL-22 nucleotide sequence or a fragment thereof, e.g., SEQ ID NO:2 (human) or SEQ ID NO:4 (murine) or a fragment thereof; or (6) a nucleotide sequence that hybridizes to one of the foregoing nucleotide sequences under stringent conditions, e.g., highly stringent conditions. The IL-22 may bind to IL-22R and/or a receptor complex of IL-22R and IL-10R2 of mammalian origin, e.g., human or mouse.

The nucleotide sequence and the predicted amino acid sequence of human IL-22 are shown in SEQ ID NO:2 and SEQ ID NO:1, respectively. The amino acid sequence of mature human IL-22 corresponds to amino acids 34-179 of SEQ ID NO:1. Analysis of recombinant human IL-22 reveals many structural domains. (Nagem et al. (2002) Structure, 10:1051-62; U.S. Patent Application No. US 2002/0187512 A1).

The term "IL-22 activity" refers to at least one cellular process initiated or interrupted as a result of IL-22 binding to a receptor complex consisting of IL-22R and IL-10R2 on the cell. IL-22 activities include at least one of, but are not limited to: (1) binding IL-22R or a receptor complex of IL-22R and IL-10R2 (e.g., human IL-22R with or without human IL-10R2); (2) associating with signal transduction molecules (e.g., JAK-1); (3) stimulating phosphorylation of STAT proteins (e.g., STAT5, STAT3, or combination thereof); (4) activating STAT proteins; and (5) modulating (e.g., increasing or decreasing) proliferation, differentiation, effector cell function, cytolytic activity, cytokine secretion, survival, or combinations thereof, of epithelial cells, fibroblasts, or immune cells. Epithelial cells include, but are not limited to, cells of the skin, gut, liver, and kidney, as well as endothelial cells. Fibroblasts include, but are not limited to, synovial fibroblasts. Immune cells may include CD8+ and CD4+ T cells, NK cells, B cells, macrophages, and megakaryocytes. IL-22 activity can be determined in vitro, for example, using the IL-22 receptor inhibition assay as described in Examples 2 and 6, the GROa secretion assay in Example 9, or the BAF3 proliferation assay of Example 7. IL-22 activity can also be determined in vivo, for example, by scoring progression of an immune response or disorder as described in Example 13.

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term excludes sequences generated by genomic rearrangement in an immune cell.

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The phrase "percent identical" or "percent identity" refers to the similarity between at least two different sequences. This percent identity can be determined by standard alignment algorithms, for example, the Basic Local Alignment Tool (BLAST) described by Altshul et al. ((1990) J. Mol. Biol., 215: 403-410); the algorithm of Needleman et al. ((1970) J. Mol. Biol., 48: 444-453); or the algorithm of Meyers et al. ((1988) Comput. Appl. Biosci., 4: 11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4. The percent identity is usually calculated by comparing sequences of similar length.

The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

The terms "specific binding" or "specifically binds" refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the association constant $K_A$ is higher than $10^6 M^{-1}$. If necessary, nonspecific binding can be reduced without substantially affecting specific binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques. Illustrative conditions are set forth in Example 3, but other conditions known to the person of ordinary skill in the art fall within the scope of this invention.

As used herein, the term "stringent" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and nonaqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5M sodium phosphate, 7% SDS at 65° C., followed by at least one wash at 0.2×SSC, 1% SDS at 65° C.

The phrase "substantially as set out," "substantially identical" or "substantially homologous" means that the relevant amino acid or nucleotide sequence (e.g., CDR(s), $V_H$, or $V_L$ domain) will be identical to or have insubstantial differences (through conserved amino acid substitutions) in comparison to the sequences which are set out. Insubstantial differences include minor amino acid changes, such as 1 or 2 substitutions in a 5 amino acid sequence of a specified region. In the case of antibodies, the second antibody has the same specificity and has at least 50% of the affinity of the first antibody.

Sequences substantially identical or homologous (e.g., at least about 85% sequence identity) to the sequences disclosed herein are also part of this application. In some embodiment, the sequence identity can be about 85%, 90%, 95%, 96%, 97%, 98%, 99% or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

The term "therapeutic agent" is a substance that treats or assists in treating a medical disorder. Therapeutic agents may include, but are not limited to, substances that modulate immune cells or immune responses in a manner that complements the IL-22 activity of anti-IL-22 antibodies. Non-limiting examples and uses of therapeutic agents are described herein.

As used herein, a "therapeutically effective amount" of an anti-IL-22 antibody refers to an amount of an antibody which is effective, upon single or multiple dose administration to a subject (such as a human patient) at treating, preventing, curing, delaying, reducing the severity of, and/or ameliorating at least one symptom of a disorder or recurring disorder, or prolonging the survival of the subject beyond that expected in the absence of such treatment.

The term "treatment" refers to a therapeutic or preventative measure. The treatment may be administered to a subject having a medical disorder or who ultimately may acquire the disorder, in order to prevent, cure, delay, reduce the severity of, and/or ameliorate one or more symptoms of a disorder or recurring disorder, or in order to prolong the survival of a subject beyond that expected in the absence of such treatment.

II. Anti-IL-22 Antibodies

The disclosure provides novel anti-IL-22 antibodies that comprise novel antigen-binding fragments.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas (see e.g., Kohler and Milstein (1975) *Nature*, 256: 495-499) in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) *Science* 228:1315-1317; Clackson et al. (1991) *Nature*, 352: 624-628; Marks et al. (1991) *J. Mol. Biol.*, 222: 581-597 WO92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.,* 80: 7308-7312, 1983; Kozbor et al., *Immunology Today,* 4: 7279, 1983; Olsson et al., *Meth. Enzymol.,* 92: 3-16, 1982), and may be made according to the teachings of PCT Publication WO92/06193 or EP 0239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

In certain embodiments, an antibody can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., *Immunomethods* 4:25-34, 1994; and de Haas et al., *J. Lab. Clin. Med.* 126:330-41, 1995).

For additional antibody production techniques, see Antibodies: A Laboratory Manual, eds. Harlow et al., Cold Spring Harbor Laboratory, 1988. The present invention is not necessarily limited to any particular source, method of production, or other special characteristics of an antibody.

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual*, Cold Spring Harbor Laboratory, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of Proteins of Immunological Interest, US Department of Health and Human Services* (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains*. In: *Antibody Engineering Lab Manual* (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops.

The Fab fragment (Fragment antigen-binding) consists of $V_H\text{-}C_H1$ and $V_L\text{-}C_L$ domains covalently linked by a disulfide bond between the constant regions. The $F_v$ fragment is smaller and consists of $V_H$ and $V_L$ domains non-covalently linked. To overcome the tendency of non-covalently linked domains to dissociate, a single chain $F_v$ fragment (scF$_v$) can be constructed. The scF$_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide may be used as a linker, but other linkers are known in the art.

The sequence of antibody genes after assembly and somatic mutation is highly varied, and these varied genes are estimated to encode $10^{10}$ different antibody molecules (Immunoglobulin Genes, 2nd ed., eds. Jonio et al., Academic Press, San Diego, Calif., 1995).

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992). In one embodiment, the bispecific antibody comprises a first binding domain polypeptide, such as a Fab' fragment, linked via an immunoglobulin constant region to a second binding domain polypeptide.

Small Modular ImmunoPharmaceuticals (SMIP™) provide an example of a variant molecule comprising a binding domain polypeptide. SMIPs and their uses and applications are disclosed in, e.g., U.S. Published Patent Application. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

A SMIP™ typically refers to a binding domain-immunoglobulin fusion protein that includes a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain, other than CH1, for example, the CH2 and CH3 regions of IgG and IgA, or the CH3 and CH4 regions of IgE (see e.g., U.S. 2005/0136049 by Ledbetter, J. et al., which is incorporated by reference, for a more complete description). The binding domain-immunoglobulin fusion protein can further include a region that includes a native or engineered immunoglobulin heavy chain CH2 constant region polypeptide (or CH3 in the case of a construct derived in whole or in part from IgE) that is fused or otherwise connected to the hinge region polypeptide and a native or engineered immunoglobulin heavy chain CH3 constant region polypeptide (or CH4 in the case of a construct derived in whole or in part from IgE) that is fused or otherwise connected to the CH2 constant region polypeptide (or CH3 in the case of a construct derived in whole or in part from IgE). Typically, such binding domain-immunoglobulin fusion proteins are capable of at least one immunological activity selected from the group consisting of antibody dependent cell-mediated cytotoxicity, complement fixation, and/or binding to a target, for example, a target antigen, such as human IL-22.

Therapeutic proteins, i.e., a protein or peptide that has a biological effect on a region in the body on which it acts or on a region of the body on which it remotely acts via intermediates, are also useful for practicing the invention. A therapeutic protein can include peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and potentially improved characteristics.

Other embodiments of therapeutic proteins include fusion proteins. These molecules generally have all or a substantial portion of a targeting peptide, for example, IL-22 or an anti IL-22 antibody, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments of antibodies, antigens, receptor proteins, enzymes, lectins, MHC proteins, cell adhesion proteins and binding proteins. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

In one embodiment, the targeting peptide, for example, IL-22 or an anti IL-22 antibody, is fused with an immunoglobulin heavy chain constant region, such as an Fc fragment, which contains two constant region domains and a hinge region but lacks the variable region (See, U.S. Pat. Nos. 6,018,026 and 5,750,375, incorporated herein by reference). The Fc region may be a naturally occurring Fc region, or may be altered to improve certain qualities, such as therapeutic qualities, circulation time, reduced aggregation, etc. Peptides and proteins fused to an Fc region typically exhibit a greater half-life in vivo than the unfused counterpart. Also, a fusion to an Fc region permits dimerization/multimerization of the fusion polypeptide.

VHH molecules (or nanobodies), as known to the skilled artisan, are heavy chain variable domains derived from immunoglobulins naturally devoid of light chains, such as those derived from Camelidae as described in WO9404678, incorporated herein by reference. Such a VHH molecule can be derived from antibodies raised in Camelidae species, for example in camel, llama, dromedary, alpaca and guanaco and is sometimes called a camelid or camelized variable domain. See e.g., Muyldermans., *J. Biotechnology* (2001) 74(4):277-302, incorporated herein by reference. Other species besides *Camelidae* may produce heavy chain antibodies naturally devoid of light chain. VHH molecules are about 10 times smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognized by antibodies generated in vitro through the use of antibody libraries or via immunization of mammals other than Camelids (see WO 9749805, which is incorporated herein by reference).

One aspect of the present invention comprises antibodies and antigen binding fragments that bind IL-22. The disclosure provides novel CDRs derived from human immunoglobulin gene libraries. The structure for carrying a CDR is generally an antibody heavy or light chain or portion thereof, where the CDR is located to a naturally occurring CDR region. The structures and locations of variable domains may be determined as described in Kabat et al., Sequences of Proteins of Immunological Interest, No. 91-3242, National Institutes of Health Publications, Bethesda, Md. (1991).

DNA and amino acid (AA) sequences of illustrative embodiments of the anti-IL-22 antibodies of this invention, including their scF$_v$ fragments, V$_H$ and V$_L$ domains, and CDRs, are set forth in FIGS. 7-10 and enumerated in Tables 1 and 7. Twenty specific embodiments of the non-germlined antibodies are identified as GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11. The CDR positions in the V$_H$ and V$_L$ domains of the non-germlined antibodies are listed in Table 2. Fifteen specific embodiments of the germlined antibodies are identified as GIL01, GIL16, GIL45, GIL60, GIL68, GIL92, 062A09, 087B03, 166B06, 166G05, 354A08, 355B06, 355E04, 356A11, and 368D04.

TABLE 1

Amino acid and Nucleotide Sequences of V$_H$ and V$_L$ Domains, Fv, and CDRs of Non-germlined Antibodies

| Region | Type | GIL01 SEQ ID | GIL16 SEQ ID | GIL45 SEQ ID | GIL60 SEQ ID | GIL68 SEQ ID | GIL92 SEQ ID | 097D09 SEQ ID | 062A09 SEQ ID | 062G05 SEQ ID | 087B03 SEQ ID |
|---|---|---|---|---|---|---|---|---|---|---|---|
| V$_H$ | AA | NO: 5 | NO: 23 | NO: 41 | NO: 59 | NO: 77 | NO: 95 | NO: 113 | NO: 131 | NO: 149 | NO: 167 |
| V$_L$ | AA | NO: 6 | NO: 24 | NO: 42 | NO: 60 | NO: 78 | NO: 96 | NO: 114 | NO: 132 | NO: 150 | NO: 168 |
| scFv | AA | NO: 7 | NO: 25 | NO: 43 | NO: 61 | NO: 79 | NO: 97 | NO: 115 | NO: 133 | NO: 151 | NO: 169 |
| H1 | AA | NO: 8 | NO: 26 | NO: 44 | NO: 62 | NO: 80 | NO: 98 | NO: 116 | NO: 134 | NO: 152 | NO: 170 |
| H2 | AA | NO: 9 | NO: 27 | NO: 45 | NO: 63 | NO: 81 | NO: 99 | NO: 117 | NO: 135 | NO: 153 | NO: 171 |
| H3 | AA | NO: 10 | NO: 28 | NO: 46 | NO: 64 | NO: 82 | NO: 100 | NO: 118 | NO: 136 | NO: 154 | NO: 172 |
| L1 | AA | NO: 11 | NO: 29 | NO: 47 | NO: 65 | NO: 83 | NO: 101 | NO: 119 | NO: 137 | NO: 155 | NO: 173 |
| L2 | AA | NO: 12 | NO: 30 | NO: 48 | NO: 66 | NO: 84 | NO: 102 | NO: 120 | NO: 138 | NO: 156 | NO: 174 |
| L3 | AA | NO: 13 | NO: 31 | NO: 49 | NO: 67 | NO: 85 | NO: 103 | NO: 121 | NO: 139 | NO: 157 | NO: 175 |
| V$_H$ | DNA | NO: 14 | NO: 32 | NO: 50 | NO: 68 | NO: 86 | NO: 104 | NO: 122 | NO: 140 | NO: 158 | NO: 176 |
| V$_L$ | DNA | NO: 15 | NO: 33 | NO: 51 | NO: 69 | NO: 87 | NO: 105 | NO: 123 | NO: 141 | NO: 159 | NO: 177 |
| scF$_v$ | DNA | NO: 16 | NO: 34 | NO: 52 | NO: 70 | NO: 88 | NO: 106 | NO: 124 | NO: 142 | NO: 160 | NO: 178 |
| H1 | DNA | NO: 17 | NO: 35 | NO: 53 | NO: 71 | NO: 89 | NO: 107 | NO: 125 | NO: 143 | NO: 161 | NO: 179 |
| H2 | DNA | NO: 18 | NO: 36 | NO: 54 | NO: 72 | NO: 90 | NO: 108 | NO: 126 | NO: 144 | NO: 162 | NO: 180 |
| H3 | DNA | NO: 19 | NO: 37 | NO: 55 | NO: 73 | NO: 91 | NO: 109 | NO: 127 | NO: 145 | NO: 163 | NO: 181 |
| L1 | DNA | NO: 20 | NO: 38 | NO: 56 | NO: 74 | NO: 92 | NO: 110 | NO: 128 | NO: 146 | NO: 164 | NO: 182 |
| L2 | DNA | NO: 21 | NO: 39 | NO: 57 | NO: 75 | NO: 93 | NO: 111 | NO: 129 | NO: 147 | NO: 165 | NO: 183 |
| L3 | DNA | NO: 22 | NO: 40 | NO: 58 | NO: 76 | NO: 94 | NO: 112 | NO: 130 | NO: 148 | NO: 166 | NO: 184 |

| Region | Type | 367D04 SEQ ID | 368D04 SEQ ID | 166B06 SEQ ID | 166G05 SEQ ID | 375G06 SEQ ID | 376B10 SEQ ID | 354A08 SEQ ID | 355B06 SEQ ID | 355E04 SEQ ID | 356A11 SEQ ID |
|---|---|---|---|---|---|---|---|---|---|---|---|
| V$_H$ | AA | NO: 185 | NO: 203 | NO: 221 | NO: 239 | NO: 257 | NO: 275 | NO: 293 | NO: 311 | NO: 329 | NO: 347 |
| V$_L$ | AA | NO: 186 | NO: 204 | NO: 222 | NO: 240 | NO: 258 | NO: 276 | NO: 294 | NO: 312 | NO: 330 | NO: 348 |
| scF$_v$ | AA | NO: 187 | NO: 205 | NO: 223 | NO: 241 | NO: 259 | NO: 277 | NO: 295 | NO: 313 | NO: 331 | NO: 349 |
| H1 | AA | NO: 188 | NO: 206 | NO: 224 | NO: 242 | NO: 260 | NO: 278 | NO: 296 | NO: 314 | NO: 332 | NO: 350 |
| H2 | AA | NO: 189 | NO: 207 | NO: 225 | NO: 243 | NO: 261 | NO: 279 | NO: 297 | NO: 315 | NO: 333 | NO: 351 |
| H3 | AA | NO: 190 | NO: 208 | NO: 226 | NO: 244 | NO: 262 | NO: 280 | NO: 298 | NO: 316 | NO: 334 | NO: 352 |
| L1 | AA | NO: 191 | NO: 209 | NO: 227 | NO: 245 | NO: 263 | NO: 281 | NO: 299 | NO: 317 | NO: 335 | NO: 353 |
| L2 | AA | NO: 192 | NO: 210 | NO: 228 | NO: 246 | NO: 264 | NO: 282 | NO: 300 | NO: 318 | NO: 336 | NO: 354 |
| L3 | AA | NO: 193 | NO: 211 | NO: 229 | NO: 247 | NO: 265 | NO: 283 | NO: 301 | NO: 319 | NO: 337 | NO: 355 |
| V$_H$ | DNA | NO: 194 | NO: 212 | NO: 230 | NO: 248 | NO: 266 | NO: 284 | NO: 302 | NO: 320 | NO: 338 | NO: 356 |
| V$_L$ | DNA | NO: 195 | NO: 213 | NO: 231 | NO: 249 | NO: 267 | NO: 285 | NO: 303 | NO: 321 | NO: 339 | NO: 357 |
| scF$_v$ | DNA | NO: 196 | NO: 214 | NO: 232 | NO: 250 | NO: 268 | NO: 286 | NO: 304 | NO: 322 | NO: 340 | NO: 358 |
| H1 | DNA | NO: 197 | NO: 215 | NO: 233 | NO: 251 | NO: 269 | NO: 287 | NO: 305 | NO: 323 | NO: 341 | NO: 359 |
| H2 | DNA | NO: 198 | NO: 216 | NO: 234 | NO: 252 | NO: 270 | NO: 288 | NO: 306 | NO: 324 | NO: 342 | NO: 360 |
| H3 | DNA | NO: 199 | NO: 217 | NO: 235 | NO: 253 | NO: 271 | NO: 289 | NO: 307 | NO: 325 | NO: 343 | NO: 361 |
| L1 | DNA | NO: 200 | NO: 218 | NO: 236 | NO: 254 | NO: 272 | NO: 290 | NO: 308 | NO: 326 | NO: 344 | NO: 362 |
| L2 | DNA | NO: 201 | NO: 219 | NO: 237 | NO: 255 | NO: 273 | NO: 291 | NO: 309 | NO: 327 | NO: 345 | NO: 363 |
| L3 | DNA | NO: 202 | NO: 220 | NO: 238 | NO: 256 | NO: 274 | NO: 292 | NO: 310 | NO: 328 | NO: 346 | NO: 364 |

TABLE 2

Positions of CDRs within Non-germlined Antibody
Amino Acid Sequences of $V_H$ and $V_L$ Domains

| CDR | GIL01 | GIL16 | GIL45 | GIL60 | GIL68 | GIL92 | 097D09 | 062A09 | 062G05 | 087B03 |
|-----|-------|-------|-------|-------|-------|-------|--------|--------|--------|--------|
| H1  | 31-35 | 31-35 | 31-35 | 31-35 | 31-35 | 31-35 | 31-35  | 31-35  | 31-35  | 31-35  |
| H2  | 50-66 | 50-66 | 50-66 | 50-66 | 50-66 | 50-66 | 50-66  | 50-66  | 50-66  | 50-66  |
| H3  | 99-108| 99-108| 99-108| 99-110| 99-108| 99-110| 99-108 | 99-108 | 99-108 | 99-110 |
| L1  | 24-34 | 24-34 | 23-36 | 23-36 | 23-33 | 23-36 | 24-34  | 24-34  | 24-34  | 23-36  |
| L2  | 50-56 | 50-56 | 52-58 | 52-58 | 49-55 | 52-58 | 50-56  | 50-56  | 50-56  | 52-58  |
| L3  | 89-97 | 89-97 | 91-100| 91-100| 88-98 | 91-101| 89-97  | 89-97  | 89-97  | 91-100 |

| CDR | 367D04 | 368D04 | 166B06 | 166G05 | 375G06 | 376B10 | 354A08 | 355B06 | 355E04 | 356A11 |
|-----|--------|--------|--------|--------|--------|--------|--------|--------|--------|--------|
| H1  | 31-35  | 31-35  | 31-35  | 31-35  | 31-35  | 31-35  | 30-34  | 31-35  | 31-35  | 31-35  |
| H2  | 50-66  | 50-66  | 50-66  | 50-66  | 50-66  | 50-66  | 49-65  | 50-66  | 50-66  | 50-66  |
| H3  | 99-110 | 99-110 | 99-108 | 99-108 | 99-108 | 99-108 | 98-109 | 99-110 | 99-110 | 99-110 |
| L1  | 23-36  | 23-36  | 23-33  | 23-33  | 23-33  | 23-33  | 23-36  | 23-36  | 23-36  | 22-35  |
| L2  | 52-58  | 52-58  | 49-55  | 49-55  | 49-55  | 49-55  | 52-58  | 52-58  | 52-58  | 51-58  |
| L3  | 91-100 | 91-100 | 88-98  | 88-98  | 88-98  | 88-98  | 91-101 | 91-101 | 91-101 | 90-100 |

Anti-IL-22 antibodies of this invention may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Constant regions are known in the art (see, for example, Kabat et al., Sequences of Proteins of Immunological Interest, No. 91-3242, National Institutes of Health Publications, Bethesda, Md. (1991)). Therefore, antibodies within the scope of this invention include $V_H$ and $V_L$ domains, or a portion thereof, combined with constant regions known in the art.

Certain embodiments comprise a $V_H$ domain, a $V_L$ domain, or a combination thereof, of the $F_v$ fragment from GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11. Another embodiment comprises a $V_H$ domain, a $V_L$ domain, or a combination thereof, of the $F_v$ fragment from an antibody chosen from 356A11, 354A08, 087B03, and 368D04. Further embodiments comprise one, two, three, four, five or six complementarity determining regions (CDRs) from the $V_H$ and $V_L$ domains. Antibodies whose CDR sequences are included within SEQ ID NO:5-13, 23-31, 41-49, 59-67, 77-85, 95-103, 113-121, 131-139, 149-157, 167-175, 185-193, 203-211, 221-229, 239-247, 257-265, 275-283, 293-301, 311-319, 329-337, 347-355, 365-373, 383-391, 401-409, 419-427, 437-445, 455-463, 473-481, 491-499, 509-517, 527-535, 545-553, 563-571, 581-589, 599-607, or 617-625 are encompassed within the scope of this invention. For example, in one embodiment, an antibody comprises a H3 fragment of the $V_H$ domain of germlined or non-germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 or from an antibody chosen from 356A11, 354A08, 087B03, and 368D04.

In certain embodiments, the $V_H$ and/or $V_L$ domains may be germlined, i.e., the framework regions (FR) of these domains are mutated using conventional molecular biology techniques to match those produced by the germline cells. In other embodiments, the FR sequences remain diverged from the consensus germline sequences. In one embodiment of this invention, germlined antibodies are shown in Table 7.

In one embodiment, the invention provides amino acid and nucleic acid sequences for the germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11. Amino acid and nucleotide sequences for the $V_H$ domain of the germlined GIL01, GIL16, GIL45, GIL60, GIL68, GIL92, 062A09, 087B03, 166B06, 166G05, 354A08, 355B06, 355E04, 356A11, and 368D04 are depicted in Table 7 and FIG. 8. Amino acid and nucleotide sequences for the $V_L$ domain of the germlined GIL01, GIL16, GIL45, GIL60, GIL68, GIL92, 062A09, 087B03, 166B06, 166G05, 354A08, 355B06, 355E04, 356A11, and 368D04 are also depicted in Table 7 and FIG. 8.

In one embodiment, mutagenesis is used to make an antibody more similar to one or more germline sequences. This may be desirable when mutations are introduced into the framework region of an antibody through somatic mutagenesis or through error prone PCR. Germline sequences for the $V_H$ and $V_L$ domains can be identified by performing amino acid and nucleic acid sequence alignments against the VBASE database (MRC Center for Protein Engineering, UK). VBASE is a comprehensive directory of all human germline variable region sequences compiled from over a thousand published sequences, including those in the current releases of the Genbank and EMBL data libraries. In some embodiments, the FR regions of the scFvs are mutated in conformity with the closest matches in the VBASE database and the CDR portions are kept intact.

In certain embodiments, antibodies of this invention specifically react with an epitope that is the same as the epitope recognized by GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11, such that they competitively inhibit the binding of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 to human IL-22. Such antibodies can be determined in competitive binding assays. In one embodiment, the antibody, or antigen binding fragment thereof, binds to an IL-22 epitope that is recognized by 368D04, such that the antibody competitively inhibits the binding of 368D04 to human IL-22. In another embodiment, the antibody, or antigen binding fragment thereof, binds to an IL-22 epitope that is recognized by 356A11, such that the antibody competitively inhibits the binding of 356A11 to human IL-22. In another embodiment, the antibody, or antigen binding fragment thereof, binds to an IL-22 epitope that is recognized by 354A08, such that the antibody competitively inhibits the binding of 354A08 to human IL-22. In another embodiment, the antibody, or antigen binding fragment thereof, binds to an IL-22 epitope that is recognized by 087B03, such that the antibody competitively inhibits the binding of 087603 to human IL-22. In one embodiment, the association constant ($K_A$) of these antibodies for human IL-22 is at least $10^6$ $M^{-1}$. In another embodiment, the association constant of these antibodies for human IL-22 is at least $10^9$ $M^{-1}$. In other embodiments, the association constant of these antibodies for human IL-22 is at least $10^{10}$ $M^{-1}$, at least $10^{11}$ $M^{-1}$, or at least $10^{12}$ $M^{-1}$. The binding affinity may be determined using techniques known in the art, such as ELISA, biosensor technology, such as biospecific interaction analysis, or other techniques including those described in this application.

It is contemplated that antibodies of this invention may bind other proteins, such as, for example, recombinant proteins comprising all or a portion of IL-22.

One of ordinary skill in the art will recognize that the disclosed antibodies may be used to detect, measure, and/or inhibit proteins that differ somewhat from IL-22. For example, these proteins may be homologs of IL-22. Anti-IL-22 antibodies are expected to bind proteins that comprise a sequence which is at least about 60%, 70%, 80%, 90%, 95%, or more identical to any sequence of at least 100, 80, 60, 40, or 20 contiguous amino acids in the sequence set forth SEQ ID NO:1.

In addition to sequence homology analyses, epitope mapping (see, e.g., Epitope Mapping Protocols, ed. Morris, Humana Press, 1996), and secondary and tertiary structure analyses can be carried out to identify specific 3D structures assumed by the presently disclosed antibodies and their complexes with antigens. Such methods include, but are not limited to, X-ray crystallography (Engstom (1974) Biochem. Exp. Biol., 11:7-13) and computer modeling of virtual representations of the present antibodies (Fletterick et al. (1986) Computer Graphics and Molecular Modeling, in Current Communications in Molecular Biology, Cold Spring Harbor Laboratory, Cold Spring Harbor, N.Y.).

The disclosure provides a method for obtaining anti-IL-22 antibodies that comprises creating antibodies with altered Table 1$V_H$ and/or $V_L$ sequence(s). Such antibodies may be derived by a skilled artisan using techniques known in the art. For example, amino acid substitutions, deletions, or additions can be introduced in FR and/or CDR regions. FR changes are usually designed to improve the stability and immunogenicity of the antibody, while CDR changes are typically designed to increase antibody affinity for its antigen. The changes that increase affinity may be tested by altering CDR sequence and measuring antibody affinity for its target (see Antibody Engineering, 2nd ed., Oxford University Press, ed. Borrebaeck, 1995).

Antibodies whose CDR sequences differ insubstantially from those included in or included within the sequences in SEQ ID NO: 5-13, 23-31, 41-49, 59-67, 77-85, 95-103, 113-121, 131-139, 149-157, 167-175, 185-193, 203-211, 221-229, 239-247, 257-265, 275-283, 293-301, 311-319, 329-337, 347-355, 365-373, 383-391, 401-409, 419-427, 437-445, 455-463, 473-481, 491-499, 509-517, 527-535, 545-553, 563-571, 581-589, 599-607, or 617-625, are encompassed within the scope of this invention. Typically, this involves substitution of an amino acid with an amino acid having similar charge, hydrophobic, or stereochemical characteristics. More drastic substitutions in FR regions, in contrast to CDR regions, may also be made as long as they do not adversely affect (e.g., reduce affinity by more than 50% as compared to unsubstituted antibody) the binding properties of the antibody. Substitutions may also be made to germline the antibody or stabilize the antigen binding site.

Conservative modifications will produce molecules having functional and chemical characteristics similar to those of the molecule from which such modifications are made. In contrast, substantial modifications in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, or (3) the size of the molecule.

For example, a "conservative amino acid substitution" may involve a substitution of a native amino acid residue with a normative residue such that there is little or no effect on the polarity or charge of the amino acid residue at that position. (See, for example, MacLennan et al., 1998, Acta Physiol. Scand. Suppl. 643:55-67; Sasaki et al., 1998, Adv. Biophys. 35:1-24).

Desired amino acid substitutions (whether conservative or non-conservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions include, but are not limited to, those set forth in Table 3.

TABLE 3

Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1, 4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |

TABLE 3-continued

Amino Acid Substitutions

| Original Residues | Exemplary Substitutions | More Conservative Substitutions |
|---|---|---|
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

In one embodiment, the method for making a variant $V_H$ domain comprises adding, deleting, or substituting at least one amino acid in the disclosed $V_H$ domains, or combining the disclosed $V_H$ domains with at least one $V_L$ domain, and testing the variant $V_H$ domain for IL-22 binding or modulation of IL-22 activity.

An analogous method for making a variant $V_L$ domain comprises adding, deleting, or substituting at least one amino acid in the disclosed $V_L$ domains, or combining the disclosed $V_L$ domains with at least one $V_H$ domain, and testing the variant $V_L$ domain for IL-22 binding or modulation of IL-22 activity.

A further aspect of the disclosure provides a method for preparing antibodies or antigen-binding fragments that specifically bind IL-22. The method comprises:

(a) providing a starting repertoire of nucleic acids encoding a $V_H$ domain which lacks at least one CDR or contains at least one CDR to be replaced;

(b) inserting into or replacing the CDR region of the starting repertoire with at least one donor nucleic acid encoding an amino acid sequence as substantially set out herein for a $V_H$ CDR, yielding a product repertoire;

(c) expressing the nucleic acids of the product repertoire;

(d) selecting a specific antigen-binding fragment that binds to IL-22; and (e) recovering the specific antigen-binding fragment or nucleic acid encoding it.

In an analogous method at least one $V_L$ CDR of the invention is combined with a repertoire of nucleic acids encoding a $V_L$ domain which lacks at least one CDR or contains at least one CDR to be replaced. The at least one $V_H$ or $V_L$ CDR may be a CDR1, a CDR2, a CDR3, or a combination thereof, including combinations of $V_H$ and $V_L$ CDRs, such as those set forth in Tables 1 or 7, including those set out in SEQ ID NO:8, 9, 10, 11, 12, 13, 26, 27, 28, 29, 30, 31, 44, 45, 46, 47, 48, 49, 62, 63, 64, 65, 66, 67, 80, 81, 82, 83, 84, 85, 98, 99, 100, 101, 102, 103, 116, 117, 118, 119, 120, 121, 134, 135, 136, 137, 138, 139, 152, 153, 154, 155, 156, 157, 170, 171, 172, 173, 174, 175, 188, 189, 190, 191, 192, 193, 206, 207, 208, 209, 210, 211, 224, 225, 226, 227, 228, 229, 242, 243, 244, 245, 246, 247, 260, 261, 262, 263, 264, 265, 278, 279, 280, 281, 282, 283, 296, 297, 298, 299, 300, 301, 314, 315, 316, 317, 318, 319, 332, 333, 334, 335, 336, 337, 350, 351, 352, 353, 354, 355, 368, 369, 370, 371, 372, 373, 386, 387, 388, 389, 390, 391, 404, 405, 406, 407, 408, 409, 422, 423, 424, 425, 426, 427, 440, 441, 442, 443, 444, 445, 458, 459, 460, 461, 462, 463, 476, 477, 478, 479, 480, 481, 494, 495, 496, 497, 498, 499, 512, 513, 514, 515, 516, 517, 530, 531, 532, 533, 534, 535, 548, 549, 550, 551, 552, 553, 566, 567, 568, 569, 570, 571, 584, 585, 586, 587, 588, 589, 602, 603, 604, 605, 606, 607, 620, 621, 622, 623, 624, or 625.

In one embodiment, the variable domain includes a CDR3 to be replaced or lacks a CDR3 encoding region and the at least one donor nucleic acid encodes an amino acid substantially as set out in SEQ ID NO:10, 13, 28, 31, 46, 49, 64, 67, 82, 85, 100, 103, 118, 121, 136, 139, 154, 157, 172, 175, 190, 193, 208, 211, 226, 229, 244, 247, 262, 265, 280, 283, 298, 301, 316, 319, 334, 337, 352, 355, 370, 373, 388, 391, 406, 409, 424, 427, 442, 445, 460, 463, 478, 481, 496, 499, 514, 517, 532, 535, 550, 553, 568, 571, 586, 589, 604, 607, 622, or 625.

In another embodiment, the variable domain includes a CDR1 to be replaced or lacks a CDR1 encoding region and the at least one donor nucleic acid encodes an amino acid sequence substantially as set out in SEQ ID NO:8, 11, 26, 29, 44, 47, 62, 65, 80, 83, 98, 101, 116, 119, 134, 137, 152, 155, 170, 173, 188, 191, 206, 209, 224, 227, 242, 245, 260, 263, 278, 281, 296, 299, 314, 317, 332, 335, 350, 353, 368, 371, 386, 389, 404, 407, 422, 425, 440, 443, 458, 461, 476, 479, 494, 497, 512, 515, 530, 533, 548, 551, 566, 569, 584, 587, 602, 605, 620, or 623.

In another embodiment, the variable domain includes a CDR2 to be replaced or lacks a CDR2 encoding region and the at least one donor nucleic acid encodes an amino acid sequence substantially as set out in SEQ ID NO:9, 12, 27, 30, 45, 48, 63, 66, 81, 84, 99, 102, 117, 120, 135, 138, 153, 156, 171, 174, 189, 192, 207, 210, 225, 228, 243, 246, 261, 264, 279, 282, 297, 300, 315, 318, 333, 336, 351, 354, 369, 372, 387, 390, 405, 408, 423, 426, 441, 444, 459, 462, 477, 480, 495, 498, 513, 516, 531, 534, 549, 552, 567, 570, 585, 588, 603, 606, 621, or 624.

In another embodiment, the variable domain includes a CDR3 to be replaced or lacks a CDR3 encoding region and further comprises a CDR1 to be replaced or lacks a CDR1 encoding region, where the at least one donor nucleic acid encodes an amino acid sequence substantially as set out in Tables 1 or 7.

In another embodiment, the variable domain includes a CDR3 to be replaced or lacks a CDR3 encoding region and further comprises a CDR2 to be replaced or lacks a CDR2 encoding region, where the at least one donor nucleic acid encodes an amino acid sequence substantially as set out in Tables 1 or 7.

In another embodiment, the variable domain includes a CDR3 to be replaced or lacks a CDR3 encoding region and further comprises a CDR1 and a CDR2 to be replaced or lacks a CDR1 and a CDR2 encoding region, where the at least one donor nucleic acid encodes an amino acid sequence substantially as set out in Tables 1 or 7.

Using recombinant DNA methodology, a disclosed CDR sequence may be introduced into a repertoire of $V_H$ or $V_L$ domains lacking the respective CDR (Marks et al. (BioTechnology (1992) 10: 779-783). For example, a primer adjacent to the 5' end of the variable domain and a primer to the third FR can be used to generate a repertoire of variable domain sequences lacking CDR3. This repertoire can be combined with a CDR3 of a disclosed antibody. Using analogous techniques, portions of a disclosed CDR sequence may be shuffled with portions of CDR sequences from other antibodies to provide a repertoire of antigen-binding fragments that bind IL-22. Either repertoire can be expressed in a host system such as phage display (described in WO 92/01047 and its corresponding U.S. Pat. No. 5,969,108) so suitable antigen-binding fragments that bind to IL-22 can be selected.

A further alternative uses random mutagenesis of the disclosed $V_H$ or $V_L$ sequences to generate variant $V_H$ or $V_L$ domains still capable of binding IL-22. A technique using error-prone PCR is described by Gram et al. (Proc. Nat. Acad. Sci. U.S.A. (1992) 89: 3576-3580).

Another method uses direct mutagenesis of the disclosed $V_H$ or $V_L$ sequences. Such techniques are disclosed by Barbas et al. (Proc. Nat. Acad. Sci. U.S.A. (1994) 91: 3809-3813) and Schier et al. (J. Mol. Biol. (1996) 263: 551-567).

A portion of a variable domain will comprise at least one CDR region substantially as set out herein and, optionally, intervening framework regions from the $V_H$ or $V_L$ domains as set out herein. The portion may include the C-terminal half of FR1 and/or the N-terminal half of FR4. Additional residues at the N-terminal or C-terminal end of the variable domain may not be the same residues found in naturally occurring antibodies. For example, construction of antibodies by recombinant DNA techniques often introduces N- or C-terminal residues from its use of linkers. Some linkers may be used to join variable domains to other variable domains (e.g., diabodies), constant domains, or proteinaceous labels.

Although the embodiments illustrated in the Examples comprise a "matching" pair of $V_H$ and $V_L$ domains, a skilled artisan will recognize that alternative embodiments may comprise antigen-binding fragments containing only a single CDR from either $V_L$ or $V_H$ domain. Either one of the single chain specific antigen-binding domains can be used to screen for complementary domains capable of forming a two-domain specific antigen-binding fragment capable of, for example, binding to IL-22. The screening may be accomplished by phage display screening methods using the so-called hierarchical dual combinatorial approach disclosed in WO 92/01047. In this approach, an individual colony containing either a H or L chain clone is used to infect a complete library of clones encoding the other chain (L or H), and the resulting two-chain specific antigen-binding domain is selected in accordance with phage display techniques as described.

In some alternative embodiments, the anti-IL-22 antibodies can be linked to a protein (e.g., albumin) by chemical cross-linking or recombinant methods. The disclosed antibodies may also be linked to a variety of nonproteinaceous polymers (e.g., polyethylene glycol, polypropylene glycol, or polyoxyalkylenes) in manners set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their half-life in blood circulation. Exemplary polymers and attachment methods are shown in U.S. Pat. Nos. 4,766,106; 4,179,337; 4,495,285; and 4,609,546.

The disclosed antibodies can be modified to alter their glycosylation; that is, at least one carbohydrate moiety can be deleted or added to the antibody. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the antibody (see WO 87/05330 and Aplin et al. (1981) *CRC Crit. Rev. Biochem.*, 22: 259-306). Removal of carbohydrate moieties can also be accomplished chemically or enzymatically (see Hakimuddin et al. (1987) *Arch. Biochem. Biophys.*, 259: 52; Edge et al. (1981) *Anal. Biochem.*, 118: 131; Thotakura et al. (1987) *Meth. Enzymol.*, 138: 350).

Methods for altering an antibody constant region are known in the art. Antibodies with altered function (e.g., altered affinity for an effector ligand such as FcR on a cell or the C1 component of complement) can be produced by replacing at least one amino acid residue in the constant portion of the antibody with a different residue (see e.g., EP 388,151 A1, U.S. Pat. No. 5,624,821 and U.S. Pat. No. 5,648, 260). Similar types of alterations could be described which if applied to a murine or other species antibody would reduce or eliminate similar functions.

For example, it is possible to alter the affinity of an Fc region of an antibody (e.g., an IgG, such as a human IgG) for FcR (e.g., Fc gamma R1) or C1 q. The affinity may be altered by replacing at least one specified residue with at least one residue having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

For example, replacing residue 297 (asparagine) with alanine in the IgG constant region significantly inhibits recruitment of effector cells, while only slightly reducing (about three fold weaker) affinity for C1q (see e.g., U.S. Pat. No. 5,624,821). The numbering of the residues in the heavy chain is that of the EU index (see Kabat et al., 1991 supra). This alteration destroys the glycosylation site and it is believed that the presence of carbohydrate is required for Fc receptor binding. Any other substitution at this site that destroys the glycosylation site is believed to cause a similar decrease in lytic activity. Other amino acid substitutions, e.g., changing any one of residues 318 (Glu), 320 (Lys) and 322 (Lys), to Ala, are also known to abolish C1q binding to the Fc region of IgG antibodies (see e.g., U.S. Pat. No. 5,624,821).

Modified antibodies can be produced which have a reduced interaction with an Fc receptor. For example, it has been shown that in human $IgG_3$, which binds to the human Fc gamma R1 receptor, changing Leu 235 to Glu destroys its interaction with the receptor. Mutations on adjacent or close sites in the hinge link region of an antibody (e.g., replacing residues 234, 236 or 237 with Ala) can also be used to affect antibody affinity for the Fc gamma R1 receptor. The numbering of the residues in the heavy chain is based in the EU index (see Kabat et al., 1991 supra).

Additional methods for altering the lytic activity of an antibody, for example, by altering at least one amino acid in the N-terminal region of the CH2 domain, are described in WO 94/29351 by Morgan et al. and U.S. Pat. No. 5,624,821.

The antibodies of this invention may be tagged with a detectable or functional label. These labels include radiolabels (e.g., $^{131}I$ or $^{99}Tc$), enzymatic labels (e.g., horseradish peroxidase or alkaline phosphatase), and other chemical moieties (e.g., biotin).

The invention may also feature an isolated antibody that binds to IL-22, in particular, human IL-22. In certain embodiments, the anti-IL-22 antibody may have at least one of the following characteristics: (1) it is a monoclonal or single specificity antibody; (2) it is a human antibody; (3) it is an in vitro generated antibody; (4) it is an in vivo generated antibody (e.g., transgenic mouse system); (5) it binds to IL-22 with an association constant of at least $10^{12}$ $M^{-1}$; (6) it binds to IL-22 with an association constant of at least $10^{11}$ $M^{-1}$; (7) it binds to IL-22 with an association constant of at least $10^{10}$ $M^{-1}$; (8) it binds to IL-22 with an association constant of at least $10^9$ $M^{-1}$; (9) it binds to IL-22 with an association constant of at least $10^6$ $M^{-1}$; (10) it binds to IL-22 with a dissociation constant of 500 nM or less; (11) it binds to IL-22 with a dissociation constant of 10 nM or less; (12) it binds to IL-22 with a dissociation constant of 150 pM or less; (13) it binds to IL-22 with a dissociation constant of 60 pM or less; (14) it inhibits binding of IL-22 to IL-22R or a receptor complex of IL-22R and IL-10R2 with an $IC_{50}$ of 10 nM or less; (15) it blocks IL-22 mediated proliferation of IL-22 receptor engineered BaF3 cells with an $IC_{50}$ of 1 nM or less in one embodiment, with an $IC_{50}$ of 150 pM or less in another embodiment, with an $IC_{50}$ of 100 pM or less in another embodiment, and with an $IC_{50}$ of 10 pM or less in another embodiment; and (16) it blocks IL-22 mediated GROa secretion from HT29 with an $IC_{50}$ of 1 nM or less in one embodiment, with an $IC_{50}$ of 150 pM or less in another embodiment, and with an $IC_{50}$ of 10 pM or less in another embodiment.

One of skill in the art will appreciate that the modifications described above are not all-exhaustive, and that many other modifications are obvious to a skilled artisan in light of the teachings of the present disclosure.

III. Nucleic Acids, Cloning and Expression Systems

The disclosure provides isolated nucleic acids encoding the disclosed antibodies. The nucleic acids may comprise DNA or RNA, and they may be synthetic (completely or partially) or recombinant (completely or partially). Reference to a nucleotide sequence as set out herein encompasses a DNA molecule with the specified sequence, and encompasses a RNA molecule with the specified sequence in which U is substituted for T.

Also provided are nucleic acids that comprise a coding sequence for one, two, or three CDR's, a $V_H$ domain, a $V_L$ domain, or combinations thereof, as disclosed herein, or a sequence substantially identical thereto (e.g., a sequence at least 85%, 90%, 95%, 96%, 97%, 98%, 99% or higher identical thereto, or which is capable of hybridizing under stringent conditions to the sequences disclosed).

In one embodiment, the isolated nucleic acids have nucleotide sequences encoding heavy chain and light chain variable regions of an anti-IL-22 antibody having at least one CDR chosen from the amino acid sequences of SEQ ID NO: 8-13, 26-31, 44-49, 62-67, 80-85, 98-103, 116-121, 134-139, 152-157, 170-175, 188-193, 206-211, 224-229, 242-247, 260-265, 278-283, 296-301, 314-319, 332-337, 350-355, 368-373, 386-391, 404-409, 422-427, 440-445, 458-463, 476-481, 494-499, 512-517, 530-535, 548-553, 566-571, 584-589, 602-607, or 620-625; or sequence encoding a CDR which differs by one or two amino acids from the sequences described herein.

The nucleic acid can encode only the light chain or the heavy chain variable region, or can also encode an antibody light or heavy chain constant region, operatively linked to the corresponding variable region. In one embodiment, the light chain variable region is linked to a constant region chosen from a kappa or a lambda constant region. The light chain constant region may also be a human kappa or lambda type. In another embodiment, the heavy chain variable region is linked to a heavy chain constant region of an antibody isotype chosen from IgG (e.g., $IgG_1$, $IgG_2$, $IgG_3$, $IgG_4$), IgM, $IgA_1$, $IgA_2$, IgD, and IgE. The heavy chain constant region may be an IgG (e.g., an $IgG_1$) isotype.

The nucleic acid compositions of the present invention, while often in the native sequence (of cDNA or genomic DNA or mixtures thereof) except for modified restriction sites and the like, may be mutated in accordance with standard techniques to provide gene sequences. For coding sequences, these mutations, may affect amino acid sequence as desired. In particular, nucleotide sequences substantially identical to or derived from native V, D, J, constant, switches and other such sequences described herein are contemplated (where "derived" indicates that a sequence is identical or modified from another sequence).

In one embodiment, the nucleic acid differs (e.g., differs by substitution, insertion, or deletion) from that of the sequences provided (e.g., as follows: by at least one but less than 10, 20, 30, or 40 nucleotides; at least one but less than 1%, 5%, 10% or 20% of the nucleotides in the subject nucleic acid). If necessary for this analysis the sequences should be aligned for maximum homology. "Looped" out sequences from deletions or insertions, or mismatches, are considered differences. The difference may be at a nucleotide(s) encoding a non-essential residue(s), or the difference may be a conservative substitution(s).

The disclosure also provides nucleic acid constructs in the form of plasmids, vectors, transcription or expression cassettes, which comprise at least one nucleic acid as described herein.

The disclosure further provides a host cell that comprises at least one nucleic acid construct described herein.

Also provided are the methods of making the encoded protein(s) from the nucleic acid(s) comprising sequence described herein. The method comprises culturing host cells under appropriate conditions so they express the protein from the nucleic acid. Following expression and production, the $V_H$ or $V_L$ domain, or specific binding member may be isolated and/or purified using any suitable technique, then used as appropriate. The method can also include the steps of fusing a nucleic acid encoding a scFv with nucleic acids encoding a Fc portion of an antibody and expressing the fused nucleic acid in a cell. The method can also include a step of germlining.

Antigen-binding fragments, $V_H$ and/or $V_L$ domains, and encoding nucleic acid molecules and vectors may be isolated and/or purified from their natural environment, in substantially pure or homogenous form, or, in the case of nucleic acid, free or substantially free of nucleic acid or genes of origin other than the sequence encoding a polypeptide with the require function.

Systems for cloning and expressing polypeptides in a variety of host cells are known in the art. Cells suitable for producing antibodies are described in, for example, Fernandez et al. (1999) Gene Expression Systems, Academic Press, eds. In brief, suitable host cells include mammalian cells, insect cells, plant cells, yeast cells, or prokaryotic cells, e.g., E. coli. Mammalian cells available in the art for heterologous polypeptide expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cell. In one embodiment, the GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11 antibodies are expressed in HEK293 or CHO cells. In another embodiment, a selection of antibodies chosen from 365A11, 354A08, 087B03, and 368D04 are expressed in HEK293 or CHO cells. In other embodiments, the nucleic acids encoding the antibodies of the invention are placed under the control of a tissue-specific promoter (e.g., a mammary specific promoter) and the antibodies are produced in transgenic animals. For example, the antibodies are secreted into the milk of the transgenic animal, such as a transgenic cow, pig, horse, sheep, goat or rodent.

Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone. For details, see Sambrook et al., Molecular Cloning: A Laboratory Manual, 2nd ed., Cold Spring Harbor Laboratory Press (1989). Many established techniques used with vectors, including the manipulation, preparation, mutagenesis, sequencing, and transfection of DNA, are described in Current Protocols in Molecular Biology, Second Edition, Ausubel et al. eds., John Wiley & Sons (1992).

A further aspect of the disclosure provides a method of introducing the nucleic acid into a host cell. For eukaryotic cells, suitable transfection techniques may include calcium phosphate, DEAE-Dextran, electroporation, liposome-mediated transfection, and transduction using retrovirus or other viruses, e.g., vaccinia or baculovirus. For bacterial cells, suitable techniques may include calcium chloride transformation, electroporation, and transfection using bacteriophage. DNA introduction may be followed by a selection method (e.g., drug resistance) to select cells that contain the nucleic acid.

IV. Uses of Anti-IL-22 Antibodies

Anti-IL-22 antibodies that act as antagonists to IL-22 can be used to regulate at least one IL-22-mediated immune response, such as acting on epithelial cells in solid tissue and indirectly modulating downstream immune responses, such as blocking expansion of T cell subsets, including, for example, $T_H17$ T cells. In one embodiment, antibodies of the invention are used in a method for regulating an immune response, the method comprising contacting IL-22 with an antibody of the invention thereby regulating the immune response. In one embodiment, the immune response comprises cell proliferation, cytolytic activity, cytokine secretion, or chemokine secretion.

Accordingly, the antibodies of the invention can be used to directly or indirectly inhibit the activity (e.g., proliferation, differentiation, and/or survival) of an immune or hematopoietic cell (e.g., a cell of myeloid, lymphoid, or erythroid lineage, or precursor cells thereof), and, thus, can be used to treat a variety of immune disorders and hyperproliferative disorders. Non-limiting examples of immune disorders that can be treated include, but are not limited to, autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD; acute inflammatory conditions, e.g., endotoxemia, sepsis and septicaemia, toxic shock syndrome and infectious disease; multiple organ failure; respiratory disease (ARD); amyloidosis; nephropathies such as glomerulosclerosis, membranous neuropathy, renal arteriosclerosis, glomerulonephritis, fibroproliferative diseases of the kidney, as well as other kidney disfunctions and renal tumors. Because of IL-22's effects on epithelia, anti-IL-22 antibodies can be used to treat epithelial cancers, e.g., carcinoma, melanoma and others. For a description of a rationale for IL-22 inhibition in these and other disease states see WO 03/083062 (pages 58-75).

Multiple sclerosis is a central nervous system disease that is characterized by inflammation and loss of myelin sheaths—the fatty material that insulates nerves and is needed for proper nerve function. Inflammation that results from an immune response that is dependent on IL-22 can be treated with the antibodies and compositions of this invention. In the experimental autoimmune encephalitis (EAE) mouse model for multiple sclerosis (Tuohy et al. (J. Immunol. (1988) 141: 1126-1130), Sobel et al. (J. Immunol. (1984) 132: 2393-2401), and Traugott (Cell Immunol. (1989) 119: 114-129), treatment of mice with GIL01, GIL16, GIL45, GIL60, GIL68, GIL92, 097D09, 062A09, 062G05, 087603, 367D04, 368D04, 166B06, 166G05, 375G06, 376B10, 354A08, 355B06, 355E04, or 356A11 injections prior (and continuously) to EAE induction may profoundly delay the onset of the disease. This can serve as a model for confirming use of the antibody of the invention. The antibodies of this invention may similarly be used to treat multiple sclerosis in humans.

Arthritis is a disease characterized by inflammation in the joints. Rheumatoid Arthritis (RA) is the most frequent form of arthritis, involving inflammation of connective tissue and the synovial membrane, a membrane that lines the joint. The inflamed synovial membrane often infiltrates the joint and damages joint cartilage and bone. IL-22 and IL-22R protein and/or transcript is associated with both human diseases. In RA synovial biopsies, IL-22 protein is detected in vimentin+ synovial fibroblasts and some CD68+ macrophages while IL-22R is detected in synovial fibroblasts. Treatment of synovial fibroblasts with IL-22 induces the production of monocyte chemoattractant protein-1, MCP-1, as well as general metabolic activity (Ikeuchi, H., et al. (2005) *Arthritis Rheum.* 52:1037-46). Inhibitors of IL-22 ameliorate symptoms of rheumatoid arthritis (WO 2005/000897 A2; U.S. Pat. No. 6,939,545). Increased secretion of inflammatory cytokines and chemokines, and more importantly, increased disease resulting from immune responses that are dependent on IL-22 may be treated with the antibodies of this invention. Similarly, the antibodies and compositions of this invention may be used to treat RA or other arthritic diseases in humans.

Transplant rejection is the immunological phenomenon where tissues from a donor are specifically "attacked" by immune cells of the host. The principle "attacking" cells are T cells, whose T cell receptors recognize the donor's MHC molecules as "foreign." This recognition activates the T cells, which proliferate and secrete a variety of cytokines and cytolytic proteins that ultimately destroy the transplant. MLR and transplantation models have been described by Current Protocols in Immunology, Second Edition, Coligan et al. eds., John Wiley & Sons, 1994; Kasaian et al. (Immunity (2002) 16: 559-569); Fulmer et al. (Am. J. Anat. (1963) 113: 273-285), and Lenschow et al. (Science (1992) 257: 789-792). The antibodies and compositions of this invention may be used to reduce the MLR and treat transplant rejection and related diseases (e.g., graft versus host disease) in humans that are dependent on IL-22.

The antibodies of this invention can also be used to treat hyperproliferative disorders associated with aberrant activity of IL-22-responsive cells and IL-22R/IL-10R2-responsive cells by administering the antibodies in an amount sufficient to inhibit or reduce hyperproliferation of IL-22 and/or IL-22R and/or IL-10R2-responsive cells in a subject and allowing the antibodies to treat or prevent the disorder. IL-22 and IL-22R expression is constitutive on epithelial cells in a number of tissues including, but not limited to, pancreas, lung, skin, gut, liver, kidney (Kotenko, S. V. et al. (2001) *J. Biol. Chem.* 276:2725-32; Xie, M. H. et al. (2000) *J. Biol. Chem.* 275:31335-9; Wolk, K. et al. (2004) *Immunity* 21:241-54). In addition, IL-22 receptor complex is also expressed on the surface of fibroblasts from the diseased joint and normal gut (Ikeuchi, H. et al. (2005) *Arthritis Rheum.* 52:1037-46; Andoh, A. et al. (2005) *Gastroenterology* 129:969-84). Neoplastic derivatives of these cell types may be hyper responsive to IL-22, modulating these cells ability to survive in the organism. Hence antibodies to IL-22 may be used to inhibit the progression of such neoplasms, e.g. squamous cell carcinomas, basal cell carcinomas, transitional cell papillomas and carcinomas, adenomas, adenocarcinoma, linitis plastica, insulinoma, glucagonoma, gastrinoma, vipoma, cholangiocarcinoma, hepatocellular carcinoma, adenoid cyctic carcinoma, carcinoid tumor of appendix, prolactinoma, oncocytoma, hurthle cell adenoma, renal cell carcinoma, Grawitz tumor, multiple endocrine adenomas, endometroid adenoma, adnexal and skin appendage neoplasms, mucoepidermoid neoplams, cystic, mucinous and serous neoplasms, cystadenoma, pseudomyxoma peritonei, ductal, lobular and medullary neoplasms, acinar cell neoplasns, complex epithelial neoplasms, Warthin's tumor, thymoma, specialized gonadal neoplasms, sex cord-stromal tumor, thecoma, granulosa cell tumor, arrhenoblastoma, sertoli-leydig cell tumor, paraganglioma, pheochromocytoma, glomus tumor, malanocytic nevus, malignant melanoma, melanoma, nodular melanoma, dysplastic nevus, lentigo maligna, superficial spreading melanoma, or acral lentiginous melanoma. While the IL-22 receptor is not detected on ex vivo naïve or activated immune cells, dysregulation of the receptor might make such derivative neoplastic cells responsive to IL-22 and thus inhibition by an antibody to IL-22.

In another aspect, the invention features a method of decreasing, inhibiting or reducing an acute phase response in a subject. The method includes administering to the subject an anti-IL-22 antibody or fragment thereof as described herein, in an amount sufficient to decrease, inhibit or reduce the acute phase response in the subject. In one embodiment, the subject is a mammal, e.g., a human suffering from an IL-22-associated disorder as described herein, including, e.g., respiratory disorders, inflammatory disorders and autoimmune disorders. In one embodiment, the IL-22 binding agent is administered locally, e.g., topically, subcutaneously, or other administrations that are not in the general circulation.

IL-22 is believed to exert its inflammatory effects locally, e.g. by acting (e.g., directly acting) as a modular or a regulator of tissue inflammation as opposed to direct systemic effects. Accordingly, inhibition of IL-22 activity using, e.g. an anti-IL-22 antibody of the present invention may provide a more effective (e.g., less toxic) tissue-specific, anti-inflammatory agent than systemic anti-inflammatory modalities. Furthermore, inhibition of local IL-22 using, e.g., an anti-IL-22 antibody or fragment thereof described herein, may provide a useful candidate for combination with systemic anti-inflammatory modalities.

V. Combination Therapy

In one embodiment, a pharmaceutical composition comprising at least one anti-IL-22 antibody and at least one therapeutic agent is administered in combination therapy. The therapy is useful for treating pathological conditions or disorders, such as immune and inflammatory disorders. The term "in combination" in this context means that the antibody composition and the therapeutic agent are given substantially contemporaneously, either simultaneously or sequentially. In one embodiment, if given sequentially, at the onset of administration of the second compound, the first of the two compounds is still detectable at effective concentrations at the site of treatment. In another embodiment, if given sequentially, at the onset of administration of the second compound, the first of the two compounds is not detectable at effective concentrations at the site of treatment.

For example, the combination therapy can include at least one anti-IL-22 antibody co-formulated with, and/or co-administered with, at least one additional therapeutic agent. The additional agents may include at least one cytokine inhibitor, growth factor inhibitor, immunosuppressant, anti-inflammatory agent, metabolic inhibitor, enzyme inhibitor, cytotoxic agent, and cytostatic agent, as described in more detail below. In one embodiment, the additional agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Arava), tumor necrosis factor inhibitors, including etanercept (Enbrel), infliximab (Remicade) (with or without methotrexate), and adalimumab (Humira), anti-CD20 antibody (e.g., Rituxan), soluble interleukin-1 receptor, such as anakinra (Kineret), gold, minocycline (Minocin), penicillamine, and cytotoxic agents, including azathioprine, cyclophosphamide, and cyclosporine. Such combination therapies may advantageously utilize lower dosages of the administered therapeutic agents, thus avoiding possible toxicities or complications associated with the various monotherapies. Moreover, the additional therapeutic agents disclosed herein act on pathways in addition to or that differ from the IL-22/IL-22R/IL-10R2 pathway, and thus are expected to enhance and/or synergize with the effects of the anti-IL-22 antibodies.

Therapeutic agents used in combination with anti-IL-22 antibodies may be those agents that interfere at different stages in the autoimmune and subsequent inflammatory response. In one embodiment, at least one anti-IL-22 antibody described herein may be co-formulated with, and/or co-administered with, at least one cytokine and/or growth factor antagonist. The antagonists may include soluble receptors, peptide inhibitors, small molecules, ligand fusions, antibodies and binding fragments thereof (that bind cytokines or growth factors or their receptors or other cell surface molecules), and "anti-inflammatory cytokines" and agonists thereof.

Non-limiting examples of the agents that can be used in combination with the anti-IL-22 antibodies described herein, include, but are not limited to, antagonists of at least one interleukin (e.g., IL-1, IL-2, IL-6, IL-7, IL-8, IL-12 (or one of its subunits p35 or p40), IL-13, IL-15, IL-16, IL-17A-F (including heterodimers thereof, for example, IL-17A/IL-17F heterodimer), IL-18, IL-19, IL-20, IL-21, and IL-23 (or one of its subunits p19 or p40)); cytokine (e.g., TNFα, LT, EMAP-II, and GM-CSF); and growth factor (e.g., FGF and PDGF). The agents may also include, but not limited to, antagonists of at least one receptor for an interleukin, cytokine, and growth factor. Anti-IL-22 antibodies can also be combined with inhibitors (e.g., antibodies or binding fragments thereof) to cell surface molecules such as CD2, CD3, CD4, CD8, CD20 (e.g. Rituxan), CD25, CD28, CD30, CD40, CD45, CD69, CD80 (B7.1), CD86 (B7.2), CD90, or their ligands (e.g., CD154 (gp39, CD40L)), or LFA-1/ICAM-1 and VLA-4NCAM-1 (Yusuf-Makagiansar et al. (2002) *Med Res Rev* 22(2):146-67)). In certain embodiments, antagonists that can be used in combination with anti-IL-22 antibodies described herein may include antagonists of IL-1, IL-12 (or one of its subunits p35 or p40), TNFα, IL-15, IL-17A-F (including heterodimers thereof, for example, IL-17A/IL-17F heterodimer), IL-18, IL-19, IL-20, IL-21, and IL-23 (or one of its subunits p19 or p40), and their receptors.

Examples of those agents include IL-12 antagonists (such as antibodies that bind IL-12 (see e.g., WO 00/56772) or one of its subunits p35 or p40); IL-12 receptor inhibitors (such as antibodies to the IL-12 receptor); and soluble IL-12 receptor and fragments thereof. Examples of IL-15 antagonists include antibodies against IL-15 or its receptor, soluble fragments of the IL-15 receptor, and IL-15-binding proteins. Examples of IL-18 antagonists include antibodies to IL-18, soluble fragments of the IL-18 receptor, and IL-18 binding proteins (IL-18BP, Mallet et al. (2001) Circ. Res. 28). Examples of IL-1 antagonists include Interleukin-1-Converting Enzyme (ICE) inhibitors (such as V×740), IL-1 antagonists (e.g., IL-1RA (ANIKINRA, AMGEN)), sIL-1RII (Immunex), and anti-IL-1 receptor antibodies.

In one embodiment, the combination therapy includes at least one anti-IL-22 antibody co-formulated with, and/or co-administered with an antagonist, such as an antibody or antigen binding fragment thereof or a soluble receptor, of at least one of IL-17A, IL-17F, IL-17A/IL-17F heterodimer, or IL-23 (or one of its subunits p19 or p40).

Examples of TNF antagonists include antibodies to TNF (e.g., human TNFα), such as D2E7 (human anti-TNFα antibody, U.S. Pat. No. 6,258,562, Humira™, BASF); CDP-571/CDP-870/BAY-10-3356 (humanized anti-TNFα antibodies, Celltech/Pharmacia); cA2 (chimeric anti-TNFα antibody, Remicade™, Centocor); and anti-TNF antibody fragments (e.g., CPD870). Other examples include soluble TNF receptor (e.g., human p55 or p75) fragments and derivatives, such as p55 kdTNFR-IgG (55 kD TNF receptor-IgG fusion protein, Lenercept™) and 75 kdTNFR-IgG (75 kD TNF receptor-IgG fusion protein, Enbrel™, Immunex, see, e.g., Arthritis & Rheumatism (1994) Vol. 37, S295; J. Invest. Med. (1996) Vol. 44, 235A). Further examples include enzyme antagonists (e.g., TNFα converting enzyme inhibitors (TACE) such as alpha-sulfonyl hydroxamic acid derivative (WO 01/55112) or N-hydroxyformamide inhibitor (GW 3333, –005, or –022)) and TNF-bp/s-TNFR (soluble TNF binding protein, see e.g., Arthritis & Rheumatism (1996) Vol. 39, No. 9 (supplement), S284; and Am. J. Physiol. Heart Circ. Physiol. (1995) Vol. 268, pp. 37-42). TNF antagonists may be soluble TNF receptor (e.g., human p55 or p75) fragments and derivatives, such as 75 kdTNFR-IgG; and TNFα converting enzyme (TACE) inhibitors.

In other embodiments, the anti-IL-22 antibodies described herein can be administered in combination with at least one of the following: IL-13 antagonists, such as soluble IL-13 receptors and/or anti-IL-13 antibodies; and IL-2 antagonists, such as IL-2 fusion proteins (e.g., DAB 486-IL-2 and/or DAB 389-IL-2, Seragen, see e.g., Arthritis & Rheumatism (1993) Vol. 36, 1223) and anti-IL-2R antibodies (e.g., anti-Tac (humanized antibody, Protein Design Labs, see Cancer Res. 1990 Mar. 1; 50(5):1495-502)). Another combination includes anti-IL-22 antibodies in combination with non-depleting anti-CD4 inhibitors such as IDEC-CE9.1/SB 210396 (anti-CD4 antibody, IDEC/SmithKline). Yet other combinations include anti-IL-22 antibodies with antagonists (such as antibodies, soluble receptors, or antagonistic ligands) of costimulatory molecules, such as CD80 (B7.1) and CD86 (B7.2); ICOSL, ICOS, CD28, and CTLA4 (e.g., CTLA4-Ig); P-selectin glycoprotein ligand (PSGL); and anti-inflammatory cytokines and agonists thereof (e.g., antibodies). The anti-inflammatory cytokines may include IL-4 (DNAX/Schering); IL-10 (SCH 52000, recombinant IL-10, DNAX/Schering); IL-13; and TGF.

In other embodiments, at least one anti-IL-22 antibody can be co-formulated with, and/or co-administered with, at least one anti-inflammatory drug, immunosuppressant, metabolic inhibitor, and enzymatic inhibitor. Non-limiting examples of the drugs or inhibitors that can be used in combination with the IL-22 antagonists described herein, include, but are not limited to, at least one of: non-steroidal anti-inflammatory drug (NSAID) (such as ibuprofen, Tenidap (see e.g., Arthritis & Rheumatism (1996) Vol. 39, No. 9 (supplement), S280)), Naproxen (see e.g., Neuro Report (1996) Vol. 7, pp. 1209-1213), Meloxicam, Piroxicam, Diclofenac, and Indomethacin); Sulfasalazine (see e.g., Arthritis & Rheumatism (1996) Vol. 39, No. 9 (supplement), S281); corticosteroid (such as prednisolone); cytokine suppressive anti-inflammatory drug (CSAID); and an inhibitor of nucleotide biosynthesis (such as an inhibitor of purine biosynthesis (e.g., folate antagonist such as methotrexate) and an inhibitor of pyrimidine biosynthesis (e.g., a dihydroorotate dehydrogenase (DHODH) inhibitor such as leflunomide (see e.g., *Arthritis & Rheumatism* (1996) Vol. 39, No. 9 (supplement), S131; Inflammation Research (1996) Vol. 45, pp. 103-107)). Therapeutic agents for use in combination with IL-22/IL-22R or IL-22/IL-10R2 antagonists may include NSAIDs, CSAIDs, DHODH inhibitors (such as leflunomide), and folate antagonists (such as methotrexate).

Examples of additional inhibitors include at least one of: corticosteroid (oral, inhaled and local injection); immunosuppressant (such as cyclosporin and tacrolimus (FK-506)); a mTOR inhibitor (such as sirolimus (rapamycin) or a rapamycin derivative (e.g., ester rapamycin derivative such as CCI-779 (Elit. L. (2002) *Current Opinion Investig. Drugs* 3(8): 1249-53; Huang, S. et al. (2002) *Current Opinion Investig. Drugs* 3(2):295-304))); an agent which interferes with the signaling of proinflammatory cytokines such as TNFα and IL-1 (e.g., IRAK, NIK, IKK, p38 or a MAP kinase inhibitor); a COX2 inhibitor (e.g., celecoxib and variants thereof (MK-966), see e.g., Arthritis & Rheumatism (1996) Vol. 39, No. 9 (supplement), S81); a phosphodiesterase inhibitor (such as R973401, see e.g., Arthritis & Rheumatism (1996) Vol. 39, No. 9 (supplement), S282)); a phospholipase inhibitor (e.g., an inhibitor of cytosolic phospholipase 2 (cPLA2) such as trifluoromethyl ketone analogs (U.S. Pat. No. 6,350,892)); an inhibitor of vascular endothelial cell growth factor (VEGF); an inhibitor of the VEGF receptor; and an inhibitor of angiogenesis. Therapeutic agents for use in combination with anti-IL-22 antibodies may include immunosuppresants (such as cyclosporine and tacrolimus (FK-506)); and mTOR inhibitors (such as sirolimus (rapamycin) or rapamycin derivatives (e.g., ester rapamycin derivatives such as CCI-779)); COX2 inhibitors (such as celecoxib and variants thereof); and phospholipase inhibitors (such as inhibitors of cytosolic phospholipase 2 (cPLA2) (e.g., trifluoromethyl ketone analogs)).

Examples of therapeutic agents that can be co-administered and/or co-formulated with at least one anti-IL-22 antibody, include, but are not limited to, at least one of: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, Lenercept™) and 75 kdTNFR-IgG (75 kD TNF receptor-IgG fusion protein, Enbrel™)); TNF enzyme antagonists (such as TACE inhibitors); antagonists of IL-12 (or one of its subunits p35 or p40), IL-15, IL-17A-F (including heterodimers thereof, for example, IL-17A/IL-17F heterodimer), IL-18, IL-19, IL-20, IL-21, IL-22, and IL-23 (or one of its subunits p19 or p40); T cell and B cell depleting agents (such as anti-CD4 or anti-CD22 antibodies); small molecule inhibitors (such as methotrexate and leflunomide); sirolimus (rapamycin) and analogs thereof (such as CCI-779); Cox-2 and cPLA2 inhibitors; p38, TPL-2, Mk-2 and NFκB inhibitors; RAGE and soluble RAGE; P-selectin and PSGL-1 inhibitors (such as antibodies to and small molecule inhibitors); and estrogen receptor beta (ERB) agonists, and ERB-NFkb antagonists. Therapeutic agents that can be co-administered and/or co-formulated with at least one anti-IL-22 antibody may include at least one of: a soluble fragment of a TNF receptor (e.g., human p55 or p75) such as 75 kdTNFR-IgG (75 kD TNF receptor-IgG fusion protein, Enbrel™); methotrexate; leflunomide; and sirolimus (rapamycin) and analogs thereof (such as CCI-779).

The anti-IL-22 antibodies disclosed herein can be used in combination with other therapeutic agents to treat specific immune disorders as discussed in further detail below.

Non-limiting examples of agents for treating arthritic disorders (e.g., rheumatoid arthritis, inflammatory arthritis, rheumatoid arthritis, juvenile rheumatoid arthritis, osteoarthritis and psoriatic arthritis), with which an anti-IL-22 antibody can be combined include at least one of the following: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, Lenercept™) and 75 kdTNFR-IgG (75 kD TNF receptor-IgG fusion protein, Enbrel™)); TNF enzyme antagonists (such as TACE inhibitors); antagonists of IL-12 (or one of its subunits p35 or p40), IL-15, IL-17A-F (including heterodimers thereof, for example, IL-17A/IL-17F heterodimer), IL-18, II-19, IL-20, IL-21, IL-22, IL-23 (or one of its subunits p19 or p40), and IL-24; T cell and B cell depleting agents (such as anti-CD4, anti-CD20, or anti-CD22 antibodies); small molecule inhibitors (such as methotrexate and leflunomide); sirolimus (rapamycin) and analogs thereof (e.g., CCI-779); Cox-2 and cPLA2 inhibitors; NSAIDs; p38, TPL-2, Mk-2, and NFκB inhibitors; RAGE or soluble RAGE; P-selectin or PSGL-1 inhibitors (such as small molecule inhibitors and antibodies to); estrogen receptor beta (ERB) agonists, and ERB-NFκB antagonists. Therapeutic agents that can be co-administered and/or co-formulated with at least one IL-22/IL-22R/IL-10R2 antagonist may include at least one of: a soluble fragment of a TNF receptor (e.g., human p55 or p75) such as 75 kdTNFR-IgG (75 kD TNF receptor-IgG fusion protein, Enbrel™); methotrexate; leflunomide; and sirolimus (rapamycin) or an analog thereof (e.g., CCI-779).

Non-limiting examples of agents for treating multiple sclerosis with which anti-IL-22 antibody can be combined include interferon-β for example, IFNβ-1a and IFMβ-1b), copaxone, corticosteroids, IL-1 inhibitors, TNF inhibitors, antibodies to CD40 ligand, antibodies to CD80, and IL-12 antagonists, including antibodies that bind IL-12 (or one of its subunits p35 or p40).

Non-limiting examples of agents for treating inflammatory bowel disease or Crohn's disease with which an anti-IL-22 antibody can be combined include budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13, and/or TGFβ or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

In other embodiments, an anti-IL-22 antibody can be used in combination with at least one antibody directed at other targets involved in regulating immune responses, e.g., transplant rejection or graft versus host disease. Non-limiting examples of agents for treating immune responses with which an IL-22/IL-22R/IL10R2 antagonist of the invention can be combined include the following: antibodies against cell surface molecules, including but not limited to CD25 (IL-2 receptor α), CD11a (LFA-1), CD54 (ICAM-1), CD4, CD45, CD28/CTLA4, CD80 (B7-1), CD86 (B7-2), or combinations thereof. In another embodiment, an anti-IL-22 antibody is used in combination with at least one general immunosuppressive agent, such as cyclosporin A or FK506.

Another aspect of the present invention accordingly relates to kits for carrying out the combined administration of the anti-IL-22 antibodies with other therapeutic agents. In one embodiment, the kit comprises at least one anti-IL-22 antibody formulated in a pharmaceutical carrier, and at least one therapeutic agent, formulated as appropriate in one or more separate pharmaceutical preparations.

VI. Diagnostic Uses

The antibodies may also be used to detect the presence of IL-22 in biological samples. By correlating the presence or level of these proteins with a medical condition, one of skill in the art can diagnose the associated medical condition. For example, IL-22 induces changes associated with those caused by inflammatory cytokines (such as IL-1 and TNFα), and inhibitors of IL-22 ameliorate symptoms of rheumatoid arthritis (WO 2005/000897 A2). Illustrative medical conditions that may be diagnosed by the antibodies of this invention include multiple sclerosis, rheumatoid arthritis, psoriasis, inflammatory bowel disease, pancreatitis, and transplant rejection.

Antibody-based detection methods are well known in the art, and include ELISA, radioimmunoassays, immunoblots, Western blots, flow cytometry, immunofluorescence, immunoprecipitation, and other related techniques. The antibodies may be provided in a diagnostic kit that incorporates at least one of these procedures to detect IL-22. The kit may contain other components, packaging, instructions, or other material to aid the detection of the protein and use of the kit.

Antibodies may be modified with detectable markers, including ligand groups (e.g., biotin), fluorophores and chromophores, radioisotopes, electron-dense reagents, or enzymes. Enzymes are detected by their activity. For example, horseradish peroxidase is detected by its ability to convert tetramethylbenzidine (TMB) to a blue pigment, quantifiable with a spectrophotometer. Other suitable binding partners include biotin and avidin, IgG and protein A, and other receptor-ligand pairs known in the art.

Antibodies can also be functionally linked (e.g., by chemical coupling, genetic fusion, non-covalent association or otherwise) to at least one other molecular entity, such as another antibody (e.g., a bispecific or a multispecific antibody), toxins, radioisotopes, cytotoxic or cytostatic agents, among others. Other permutations and possibilities are apparent to those of ordinary skill in the art, and they are considered equivalents within the scope of this invention.

VII. Pharmaceutical Compositions and Methods of Administration

Certain embodiments of the invention include compositions comprising the disclosed antibodies. The compositions may be suitable for pharmaceutical use and administration to patients. The compositions comprise an antibody of the present invention and a pharmaceutical excipient. As used herein, "pharmaceutical excipient" includes solvents, dispersion media, coatings, antibacterial and antifungal agents, isotonic and absorption delaying agents, etc., that are compatible with pharmaceutical administration. Use of these agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. Pharmaceutical compositions may be topically or orally administered, or capable of transmission across mucous membranes. Examples of administration of a pharmaceutical composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin.

Oral compositions include an inert diluent or edible carrier. The composition can be enclosed in gelatin or compressed into tablets. For the purpose of oral administration, the antibodies can be incorporated with excipients and placed in tablets, troches, or capsules. Pharmaceutically compatible binding agents or adjuvant materials can be included in the composition. The tablets, troches, and capsules, may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

The composition may also be administered by a transmucosal or transdermal route. For example, antibodies that comprise a Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used. For administration by inhalation, the antibodies are delivered in an aerosol spray from a pressured container or dispenser, which contains a propellant (e.g., liquid or gas) or a nebulizer.

In certain embodiments, the antibodies of this invention are prepared with carriers to protect the antibodies against rapid elimination from the body. Biodegradable polymers (e.g., ethylene vinyl acetate, polyanhydrides, polyglycolic acid, collagen, polyorthoesters, polylactic acid) are often used. Methods for the preparation of such formulations are known by those skilled in the art. Liposomal suspensions can be used as pharmaceutically acceptable carriers too. The liposomes can be prepared according to established methods known in the art (U.S. Pat. No. 4,522,811).

The antibodies or antibody compositions of the invention are administered in therapeutically effective amounts as described. Therapeutically effective amounts may vary with the subject's age, condition, sex, and severity of medical condition. Appropriate dosage may be determined by a physician based on clinical indications. The antibodies or compositions may be given as a bolus dose to maximize the circulating levels of antibodies for the greatest length of time. Continuous infusion may also be used after the bolus dose.

As used herein, the term "subject" is intended to include human and non-human animals. Subjects may include a human patient having a disorder characterized by cells that express IL-22, e.g., a cancer cell or an immune cell. The term "non-human animals" of the invention includes all vertebrates, such as non-human primates, sheep, dogs, cows, chickens, amphibians, reptiles, etc.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics. Dosages can also be administered via continuous infusion (such as through a pump). The administered dose may also depend on the route of administration. For example, subcutaneous administration may require a higher dosage than intravenous administration.

In certain circumstances it may be advantageous to formulate compositions in dosage unit form for ease of administration and uniformity of dosage. Dosage unit form as used herein refers to physically discrete units suited for the patient. Each dosage unit contains a predetermined quantity of antibody calculated to produce a therapeutic effect in association with the carrier. The dosage unit depends on the characteristics of the antibodies and the particular therapeutic effect to be achieved.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

The data obtained from the cell culture assays and animal studies can be used to formulate a dosage range in humans. The dosage of these compounds may lie within the range of circulating antibody concentrations in the blood, that includes an $ED_{50}$ with little or no toxicity. The dosage may vary within this range depending upon the dosage composition form employed and the route of administration. For any antibody used in the present invention, the therapeutically effective dose can be estimated initially using cell culture assays. A dose may be formulated in animal models to achieve a circulating plasma concentration range that includes the $IC_{50}$ (i.e., the concentration of antibody which achieves a half-maximal inhibition of symptoms). The effects of any particular dosage can be monitored by a suitable bioassay. Examples of suitable bioassays include DNA replication assays, transcription-based assays, IL-22/IL-22R binding assays, IL-22/IL-10R2 binding assays, IL-22/IL-22R/IL-10R2, and other immunological assays.

EXAMPLES

Example 1

Selection of Anti-IL-22 scFv's

Selection of Parents GIL01 and GIL68

GIL01 and GIL68 were isolated from scFv libraries by soluble selection on IL-22. Soluble selections were carried out using biotinylated IL-22 with an N-terminal His/FLAG tagged protein (bio.IL-22H/F). Bio.IL-22H/F was initially used at a concentration of 100 nM. An scFv phagemid library, which is an expanded version of the $1.38 \times 10^{10}$ library described (Vaughan et al., 1996), was used to select antibodies specific for IL-22. Purified scFv phage ($10^{12}$ transducing units (tu)) were blocked for 30 minutes in 100 µl 3% MPBS (3% milk powder in PBS), then bio.IL-22H/F was added and incubated at room temperature for 1 hour. Phage/antigen was added to 50 µl of Dynal M280 Streptavidin magnetic beads, which had been blocked for 1 hour at 37° C. in 1 ml of 3% MPBS, then incubated for a further 15 minutes at room temperature. Beads were captured using a magnetic rack and washed 4× in 1 ml of 3% MPBS/0.1% (v/v) Tween 20 followed by three washes in PBS. After the last wash, beads were resuspended in 100 µl PBS and used to infect 5 ml exponentially growing E. coli TG-1 cells. Cells and phage on beads were incubated for 1 hour at 37° C. (30 minutes stationary, 30 minutes shaking at 250 rpm), then spread on 2TYAG plates. Plates were incubated at 30° C. overnight and colonies visualized the next day. Colonies were scraped off the plates into 10 ml 2TY broth and 15% glycerol added for storage at $-70°$ C.

Glycerol stock cultures from the first round panning selection were superinfected with helper phage and rescued to give scFv antibody-expressing phage particles for the second round of selection. A second and third round of soluble selection was carried out as described above, dropping the concentration of bio.IL-22H/F to 50 nM.

Isolation of Parents GIL16, GIL45, GIL60 and GIL92

GIL16, GIL45, GIL60 and GIL92 were isolated from scFv libraries by a combination of panning on an IL-22 fusion protein and soluble selection on bio.IL-22H/F. Wells of a microtiter plate were coated with 10 µg/ml (Dulbecco's PBS, pH 7.4) human IL-22 fusion protein and incubated overnight at 4° C. Wells were washed in PBS and blocked for 2 hours at 37° C. in 3% MPBS. Purified phage ($10^{12}$ tu) in 100 µl of 3% MPBS were added to blocked wells and incubated at room temperature for 1 hour. Wells were washed 10 times with PBST (PBS containing 0.1% v/v Tween20), then 10 times with PBS. Bound phage particles were eluted with 100 µl trypsin solution (0.5 µg/ml trypsin in 50 mM Tris pH 8, 1 mM $CaCl_2$) for 30 minutes at 37° C. The eluted phage were used to infect 10 ml exponentially growing E. coli TG1. Infected cells were grown in 2TY broth for 1 hour at 37° C., as above, then streaked onto 2TYAG plates and incubated overnight at 30° C. Output colonies were scraped off the plates and phage rescued as described above. A second round of soluble selection was carried out as described above, using 100 nM bio.IL-22H/F.

Example 2

ScFv Blocks Binding of IL-22 to IL-22R

Inhibition assays were performed on the parent antibodies GIL01, GIL16, GIL45, GIL60, GIL68, and GIL92 to identify antibodies that block or alter binding of IL-22 to IL-22R and/or IL-22 receptor complex. Crude scFv containing periplasmic extracts were screened for the ability to inhibit the binding of bio.IL-22H/F to a human IL-22 receptor protein (hIL-22R). Output colonies from selections were picked into 96 well plates containing 100 µl 2TYAG. ScFv production was induced by addition of 1 mM IPTG to exponentially growing cultures and overnight incubation at 30° C. Periplasmic extracts were prepared (Griffiths et al., 1993) in 50 mM MOPS pH 7.4/0.5 mM EDTA/0.5M Sorbitol.

Microtiter plates were coated with 1.25 µg/ml of an IL-22 receptor protein antibody (in PBS) for 1.5 hours at room temperature. Plates were then washed three times in PBS, and blocked for 1 hour at room temperature with PBS containing 2% milk powder (2% MPBS). After a further 3 washes, 50 µl of 25% cell conditioned medium containing an IL-22 receptor protein was added to each well, and incubated overnight at 4° C. The following day, 25 µl of sample and 250 of bio.IL-22H/F (54 ng/ml in PBS/0.05% BSA/0.05% Tween) were added to the washed plates, and incubated for 1.5 hours at room temperature. After 3 washes in PBST, binding of bio.IL-22H/F was detected with Europium-Streptavidin and TRF detected with the DELFIA® reagent kit and Victor 2™ Plate Reader (Perkin Elmer).

Clones that showed inhibition of IL-22 binding were retested as purified scFv. Both the IL-22/IL-22R binding assay (described above) and the IL-22/IL-22 receptor complex assay (described below) were used. ScFv concentrations were titrated in order to establish the clone potencies as measured by assay $IC_{50}$ values. These were determined using GraphPad Prism software and four-parameter logistic equation curve fitting. Sample results from the IL-22 receptor complex assay are shown in FIG. 1.

Example 3

Verification of IL-22 Binding by Phage ELISA

To establish the specificity of the scFv's for IL-22, a phage ELISA was performed using IL-22 fusion protein, IL-22H/F and an unrelated protein. Individual *E. coli* colonies containing phagemid were inoculated into 96 well plates containing 100 µl 2TYAG medium per well. M13K07 helper phage were added to a multiplicity of infection (moi) of 10 to the exponentially growing culture and the plates incubated an additional 1 hour at 37° C. Plates were centrifuged in a benchtop centrifuge at 2000 rpm for 10 minutes. The supernatant was removed and cell pellets were resuspended in 100 µl 2TYAK and incubated at 30° C. overnight with shaking. The next day, plates were centrifuged at 2000 rpm for 10 minutes and 100 µl phage-containing supernatant from each well was transferred to a fresh 96 well plate. Phage samples were blocked in a final concentration of 3% MPBS for 1 hour at room temperature.

Microtiter plates were coated with 1 µg/ml IL-22 fusion protein, IL-22H/F or an unrelated protein and incubated overnight at 4° C. After coating, the solutions were removed from the wells, and the plates blocked for 1 hour at room temperature in 3% MPBS. Plates were rinsed with PBS then 50 µl of pre-blocked phage was added to each well. The plates were incubated at room temperature for 1 hour, then washed with 3 changes of PBST followed by 3 changes of PBS. To each well, 50 µl of a 1:5000 dilution of anti-M13-HRP conjugate (Pharmacia) was added and the plates incubated at room temperature for 1 hour. Plates were washed 3 times with PBST then 3 times with PBS. Fifty µl of TMB substrate was added to each well and incubated until color development. The reaction was stopped by the addition of 25 µl of 0.5 M $H_2SO_4$, and the absorbance at 450 nm measured. These experiments confirmed the specific binding of scFv clones to IL-22.

Example 4

Conversion of $scF_v$ to IgG

Heavy and light chain V regions from scFv clones were amplified with clone-specific primers. PCR products were digested with appropriate restriction enzymes and subcloned into vectors containing human IgG4 heavy chain constant domain (for $V_H$ domains) or vectors containing human lambda or kappa light chain constant domains as appropriate ($V_L$ domains). The closest human germlines of the $V_H$ and $V_L$ segments were determined and this information was used to indicate whether kappa or lambda light chain constant domains were used (Table 4). Correct insertion of V region domains into plasmids was verified by sequencing of plasmid DNA from individual *E. coli* colonies. Plasmids were prepared from *E. coli* cultures by standard techniques and heavy and light chain constructs co-transfected into HEK 293 EBNA cells using standard techniques. Secreted IgG was purified using protein A sepharose (Pharmacia) and buffer exchanged into PBS.

TABLE 4

$V_H$ and $V_L$ germlines of IL-22 neutralizing clones

| Clone | $V_H$ germline | $V_L$ germline |
|---|---|---|
| GIL01 | 3-11 (DP35) | Vk1:L12 |
| GIL16 | 1-18 (DP14) | Vk1:L12 |
| GIL45 | 3-33 (DP50) | VL2:2a2 (DPL11) |
| GIL60 | 3-20 (DP32) | VL2:2a2 (DPL11) |
| GIL68 | 1-2 (DP8) | VL3:3h |
| GIL92 | 1-2 (DP8) | VL1:1e (DPL8) |

Potency of purified IgG was verified in the biochemical IL-22 receptor complex inhibition assay as described below. IgG concentrations were titrated in order to obtain potency values. Sample potency data is shown in Table 5.

TABLE 5

Potency of IL-22 scFv and IgG in the IL-22 receptor complex inhibition assay

| Clone | ScFv potency (nM) | IgG potency (nM) |
|---|---|---|
| GIL01 | 104 | 13 |
| GIL16 | 49 | 10 |
| GIL60 | 43 | 15 |
| GIL68 | 7 | 2 |
| GIL92 | 16 | unobtainable |
| GIL45 | 358 | 180 |

Example 5

IL-22 Antibody Optimization

Large ribosome display libraries were created and screened for scFv's that specifically recognized recombinant human IL-22, essentially as described in Hanes et al. (2000). Initially the five parent clones (GIL01, GIL16, GIL60, GIL68 and GIL92) were converted to ribosome display format, and this template was subsequently used for library creation. On the DNA level, a T7 promoter was added at the 5'-end for efficient transcription to mRNA. On the mRNA level, the construct contained a prokaryotic ribosome-binding site (Shine-Dalgarno sequence) and 5' & 3' stem loops for mRNA stability. At the 3' end of the single chain, the stop codon was removed and a portion of gIII was added to act as a spacer, allowing folding of the scFv away from the ribosomal tunnel (Hanes et al. 2000).

Ribosome display libraries derived from the lead clones were created by mutagenesis of the single chain complementarity determining regions (CDRs) using PCR with non-proofreading Taq DNA polymerase. Affinity based selections were performed where the library was incubated with bio.IL-22H/F, followed by streptavidin coated paramagnetic beads (Dynal M280). Tertiary complexes (mRNA-ribosome-scFv) were recovered by magnetic separation, while unbound complexes were washed away. The mRNAs encoding the bound scFvs were then rescued by RT-PCR as described (Hanes et al., 2000) and the selection process repeated with decreasing concentrations (100 nM-10 pM over 5 rounds) of bio.IL-22H/F.

Error prone PCR was introduced to further increase library size. The error rate that was employed created, on average, 7.2 mutations per 1,000 bp after a standard PCR reaction based on the method of Cadwell and Joyce (1992). Initial error prone PCR reactions took place between the first and second rounds of selection.

$V_H/V_L$ recombination libraries for each parent clone were prepared from the $V_H$ and $V_L$ CDR ribosome display outputs after either the second or fourth round of selections. The $V_H$ portion of the $V_H$ CDR selection output for a particular lineage was specifically PCR amplified, using clone specific primers. The $V_L$ portion of the $V_L$ CDR selection output for the same lineage was amplified separately. These two PCR products were recombined via an overlapping PCR reaction. This created a complete library of scFv products containing all components required for further rounds of ribosome display selection.

For some clones, phage display libraries were also utilized. Phage libraries were created by mutagenesis of single chain CDRs using PCR reactions with appropriate primers, and selected as described above. These outputs were also combined with ribosome display selection outputs to create $V_H/V_L$ recombination libraries. The $V_H$ selection outputs from the fourth round of ribosome display, together with the outputs from the third round of phage display, were recombined with the $V_L$ outputs from the same lineage. This was achieved using clone specific primers and over-lapping PCR to produce $V_H/V_L$ recombination libraries. Selections with soluble bio.IL-22H/F continued in ribosome display format, as described above. The scFv regions of selection outputs were directionally cloned into pCANTAB6 for production of scFv for biochemical high throughput screening.

Example 6

Identification of Optimized Clones

Two assays were used for high throughput screening of selection outputs. Outputs derived from clones GIL01, GIL16 and GIL68 were screened in a homogeneous time resolved fluorescence assay (HTRF®, Cis Biointernational), while GIL60 and GIL92 outputs were screened in a DELFIA® (Perkin Elmer) assay.

HTRF® Epitope Competition Assay

Crude scFv containing culture supernatants from GIL01, GIL16 and GIL68 output clones were prepared as described above and screened for inhibition of bio.IL-22H/F binding GIL68 in an HTRF assay.

Cryptate labeled GIL68 IgG (labeling kit from Cis Biointernational) was diluted 400 fold in assay buffer (PBS/0.4M KF/0.05% BSA/0.05% Tween), followed by the addition of 7.5 nM Streptavidin XL665 (Xlent, Cis Biointernational). This solution was mixed with crude scFv sample (diluted 125x), and bio.IL-22H/F in a Packard black 384 well Optiplate (Perkin Elmer). Plates were incubated for 1 hour at room temperature then read using a Victor 2™ Plate Reader (Perkin Elmer). The 665 nM/620 nM emission ratio was used to calculate the percentage of specific binding in each well.

DELFIA® Time Resolved Fluorescence Assay

GIL60 and GIL92 output clones were screened for inhibition of bio.IL-22H/F binding to an IL-22 receptor complex.

Microtiter plates were coated with an IL-22 receptor complex antibody (1 μg/ml in PBS), and incubated for 1.5 hours at room temperature. Plates were washed three times in PBST, and blocked for 1 hour at room temperature with 2% MPBS. After a further 3 washes, diluted cell conditioned medium containing an IL-22 receptor complex was added and incubated overnight at 4° C. Crude scFv supernatants were prepared as described above. The following day, 25 μl of diluted scFv sample and 25 μl of bio.IL-22 H/F (6 ng/ml) were added to the washed plates, and incubated for 1.5 hours at room temperature. Plates were washed 3 times in PBST, then binding of bio.IL-22H/F to the IL-22 receptor complex was detected with Europium-Streptavidin and the DELFIA® reagent kit (PerkinElmer). Time Resolved Fluorescence was measured using a Victor 2™ Plate Reader (Perkin Elmer).

Purified scFv from positive clones identified from the screening were tested in the DELFIA® IL-22 receptor complex competition assay as described above. A titration of scFv concentrations was used in order to establish the clone potency as measured by $IC_{50}$ values in the assay. Sample results are shown in FIG. 2. Fourteen optimized clones were designated 097D09, 062A09, 062G05, 087B03, 367D04, 368D04, 166B06, 166G05, 375G06, 376B10, 354A08, 355B06, 355E04, and 356A11.

Example 7

Ranking of Optimized Clones in the BAF3-IL-22 Proliferation Assay

Proliferation assays were performed to assess the antibody's ability to block the IL-22 mediated BaF3 cell proliferation. BaF3 cells expressing hIL22Ft/hIL10R2 were generated by co-transfection of BaF3 cells with hIL22R-GFP and hIL10R2-YFP. BaF3 cells expressing both hIL22R and hIL10R2 (BaF3-IL-22 receptor cells) were sorted and collected by FACS.

BaF3-IL-22 receptor cells were routinely maintained in RPMI1640 with 10% FBS and 1 ng/mL murine IL-J. Immediately before assay setup, cells were washed 4 times in assay medium (RPMI1640 with 10% FBS, 100 U/ml Penicillin and 100 μl/ml Streptomycin), resuspended in assay medium and incubated at 37° C., 5% $CO_2$ for 6-8 hours. To prepare assay plates, 100 μl of cells ($1 \times 10^5$/ml in assay medium) were added to the central 60 wells of a 96 well flat-bottomed tissue culture plate (Costar). Test scFv or IgG samples were prepared by diluting the stock sample in assay medium followed by filtration through a 0.22 μM filter. Serial 5-fold dilutions of samples were prepared in a separate dilution plate. Cell containing wells were treated with 50 μl of sample followed by 50 μl of human IL-22, (40 ng/ml in assay medium), and were then incubated for 40 hours at 37° C. in 5% $CO_2$. Control wells included media alone and cells either alone or in the presence of 10 ng/mL human IL-22.

Cell proliferation was detected by the addition of 20 μl of Alamar Blue (Serotec) to wells, followed by incubation for 5 hours±30 mins at 37° C. in 5% $CO_2$. Plates were mixed by gentle tapping to ensure even signal throughout the wells before measurement of fluorescence (excitation=560 nM, emission=590 nM). $EC_{50}$ and $IC_{50}$ values were estimated using four-parameter logistic curve fitting (Graphpad Prism 2 Software) and were used to rank antibodies. Sample potency data for optimized scFvs and IgGs are shown in Table 6.

TABLE 6

$IC_{50}$ values of scFv and IgG clones in BaF3-IL-22 proliferation assay

| Clone | Parent | $IC_{50}$ of scFv (pM) | $IC_{50}$ of IgG (pM) |
|---|---|---|---|
| 097D09 | GIL01 | 298 ± 246 | 197 ± 42 |
| 062A09 | GIL16 | 267 | 83 ± 37 |
| 062G05 | GIL16 | 182 | 112 ± 30 |
| 087B03 | GIL60 | 212 | 105 ± 17 |

TABLE 6-continued

IC$_{50}$ values of scFv and IgG clones in BaF3-IL-22 proliferation assay

| Clone | Parent | IC$_{50}$ of scFv (pM) | IC$_{50}$ of IgG (pM) |
|---|---|---|---|
| 367D04 | GIL60 | 160 ± 49 | 126 ± 6 |
| 368D04 | GIL60 | 186 ± 66 | 127 ± 10 |
| 166B06 | GIL68 | 460 | 71 ± 23 |
| 166G05 | GIL68 | 204 | 97 ± 23 |
| 375G06 | GIL68 | 118 ± 98 | 100 ± 1 |
| 376B10 | GIL68 | 104 ± 47 | 119 ± 6 |
| 354A08 | GIL92 | 219 ± 83 | 79 ± 15* |
| 355B06 | GIL92 | 183 ± 3 | 92 ± 14* |
| 355E04 | GIL92 | 192 ± 47 | 100 ± 14* |
| 356A11 | GIL92 | 124 ± 21 | 53 ± 5* |

*GIL92-derived clones were tested as germlined IgGs.

Example 8

Germlining

Sequence data for the six parent clones was used to identify the nearest germ line sequence for the heavy and light chain of each clone. Appropriate mutations were made using standard site directed mutagenesis techniques with the appropriate mutagenic primers. Mutation of sequences was confirmed by sequence analysis. The sequences for the germlined clones and their scFv and V$_H$ and V$_L$ domains are shown in Table 7. Purified scFv from the germlined parent clones were tested in the biotinylated IL-22 binding IL-22 receptor complex competition assay as described earlier, in order to establish the clone potency as measured by IC$_{50}$ values in the assay. Results are summarized in Table 8.

TABLE 7

A: Amino Acid and Nucleotide Sequences of V$_H$ and V$_L$ Domains, F$_V$, and CDRs of Germlined Antibodies (GIL01, GIL16, GIL45, GIL60, GIL68, GIL92, 062A09, and 087B03)

| Region | Type | GIL01 SEQ ID | GIL16 SEQ ID | GIL45 SEQ ID | GIL60 SEQ ID | GIL68 SEQ ID | GIL92 SEQ ID | 062A09 SEQ ID | 087B03 SEQ ID |
|---|---|---|---|---|---|---|---|---|---|
| V$_H$ | AA | NO: 365 | NO: 383 | NO: 401 | NO: 419 | NO: 437 | NO: 455 | NO: 473 | NO: 491 |
| V$_L$ | AA | NO: 366 | NO: 384 | NO: 402 | NO: 420 | NO: 438 | NO: 456 | NO: 474 | NO: 492 |
| scF$_v$ | AA | NO: 367 | NO: 385 | NO: 403 | NO: 421 | NO: 439 | NO: 457 | NO: 475 | NO: 493 |
| H1 | AA | NO: 368 | NO: 386 | NO: 404 | NO: 422 | NO: 440 | NO: 458 | NO: 476 | NO: 494 |
| H2 | AA | NO: 369 | NO: 387 | NO: 405 | NO: 423 | NO: 441 | NO: 459 | NO: 477 | NO: 495 |
| H3 | AA | NO: 370 | NO: 388 | NO: 406 | NO: 424 | NO: 442 | NO: 460 | NO: 478 | NO: 496 |
| L1 | AA | NO: 371 | NO: 389 | NO: 407 | NO: 425 | NO: 443 | NO: 461 | NO: 479 | NO: 497 |
| L2 | AA | NO: 372 | NO: 390 | NO: 408 | NO: 426 | NO: 444 | NO: 462 | NO: 480 | NO: 498 |
| L3 | AA | NO: 373 | NO: 391 | NO: 409 | NO: 427 | NO: 445 | NO: 463 | NO: 481 | NO: 499 |
| V$_H$ | DNA | NO: 374 | NO: 392 | NO: 410 | NO: 428 | NO: 446 | NO: 464 | NO: 482 | NO: 500 |
| V$_L$ | DNA | NO: 375 | NO: 393 | NO: 411 | NO: 429 | NO: 447 | NO: 465 | NO: 483 | NO: 501 |
| scF$_v$ | DNA | NO: 376 | NO: 394 | NO: 412 | NO: 430 | NO: 448 | NO: 466 | NO: 484 | NO: 502 |
| H1 | DNA | NO: 377 | NO: 395 | NO: 413 | NO: 431 | NO: 449 | NO: 467 | NO: 485 | NO: 503 |
| H2 | DNA | NO: 378 | NO: 396 | NO: 414 | NO: 432 | NO: 450 | NO: 468 | NO: 486 | NO: 504 |
| H3 | DNA | NO: 379 | NO: 397 | NO: 415 | NO: 433 | NO: 451 | NO: 469 | NO: 487 | NO: 505 |
| L1 | | NO: 380 | NO: 398 | NO: 416 | NO: 434 | NO: 452 | NO: 470 | NO: 488 | NO: 506 |
| L2 | DNA | NO: 381 | NO: 399 | NO: 417 | NO: 435 | NO: 453 | NO: 471 | NO: 489 | NO: 507 |
| L3 | DNA | NO: 382 | NO: 400 | NO: 418 | NO: 436 | NO: 454 | NO: 472 | NO: 490 | NO: 508 |

B: Amino Acid and Nucleotide Sequences of V$_H$ and V$_L$ Domains, F$_V$, and CDRs of Germlined Antibodies (166B06, 166G05, 354A08, 355B06, 355E04, 356A11, and 368D04)

| Region | Type | 166B06 SEQ ID | 166G05 SEQ ID | 354A08 | 355B06 SEQ ID | 355E04 SEQ ID | 356A11 SEQ ID | 368D04 SEQ ID |
|---|---|---|---|---|---|---|---|---|
| V$_H$ | AA | NO: 509 | NO: 527 | NO: 545 | NO: 563 | NO: 581 | NO: 599 | NO: 617 |
| V$_L$ | AA | NO: 510 | NO: 528 | NO: 546 | NO: 564 | NO: 582 | NO: 600 | NO: 618 |
| scF$_v$ | AA | NO: 511 | NO: 529 | NO: 547 | NO: 565 | NO: 583 | NO: 601 | NO: 619 |
| H1 | AA | NO: 512 | NO: 530 | NO: 548 | NO: 566 | NO: 584 | NO: 602 | NO: 620 |
| H2 | AA | NO: 513 | NO: 531 | NO: 549 | NO: 567 | NO: 585 | NO: 603 | NO: 621 |
| H3 | AA | NO: 514 | NO: 532 | NO: 550 | NO: 568 | NO: 586 | NO: 604 | NO: 622 |
| L1 | AA | NO: 515 | NO: 533 | NO: 551 | NO: 569 | NO: 587 | NO: 605 | NO: 623 |
| L2 | AA | NO: 516 | NO: 534 | NO: 552 | NO: 570 | NO: 588 | NO: 606 | NO: 624 |
| L3 | AA | NO: 517 | NO: 535 | NO: 553 | NO: 571 | NO: 589 | NO: 607 | NO: 625 |
| V$_H$ | DNA | NO: 518 | NO: 536 | NO: 554 | NO: 572 | NO: 590 | NO: 608 | NO: 626 |
| V$_L$ | DNA | NO: 519 | NO: 537 | NO: 555 | NO: 573 | NO: 591 | NO: 609 | NO: 627 |
| scF$_v$ | DNA | NO: 520 | NO: 538 | NO: 556 | NO: 574 | NO: 592 | NO: 610 | NO: 628 |
| H1 | DNA | NO: 521 | NO: 539 | NO: 557 | NO: 575 | NO: 593 | NO: 611 | NO: 629 |
| H2 | DNA | NO: 522 | NO: 540 | NO: 558 | NO: 576 | NO: 594 | NO: 612 | NO: 630 |
| H3 | DNA | NO: 523 | NO: 541 | NO: 559 | NO: 577 | NO: 595 | NO: 613 | NO: 631 |
| L1 | DNA | NO: 524 | NO: 542 | NO: 560 | NO: 578 | NO: 596 | NO: 614 | NO: 632 |
| L2 | DNA | NO: 525 | NO: 543 | NO: 561 | NO: 579 | NO: 597 | NO: 615 | NO: 633 |
| L3 | DNA | NO: 526 | NO: 544 | NO: 562 | NO: 580 | NO: 598 | NO: 616 | NO: 634 |

TABLE 8

ScFv potencies of ungermlined and germlined parent clones in the IL-22 receptor competition assay

| Parent clone | Average IC$_{50}$ nM in IL-22 competition assay | |
|---|---|---|
| scFv | Parent | Fully germlined |
| GIL01 | 124 ± 50 | 143 ± 45 |
| GIL16 | 44 ± 1 | 38 ± 1 |
| GIL60 | 51 ± 16 | 82 ± 3 |
| GIL68 | 9 ± 1 | 14 + 1 |
| GIL92 | 18 ± 2 | 40 ± 11 |

Nine of the optimized antibodies were germlined as described above. Eight germlined IgGs were tested in the BaF3-IL-22 proliferation assay as described above. Antibody IC$_{50}$ values from a representative experiment are shown in Table 9.

Antibody sequences were then sent to GENEART North America (28 Kirk Bradden Rd. East, Toronto, ON, Canada M8Y2E6), where they were synthesized for optimized expression in CHO cells using GENEART's proprietary optimization algorithm.

TABLE 9

IgG potencies of germlined optimized clones in the BaF3-IL-22R proliferation assay

| Clone | Parent | IC$_{50}$ (pM) of non-germlined IgG | IC$_{50}$ (pM) of germlined IgG |
|---|---|---|---|
| 087B03 | GIL60 | 72 ± 6 | 118 ± 19 |
| 166B06 | GIL68 | 109 ± 16 | 169 ± 32 |
| 166G05 | GIL68 | 366 ± 226* | 109 ± 31 |
| 356A11 | GIL92 | ND | 53 ± 5 |
| 355B06 | GIL92 | ND | 92 ± 14 |
| 355E04 | GIL92 | ND | 100 ± 14 |
| 354A08 | GIL92 | ND | 79 ± 15 |
| 062A09 | GIL16 | 108 ± 23 | unobtainable |

*sample contained precipitate
ND = not determined

Example 9

Antibody Inhibits IL-22 Induced GROa Secretion from HT29 Cells

GROa assays were performed to assess the antibody's ability to block the IL-22 induced GROa secretion from HT29 cells. HT29 cells were seeded in 96 well flat bottom tissue culture plate (Corning Inc. Cat. #3595) in DMEM medium (DMEM+10% FBS+100 unit/ml penicillin and streptomycin+2 mM Glutamine) at 5×10$^4$/well. 10 ng/ml IL-22 was mixed with serially diluted antibody in DMEM medium and incubated for 30 min at 37° C. 24 hours after seeding, medium was removed from HT29 cells and pre-mixed IL-22 and antibody were added to the cells in 96 well plate.

Figure 3A:
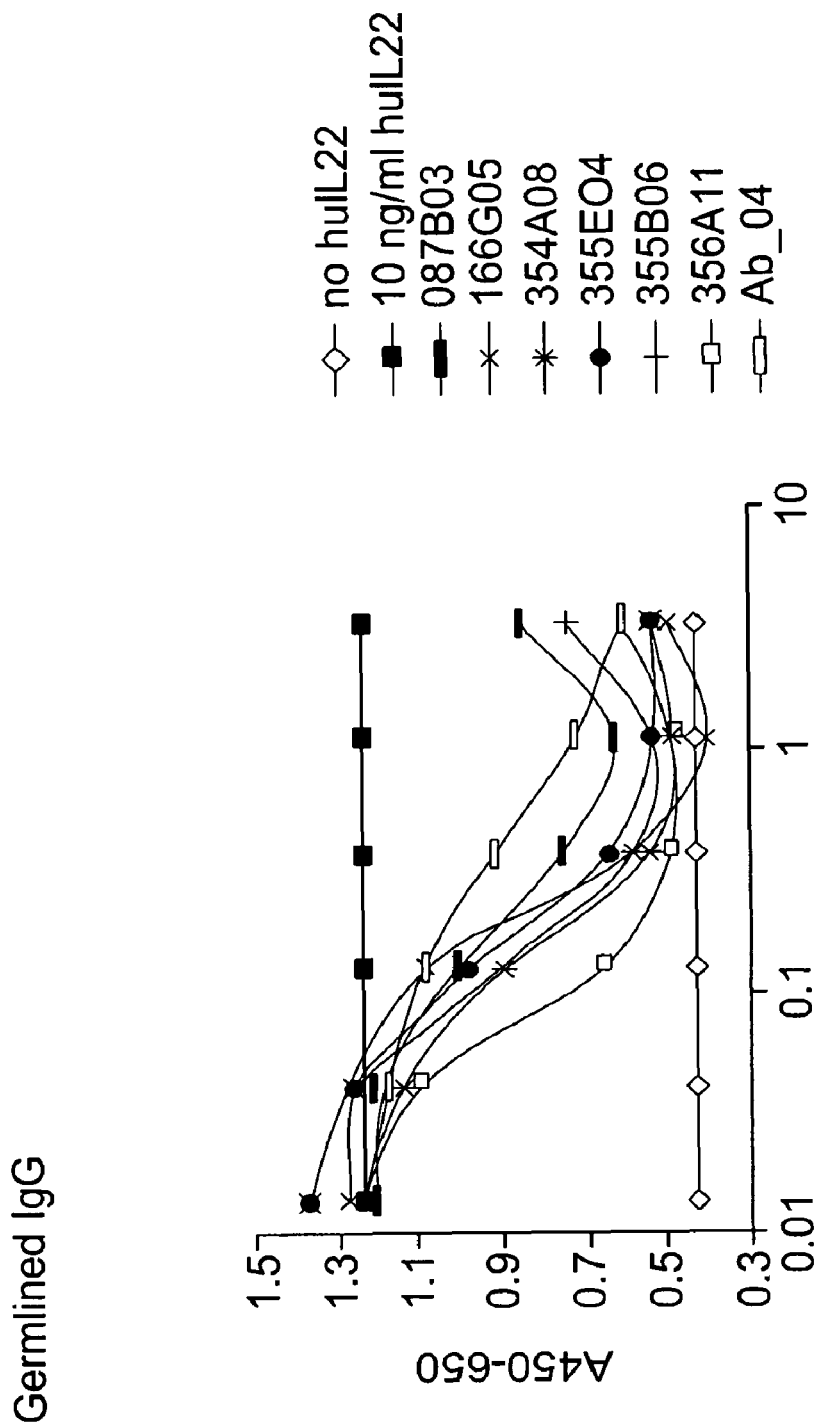
FIG. 3. IgG potency in GROa cell based assays. Optimized GIL-IgGs in huIL-22 GROa assay. (A) Germlined IgG. (B) Non-germlined IgG.
Figure 3B:
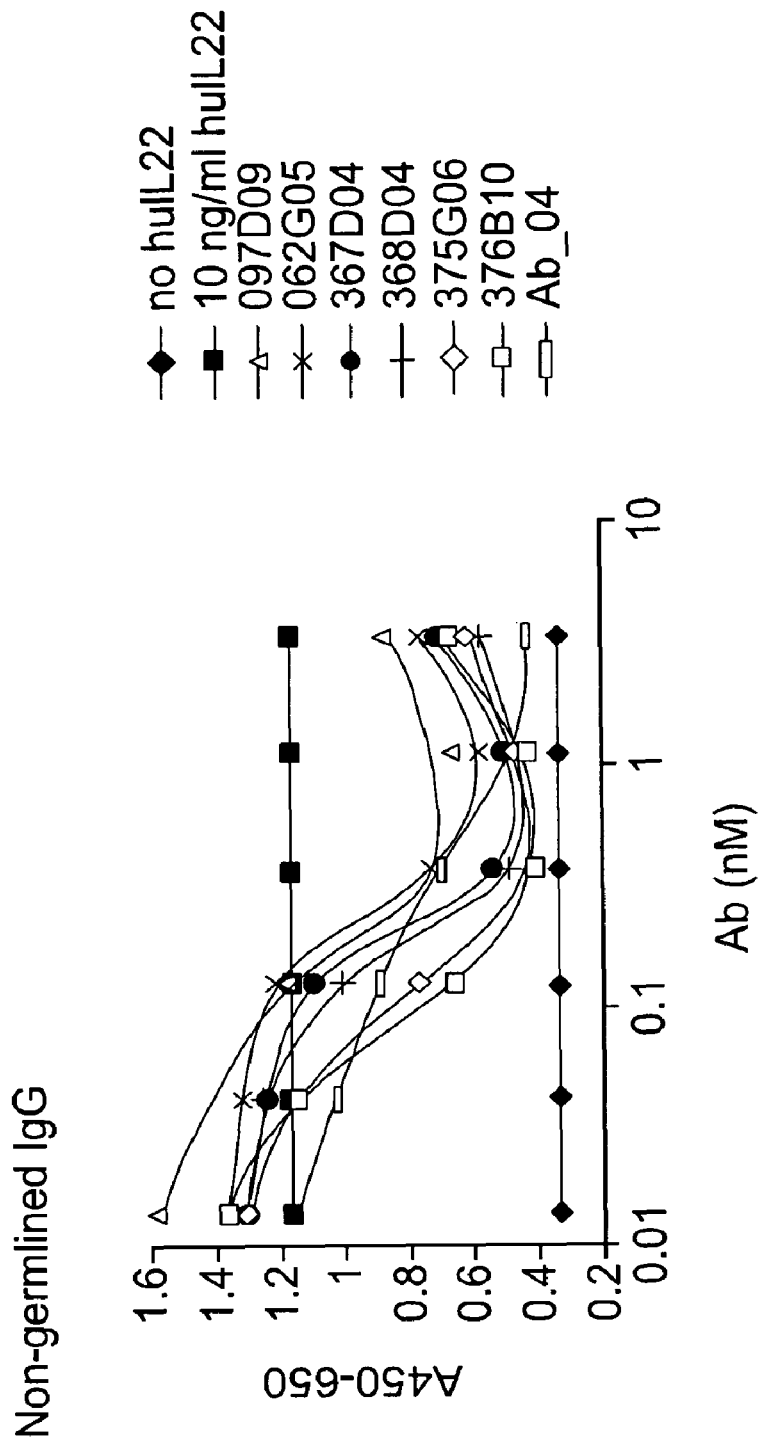

After 48 hours of incubation at 37° C. with 5% CO$_2$, medium was collected and secreted GROa was tested using Human GROa Immunoassay kit (R&D Systems, Cat. DGR00), according to the manufacturer's directions. Results are presented in FIG. 3.

Example 10

Antibody Binds to and Inhibits Different Species IL-22

Figure 4A:
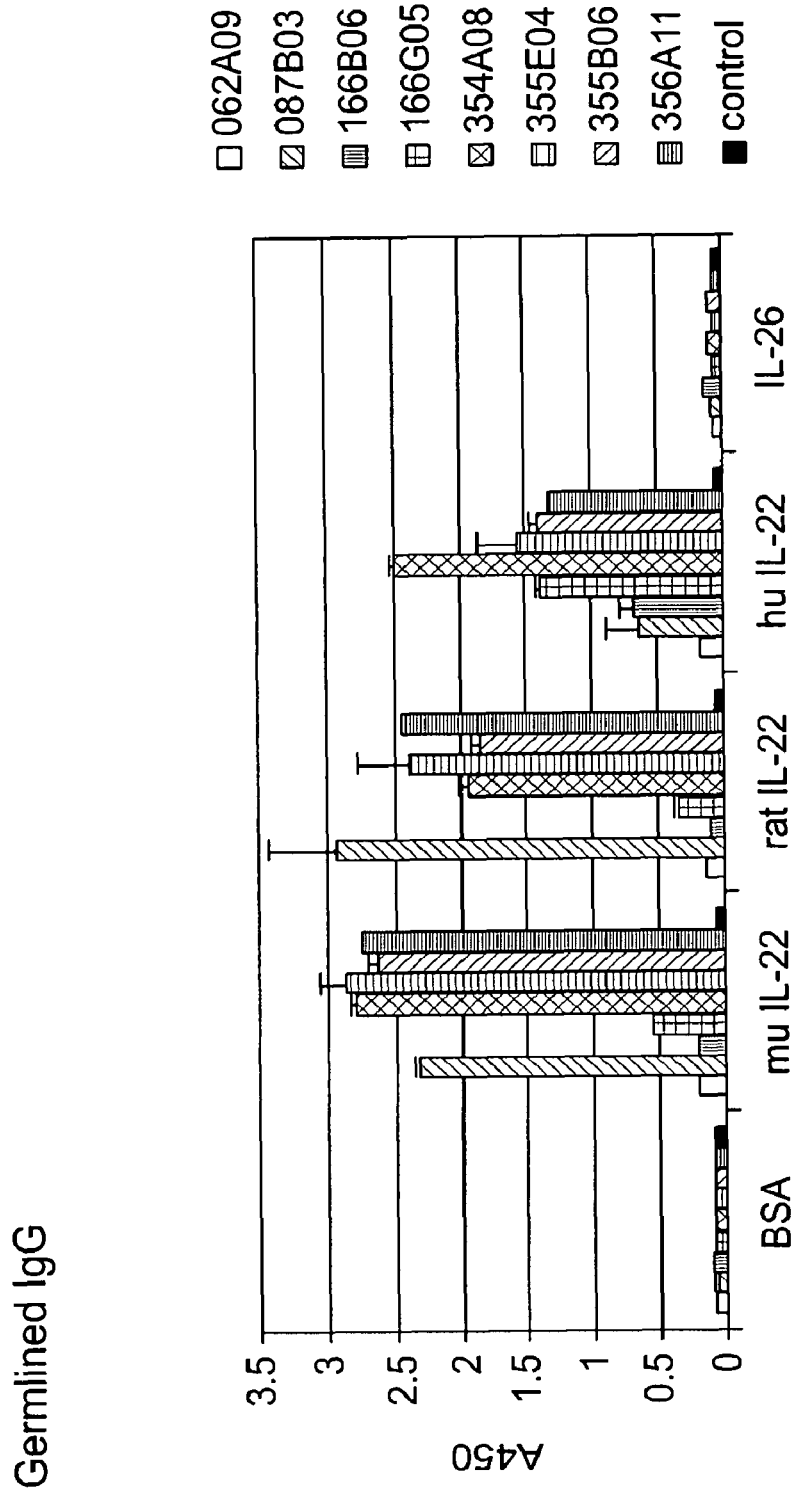
FIG. 4. Cross species reactivity of IL-22 antibodies by ELISA. Optimized GIL-IgGs specifically bind to IL-22. (A) Germlined IgG. (B) Non-germlined IgG.
Figure 4B:
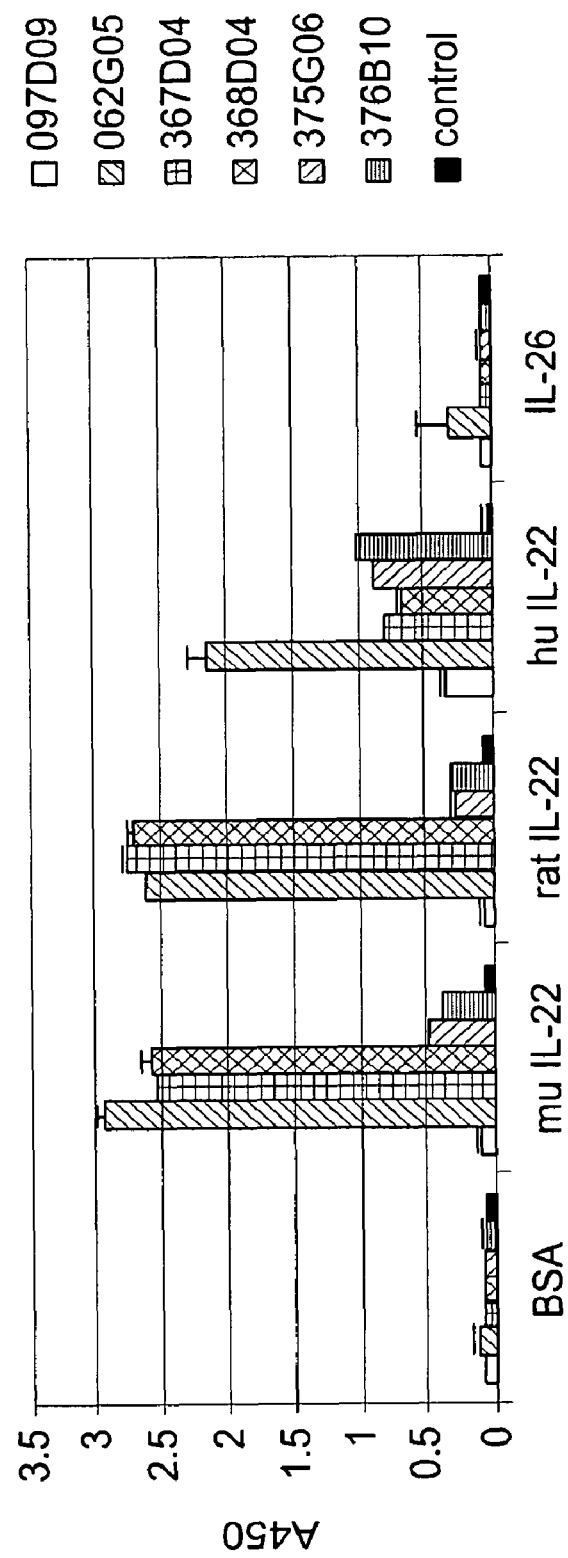

Cross species reactivity of germlined and non-germlined optimized antibodies were determined as follows: ELISA plates (Costar, Cat. #3590) were coated overnight with 1 µg/ml of rat, mouse, or human IL-22 or human IL-26 in PBS buffer. Plates were washed with PBST buffer (0.05% Tween20 in PBS) 3 times, then blocked with 1% BSA (Sigma A8918)/PBST for 1 hr at RT. Antibodies were added at 1 µg/ml, incubated 1 hr at 25° C. The plates were washed, then HRP-conjugated goat anti-human IgG antibody (Southern Biotech Association, Cat. #2040-05) was added. The plates were incubated for 1 hour at 25° C., then washed with PBST, and developed with TMB (KPL, Cat. #50-76-04). Reaction was stopped with 0.18 M H$_2$S0$_4$. Plates were read at OD 450 nm. Results are presented in FIG. 4.

These antibodies were also evaluated in both the GROa cell assay and BaF3-IL-22 proliferation assay. As shown in Tables 10(a) and 10(b), the antibodies blocked the activity of human, monkey, rat, and mouse IL-22 signalling via a human IL-22 receptor. 356A11 and 368D04 also demonstrated cross-species reactivity against murine, rat, and monkey IL-22 using real-time biospecific interaction analysis (BIA), as discussed further in Example 11.

TABLE 10(a)

IL-22 antibodies are highly potent for blocking other species of IL-22 as shown in the GROa cell based assay system.

| Protein ID | human IL-22 | murine IL-22 | rat IL-22 | monkey IL-22 |
|---|---|---|---|---|
| 356A11 | 123.64 | 143.76 | 210.91 | 89.57 |
| 368D04 | 154.07 | 156.25 | 281.12 | 184.10 |
| control 1 | 353.18 | 468.34 | 1161.57 | 343.19 |
| control 2 | 1955.80 | 3399.79 | 10697.17 | 1459.27 |

Values shown represent IC$_{50}$ values in pM.

TABLE 10(b)

IL-22 antibodies are highly potent for blocking other species of IL-22 as shown in the BaF3 cell based assay system.

| Protein ID | human IL-22 | murine IL-22 | rat IL-22 | monkey IL-22 |
|---|---|---|---|---|
| 356A11 | 3.57 | 2.53 | 10.69 | 2.58 |
| 368D04 | 3.63 | 1.47 | 12.07 | 3.87 |
| control 1 | 6.40 | 5~6 | 27.37 | 7.18 |
| control 2 | 204.98 | 1033.26 | 2500.00 | 134.27 |

Values shown represent IC$_{50}$ values in pM.

Example 11

Comparison of Binding Kinetics Between Rat Anti-IL-22 Monoclonal Antibodies and Human Anti-IL-22 Monoclonal Antibodies The binding kinetics of human, monoclonal anti-IL-22 antibodies (356A11 and 368D04) and rat, monoclonal anti-IL-22 antibodies (P3/3 (Ab-02) and P3/2 (Ab-04) from WO 2005/000897 and WO 02/068476) to human IL-22 were evaluated by real-time biospecific interaction analysis (BIA) using surface plasmon resonance technology.

To prepare the biosensor surface for the rat monoclonal antibodies, Protein A/G (Pierce #21186, Rockford, Ill.) was immobilized onto a research-grade carboxymethyl dextran chip (CM5) using amine coupling. The surface was activated with EDC/NHS. The protein NG was injected at a concentration of 50 μg/ml in sodium acetate buffer (pH 4.0). The immobilization was done using the wizard tools with aim of 3000 (RUs) for the protein A/G. Remaining activated groups were blocked with 1.0 M ethanolamine (pH 8.0). The first flow cell was used as a reference surface to correct for bulk refractive index, matrix effects, and non-specific binding. The second, third, and fourth flow cells were coated with the capturing molecule. The rat monoclonal antibodies Ab-02 and Ab-04, which bind to protein A/G, were captured onto the protein NG surface by injecting 30 μl of a 1 μg/ml solution. The net difference between the baseline and the point approximately 90 seconds after completing Ab-02 or Ab-04 injection was used to represent the amount of ligand bound.

To prepare the biosensor surface for the human monoclonal antibodies, either human monoclonal antibody (356A11 or 368D04) or control antibody PD-1 (#17) were immobilized onto a research-grade carboxymethyl dextran chip (CM5) using standard amine coupling. The surface was activated with EDC/NHS. The capturing antibodies were injected at a concentration of 1 μg/ml in sodium acetate buffer (pH 5.5). Remaining activated groups were blocked with 1.0 M ethanolamine (pH 8.0). The first flow cell was used as a reference surface to correct for bulk refractive index, matrix effects, and non-specific binding. The second, third, and fourth flow cells were coated with the capturing molecule.

For Ab-02 and Ab-04, solutions of human IL-22 at 300, 100, 50, 25, 12.5, 6.4, 3.2, 1.6 and 0 nM concentrations were injected in triplicates at a flow rate of 30 μl per minute for 3 minutes and the amount of bound material as a function of time was recorded as sensorgrams. The dissociation phase was monitored in HBS/EP buffer for 10 minutes at the same flow rate followed by a 5 μl injection of 0.1% TFA and a 5 μl injection of glycine pH 1.5 to regenerate a fully active capturing surface.

For 356A11 and 368D04, solutions of human IL-22 at 400, 200, 100, 50, 25, 12.5, 6.25 and 0 nM were injected in triplicates at a flow rate of 100 μl per minute (high flow to avoid non specific binding) for 3 minutes, and the amount of bound material as a function of time was recorded as sensorgrams. The dissociation phase was monitored in HBS/EP buffer for 60 minutes at the same flow rate followed by two 5 μl injections of glycine pH 1.5 to regenerate a fully active capturing surface.

All kinetic experiments were done at 22.5° C. in HBS/EP buffer. Blank and buffer effects were subtracted for each sensorgram using double referencing. In control experiments the first injection contained buffer.

The kinetic data were analyzed using BIAevaluation software 3.0.2 applied to a 1:1 model. The apparent dissociation ($K_d$) and association ($K_a$) rate constants were calculated from the appropriate regions of the sensorgrams using a global analysis. The affinity constants of the interaction between antibody and analyte were calculated from the kinetic rate constants by the following formulae: $K_D=K_d/K_a$, where $K_D$ is the dissociation constant and $K_A=K_a/K_d$, where $K_A$ is the association constant. The binding data for Ab-02 and AB-04 are summarized in Tables 11A and 11B. The binding data for 356A11 and 368D04 are summarized in Table 12.

TABLE 11A

Kinetic parameters for the interaction between human IL-22 and anti-IL-22 antibodies Ab-02 and Ab-04

| | Ab-02 $k_a$ ($M^{-1}s^{-1}$) | Ab-02 $k_d$ ($s^{-1}$) | Ab-04 $k_a$ ($M^{-1}s^{-1}$) | Ab-04 $k_d$ ($s^{-1}$) |
|---|---|---|---|---|
| Protein A/G | 2.78E+05 | 1.45E−03 | 5.15E+05 | 1.23E−03 |

TABLE 11B

Kinetic data of rat monoclonal antibodies for human IL-22

| Antibody | Ka (1/Ms) | Kd (1/s) | KA (1/M) | KD (M) | Chi2 |
|---|---|---|---|---|---|
| Ab-02 | 2.78E+05 | 1.45E−03 | 1.92E+08 | 5.22E−08 | 0.49 |
| Ab-04 | 5.15E+05 | 1.23E−03 | 4.22E+08 | 2.38E−09 | 0.53 |

TABLE 12

Kinetic data of human monoclonal antibodies for human IL-22

| Antibody | Ka (1/Ms) | Kd (1/s) | KA (1/M) | KD (M) | Chi2 |
|---|---|---|---|---|---|
| 356A11 | 7.91E+04 | 4.27E−06 | 1.85E+10 | 5.40E−11 | 0.223 |
| 368D04 | 1.89E+05 | 2.50E−05 | 7.56E+09 | 1.32E−10 | 0.298 |

These results show that the human monoclonal anti-IL-22 antibodies of this invention have a significantly higher affinity for human IL-22 than the rat monoclonal anti-IL-22 antibodies Ab-02 and Ab-04, described in WO 2005/000897 and WO 02/068476 as having the ability to neutralize human IL-22. Specifically, the dissociation constant of 356A11 ($K_D$=5.40× $10^{-11}$ M or 0.054 nM) for human IL-22 is approximately 1000-fold and more than 40-fold greater than the dissociation constants of Ab-02 ($K_D$=5.22×$10^{-8}$M or 52 nM) and Ab-04 ($K_D$=2.38×$10^{-9}$ M or 2.38 nM), respectively. Similarly, 368D04 ($K_D$=1.32×$10^{-10}$ M or 0.132 nM) has an approximately 400-fold and 18-fold stronger affinity for human IL-22 than Ab-02 and Ab-04, respectively. The binding profiles of 356A11 and 36804 for monkey, murine, and rat IL-22 were similar to that of human IL-22 (data not shown).

The binding specificities of 356A11 and 368D04 were also evaluated using BIA. Neither antibody showed cross reactivity with human IL-10, human IL-19, human IL-20, human IL-24, human IL-28A, human IL-29, human IFN-α2c, or human IFN-ω (data not shown).

Example 12

Model for Treatment of Arthritis

Arthritis is a disease characterized by inflammation in the joints. Rheumatoid Arthritis (RA) is the most frequent form of arthritis, involving inflammation of connective tissue and the synovial membrane, a membrane that lines the joint. The inflamed synovial membrane often infiltrates the joint and damages joint cartilage and bone. Both IL-22 and IL-22R protein and/or transcript are associated with human disease. In RA synovial biopsies, IL-22 protein is detected in vimentin+ synovial fibroblasts and some CD68+ macrophages while IL-22R is detected in synovial fibroblasts. Treatment of synovial fibroblasts with IL-22 induces the production of monocyte chemoattractant protein-1, MCP-1, as well as general metabolic activity (Ikeuchi, H. et al. (2005) *Arthritis Rheum.* 52:1037-46).

IL-22 is used to study its effect on cells from the synovial membrane, the membrane that lines the joints. Human fibroblast-like synoviocytes (HFLS) (Cell Applications (San Diego, Calif.)) are isolated from synovial tissues of rheumatoid arthritis patients undergoing joint surgery. HFLS are cultured with human IL-22 for 48 hours, and the supernatants are removed and tested for chemokines and cytokines by ELISA. IL-22 will increase HFLS secretion of chemokines MCP-1, Eotaxin, and IP-10, and cytokines TNFα, IL-6, and IL-8. These chemokines and cytokines are known in the art to promote inflammation through a number of activities, and increased concentrations in the joints caused by IL-22 exacerbates inflammation and RA.

IL-22 is used to regulate the clinical progression of CIA (Collagen Induced Arthritis). CIA is the standard mouse and rat model for studying rheumatoid arthritis, see e.g., Holmdahl et al., (2002) *Ageing Res. Rev.*, 1:135. On day 0, mice are injected with 100 μg of Collagen Type II in complete Freund's adjuvant, and on day 21, the mice are boosted with 100 μg of Collagen Type II in incomplete Freund's adjuvant. On day 21, the mice are also injected daily with 1 μg of IL-22, and each day, the mice are examined for disease. The clinical signs are scored as follows: 0=no swelling, 1=1 to 2 swollen digits or swollen ankle, 2=more than 2 swollen digits or mild paw swelling, 3=extensive paw swelling, and 4=ankylosis of paw. Mice injected with PBS after the collagen injections progressively develop disease. Mice that are injected with IL-22 after the collagen injections progressively develop more severe disease. Because treatment with IL-22 specifically exacerbates CIA, treatment with anti-IL-22 antibodies, for example with germlined 087B03, 368D04, 354A08 or 356A11, is expected to suppress or delay CIA. Thus, since this model predicts treatment efficacy for RA, treatment with anti-IL-22 antibodies, including germlined or non-germlined 087B03, 368D04, 354A08 or 356A11, is expected to suppress or delay RA in humans.

Example 13

Treatment of Patients

Patients with an autoimmune disorder, respiratory disorder, inflammatory condition of the skin, cardiovascular system, nervous system, kidneys, liver and pancreas or transplant patients are among the types of patients that may be treated with the antibodies of the invention. Exemplary treatment regimens and expected outcomes of antibodies according to this invention, including 087B03, 368D04, 354A08, and 356A11, are provided below. Dosages and frequencies of administration other than those in Table 13 may also be used. The skilled artisan can adjust treatment regimens as necessary based on route of administration or other known variables, such as the age, weight, condition, sex, severity of medical condition, etc. of the patient to be treated.

TABLE 13

Treatment Regimens

| Disorder | Treated with | Dosage Range | Frequency | Expected Outcome |
|---|---|---|---|---|
| Multiple Sclerosis | 087B03, 368D04, 356A11, or 354A08 | 250 μg/kg to 2 mg/kg | weekly, biweekly, or monthly | improvement or stabilization of condition |
| Rheumatoid Arthritis | 087B03, 368D04, 356A11, or 354A08 | 250 μg/kg to 2 mg/kg | weekly, biweekly, or monthly | improvement or stabilization of condition |
| Psoriasis | 087B03, 368D04, 356A11, or 354A08 | 250 μg/kg to 2 mg/kg | weekly, biweekly, or monthly | improvement or stabilization of condition |
| IBD | 087B03, 368D04, 356A11, or 354A08 | 250 μg/kg to 2 mg/kg | monthly, biweekly, or monthly | improvement or stabilization of condition |
| Alzheimer's Disease | 087B03, 368D04, 356A11, or 354A08 | 250 μg/kg to 2 mg/kg | monthly, biweekly, or monthly | improvement or stabilization of condition |

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supercede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated antibody, or antigen-binding fragment thereof, that specifically binds to IL-22, wherein the antibody, or antigen-binding fragment thereof, comprises a $V_H$ domain comprising an amino acid sequence which is at least 95% identical to the amino acid sequence shown in SEQ ID NO:599 or a $V_L$ domain comprising an amino acid sequence which is at least 95% identical to the amino acid sequence shown in SEQ ID NO:600.

2. The antibody of claim 1, wherein the $V_L$ domain comprises three complementarity determining regions (CDRs) comprising the amino acid sequences of SEQ ID NO:605, 606, and 607.

3. The antibody of claim 1, wherein the $V_H$ domain comprises three complementarity determining regions (CDRs) comprising the amino acid sequences of SEQ ID NO: 602, 603, and 604.

4. The antibody of claim 1, wherein the association constant of the antibody for human IL-22 is at least $10^{10}$ M$^{-1}$.

5. The antibody of claim 1, wherein the antibody blocks IL-22 mediated proliferation of BaF3 cells with an IC$_{50}$ of 150 pM or less and wherein the BaF3 cells comprise a human IL-22 receptor.

6. The antibody of claim 1, wherein the antibody blocks IL-22 mediated GROa secretion from HT29 cells with an IC$_{50}$ of 150 pM or less.

7. The antibody of claim 1, wherein the antibody inhibits the binding of IL-22 to IL-22R or a receptor complex comprising IL-22R and IL-10R2.

8. The antibody of claim 1, wherein the antibody is human.

9. The antibody of claim 1, wherein the antibody is IgG1 or IgG4.

10. A pharmaceutical composition comprising the antibody of claim 1.

11. An isolated antibody, or antigen-binding fragment thereof, that specifically binds to IL-22, wherein the antibody, or antigen-binding fragment thereof, comprises 1) a $V_H$ domain comprising an amino acid sequence that is at least 85% identical to the amino acid sequence of SEQ ID NO:599 and 2) a $V_L$ domain comprising an amino acid sequence that is at least 85% identical to the amino acid sequence of SEQ ID NO:600.

12. The antibody of claim 11, wherein the $V_H$ domain comprises an amino acid sequence that is at least 90% identical to the amino acid sequence of SEQ ID NO:599 and the $V_L$ domain comprises an amino acid sequence that is at least 90% identical to the amino acid sequence of SEQ ID NO:600.

13. The antibody of claim 11, wherein the $V_H$ domain comprises an amino acid sequence that is at least 95% identical to the amino acid sequence of SEQ ID NO:599 and the $V_L$ domain comprises an amino acid sequence that is at least 95% identical to the amino acid sequence of SEQ ID NO:600.

14. The antibody of claim 11, wherein the $V_H$ domain comprises an amino acid sequence that is at least 98% identical to the amino acid sequence of SEQ ID NO:599 and the $V_L$ domain comprises an amino acid sequence that is at least 98% identical to the amino acid sequence of SEQ ID NO:600.

15. The antibody of claim 11, wherein the $V_H$ domain differs by no more than 5 amino acids from the amino acid sequence of SEQ ID NO:599 and wherein the $V_L$ domain differs by no more than 5 amino acids from the amino acid sequence of SEQ ID NO:600.

16. An isolated antibody, or antigen-binding fragment thereof, that specifically binds to IL-22, wherein the antibody, or antigen-binding fragment thereof, comprises 1) a $V_H$ domain comprising an amino acid sequence that is at least 85% identical to SEQ ID NO:599, wherein the $V_H$ domain comprises three complementarity determining regions (CDRs) comprising the amino acid sequences of SEQ ID NO:602, 603, and 604, and 2) a $V_L$ domain comprising an amino acid sequence that is at least 85% identical to SEQ ID NO:600, wherein the $V_L$ domain comprises three CDRs comprising the amino acid sequences of SEQ ID NO:605, 606, and 607.

17. The antibody of claim 16, wherein the $V_H$ domain comprises an amino acid sequence that is at least 90% identical to SEQ ID NO:599 and the $V_L$ domain comprises an amino acid sequence that is at least 90% identical to SEQ ID NO:600.

18. The antibody of claim 16, wherein the $V_H$ domain comprises an amino acid sequence that is at least 95% identical to SEQ ID NO:599 and the $V_L$ domain comprises an amino acid sequence that is at least 95% identical to SEQ ID NO:600.

19. The antibody of claim 16, wherein the $V_H$ domain comprises an amino acid sequence that is at least 98% identical to SEQ ID NO:599 and the $V_L$ domain comprises an amino acid sequence that is at least 98% identical to SEQ ID NO:600.

20. The antibody of claim 16, wherein the $V_H$ domain differs by no more than 5 amino acids from the amino acid sequence of SEQ ID NO:599 and wherein the $V_L$ domain differs by no more than 5 amino acids from the amino acid sequence of SEQ ID NO:600.

* * * * *

SEQUENCE LISTING

<160> NUMBER OF SEQ ID NOS: 634

<210> SEQ ID NO 1
<211> LENGTH: 178
<212> TYPE: PRT
<213> ORGANISM: Homo sapiens

<400> SEQUENCE: 1

Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Trp Pro Phe Leu Ala Arg Leu Ser Asn Arg Leu
        115                 120                 125

Ser Thr Cys His Ile Glu Gly Asp Asp Leu His Ile Gln Arg Asn Val
    130                 135                 140

Gln Lys Leu Lys Asp Thr Val Lys Lys Leu Gly Glu Ser Gly Glu Ile
145                 150                 155                 160

Lys Ala Ile Gly Glu Leu Asp Leu Leu Phe Met Ser Leu Arg Asn Ala
                165                 170                 175

Cys Ile

<210> SEQ ID NO 2
<211> LENGTH: 1191
<212> TYPE: DNA
<213> ORGANISM: Homo sapiens

<400> SEQUENCE: 2
gaattcggcc aaagaggcct acaggttctc cttccccagt caccagttgc tcgagttaga      60
attgtctgca atggccgccc tgcagaaatc tgtgagctct ttccttatgg ggaccctggc     120
caccagctgc tccttctct tggccctctt ggtacaggga ggagcagctg cgccatcag      180 ctcccactgc aggcttgaca gtccaactt ccagcagccc tatatcacca accgcacctt     240
catgctggct aaggaggcta gcttggctga taacaacaca gacgttcgtc tcattgggga     300
gaaactgttc cacggagtca gtatgagtga gcgctgctat ctgatgaagc aggtgctgaa     360
cttcaccctt gaagaagtgc tgttccctca atctgatagg ttccagcctt atatgcagga     420
ggtggtgccc ttcctggcca ggctcagcaa caggctaagc acatgtcata ttgaaggtga     480
tgacctgcat atccagagga atgtgcaaaa gctgaaggac acagtgaaaa agcttggaga     540
gagtggagag atcaaagcaa ttggagaact ggatttgctg tttatgtctc tgagaaatgc     600
ctgcatttga ccagagcaaa gctgaaaat gaataactaa ccccttttcc ctgctagaaa     660
taacaattag atgccccaaa gcgatttttt ttaaccaaaa ggaagatggg aagccaaact     720
ccatcatgat gggtggattc caaatgaacc cctgcgttag ttacaaagga aaccaatgcc     780

```
actttttgttt ataagaccag aaggtagact ttctaagcat agatatttat tgataacatt      840
tcattgtaac tggtgttcta tacacagaaa acaatttatt ttttaaataa ttgtcttttt       900
ccataaaaaa gattactttc cattcccttta ggggaaaaaa cccctaaata gcttcatgtt      960
tccataatca gtactttata tttataaatg tatttattat tattataaga ctgcatttta     1020
tttatatcat tttattaata tggatttatt tatagaaaca tcattcgata ttgctacttg     1080
agtgtaaggc taatattgat atttatgaca ataattatag agctataaca tgtttatttg     1140
acctcaataa acacttggat atcctaaaaa aaaaaaaaaa aaagcggccg c              1191
```

<210> SEQ ID NO 3
<211> LENGTH: 179
<212> TYPE: PRT
<213> ORGANISM: Mus musculus

<400> SEQUENCE: 3

```
Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val
```

<210> SEQ ID NO 4
<211> LENGTH: 540
<212> TYPE: DNA
<213> ORGANISM: Mus musculus

<400> SEQUENCE: 4

```
atggctgtcc tgcagaaatc tatgagtttt tcccttatgg ggactttggc cgccagctgc       60
ctgcttctca ttgccctgtg ggcccaggag gcaaatgcgc tgcccgtcaa cacccggtgc      120
aagcttgagg tgtccaactt ccagcagccg tacatcgtca accgcacctt tatgctggcc      180
aaggaggcca gccttgcaga taacaacaca gacgtccggc tcatcgggga gaaactgttc      240
cgaggagtca gtgctaaaga tcagtgctac ctgatgaagc aggtgctcaa cttcacccttg     300 gaagacgttc tgctccccca gtcagacagg ttcagcccct acatgcagga ggtggtacct      360
ttcctgacca aactcagcaa tcagctcagc tcctgtcaca tcagcggtga cgaccagaac      420
```

```
atccagaaga atgtcagaag gctgaaggag acagtgaaaa agcttggaga gagtggagag    480
atcaaggcga ttggggaact ggacctgctg tttatgtctc tgagaaatgc ttgcgtctga    540
```

<210> SEQ ID NO 5
<211> LENGTH: 119
<212> TYPE: PRT
<213> ORGANISM: Homo sapiens

<400> SEQUENCE: 5

```
Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Arg Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Ser Ser Leu Arg Ser Glu Asp Thr Ala Val Tyr Tyr Cys
            85                  90                  95

Ala Arg Gly Leu Trp Val Trp Asp Pro Leu Asp Tyr Trp Gly Arg Gly
            100                 105                 110

Thr Leu Val Thr Val Ser Ser
        115
```

<210> SEQ ID NO 6
<211> LENGTH: 108
<212> TYPE: PRT
<213> ORGANISM: Homo sapiens

<400> SEQUENCE: 6

```
Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
            85                  90                  95

Thr Phe Gly Gly Gly Thr Lys Leu Glu Ile Lys Arg
            100                 105
```

<210> SEQ ID NO 7
<211> LENGTH: 245
<212> TYPE: PRT
<213> ORGANISM: Homo sapiens

<400> SEQUENCE: 7

```
Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Arg Gly Leu Glu Trp Val
```

```
                   35                  40                  45
Ser Ala Ile Ser Gly Ser Gly Gly Ser Thr Tyr Tyr Ala Asp Ser Val
 50                  55                  60

Lys Gly Arg Ile Thr Ile Ser Arg Asp Asn Ala Lys Asn Ser Leu Tyr
 65                  70                  75                  80

Leu Gln Met Ser Ser Leu Arg Ser Glu Asp Thr Ala Val Tyr Tyr Cys
                 85                  90                  95

Ala Arg Gly Leu Trp Val Trp Asp Pro Leu Asp Tyr Trp Gly Arg Gly
                100                 105                 110

Thr Leu Val Thr Val Ser Ser Gly Gly Gly Ser Gly Gly Gly
                115                 120                 125

Ser Gly Gly Gly Ser Asp Ile Gln Met Thr Gln Ser Pro Ser Thr
    130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
                180                 185                 190

Pro Ser Arg Phe Ser Gly Ser Gly Ser Gly Thr Asp Phe Thr Leu Thr
                195                 200                 205

Ile Ser Ser Leu Gln Pro Asp Asp Phe Ala Thr Tyr Tyr Cys Gln Gln
210                 215                 220

Tyr Ser Asn Tyr Pro Leu Thr Phe Gly Gly Gly Thr Lys Leu Glu Ile
225                 230                 235                 240

Lys Arg Ala Ala Ala
                245

<210> SEQ ID NO 8
<211> LENGTH: 5
<212> TYPE: PRT
<213> ORGANISM: Homo sapiens

<400> SEQUENCE: 8

Asp Tyr Tyr Met Ser
1               5

<210> SEQ ID NO 9
<211> LENGTH: 17
<212> TYPE: PRT
<213> ORGANISM: Homo sapiens

<400> SEQUENCE: 9

Ala Ile Ser Gly Ser Gly Gly Ser Thr Tyr Tyr Ala Asp Ser Val Lys
1               5                   10                  15

Gly

<210> SEQ ID NO 10
<211> LENGTH: 10
<212> TYPE: PRT
<213> ORGANISM: Homo sapiens

<400> SEQUENCE: 10

Gly Leu Trp Val Trp Asp Pro Leu Asp Tyr
1               5                   10

<210> SEQ ID NO 11
<211> LENGTH: 11
<212> TYPE: PRT
```

<213> ORGANISM: Homo sapiens

<400> SEQUENCE: 11

Arg Ala Ser Glu Gly Ile Tyr His Trp Leu Ala
1               5                   10

<210> SEQ ID NO 12
<211> LENGTH: 7
<212> TYPE: PRT
<213> ORGANISM: Homo sapiens

<400> SEQUENCE: 12

Lys Ala Ser Ser Leu Ala Ser
1               5

<210> SEQ ID NO 13
<211> LENGTH: 9
<212> TYPE: PRT
<213> ORGANISM: Homo sapiens

<400> SEQUENCE: 13

Gln Gln Tyr Ser Asn Tyr Pro Leu Thr
1               5

<210> SEQ ID NO 14
<211> LENGTH: 357
<212> TYPE: DNA
<213> ORGANISM: Homo sapiens

<400> SEQUENCE: 14

```
gaggtgcagt tggtggagtc tgggggaggc ttggtcacgc ctggagggtc cctgagactc      60
tcctgtgcag cctctggatt caccttcagt gactactaca tgagctggat ccgccaggct     120
ccagggaggg gctggagtg gtctcagct attagtggta gtggtggtag cacatactac       180
gcagactccg tgaagggccg gatcaccatc tccagagaca cgccaagaa ctcactgtat      240
ctgcaaatga gcagcctgag atctgaggac acggccgtgt attactgtgc gagagggctt    300
tgggtttggg atcctcttga ctactggggc agaggaaccc tggtcaccgt ctcctca       357
```

<210> SEQ ID NO 15
<211> LENGTH: 324
<212> TYPE: DNA
<213> ORGANISM: Homo sapiens

<400> SEQUENCE: 15

```
gacatccaga tgacccagtc tccttccacc ctgtctgcat ctattggaga cagagtcacc      60
atcacctgcc gggccagtga gggtatttat cactggttgg cctggtatca gcagaagcca    120
gggaaagccc ctaaactcct gatctataag gcctctagtt tagccagtgg ggccccatca    180
aggttcagcg gcagtggatc tgggacagat ttcactctca ccatcagcag cctgcagcct    240
gatgattttg caactattat ctgccaacaa tatagtaatt atccgctcac tttcggcgga    300
gggaccaagc tggagatcaa acgt                                            324
```

<210> SEQ ID NO 16
<211> LENGTH: 735
<212> TYPE: DNA
<213> ORGANISM: Homo sapiens

<400> SEQUENCE: 16

```
gaagtgcagc tggtggagtc tgggggaggc ttggtcacgc ctggagggtc cctgagactc      60
tcctgtgcag cctctggatt caccttcagt gactactaca tgagctggat ccgccaggct    120
```

```
ccagggaggg ggctggagtg ggtctcagct attagtggta gtggtggtag cacatactac    180
gcagactccg tgaagggccg gatcaccatc tccagagaca acgccaagaa ctcactgtat    240
ctgcaaatga gcagcctgag atctgaggac acggccgtgt attactgtgc gagagggctt    300
tgggtttggg atcctcttga ctactgggc agaggaaccc tggtcaccgt ctcttcaggt     360
ggaggcggtt caggcggagg tggcagcggc ggtggcggat cggacatcca gatgacccag    420
tctccttcca ccctgtctgc atctattgga gacagagtca ccatcacctg ccgggccagt    480
gagggtattt atcactggtt ggcctggtat cagcagaagc cagggaaagc ccctaaactc    540
ctgatctata aggcctctag tttagccagt ggggcccat caaggttcag cggcagtgga     600
tctgggacag atttcactct caccatcagc agcctgcagc ctgatgattt tgcaacttat    660
tactgccaac aatatagtaa ttatccgctc actttcggcg gagggaccaa gctggagatc    720
aaacgtgcgg ccgca                                                    735
```

```
<210> SEQ ID NO 17
<211> LENGTH: 15
<212> TYPE: DNA
<213> ORGANISM: Homo sapiens

<400> SEQUENCE: 17
gactactaca tgagc                                                     15
```

```
<210> SEQ ID NO 18
<211> LENGTH: 51
<212> TYPE: DNA
<213> ORGANISM: Homo sapiens

<400> SEQUENCE: 18
gctattagtg gtagtggtgg tagcacatac tacgcagact ccgtgaaggg c              51
```

```
<210> SEQ ID NO 19
<211> LENGTH: 30
<212> TYPE: DNA
<213> ORGANISM: Homo sapiens

<400> SEQUENCE: 19
gggctttggg tttgggatcc tcttgactac                                      30
```

```
<210> SEQ ID NO 20
<211> LENGTH: 33
<212> TYPE: DNA
<213> ORGANISM: Homo sapiens

<400> SEQUENCE: 20
cgggccagtg agggtattta tcactggttg gcc                                  33
```

```
<210> SEQ ID NO 21
<211> LENGTH: 21
<212> TYPE: DNA
<213> ORGANISM: Homo sapiens

<400> SEQUENCE: 21
aaggcctcta gtttagccag t                                               21
```

```
<210> SEQ ID NO 22
<211> LENGTH: 27
<212> TYPE: DNA
<213> ORGANISM: Homo sapiens

<400> SEQUENCE: 22
```

```
caacaatata gtaattatcc gctcact                                        27
```

<210> SEQ ID NO 23
<211> LENGTH: 119
<212> TYPE: PRT
<213> ORGANISM: Homo sapiens

<400> SEQUENCE: 23

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser
        115

<210> SEQ ID NO 24
<211> LENGTH: 108
<212> TYPE: PRT
<213> ORGANISM: Homo sapiens

<400> SEQUENCE: 24

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys Arg
            100                 105

<210> SEQ ID NO 25
<211> LENGTH: 245
<212> TYPE: PRT
<213> ORGANISM: Homo sapiens

<400> SEQUENCE: 25

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

```
Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Ser Gly Thr Asp Phe Thr Leu Thr
        195                 200                 205

Ile Ser Ser Leu Gln Pro Asp Asp Phe Ala Thr Tyr Tyr Cys Gln Gln
210                 215                 220

Tyr Ser Asn Tyr Pro Leu Thr Phe Gly Gly Gly Thr Lys Leu Glu Ile
225                 230                 235                 240

Lys Arg Ala Ala Ala
            245

<210> SEQ ID NO 26
<211> LENGTH: 5
<212> TYPE: PRT
<213> ORGANISM: Homo sapiens

<400> SEQUENCE: 26

Ser Tyr Gly Ile Ser
1               5

<210> SEQ ID NO 27
<211> LENGTH: 17
<212> TYPE: PRT
<213> ORGANISM: Homo sapiens

<400> SEQUENCE: 27

Trp Ile Ser Ala Tyr Thr Gly Asn Thr Asn Tyr Ala Gln Lys Phe Gln
1               5                   10                  15

Gly

<210> SEQ ID NO 28
<211> LENGTH: 10
<212> TYPE: PRT
<213> ORGANISM: Homo sapiens

<400> SEQUENCE: 28

Asp Arg Gly Tyr Tyr Asp Ala Phe Asp Ile
1               5                   10

<210> SEQ ID NO 29
<211> LENGTH: 11
<212> TYPE: PRT
<213> ORGANISM: Homo sapiens
```

<400> SEQUENCE: 29

Arg Ala Ser Glu Gly Ile Tyr His Trp Leu Ala
1               5                   10

<210> SEQ ID NO 30
<211> LENGTH: 7
<212> TYPE: PRT
<213> ORGANISM: Homo sapiens

<400> SEQUENCE: 30

Lys Ala Ser Ser Leu Ala Ser
1               5

<210> SEQ ID NO 31
<211> LENGTH: 9
<212> TYPE: PRT
<213> ORGANISM: Homo sapiens

<400> SEQUENCE: 31

Gln Gln Tyr Ser Asn Tyr Pro Leu Thr
1               5

<210> SEQ ID NO 32
<211> LENGTH: 357
<212> TYPE: DNA
<213> ORGANISM: Homo sapiens

<400> SEQUENCE: 32
caggtgcagc tggtggagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg atcagcgctt acactggtaa cacaaactat      180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgcttttga tatctggggc caaggcaccc tggtcaccgt ctcctca        357

<210> SEQ ID NO 33
<211> LENGTH: 324
<212> TYPE: DNA
<213> ORGANISM: Homo sapiens

<400> SEQUENCE: 33
gacatccaga tgacccagtc tccttccacc ctgtctgcat ctattggaga cagagtcacc      60
atcacctgcc gggccagtga gggtatttat cactggttgg cctggtatca gcagaagcca     120
gggaaagccc ctaaactcct gatctataag gcctctagtt tagccagtgg ggccccatca     180
aggttcagcg gcagtggatc tgggacagat ttcactctca ccatcagcag cctgcagcct     240
gatgattttg caacttatta ctgccaacaa tatagtaatt atccgctcac tttcggcgga     300
gggaccaagc tggagatcaa acgt                                            324

<210> SEQ ID NO 34
<211> LENGTH: 735
<212> TYPE: DNA
<213> ORGANISM: Homo sapiens

<400> SEQUENCE: 34
caggtgcagc tggtggagtc tggagctgag gtgaagaagc ctggggcctc agtgaaggtc      60
tcctgcaagg cttctggtta cacctttacc agttatggta tcagctgggt gcgacaggcc     120

```
cctggacaag ggcttgagtg gatgggatgg atcagcgctt acactggtaa cacaaactat      180
gcacagaagt tccagggcag agtcaccatg accacagaca catccacgag cacagcctac      240
atggaactga ggagcctgag atctgacgac acggccgtgt attactgtgc gagagatcgt      300
ggatactatg atgcttttga tatctggggc caaggcaccc tggtcaccgt ctcctcaggt      360
ggaggcggtt caggcggagg tggcagcggc ggtggcggat cggacatcca gatgacccag      420
tctccttcca ccctgtctgc atctattgga gacagagtca ccatcacctg ccgggccagt      480
gagggtattt atcactggtt ggcctggtat cagcagaagc cagggaaagc ccctaaactc      540
ctgatctata aggcctctag tttagccagt ggggccccat caaggttcag cggcagtgga      600
tctgggacag atttcactct caccatcagc agcctgcagc tgatgatttt gcaacttat       660 tactgccaac aatatagtaa ttatccgctc actttcggcg gagggaccaa gctggagatc      720
aaacgtgcgg ccgca                                                      735
```

<210> SEQ ID NO 35
<211> LENGTH: 15
<212> TYPE: DNA
<213> ORGANISM: Homo sapiens

<400> SEQUENCE: 35

```
agttatggta tcagc                                                       15
```

<210> SEQ ID NO 36
<211> LENGTH: 51
<212> TYPE: DNA
<213> ORGANISM: Homo sapiens

<400> SEQUENCE: 36

```
tggatcagcg cttacactgg taacacaaac tatgcacaga agttccaggg c                51
```

<210> SEQ ID NO 37
<211> LENGTH: 30
<212> TYPE: DNA
<213> ORGANISM: Homo sapiens

<400> SEQUENCE: 37

```
gatcgtggat actatgatgc ttttgatatc                                       30
```

<210> SEQ ID NO 38
<211> LENGTH: 33
<212> TYPE: DNA
<213> ORGANISM: Homo sapiens

<400> SEQUENCE: 38

```
cgggccagtg agggtattta tcactggttg gcc                                   33
```

<210> SEQ ID NO 39
<211> LENGTH: 21
<212> TYPE: DNA
<213> ORGANISM: Homo sapiens

<400> SEQUENCE: 39

```
aaggcctcta gtttagccag t                                                21
```

<210> SEQ ID NO 40
<211> LENGTH: 27
<212> TYPE: DNA
<213> ORGANISM: Homo sapiens

<400> SEQUENCE: 40
caacaatata gtaattatcc gctcact				27

<210> SEQ ID NO 41
<211> LENGTH: 119
<212> TYPE: PRT
<213> ORGANISM: Homo sapiens

<400> SEQUENCE: 41

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala His Ile Trp Tyr Asp Gly Ser Asn Glu Lys Tyr Ala Asp Ser Val
    50                  55                  60

Lys Gly Arg Met Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gln His Trp Ile Thr Ala Phe Asp Ile Trp Gly Lys Gly
            100                 105                 110

Thr Leu Val Thr Val Ser Ser
        115

<210> SEQ ID NO 42
<211> LENGTH: 111
<212> TYPE: PRT
<213> ORGANISM: Homo sapiens

<400> SEQUENCE: 42

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu Gly
            100                 105                 110

<210> SEQ ID NO 43
<211> LENGTH: 249
<212> TYPE: PRT
<213> ORGANISM: Homo sapiens

<400> SEQUENCE: 43

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala His Ile Trp Tyr Asp Gly Ser Asn Glu Lys Tyr Ala Asp Ser Val
          50                  55                  60

Lys Gly Arg Met Thr Val Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gln His Trp Ile Thr Ala Phe Asp Ile Trp Gly Lys Gly
            100                 105                 110

Thr Leu Val Thr Val Ser Ser Gly Gly Gly Ser Gly Ala Gly Gly
        115                 120                 125

Ser Gly Gly Gly Ser Gln Ser Val Leu Thr Gln Pro Ala Ser Val
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Glu Gly Ser Lys Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Gln Ala Glu Asp Glu Ala Asp Tyr Tyr Cys
    210                 215                 220

Ser Ser Tyr Thr Thr Arg Ser Thr Arg Val Phe Gly Gly Gly Thr Lys
225                 230                 235                 240

Leu Thr Val Leu Gly Ala Ala Ala His
                245

<210> SEQ ID NO 44
<211> LENGTH: 5
<212> TYPE: PRT
<213> ORGANISM: Homo sapiens

<400> SEQUENCE: 44

Asn Tyr Gly Met Tyr
1               5

<210> SEQ ID NO 45
<211> LENGTH: 17
<212> TYPE: PRT
<213> ORGANISM: Homo sapiens

<400> SEQUENCE: 45

His Ile Trp Tyr Asp Gly Ser Asn Glu Lys Tyr Ala Asp Ser Val Lys
1               5                   10                  15

Gly

<210> SEQ ID NO 46
<211> LENGTH: 10
<212> TYPE: PRT
<213> ORGANISM: Homo sapiens

<400> SEQUENCE: 46

Glu Gln His Trp Ile Thr Ala Phe Asp Ile
1               5                   10

<210> SEQ ID NO 47
<211> LENGTH: 14
<212> TYPE: PRT
<213> ORGANISM: Homo sapiens -continued

```
<400> SEQUENCE: 47

Thr Gly Thr Ser Ser Asp Val Gly Gly Tyr Asn Tyr Val Ser
1               5                   10

<210> SEQ ID NO 48
<211> LENGTH: 7
<212> TYPE: PRT
<213> ORGANISM: Homo sapiens

<400> SEQUENCE: 48

Glu Gly Ser Lys Arg Pro Ser
1               5

<210> SEQ ID NO 49
<211> LENGTH: 10
<212> TYPE: PRT
<213> ORGANISM: Homo sapiens

<400> SEQUENCE: 49

Ser Ser Tyr Thr Thr Arg Ser Thr Arg Val
1               5                   10

<210> SEQ ID NO 50
<211> LENGTH: 357
<212> TYPE: DNA
<213> ORGANISM: Homo sapiens

<400> SEQUENCE: 50
cagatgcagc tggtgcagtc tgggggaggc gtggtccagc ctggggaggtc cctgagactc      60
tcctgtgcag cctctggatt caccttcagt aactatggca tgtactgggt ccgccaggct     120
ccaggcaagg ggctggagtg ggtggcacat atttggtatg atggaagtaa tgaaaagtat     180
gcagactccg tgaagggccg aatgaccgtc tccagagaca attccaggaa cacgttgtat     240
ttgcaaatga acagcctgag agccgaggac acggctgtgt attactgtgc gacagagcaa     300
cactggatta ctgcttttga tatctggggc aaaggcaccc tggtcaccgt ctcctca       357

<210> SEQ ID NO 51
<211> LENGTH: 333
<212> TYPE: DNA
<213> ORGANISM: Homo sapiens

<400> SEQUENCE: 51
cagtctgtgc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca aagcccccaa actcatgatt tatgagggca gtaagcggcc ctcagggggtt     180
tctaatcgct tctctggctc caagtctggc aacacggcct ccctgacaat ctctgggctc     240
caggctgagg acgaggctga ttattactgc agctcatata caaccaggag cactcgagtt     300
ttcggcggag ggaccaagct gaccgtccta ggt                                  333

<210> SEQ ID NO 52
<211> LENGTH: 744
<212> TYPE: DNA
<213> ORGANISM: Homo sapiens

<400> SEQUENCE: 52
cagatgcagc tggtgcagtc tgggggaggc gtggtccagc ctggggaggtc cctgagactc      60
tcctgtgcag cctctggatt caccttcagt aactatggca tgtactgggt ccgccaggct     120
ccaggcaagg ggctggagtg ggtggcacat atttggtatg atggaagtaa tgaaaagtat     180
```

```
gcagactccg tgaagggccg aatgaccgtc tccagagaca attccaggaa cacgttgtat    240
ttgcaaatga acagcctgag agccgaggac acggctgtgt attactgtgc gacagagcaa    300
cactggatta ctgcttttga tatctggggc aaaggcaccc tggtcaccgt ctcctcaggt    360
ggaggcggtt caggcgcagg tggcagcggc ggtggcggat cgcagtctgt gctgactcag    420
cctgcctccg tgtctgggtc tcctggacag tcgatcacca tctcctgcac tggaaccagc    480
agtgacgttg gtggttataa ctatgtctcc tggtaccaac aacacccagg caaagccccc    540
aaactcatga tttatgaggg cagtaagcgg ccctcagggg tttctaatcg cttctctggc    600
tccaagtctg gcaacacggc ctccctgaca atctctgggc tccaggctga ggacgaggct    660
gattattact gcagctcata caaaccagg agcactcgag ttttcggcgg agggaccaag    720
ctgaccgtcc taggtgcggc cgca                                           744
```

<210> SEQ ID NO 53
<211> LENGTH: 15
<212> TYPE: DNA
<213> ORGANISM: Homo sapiens

<400> SEQUENCE: 53

```
aactatggca tgtac                                                      15
```

<210> SEQ ID NO 54
<211> LENGTH: 51
<212> TYPE: DNA
<213> ORGANISM: Homo sapiens

<400> SEQUENCE: 54

```
catatttggt atgatggaag taatgaaaag tatgcagact ccgtgaaggg c              51
```

<210> SEQ ID NO 55
<211> LENGTH: 30
<212> TYPE: DNA
<213> ORGANISM: Homo sapiens

<400> SEQUENCE: 55

```
gagcaacact ggattactgc ttttgatatc                                      30
```

<210> SEQ ID NO 56
<211> LENGTH: 42
<212> TYPE: DNA
<213> ORGANISM: Homo sapiens

<400> SEQUENCE: 56

```
actggaacca gcagtgacgt tggtggttat aactatgtct cc                        42
```

<210> SEQ ID NO 57
<211> LENGTH: 21
<212> TYPE: DNA
<213> ORGANISM: Homo sapiens

<400> SEQUENCE: 57

```
gagggcagta agcggccctc a                                               21
```

<210> SEQ ID NO 58
<211> LENGTH: 30
<212> TYPE: DNA
<213> ORGANISM: Homo sapiens

<400> SEQUENCE: 58

```
agctcatata caaccaggag cactcgagtt                                      30
```

-continued

<210> SEQ ID NO 59
<211> LENGTH: 121
<212> TYPE: PRT
<213> ORGANISM: Homo sapiens

<400> SEQUENCE: 59

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ser Phe Tyr Tyr Phe Tyr Tyr Trp Gly
            100                 105                 110

Arg Gly Thr Leu Val Thr Val Ser Ser
        115                 120

<210> SEQ ID NO 60
<211> LENGTH: 111
<212> TYPE: PRT
<213> ORGANISM: Homo sapiens

<400> SEQUENCE: 60

Gln Ala Val Leu Thr Gln Pro Ser Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Tyr Cys Ser Ser Tyr Thr Ser Thr
                85                  90                  95

Phe Ser Val Val Phe Gly Gly Gly Thr Lys Val Thr Val Leu Gly
            100                 105                 110

<210> SEQ ID NO 61
<211> LENGTH: 250
<212> TYPE: PRT
<213> ORGANISM: Homo sapiens

<400> SEQUENCE: 61

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Gly Asn Gly Gly Thr Arg Asp Tyr Ala Ala Ser Val

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Trp Tyr Ser Gly Ser Phe Tyr Tyr Phe Gly Tyr Trp Gly
                100                 105                 110

Arg Gly Thr Leu Val Thr Val Ser Gly Gly Gly Ser Gly Gly
            115                 120                 125

Gly Gly Ser Gly Gly Gly Ser Ala Gln Ala Val Leu Thr Gln Pro
        130                 135                 140

Ser Ser Val Ser Gly Ser Pro Gly Gln Ser Ile Thr Ile Ser Cys Thr
145                 150                 155                 160

Gly Ala Ser Gly Asp Val Gly Ala Tyr Asn Phe Val Ser Trp Tyr Gln
                165                 170                 175

Gln His Pro Gly Lys Thr Pro Lys Leu Ile Ile Tyr Asp Val Asn Lys
                180                 185                 190

Arg Pro Ser Gly Val Ser Asn Arg Phe Ser Gly Ser Lys Ser Gly Asn
                195                 200                 205

Thr Ala Ser Leu Thr Ile Ser Gly Leu Gln Ala Glu Asp Glu Ser Asp
210                 215                 220

Tyr Tyr Cys Ser Ser Tyr Thr Ser Thr Phe Ser Val Val Phe Gly Gly
225                 230                 235                 240

Gly Thr Lys Val Thr Val Leu Gly Ala Ala
                245                 250
```

<210> SEQ ID NO 62
<211> LENGTH: 5
<212> TYPE: PRT
<213> ORGANISM: Homo sapiens

<400> SEQUENCE: 62

```
Asp Tyr Gly Met Asn
 1               5
```

<210> SEQ ID NO 63
<211> LENGTH: 17
<212> TYPE: PRT
<213> ORGANISM: Homo sapiens

<400> SEQUENCE: 63

```
Gly Val Asn Trp Asn Gly Gly Thr Arg Asp Tyr Ala Ala Ser Val Lys
 1               5                   10                  15
Gly
```

<210> SEQ ID NO 64
<211> LENGTH: 12
<212> TYPE: PRT
<213> ORGANISM: Homo sapiens

<400> SEQUENCE: 64

```
Gly Trp Tyr Ser Gly Ser Phe Tyr Tyr Phe Gly Tyr
 1               5                   10
```

<210> SEQ ID NO 65
<211> LENGTH: 14
<212> TYPE: PRT
<213> ORGANISM: Homo sapiens

<400> SEQUENCE: 65

Thr Gly Ala Ser Gly Asp Val Gly Ala Tyr Asn Phe Val Ser
1               5                   10

<210> SEQ ID NO 66
<211> LENGTH: 7
<212> TYPE: PRT
<213> ORGANISM: Homo sapiens

<400> SEQUENCE: 66

Asp Val Asn Lys Arg Pro Ser
1               5

<210> SEQ ID NO 67
<211> LENGTH: 10
<212> TYPE: PRT
<213> ORGANISM: Homo sapiens

<400> SEQUENCE: 67

Ser Ser Tyr Thr Ser Thr Phe Ser Val Val
1               5                   10

<210> SEQ ID NO 68
<211> LENGTH: 363
<212> TYPE: DNA
<213> ORGANISM: Homo sapiens

<400> SEQUENCE: 68
gaggtgcagc tggtggagtc gggggaggt gtggtacggc ctgggggtc cctgagactc      60 tcctgtgcag cctctggatt cacctttgac gattatggca tgaactgggt ccgccaagct     120
ccagggaagg gctggagtg gtctctggt gttaattgga tggtggtac cagagattat       180 gcagcctccg tgaagggccg attcaccatc tccagagaca cgccaagaa ctccctgtat     240 ctgcaaatga acagtctgag agccgaggac acggccttgt attactgtgc gagaggatgg    300
tatagtggga gcttctacta ctttggctac tggggccgag aaccctggt caccgtctcc     360 tca                                                                     363

<210> SEQ ID NO 69
<211> LENGTH: 333
<212> TYPE: DNA
<213> ORGANISM: Homo sapiens

<400> SEQUENCE: 69
caggctgtgc tgactcagcc gtcctccgtg tctgggtctc ctggacagtc gatcaccatc      60
tcctgcactg gagccagcgg tgacgttggt gcttataact ttgtctcctg gtaccaacaa     120
cacccaggca aaaccccaa actcataatt tatgatgtca ataagcggcc ctcagggggtt    180 tctaatcgct tctctggctc caagtctggc aacacggcct ccctgaccat ctctgggctc     240
caggccgagg acgagtctga ttattactgc agctcatata caagcacctt ctctgtggta    300
tttggcggag ggaccaaggt caccgtccta ggt                                  333

<210> SEQ ID NO 70
<211> LENGTH: 750
<212> TYPE: DNA
<213> ORGANISM: Homo sapiens

<400> SEQUENCE: 70
gaggtgcagc tggtggagtc gggggaggt gtggtacggc ctgggggtc cctgagactc      60 tcctgtgcag cctctggatt cacctttgac gattatggca tgaactgggt ccgccaagct     120

| | |
|---|---|
| ccagggaagg ggctggagtg ggtctctggt gttaatggga atggtggtac cagagattat | 180 |
| gcagcctccg tgaagggccg attcaccatc tccagagaca cgccaagaa ctccctgtat | 240 |
| ctgcaaatga acagtctgag agccgaggac acggccttgt attactgtgc gagaggatgg | 300 |
| tatagtggga gcttctacta ctttggctac tggggccgag aaccctggt caccgtctcg | 360 |
| agtggaggcg gcggttcagg cggaggtggc tctggcggtg gcggaagtgc acaggctgtg | 420 |
| ctgactcagc cgtcctccgt gtctgggtct cctggacagt cgatcaccat ctcctgcact | 480 |
| ggagccagcg gtgacgttgg tgcttataac tttgtctcct ggtaccaaca cacccaggc | 540 |
| aaaaccccca aactcataat ttatgatgtc aataagcggc cctcaggggt ttctaatcgc | 600 |
| ttctctggct ccaagtctgg caacacggcc tccctgacca tctctgggct ccaggccgag | 660 |
| gacgagtctg attattactg cagctcatat acaagcacct tctctgtggt atttggcgga | 720 |
| gggaccaagg tcaccgtcct aggtgcggcc | 750 |

<210> SEQ ID NO 71
<211> LENGTH: 15
<212> TYPE: DNA
<213> ORGANISM: Homo sapiens

<400> SEQUENCE: 71

| | |
|---|---|
| gattatggca tgaac | 15 |

<210> SEQ ID NO 72
<211> LENGTH: 51
<212> TYPE: DNA
<213> ORGANISM: Homo sapiens

<400> SEQUENCE: 72

| | |
|---|---|
| ggtgttaatt ggaatggtgg taccagagat tatgcagcct ccgtgaaggg c | 51 |

<210> SEQ ID NO 73
<211> LENGTH: 36
<212> TYPE: DNA
<213> ORGANISM: Homo sapiens

<400> SEQUENCE: 73

| | |
|---|---|
| ggatggtata gtgggagctt ctactacttt ggctac | 36 |

<210> SEQ ID NO 74
<211> LENGTH: 42
<212> TYPE: DNA
<213> ORGANISM: Homo sapiens

<400> SEQUENCE: 74

| | |
|---|---|
| actggagcca gcggtgacgt tggtgcttat aactttgtct cc | 42 |

<210> SEQ ID NO 75
<211> LENGTH: 21
<212> TYPE: DNA
<213> ORGANISM: Homo sapiens

<400> SEQUENCE: 75

| | |
|---|---|
| gatgtcaata agcggccctc a | 21 |

<210> SEQ ID NO 76
<211> LENGTH: 30
<212> TYPE: DNA
<213> ORGANISM: Homo sapiens

<400> SEQUENCE: 76
agctcatata caagcacctt ctctgtggta    30

<210> SEQ ID NO 77
<211> LENGTH: 119
<212> TYPE: PRT
<213> ORGANISM: Homo sapiens

<400> SEQUENCE: 77

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 78
<211> LENGTH: 109
<212> TYPE: PRT
<213> ORGANISM: Homo sapiens

<400> SEQUENCE: 78

Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Ser Ser Thr Asp Arg
                85                  90                  95

Pro Leu Phe Gly Gly Gly Thr Lys Leu Thr Val Leu Gly
            100                 105

<210> SEQ ID NO 79
<211> LENGTH: 247
<212> TYPE: PRT
<213> ORGANISM: Homo sapiens

<400> SEQUENCE: 79

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

-continued

Gly Trp Val Asn Pro Asp Thr Gly Thr Arg Tyr Ala Gln Lys Phe
    50                  55                  60

Gln Gly Trp Val Thr Met Thr Arg Asp Met Ser Asn Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Ser Gly Gly Gly
        115                 120                 125

Ser Gly Gly Gly Ser Ala Gln Ser Val Leu Thr Gln Pro Pro Ser
    130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
            195                 200                 205

Ile Ser Arg Val Glu Ala Gly Asp Glu Ala Asp Phe Tyr Cys Gln Val
210                 215                 220

Trp Asp Ser Ser Thr Asp Arg Pro Leu Phe Gly Gly Gly Thr Lys Leu
225                 230                 235                 240

Thr Val Leu Gly Ala Ala Ala
            245

<210> SEQ ID NO 80
<211> LENGTH: 5
<212> TYPE: PRT
<213> ORGANISM: Homo sapiens

<400> SEQUENCE: 80

Asp Tyr Tyr Ile His
1               5

<210> SEQ ID NO 81
<211> LENGTH: 17
<212> TYPE: PRT
<213> ORGANISM: Homo sapiens

<400> SEQUENCE: 81

Trp Val Asn Pro Asp Thr Gly Gly Thr Arg Tyr Ala Gln Lys Phe Gln
1               5                   10                  15

Gly

<210> SEQ ID NO 82
<211> LENGTH: 10
<212> TYPE: PRT
<213> ORGANISM: Homo sapiens

<400> SEQUENCE: 82

Asp Leu Thr Gly Phe Asp Pro Phe Asp Ile
1               5                   10

<210> SEQ ID NO 83
<211> LENGTH: 11
<212> TYPE: PRT
<213> ORGANISM: Homo sapiens

<400> SEQUENCE: 83

Gly Gly Asn Asn Phe Arg Asn Lys Arg Val His
1               5                   10

<210> SEQ ID NO 84
<211> LENGTH: 7
<212> TYPE: PRT
<213> ORGANISM: Homo sapiens

<400> SEQUENCE: 84

Tyr Asp Ser Asp Arg Pro Ser
1               5

<210> SEQ ID NO 85
<211> LENGTH: 11
<212> TYPE: PRT
<213> ORGANISM: Homo sapiens

<400> SEQUENCE: 85

Gln Val Trp Asp Ser Ser Thr Asp Arg Pro Leu
1               5                   10

<210> SEQ ID NO 86
<211> LENGTH: 357
<212> TYPE: DNA
<213> ORGANISM: Homo sapiens

<400> SEQUENCE: 86
gaggtgcagc tggtgcagtc tggggctgag gtgaagaagc ctggggcctc agtgaaggtc       60
tcctgtcagg cttctggata caccttcagc gattactata ttcactgggt gcgacagacc      120
cctggacaag ggtttgagtg gatgggatgg gtcaaccctg acactggtgg cacaagatac      180
gcgcagaagt tcagggctg gtcacaatg accagggaca tgtccaacac cacagcctac        240
atggagctgc ccaggctgag agacgacgac acggccgtat attactgtgc gagagatcta      300
actggatttg atccttttga tatctggggc cagggaaccc tggtcaccgt ctcctca         357

<210> SEQ ID NO 87
<211> LENGTH: 327
<212> TYPE: DNA
<213> ORGANISM: Homo sapiens

<400> SEQUENCE: 87
cagtctgtgc tgactcagcc accctcagtg tcagtggccc caggaaagac ggccacgatt       60
acctgtgggg gaaacaactt tcgaaataaa agagtacact ggtatcagca gaggccaggc      120
caggcccctg tcctggtcat ctattatgat tcagaccggc cctcaggat ccctgagcga       180
ttctctggct cccgctctgg gaacacggcc accctgacca tcagcagggt cgaggccggg      240
gatgaggccg acttttactg tcaggtgtgg atagtagta ctgatcgtcc gctgttcggc       300
ggagggacca agctgaccgt cctaggt                                           327

<210> SEQ ID NO 88
<211> LENGTH: 741
<212> TYPE: DNA
<213> ORGANISM: Homo sapiens

<400> SEQUENCE: 88
gaagtgcagc tggtgcagtc tggggctgag gtgaagaagc ctggggcctc agtgaaggtc       60
tcctgtcagg cttctggata caccttcagc gattactata ttcactgggt gcgacagacc      120
cctggacaag ggtttgagtg gatgggatgg gtcaaccctg acactggtgg cacaagatac      180

-continued

```
gcgcagaagt tcagggctg ggtcaccatg accagggaca tgtccaacac cacagcctac    240
atggagctgc ccaggctgag agacgacgac acggccgtat attactgtgc gagagatcta    300
actggatttg atccttttga tatctggggc cagggaaccc tggtcaccgt ctcgagtgga    360
ggcggcggtt caggcggagg tggctctggc ggtggcggaa gtgcacagtc tgtgctgact    420
cagccaccct cagtgtcagt ggccccagga aagacggcca cgattacctg tgggggaaac    480
aactttcgaa ataaaagagt acactggtat cagcagaggc caggccaggc ccctgtcctg    540
gtcatctatt atgattcaga ccggccctca gggatccctg agcgattctc tggctcccgc    600
tctgggaaca cggccaccct gaccatcagc agggtcgagg ccggggatga ggccgacttt    660
tactgtcagg tgtgggatag tagtactgat cgtccgctgt tcggcggagg gaccaagctg    720
accgtcctag gtgcggccgc a                                              741
```

<210> SEQ ID NO 89
<211> LENGTH: 15
<212> TYPE: DNA
<213> ORGANISM: Homo sapiens

<400> SEQUENCE: 89

```
gattactata ttcac                                                      15
```

<210> SEQ ID NO 90
<211> LENGTH: 51
<212> TYPE: DNA
<213> ORGANISM: Homo sapiens

<400> SEQUENCE: 90

```
tgggtcaacc ctgacactgg tggcacaaga tacgcgcaga gtttcaggg c               51
```

<210> SEQ ID NO 91
<211> LENGTH: 30
<212> TYPE: DNA
<213> ORGANISM: Homo sapiens

<400> SEQUENCE: 91

```
gatctaactg gatttgatcc ttttgatatc                                      30
```

<210> SEQ ID NO 92
<211> LENGTH: 33
<212> TYPE: DNA
<213> ORGANISM: Homo sapiens

<400> SEQUENCE: 92

```
gggggaaaca actttcgaaa taaaagagta cac                                  33
```

<210> SEQ ID NO 93
<211> LENGTH: 21
<212> TYPE: DNA
<213> ORGANISM: Homo sapiens

<400> SEQUENCE: 93

```
tatgattcag accggccctc a                                               21
```

<210> SEQ ID NO 94
<211> LENGTH: 33
<212> TYPE: DNA
<213> ORGANISM: Homo sapiens

<400> SEQUENCE: 94

```
caggtgtggg atagtagtac tgatcgtccg ctg                                  33
```

<210> SEQ ID NO 95
<211> LENGTH: 121
<212> TYPE: PRT
<213> ORGANISM: Homo sapiens

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Asp Phe Trp Gly Gly Asp Asn Trp Gly
            100                 105                 110

Arg Gly Thr Met Val Thr Val Ser Ser
        115                 120

<210> SEQ ID NO 96
<211> LENGTH: 112
<212> TYPE: PRT
<213> ORGANISM: Homo sapiens

<400> SEQUENCE: 96

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Gln Leu Thr Val Leu Gly
            100                 105                 110

<210> SEQ ID NO 97
<211> LENGTH: 252
<212> TYPE: PRT
<213> ORGANISM: Homo sapiens

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe

```
                50                  55                  60
Arg Gly Arg Val Thr Met Thr Arg Asp Thr Ser Ile Asn Thr Ala Tyr
 65                  70                  75                  80

Met Glu Leu Ser Arg Leu Gly Ser Asp Thr Ala Val Tyr Tyr Cys
                 85                  90                  95

Ala Arg Glu Pro Glu Lys Phe Asp Phe Trp Gly Gly Asp Asn Trp Gly
                100                 105                 110

Arg Gly Thr Met Val Thr Val Ser Ser Gly Gly Gly Ser Gly Gly
                115                 120                 125

Gly Gly Ser Gly Gly Gly Ser Ala Gln Ala Val Leu Thr Gln Pro
            130                 135                 140

Ser Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
                180                 185                 190

Arg Pro Ser Gly Val Pro Asp Arg Phe Ser Gly Ser Lys Ser Gly Thr
            195                 200                 205

Ser Ala Ser Leu Ala Ile Thr Gly Leu Gln Ala Glu Asp Glu Ala Asp
210                 215                 220

Tyr Tyr Cys Gln Ser Tyr Asp Ser Ser Leu Ser Gly Tyr Val Phe Gly
225                 230                 235                 240

Thr Gly Thr Gln Leu Thr Val Leu Ser Ala Ala Ala
                245                 250

<210> SEQ ID NO 98
<211> LENGTH: 5
<212> TYPE: PRT
<213> ORGANISM: Homo sapiens

<400> SEQUENCE: 98

Asp Tyr Tyr Met His
1               5

<210> SEQ ID NO 99
<211> LENGTH: 17
<212> TYPE: PRT
<213> ORGANISM: Homo sapiens

<400> SEQUENCE: 99

Trp Ile Asn Pro Tyr Thr Gly Gly Ala Phe Tyr Ala Gln Lys Phe Arg
1               5                   10                  15

Gly

<210> SEQ ID NO 100
<211> LENGTH: 12
<212> TYPE: PRT
<213> ORGANISM: Homo sapiens

<400> SEQUENCE: 100

Glu Pro Glu Lys Phe Asp Phe Trp Gly Gly Asp Asn
1               5                   10

<210> SEQ ID NO 101
<211> LENGTH: 14
<212> TYPE: PRT
<213> ORGANISM: Homo sapiens

<400> SEQUENCE: 101
```

Thr Gly Ser Ser Ser Asn Ile Gly Ala Gly Tyr Gly Val His
1               5                   10

<210> SEQ ID NO 102
<211> LENGTH: 7
<212> TYPE: PRT
<213> ORGANISM: Homo sapiens

<400> SEQUENCE: 102

Gly Asn Ser Asn Arg Pro Ser
1               5

<210> SEQ ID NO 103
<211> LENGTH: 11
<212> TYPE: PRT
<213> ORGANISM: Homo sapiens

<400> SEQUENCE: 103

Gln Ser Tyr Asp Ser Ser Leu Ser Gly Tyr Val
1               5                   10

<210> SEQ ID NO 104
<211> LENGTH: 363
<212> TYPE: DNA
<213> ORGANISM: Homo sapiens

<400> SEQUENCE: 104
caggtccagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gtgggatgg atcaaccctt atactggtgg cgcattctat       180
gcacagaagt ttcggggcag ggtcacaatg accaggaca cgtccatcaa cacagcctac      240
atggagctga gcagactggg atctgacgac acggccgtgt attattgtgc gagagaacct    300
gaaaaattcg atttttgggg gggtgacaac tggggccggg gacaatggt caccgtctcc     360 tca                                                                  363

<210> SEQ ID NO 105
<211> LENGTH: 336
<212> TYPE: DNA
<213> ORGANISM: Homo sapiens

<400> SEQUENCE: 105
caggctgtgc tgactcagcc gtcctcagtg tctggggccc cagggcagag ggtcaccatc     60
tcctgcactg ggagcagctc caacatcggg gcaggttatg gtgtacactg gtaccaacag    120
cttccaggaa cagccccaa actcctcatc tatggtaaca gcaatcggcc ctcagggtc      180 cctgaccgat tctctggctc caagtctggc acctcagcct ccctggccat cactgggctc    240
caggctgagg atgaggctga ttattactgc cagtcctatg acagcagcct gagtggttat    300
gtcttcggaa ctgggaccca gctcaccgtc ctaggt                              336

<210> SEQ ID NO 106
<211> LENGTH: 756
<212> TYPE: DNA
<213> ORGANISM: Homo sapiens

<400> SEQUENCE: 106
caggtccagc tggtgcagtc tggggctgag gtgaagaagc ctggggcctc agtgaaggtc      60
tcctgcaagg cttctggata caccttcacc gactactata tgcactgggt gcgacaggcc    120

```
cctggacaag ggcttgagtg ggtgggatgg atcaacccct atactggtgg cgcattctat    180
gcacagaagt ttcggggcag ggtcaccatg accagggaca cgtccatcaa cacagcctac    240
atggagctga gcagactggg atctgacgac acggccgtgt attattgtgc gagagaacct    300
gaaaaattcg attttggggg gggtgacaac tgggccggg gacaatggt caccgtctcg     360 agtggaggcg gcggttcagg cggaggtggc tctggcggtg gcggaagtgc acaggctgtg    420
ctgactcagc cgtcctcagt gtctgggccc ccagggcaga gggtcaccat ctcctgcact    480
gggagcagct ccaacatcgg ggcaggttat ggtgtacact ggtaccaaca gcttccagga    540
acagccccca aactcctcat ctatggtaac agcaatcggc cctcagggt ccctgaccga     600 ttctctggct ccaagtctgg cacctcagcc tccctggcca tcactgggct ccaggctgag    660
gatgaggctg attattactg ccagtcctat gacagcagcc tgagtggtta tgtcttcgga    720
actgggaccc agctcaccgt tttaagtgcg gccgca                             756
```

```
<210> SEQ ID NO 107
<211> LENGTH: 15
<212> TYPE: DNA
<213> ORGANISM: Homo sapiens

<400> SEQUENCE: 107
gactactata tgcac                                                     15

<210> SEQ ID NO 108
<211> LENGTH: 51
<212> TYPE: DNA
<213> ORGANISM: Homo sapiens

<400> SEQUENCE: 108
tggatcaacc cttatactgg tggcgcattc tatgcacaga gtttcggggg c              51

<210> SEQ ID NO 109
<211> LENGTH: 36
<212> TYPE: DNA
<213> ORGANISM: Homo sapiens

<400> SEQUENCE: 109
gaacctgaaa aattcgattt tggggggt gacaac                                36

<210> SEQ ID NO 110
<211> LENGTH: 42
<212> TYPE: DNA
<213> ORGANISM: Homo sapiens

<400> SEQUENCE: 110
actgggagca gctccaacat cggggcaggt tatggtgtac ac                        42

<210> SEQ ID NO 111
<211> LENGTH: 21
<212> TYPE: DNA
<213> ORGANISM: Homo sapiens

<400> SEQUENCE: 111
ggtaacagca atcggccctc a                                              21

<210> SEQ ID NO 112
<211> LENGTH: 33
<212> TYPE: DNA
<213> ORGANISM: Homo sapiens

<400> SEQUENCE: 112
```
cagtcctatg acagcagcct gagtggttat gtc         33

<210> SEQ ID NO 113
<211> LENGTH: 119
<212> TYPE: PRT
<213> ORGANISM: Homo sapiens

<400> SEQUENCE: 113

Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Arg Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Ser Ser Leu Arg Ser Glu Asp Thr Ala Val Tyr Tyr Cys
                85                  90                  95

Ala Arg Gly Leu Trp Val Trp Asp Pro Leu Asp Tyr Trp Gly Arg Gly
            100                 105                 110

Thr Leu Val Thr Val Ser Ser
        115

<210> SEQ ID NO 114
<211> LENGTH: 108
<212> TYPE: PRT
<213> ORGANISM: Homo sapiens

<400> SEQUENCE: 114

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Phe Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Glu Phe Ala Trp
                85                  90                  95

Thr Phe Gly Gly Gly Thr Lys Leu Glu Ile Lys Arg
            100                 105

<210> SEQ ID NO 115
<211> LENGTH: 246
<212> TYPE: PRT
<213> ORGANISM: Homo sapiens

<400> SEQUENCE: 115

Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Arg Gly Leu Glu Trp Val
        35                  40                  45

```
Ser Ala Ile Ser Gly Ser Gly Gly Ser Thr Tyr Tyr Ala Asp Ser Val
    50                  55                  60
Lys Gly Arg Ile Thr Ile Ser Arg Asp Asn Ala Lys Asn Ser Leu Tyr
 65                  70                  75                  80
Leu Gln Met Ser Ser Leu Arg Ser Glu Asp Thr Ala Val Tyr Tyr Cys
                 85                  90                  95
Ala Arg Gly Leu Trp Val Trp Asp Pro Leu Asp Tyr Trp Gly Arg Gly
                100                 105                 110
Thr Leu Val Thr Val Ser Ser Gly Gly Gly Ser Gly Gly Gly Gly
                115                 120                 125
Ser Gly Gly Gly Gly Ser Asp Ile Gln Met Thr Gln Ser Pro Ser Thr
    130                 135                 140
Leu Ser Ala Ser Ile Gly Asp Arg Val Thr Ile Thr Cys Arg Ala Ser
145                 150                 155                 160
Glu Gly Ile Tyr His Trp Leu Ala Trp Tyr Gln Gln Lys Pro Gly Lys
                165                 170                 175
Ala Pro Lys Leu Leu Ile Tyr Lys Ala Ser Ser Leu Ala Ser Gly Ala
                180                 185                 190
Pro Ser Arg Phe Ser Gly Ser Gly Phe Gly Thr Asp Phe Thr Leu Thr
                195                 200                 205
Ile Ser Ser Leu Gln Pro Asp Asp Phe Ala Thr Tyr Tyr Cys Gln Gln
                210                 215                 220
Tyr Ser Glu Phe Ala Trp Thr Phe Gly Gly Gly Thr Lys Leu Glu Ile
225                 230                 235                 240
Lys Arg Ala Ala Ala His
                245

<210> SEQ ID NO 116
<211> LENGTH: 5
<212> TYPE: PRT
<213> ORGANISM: Homo sapiens

<400> SEQUENCE: 116

Asp Tyr Tyr Met Ser
1               5

<210> SEQ ID NO 117
<211> LENGTH: 17
<212> TYPE: PRT
<213> ORGANISM: Homo sapiens

<400> SEQUENCE: 117

Ala Ile Ser Gly Ser Gly Gly Ser Thr Tyr Tyr Ala Asp Ser Val Lys
1               5                   10                  15
Gly

<210> SEQ ID NO 118
<211> LENGTH: 10
<212> TYPE: PRT
<213> ORGANISM: Homo sapiens

<400> SEQUENCE: 118

Gly Leu Trp Val Trp Asp Pro Leu Asp Tyr
1               5                   10

<210> SEQ ID NO 119
<211> LENGTH: 11
<212> TYPE: PRT
<213> ORGANISM: Homo sapiens
```

<400> SEQUENCE: 119

Arg Ala Ser Glu Gly Ile Tyr His Trp Leu Ala
1               5                   10

<210> SEQ ID NO 120
<211> LENGTH: 7
<212> TYPE: PRT
<213> ORGANISM: Homo sapiens

<400> SEQUENCE: 120

Lys Ala Ser Ser Leu Ala Ser
1               5

<210> SEQ ID NO 121
<211> LENGTH: 9
<212> TYPE: PRT
<213> ORGANISM: Homo sapiens

<400> SEQUENCE: 121

Gln Gln Tyr Ser Glu Phe Ala Trp Thr
1               5

<210> SEQ ID NO 122
<211> LENGTH: 357
<212> TYPE: DNA
<213> ORGANISM: Homo sapiens

<400> SEQUENCE: 122
gaggtgcagc tggtggagtc tgggggaggc ttggtcacgc ctggagggtc cctgagactc      60
tcctgtgcag cctctggatt caccttcagt gactactaca tgagctgggt ccgccaggct     120
ccagggaggg gctggagtg gtctcagct attagtggta gtggtggtag cacatactac      180
gcagactccg tgaagggccg gatcaccatc tccagagaca acgccaagaa ctcactgtat     240
ctgcaaatga gcagcctgag atctgaggac acggccgtgt attactgtgc gagagggctt     300
tgggtttggg atcctcttga ctactggggc agaggaaccc tggtcaccgt ctcctca        357

<210> SEQ ID NO 123
<211> LENGTH: 324
<212> TYPE: DNA
<213> ORGANISM: Homo sapiens

<400> SEQUENCE: 123
gacatccaga tgacccagtc tccttccacc ctgtctgcat ctattggaga cagagtcacc      60
atcacctgcc gggccagtga gggtatttat cactggttgg cctggtatca gcagaagcca     120
gggaaagccc ctaaactcct gatctataag gcctctagtt tagccagtgg ggccccatca     180
aggttcagcg gcagtggatt tgggaccgat ttcactctca ccatcagcag cctgcagcct     240
gatgattttg caacttatta ctgccaacaa tacagcgagt tcgcctggac cttcggcgga     300
gggaccaagc tggagatcaa acgt                                             324

<210> SEQ ID NO 124
<211> LENGTH: 738
<212> TYPE: DNA
<213> ORGANISM: Homo sapiens

<400> SEQUENCE: 124
gaggtgcagc tggtggagtc tgggggaggc ttggtcacgc ctggagggtc cctgagactc      60
tcctgtgcag cctctggatt caccttcagt gactactaca tgagctgggt ccgccaggct     120
ccagggaggg gctggagtg gtctcagct attagtggta gtggtggtag cacatactac      180

-continued

| | |
|---|---|
| gcagactccg tgaagggccg gatcaccatc tccagagaca acgccaagaa ctcactgtat | 240 |
| ctgcaaatga gcagcctgag atctgaggac acggccgtgt attactgtgc gagagggctt | 300 |
| tgggtttggg atcctcttga ctactggggc agaggaaccc tggtcaccgt ctcttcaggt | 360 |
| gggggcggtt caggcggagg tggcagcggc ggtggcggat cggacatcca gatgacccag | 420 |
| tccccttcca ccctgtctgc atctattgga gacagagtca ccatcacctg ccgggccagt | 480 |
| gagggtattt atcactggtt ggcctggtat cagcagaagc cagggaaagc ccctaaactc | 540 |
| ctgatctata aggcctctag tttagccagt ggggcccat caaggttcag cggcagtgga | 600 |
| tttgggacag atttcactct caccatcagc agcctgcagc ctgatgattt tgcaacttat | 660 |
| tactgccaac aatacagcga gttcgcctgg accttcggcg agggaccaa gctggagatc | 720 |
| aaacgtgcgg ccgcacat | 738 |

<210> SEQ ID NO 125
<211> LENGTH: 15
<212> TYPE: DNA
<213> ORGANISM: Homo sapiens

<400> SEQUENCE: 125
gactactaca tgagc    15

<210> SEQ ID NO 126
<211> LENGTH: 51
<212> TYPE: DNA
<213> ORGANISM: Homo sapiens

<400> SEQUENCE: 126
gctattagtg gtagtggtgg tagcacatac tacgcagact ccgtgaaggg c    51

<210> SEQ ID NO 127
<211> LENGTH: 30
<212> TYPE: DNA
<213> ORGANISM: Homo sapiens

<400> SEQUENCE: 127
gggctttggg tttgggatcc tcttgactac    30

<210> SEQ ID NO 128
<211> LENGTH: 33
<212> TYPE: DNA
<213> ORGANISM: Homo sapiens

<400> SEQUENCE: 128
cgggccagtg agggtattta tcactggttg gcc    33

<210> SEQ ID NO 129
<211> LENGTH: 21
<212> TYPE: DNA
<213> ORGANISM: Homo sapiens

<400> SEQUENCE: 129
aaggcctcta gtttagccag t    21

<210> SEQ ID NO 130
<211> LENGTH: 27
<212> TYPE: DNA
<213> ORGANISM: Homo sapiens

<400> SEQUENCE: 130
caacaataca gcgagttcgc ctggacc    27

<210> SEQ ID NO 131
<211> LENGTH: 119
<212> TYPE: PRT
<213> ORGANISM: Homo sapiens

<400> SEQUENCE: 131

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Val Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Gly Leu Arg Ser Asp Asp Thr Ala Val Tyr Tyr Cys
                85                  90                  95

Ala Arg Asp Arg Gly Tyr Tyr Ala Phe Asp Ile Trp Gly Gln Gly
            100                 105                 110

Thr Leu Val Thr Val Ser Ser
        115

<210> SEQ ID NO 132
<211> LENGTH: 108
<212> TYPE: PRT
<213> ORGANISM: Homo sapiens

<400> SEQUENCE: 132

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gly Ile Tyr His Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Ala Ser Gly Ala Pro Ser Arg Phe Ser Gly
    50                  55                  60

Ser Gly Phe Gly Thr Asp Phe Thr Leu Thr Ile Ser Ser Leu Gln Pro
65                  70                  75                  80

Asp Asp Phe Ala Thr Tyr Tyr Cys Gln Gln Met Gly Glu Tyr Asn Ala
                85                  90                  95

Thr Ile Gly Gly Gly Thr Lys Leu Glu Ile Lys Arg
            100                 105

<210> SEQ ID NO 133
<211> LENGTH: 246
<212> TYPE: PRT
<213> ORGANISM: Homo sapiens

<400> SEQUENCE: 133

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Val Ser Ala Tyr Thr Gly Asn Thr Asn Tyr Ala Gln Lys Phe

-continued

```
                50                  55                  60
Gln Gly Arg Val Thr Met Thr Thr Asp Thr Ser Thr Ser Thr Ala Tyr
 65                  70                  75                  80

Met Glu Leu Arg Gly Leu Arg Ser Asp Thr Ala Val Tyr Tyr Cys
                 85                  90                  95

Ala Arg Asp Arg Gly Tyr Tyr Asp Ala Tyr Asp Ile Trp Gly Gln Gly
                100                 105                 110

Thr Leu Val Thr Val Ser Ser Gly Gly Gly Ser Gly Gly Gly
            115                 120                 125

Ser Gly Gly Gly Ser Asp Ile Gln Met Thr Gln Ser Pro Ser Thr
130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Phe Gly Thr Asp Phe Thr Leu Thr
            195                 200                 205

Ile Ser Ser Leu Gln Pro Asp Asp Phe Ala Thr Tyr Tyr Cys Gln Gln
    210                 215                 220

Met Gly Glu Tyr Asn Ala Thr Ile Gly Gly Thr Lys Leu Glu Ile
225                 230                 235                 240

Lys Arg Ala Ala Ala His
                245
```

<210> SEQ ID NO 134
<211> LENGTH: 5
<212> TYPE: PRT
<213> ORGANISM: Homo sapiens

<400> SEQUENCE: 134

```
Ser Tyr Gly Ile Ser
1               5
```

<210> SEQ ID NO 135
<211> LENGTH: 17
<212> TYPE: PRT
<213> ORGANISM: Homo sapiens

<400> SEQUENCE: 135

```
Trp Val Ser Ala Tyr Thr Gly Asn Thr Asn Tyr Ala Gln Lys Phe Gln
1               5                   10                  15
Gly
```

<210> SEQ ID NO 136
<211> LENGTH: 10
<212> TYPE: PRT
<213> ORGANISM: Homo sapiens

<400> SEQUENCE: 136

```
Asp Arg Gly Tyr Tyr Asp Ala Phe Asp Ile
1               5                   10
```

<210> SEQ ID NO 137
<211> LENGTH: 11
<212> TYPE: PRT
<213> ORGANISM: Homo sapiens

<400> SEQUENCE: 137

Arg Ala Ser Glu Gly Ile Tyr His Trp Leu Ala
1               5                   10

<210> SEQ ID NO 138
<211> LENGTH: 7
<212> TYPE: PRT
<213> ORGANISM: Homo sapiens

<400> SEQUENCE: 138

Lys Ala Ser Ser Leu Ala Ser
1               5

<210> SEQ ID NO 139
<211> LENGTH: 9
<212> TYPE: PRT
<213> ORGANISM: Homo sapiens

<400> SEQUENCE: 139

Gln Gln Met Gly Glu Tyr Asn Ala Thr
1               5

<210> SEQ ID NO 140
<211> LENGTH: 357
<212> TYPE: DNA
<213> ORGANISM: Homo sapiens

<400> SEQUENCE: 140
caggtgcagc tggtggagtc tggggctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg gtcagcgctt acactggtaa cacaaactat      180
gcacagaagt tccagggcag agtcaccatg accacagaca catccacgag cacagcctac     240
atggaactga ggggcctgag atctgacgac acggccgtgt attactgtgc gagagatcgt     300
ggatactatg atgcttttga tatctggggc caaggcaccc tggtcaccgt ctcctca       357

<210> SEQ ID NO 141
<211> LENGTH: 324
<212> TYPE: DNA
<213> ORGANISM: Homo sapiens

<400> SEQUENCE: 141
gacatccaga tgacccagtc tccttccacc ctgtctgcat ctattggaga cagagtcacc      60
atcacctgcc gggccagtga gggtatttat cactggttgg cctggtatca gcagaagcca     120
gggaaagccc ctaaactcct gatctataag gcctctagtt tagccagtgg ggccccatca     180
aggttcagcg gcagtggatt tgggacagat ttcactctca ccatcagcag cctgcagcct     240
gatgattttg caacttatta ctgccaacaa atgggcgagt acaacgccac catcggcgga     300
gggaccaagc tggagatcaa acgt                                            324

<210> SEQ ID NO 142
<211> LENGTH: 738
<212> TYPE: DNA
<213> ORGANISM: Homo sapiens

<400> SEQUENCE: 142
caggtgcagc tggtggagtc tggggctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg gtcagcgctt acactggtaa cacaaactat      180

```
gcacagaagt tccagggcag agtcaccatg accacagaca catccacgag cacagcctac    240
atggaactga ggggcctgag atctgacgac acggccgtgt attactgtgc gagagatcgt    300
ggatactatg atgcttatga tatctggggc caaggcaccc tggtcaccgt ctcctcaggt    360
ggaggcggtt caggcggagg tggcagcggc ggtggcggat cggacatcca gatgacccag    420
tctccttcca ccctgtctgc atctattgga gacagagtca ccatcacctg ccgggccagt    480
gagggtattt atcactggtt ggcctggtat cagcagaagc cagggaaagc ccctaaactc    540
ctgatctata aggcctctag tttagccagt ggggccccat caaggttcag cggcagtgga    600
tttgggacag atttcactct caccatcagc agcctgcagc ctgatgattt tgcaacttat    660
tactgccaac aaatgggcga gtacaacgcc accatcggcg agggaccaa gctggagatc    720 aaacgtgcgg ccgcacat                                                 738
```

<210> SEQ ID NO 143
<211> LENGTH: 15
<212> TYPE: DNA
<213> ORGANISM: Homo sapiens

<400> SEQUENCE: 143

```
agttatggta tcagc                                                     15
```

<210> SEQ ID NO 144
<211> LENGTH: 51
<212> TYPE: DNA
<213> ORGANISM: Homo sapiens

<400> SEQUENCE: 144

```
tgggtcagcg cttacactgg taacacaaac tatgcacaga agttccaggg c              51
```

<210> SEQ ID NO 145
<211> LENGTH: 30
<212> TYPE: DNA
<213> ORGANISM: Homo sapiens

<400> SEQUENCE: 145

```
gatcgtggat actatgatgc ttttgatatc                                     30
```

<210> SEQ ID NO 146
<211> LENGTH: 33
<212> TYPE: DNA
<213> ORGANISM: Homo sapiens

<400> SEQUENCE: 146

```
cgggccagtg agggtatttta tcactggttg gcc                                33
```

<210> SEQ ID NO 147
<211> LENGTH: 21
<212> TYPE: DNA
<213> ORGANISM: Homo sapiens

<400> SEQUENCE: 147

```
aaggcctcta gtttagccag t                                              21
```

<210> SEQ ID NO 148
<211> LENGTH: 27
<212> TYPE: DNA
<213> ORGANISM: Homo sapiens

<400> SEQUENCE: 148

```
caacaaatgg gcgagtacaa cgccacc                                        27
```

<210> SEQ ID NO 149
<211> LENGTH: 119
<212> TYPE: PRT
<213> ORGANISM: Homo sapiens

<400> SEQUENCE: 149

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser
        115

<210> SEQ ID NO 150
<211> LENGTH: 108
<212> TYPE: PRT
<213> ORGANISM: Homo sapiens

<400> SEQUENCE: 150

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Phe Gly Thr Asp Phe Thr Leu Thr Ile Ser Ser Leu Gln Pro
65                  70                  75                  80

Asp Asp Phe Ala Thr Tyr Tyr Cys Gln Gln Met Gly Glu Trp Lys Ala
                85                  90                  95

Ala Phe Gly Gly Gly Thr Lys Leu Glu Ile Lys Arg
            100                 105

<210> SEQ ID NO 151
<211> LENGTH: 246
<212> TYPE: PRT
<213> ORGANISM: Homo sapiens

<400> SEQUENCE: 151

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

```
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Arg Gly Tyr Tyr Asp Ala Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Asp Ile Gln Met Thr Gln Ser Pro Ser Thr
    130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Phe Gly Thr Asp Phe Thr Leu Thr
        195                 200                 205

Ile Ser Ser Leu Gln Pro Asp Asp Phe Ala Thr Tyr Tyr Cys Gln Gln
210                 215                 220

Met Gly Glu Trp Lys Ala Ala Phe Gly Gly Gly Thr Lys Leu Glu Ile
225                 230                 235                 240

Lys Arg Ala Ala Ala His
                245

<210> SEQ ID NO 152
<211> LENGTH: 5
<212> TYPE: PRT
<213> ORGANISM: Homo sapiens

<400> SEQUENCE: 152

Ser Tyr Gly Ile Ser
1               5

<210> SEQ ID NO 153
<211> LENGTH: 17
<212> TYPE: PRT
<213> ORGANISM: Homo sapiens

<400> SEQUENCE: 153

Trp Ile Ser Ala Tyr Thr Gly Asn Thr Asn Tyr Ala Gln Lys Phe Gln
1               5                   10                  15

Gly

<210> SEQ ID NO 154
<211> LENGTH: 10
<212> TYPE: PRT
<213> ORGANISM: Homo sapiens

<400> SEQUENCE: 154

Asp Arg Gly Tyr Tyr Asp Ala Phe Asp Ile
1               5                   10

<210> SEQ ID NO 155
<211> LENGTH: 11
<212> TYPE: PRT
<213> ORGANISM: Homo sapiens

<400> SEQUENCE: 155
```

Arg Ala Ser Glu Gly Ile Tyr His Trp Leu Ala
1               5                   10

<210> SEQ ID NO 156
<211> LENGTH: 7
<212> TYPE: PRT
<213> ORGANISM: Homo sapiens

<400> SEQUENCE: 156

Lys Ala Ser Ser Leu Ala Ser
1               5

<210> SEQ ID NO 157
<211> LENGTH: 9
<212> TYPE: PRT
<213> ORGANISM: Homo sapiens

<400> SEQUENCE: 157

Gln Gln Met Gly Glu Trp Lys Ala Ala
1               5

<210> SEQ ID NO 158
<211> LENGTH: 357
<212> TYPE: DNA
<213> ORGANISM: Homo sapiens

<400> SEQUENCE: 158

| | |
|---|---|
| caggtgcagc tggtggagtc tggagctgag gtgaagaagc ctggggcctc agtgaaggtc | 60 |
| tcctgcaagg cttctggtta cacctttacc agttatggta tcagctgggt gcgacaggcc | 120 |
| cctggacaag ggcttgagtg gatgggatgg atcagcgctt acactggtaa cacaaactat | 180 |
| gcacagaagt tccagggcag agtcaccatg accacagaca catccacgag cacagcctac | 240 |
| atggaactga ggagcctgag atctgacgac acggccgtgt attactgtgc gagagatcgt | 300 |
| ggatactatg atgctttcga tatctggggc caaggcaccc tggtcaccgt ctcctca | 357 |

<210> SEQ ID NO 159
<211> LENGTH: 324
<212> TYPE: DNA
<213> ORGANISM: Homo sapiens

<400> SEQUENCE: 159

| | |
|---|---|
| gacatccaga tgacccagtc tccttccacc ctgtctgcat ctattggaga cagagtcacc | 60 |
| atcacctgcc gggccagtga gggtatttat cactggttgg cctggtatca gcagaagcca | 120 |
| gggaaagccc ctaaactcct gatctataag gcctctagtt tagccagtgg ggccccatca | 180 |
| aggttcagcg gcagtggatt tgggacagat ttcactctca ccatcagcag cctgcagcct | 240 |
| gatgattttg caacttatta ctgccaacaa atgggggagt ggaaggcggc cttcggcgga | 300 |
| gggaccaagc tggagatcaa acgt | 324 |

<210> SEQ ID NO 160
<211> LENGTH: 738
<212> TYPE: DNA
<213> ORGANISM: Homo sapiens

<400> SEQUENCE: 160

| | |
|---|---|
| caggtgcagc tggtggagtc tggagctgag gtgaagaagc ctggggcctc agtgaaggtc | 60 |
| tcctgcaagg cttctggtta cacctttacc agttatggta tcagctgggt gcgacaggcc | 120 |
| cctggacaag ggcttgagtg gatgggatgg atcagcgctt acactggtaa cacaaactat | 180 |
| gcacagaagt tccagggcag agtcaccatg accacagaca catccacgag cacagcctac | 240 |

```
atggaactga ggagcctgag atctgacgac acggccgtgt attactgtgc gagagatcgt    300
ggatactatg atgctttcga tatctggggc caaggcaccc tggtcaccgt ctcctcaggt    360
gggggcggtt caggcggagg tggcagcggc ggtggcggat cggacatcca gatgacccag    420
tctccttcca ccctgtctgc atctattgga gacagagtca ccatcacctg ccgggccagt    480
gagggtattt atcactggtt ggcctggtat cagcagaagc cagggaaagc ccctaaactc    540
ctgatctata aggcctctag tttagccagt ggggcccat caaggttcag cggcagtgga    600
tttgggacag atttcactct caccatcagc agcctgcagc ctgatgattt tgcaacttat    660
tactgccaac aaatggggga gtggaaggcg gccttcggcg agggaccaa gctggagatc    720 aaacgtgcgg ccgcacat                                                 738
```

<210> SEQ ID NO 161
<211> LENGTH: 15
<212> TYPE: DNA
<213> ORGANISM: Homo sapiens

<400> SEQUENCE: 161

```
agttatggta tcagc                                                    15
```

<210> SEQ ID NO 162
<211> LENGTH: 51
<212> TYPE: DNA
<213> ORGANISM: Homo sapiens

<400> SEQUENCE: 162

```
tggatcagcg cttacactgg taacacaaac tatgcacaga gttccaggg c              51
```

<210> SEQ ID NO 163
<211> LENGTH: 30
<212> TYPE: DNA
<213> ORGANISM: Homo sapiens

<400> SEQUENCE: 163

```
gatcgtggat actatgatgc tttcgatatc                                    30
```

<210> SEQ ID NO 164
<211> LENGTH: 33
<212> TYPE: DNA
<213> ORGANISM: Homo sapiens

<400> SEQUENCE: 164

```
cgggccagtg agggtattta tcactggttg gcc                                33
```

<210> SEQ ID NO 165
<211> LENGTH: 21
<212> TYPE: DNA
<213> ORGANISM: Homo sapiens

<400> SEQUENCE: 165

```
aaggcctcta gtttagccag t                                             21
```

<210> SEQ ID NO 166
<211> LENGTH: 27
<212> TYPE: DNA
<213> ORGANISM: Homo sapiens

<400> SEQUENCE: 166

```
caacaaatgg gggagtggaa ggcggcc                                       27
```

```
<210> SEQ ID NO 167
<211> LENGTH: 121
<212> TYPE: PRT
<213> ORGANISM: Homo sapiens

<400> SEQUENCE: 167

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120

<210> SEQ ID NO 168
<211> LENGTH: 111
<212> TYPE: PRT
<213> ORGANISM: Homo sapiens

<400> SEQUENCE: 168

Gln Ala Val Leu Thr Gln Pro Ser Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Ser Asn Thr Ala Ser Leu Thr Ile Ser Gly Leu
65                  70                  75                  80

Gln Ala Glu Asp Glu Ser Asp Tyr Tyr Cys Ser Ser Tyr Thr Ser Thr
                85                  90                  95

Phe Ser Val Val Phe Gly Gly Gly Thr Lys Val Thr Val Leu Gly
            100                 105                 110

<210> SEQ ID NO 169
<211> LENGTH: 252
<212> TYPE: PRT
<213> ORGANISM: Homo sapiens

<400> SEQUENCE: 169

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Gly Gly Gly Ser Gly Gly
        115                 120                 125

Gly Gly Ser Gly Gly Gly Ser Ala Gln Ala Val Leu Thr Gln Pro
130                 135                 140

Ser Ser Val Ser Gly Ser Pro Gly Gln Ser Ile Thr Ile Ser Cys Thr
145                 150                 155                 160

Gly Ala Ser Gly Asp Val Gly Ala Tyr Asn Phe Val Ser Trp Tyr Gln
                165                 170                 175

Gln His Pro Gly Lys Thr Pro Lys Leu Ile Ile Tyr Asp Val Asn Lys
            180                 185                 190

Arg Pro Ser Gly Val Ser Asn Arg Phe Ser Gly Ser Lys Ser Ser Asn
        195                 200                 205

Thr Ala Ser Leu Thr Ile Ser Gly Leu Gln Ala Glu Asp Glu Ser Asp
    210                 215                 220

Tyr Tyr Cys Ser Ser Tyr Thr Ser Thr Phe Ser Val Val Phe Gly Gly
225                 230                 235                 240

Gly Thr Lys Val Thr Val Leu Gly Ala Ala Ala His
                245                 250

<210> SEQ ID NO 170
<211> LENGTH: 5
<212> TYPE: PRT
<213> ORGANISM: Homo sapiens

<400> SEQUENCE: 170

Asp Tyr Gly Met Asn
1               5

<210> SEQ ID NO 171
<211> LENGTH: 17
<212> TYPE: PRT
<213> ORGANISM: Homo sapiens

<400> SEQUENCE: 171

Gly Val Asn Trp Asn Gly Gly Thr Arg Asp Tyr Ala Ala Ser Val Lys
1               5                   10                  15

Gly

<210> SEQ ID NO 172
<211> LENGTH: 12
<212> TYPE: PRT
<213> ORGANISM: Homo sapiens

<400> SEQUENCE: 172

Gly Trp Tyr Ser Gly Ala Ala Trp Asn Met Gly Tyr
1               5                   10

<210> SEQ ID NO 173
<211> LENGTH: 14
<212> TYPE: PRT
<213> ORGANISM: Homo sapiens

<400> SEQUENCE: 173

Thr Gly Ala Ser Gly Asp Val Gly Ala Tyr Asn Phe Val Ser
```

<210> SEQ ID NO 174
<211> LENGTH: 7
<212> TYPE: PRT
<213> ORGANISM: Homo sapiens

<400> SEQUENCE: 174

Asp Val Asn Lys Arg Pro Ser
1               5

<210> SEQ ID NO 175
<211> LENGTH: 10
<212> TYPE: PRT
<213> ORGANISM: Homo sapiens

<400> SEQUENCE: 175

Ser Ser Tyr Thr Ser Thr Phe Ser Val Val
1               5                   10

<210> SEQ ID NO 176
<211> LENGTH: 363
<212> TYPE: DNA
<213> ORGANISM: Homo sapiens

<400> SEQUENCE: 176

```
gaggtgcagc tggtggagtc cggggggaggt gtggtacggc ctggggggtc cctgagactc      60
tcctgtgcag cctctggatt cacctttgac gattatggca tgaactgggt ccgccaagct     120
ccagggaagg gctggagtg gtctctggt gttaattgga atggtggtac cagagattat      180
gcagcctccg tgaagggccg attcaccatc tccagagaca cgccaagaa ctccctgtat      240 ctgcaaatga acagtctgag agccgaggac acggccttgt attactgtgc gagaggatgg      300
tatagtgggg ccgcgtggaa catgggctac tggggccgag aacccctggt caccgtctcc      360
tca                                                                    363
```

<210> SEQ ID NO 177
<211> LENGTH: 333
<212> TYPE: DNA
<213> ORGANISM: Homo sapiens

<400> SEQUENCE: 177

```
caggctgtgc tgactcagcc gtcctccgtg tctgggtctc ctggacagtc gatcaccatc      60
tcctgcactg gagccagcgg tgacgttggt gcttataact ttgtctcctg gtaccaacaa     120
cacccaggca aaaccccaa actcataatt tatgatgtca ataagcggcc ctcaggggtt      180
tctaatcgct tctctggctc caagtctagc aacacggcct ccctgaccat ctctgggctc      240
caggccgagg acgagtctga ttattactgc agctcatata caagcacctt ctctgtggta      300
tttggcggag ggaccaaggt caccgtccta ggt                                   333
```

<210> SEQ ID NO 178
<211> LENGTH: 757
<212> TYPE: DNA
<213> ORGANISM: Homo sapiens

<400> SEQUENCE: 178

```
cgaggtgcag ctggtggagt ccggggggagg tgtggtacgg cctgggggt ccctgagact      60 ctcctgtgca gcctctggat tcacctttga cgattatggc atgaactggg tccgccaagc     120
tccagggaag gggctggagt gggtctctgg tgttaattgg aatggtggta ccagagatta     180
```

-continued

| | |
|---|---|
| tgcagcctcc gtgaagggcc gattcaccat ctccagagac aacgccaaga actccctgta | 240 |
| tctgcaaatg aacagtctga gagccgagga cacggccttg tattactgtg cgagaggatg | 300 |
| gtatagtggg gccgcgtgga acatgggcta ctggggccga ggaaccctgg tcaccgtctc | 360 |
| gagtggaggc ggcggttcag gcggaggtgg ctctggcggt ggcggaagtg cacaggctgt | 420 |
| gctgactcag ccgtcctccg tgtctgggtc tcctggacag tcgatcacca tctcctgcac | 480 |
| tggagccagc ggtgacgttg gtgcttataa ctttgtctcc tggtaccaac aacacccagg | 540 |
| caaaaccccc aaactcataa tttatgatgt caataagcgg ccctcagggg tttctaatcg | 600 |
| cttctctggc tccaagtcta gcaacacggc ctccctgacc atctctgggc tccaggccga | 660 |
| ggacgagtct gattattact gcagctcata caagcacc ttctctgtgg tatttggcgg | 720 |
| agggaccaag gtcaccgtcc taggtgcggc cgcacat | 757 |

<210> SEQ ID NO 179
<211> LENGTH: 15
<212> TYPE: DNA
<213> ORGANISM: Homo sapiens

<400> SEQUENCE: 179

| | |
|---|---|
| gattatggca tgaac | 15 |

<210> SEQ ID NO 180
<211> LENGTH: 51
<212> TYPE: DNA
<213> ORGANISM: Homo sapiens

<400> SEQUENCE: 180

| | |
|---|---|
| ggtgttaatt ggaatggtgg taccagagat tatgcagcct ccgtgaaggg c | 51 |

<210> SEQ ID NO 181
<211> LENGTH: 36
<212> TYPE: DNA
<213> ORGANISM: Homo sapiens

<400> SEQUENCE: 181

| | |
|---|---|
| ggatggtata gtggggccgc gtggaacatg ggctac | 36 |

<210> SEQ ID NO 182
<211> LENGTH: 42
<212> TYPE: DNA
<213> ORGANISM: Homo sapiens

<400> SEQUENCE: 182

| | |
|---|---|
| actggagcca gcggtgacgt tggtgcttat aactttgtct cc | 42 |

<210> SEQ ID NO 183
<211> LENGTH: 21
<212> TYPE: DNA
<213> ORGANISM: Homo sapiens

<400> SEQUENCE: 183

| | |
|---|---|
| gatgtcaata agcggccctc a | 21 |

<210> SEQ ID NO 184
<211> LENGTH: 30
<212> TYPE: DNA
<213> ORGANISM: Homo sapiens

<400> SEQUENCE: 184

| | |
|---|---|
| agctcatata caagcacctt ctctgtggta | 30 |

<210> SEQ ID NO 185
<211> LENGTH: 121
<212> TYPE: PRT
<213> ORGANISM: Homo sapiens

<400> SEQUENCE: 185

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ser Pro Trp Ser Leu Gly His Trp Gly
            100                 105                 110

Arg Gly Thr Leu Val Thr Val Ser Ser
        115                 120

<210> SEQ ID NO 186
<211> LENGTH: 111
<212> TYPE: PRT
<213> ORGANISM: Homo sapiens

<400> SEQUENCE: 186

Gln Ala Val Leu Thr Gln Pro Ser Ser Val Ser Gly Ser Pro Gly Gln
1               5                   10                  15

Ser Val Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Arg Leu
65                  70                  75                  80

Gln Ala Glu Asp Glu Ser Asp Tyr Tyr Cys Ser Ser Tyr Thr Ser Arg
                85                  90                  95

Tyr Thr Thr Glu Phe Gly Gly Gly Thr Lys Val Thr Val Leu Gly
            100                 105                 110

<210> SEQ ID NO 187
<211> LENGTH: 271
<212> TYPE: PRT
<213> ORGANISM: Homo sapiens

<400> SEQUENCE: 187

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Trp Tyr Ser Gly Ser Pro Trp Ser Leu Gly His Trp Gly
            100                 105                 110

Arg Gly Thr Leu Val Thr Val Ser Ser Gly Gly Gly Ser Gly Gly Gly
        115                 120                 125

Gly Gly Ser Gly Gly Ser Gly Gly Ser Gly Gly Ser Gly Gly Gly
        130                 135                 140

Ser Ser Gly Gly Ser Gly Gly Gly Ser Ala Gln Ala Val Leu
145                 150                 155                 160

Thr Gln Pro Ser Ser Val Ser Gly Ser Pro Gln Ser Val Thr Ile
                165                 170                 175

Ser Cys Thr Gly Ala Ser Gly Asp Val Gly Ala Tyr Asn Phe Val Ser
            180                 185                 190

Trp Tyr Gln Gln His Pro Gly Lys Thr Pro Lys Leu Ile Ile Tyr Asp
        195                 200                 205

Val Asn Lys Arg Pro Ser Gly Val Ser Asn Arg Phe Ser Gly Ser Lys
210                 215                 220

Ser Gly Asn Thr Ala Ser Leu Thr Ile Ser Arg Leu Gln Ala Glu Asp
225                 230                 235                 240

Glu Ser Asp Tyr Tyr Cys Ser Ser Tyr Thr Ser Arg Tyr Thr Glu
                245                 250                 255

Phe Gly Gly Gly Thr Lys Val Thr Val Leu Gly Ala Ala Ala His
        260                 265                 270

<210> SEQ ID NO 188
<211> LENGTH: 5
<212> TYPE: PRT
<213> ORGANISM: Homo sapiens

<400> SEQUENCE: 188

Asp Tyr Gly Met Asn
1               5

<210> SEQ ID NO 189
<211> LENGTH: 17
<212> TYPE: PRT
<213> ORGANISM: Homo sapiens

<400> SEQUENCE: 189

Gly Val Asn Trp Asn Gly Gly Thr Arg Asp Tyr Ala Ala Ser Val Lys
1               5                   10                  15

Gly

<210> SEQ ID NO 190
<211> LENGTH: 12
<212> TYPE: PRT
<213> ORGANISM: Homo sapiens

<400> SEQUENCE: 190

Gly Trp Tyr Ser Gly Ser Pro Trp Ser Leu Gly His
1               5                   10

<210> SEQ ID NO 191
<211> LENGTH: 14
<212> TYPE: PRT
<213> ORGANISM: Homo sapiens
```

```
<400> SEQUENCE: 191

Thr Gly Ala Ser Gly Asp Val Gly Ala Tyr Asn Phe Val Ser
1               5                   10

<210> SEQ ID NO 192
<211> LENGTH: 7
<212> TYPE: PRT
<213> ORGANISM: Homo sapiens

<400> SEQUENCE: 192

Asp Val Asn Lys Arg Pro Ser
1               5

<210> SEQ ID NO 193
<211> LENGTH: 10
<212> TYPE: PRT
<213> ORGANISM: Homo sapiens

<400> SEQUENCE: 193

Ser Ser Tyr Thr Ser Arg Tyr Thr Thr Glu
1               5                   10

<210> SEQ ID NO 194
<211> LENGTH: 363
<212> TYPE: DNA
<213> ORGANISM: Homo sapiens

<400> SEQUENCE: 194
gaggtgcagc tggtggagtc cggggggaggt gtggtacggc ctgggggggtc cctgagactc      60 tcctgtgcag cctctggatt cacctttgac gattatggca tgaactgggt ccgccaagct     120
ccagggaagg ggctggagtg ggtctctggt gttaattgga tggtggtac cagagattat      180 gcagcctccg tgaagggccg attcaccatc tccagagaca cgccaagaa ctccctgtat      240 ctgcaaatga acagtctgag agccgaggac acggccttgt attactgtgc gagaggatgg     300
tatagtggga gcccgtggtc gctgggccac tggggccgag aaccctggt caccgtctcc      360 tca                                                                    363

<210> SEQ ID NO 195
<211> LENGTH: 333
<212> TYPE: DNA
<213> ORGANISM: Homo sapiens

<400> SEQUENCE: 195
caggctgtgc tgactcagcc gtcctccgtg tctgggtctc ctggacagtc ggtcaccatc      60
tcctgcactg gagccagcgg tgacgttggt gcttataact ttgtctcctg gtaccaacaa     120
cacccaggca aaccccccaa actcataatt tatgatgtca ataagcggcc ctcaggggtt     180
tctaatcgct tctctggctc caagtctggc aacacggcct ccctgaccat ctctaggctc     240
caggccgagg acgagtctga ttattactgc agctcatata tcgaggta cacgaccgag      300 tttggcggag ggaccaaggt caccgtccta ggt                                  333

<210> SEQ ID NO 196
<211> LENGTH: 813
<212> TYPE: DNA
<213> ORGANISM: Homo sapiens

<400> SEQUENCE: 196
gaggtgcagc tggtggagtc cggggggaggt gtggtacggc ctgggggggtc cctgagactc      60
```

```
tcctgtgcag cctctggatt cacctttgac gattatggca tgaactgggt ccgccaagct      120
ccagggaagg ggctggagtg ggtctctggt gttaattgga atggtggtac cagagattat      180
gcagcctccg tgaagggccg attcaccatc tccagagaca acgccaagaa ctccctgtat      240
ctgcaaatga acagtctgag agccgaggac acggccttgt attactgtgc gagaggatgg      300
tatagtggga gcccgtggtc gctgggccac tggggccgag aaccctggt caccgtctcg       360 agtggaggcg gcggttcagg cggaggtggc tctggcggta gcgaggtggg ctctggcggt      420
agcggaggtg gctctagcgg aggtggctct ggcggtggcg aagtgcaca ggctgtgctg       480 actcagccgt cctccgtgtc tgggtctcct ggacagtcgg tcaccatctc ctgcactgga      540
gccagcggtg acgttggtgc ttataacttt gtctcctggt accaacaaca cccaggcaaa      600 accccaaac tcataattta tgatgtcaat aagcggccct caggggtttc taatcgcttc       660
tctggctcca agtctggcaa cacggcctcc ctgaccatct ctaggctcca ggccgaggac      720
gagtctgatt attactgcag ctcatataca tcgaggtaca cgaccgagtt tggcggaggg     780
accaaggtca ccgtcctagg tgcggccgca cat                                  813

<210> SEQ ID NO 197
<211> LENGTH: 15
<212> TYPE: DNA
<213> ORGANISM: Homo sapiens

<400> SEQUENCE: 197
gattatggca tgaac                                                       15

<210> SEQ ID NO 198
<211> LENGTH: 51
<212> TYPE: DNA
<213> ORGANISM: Homo sapiens

<400> SEQUENCE: 198
ggtgttaatt ggaatggtgg taccagagat tatgcagcct ccgtgaaggg c               51

<210> SEQ ID NO 199
<211> LENGTH: 36
<212> TYPE: DNA
<213> ORGANISM: Homo sapiens

<400> SEQUENCE: 199
ggatggtata gtgggagccc gtggtcgctg ggccac                                36

<210> SEQ ID NO 200
<211> LENGTH: 42
<212> TYPE: DNA
<213> ORGANISM: Homo sapiens

<400> SEQUENCE: 200
actggagcca gcggtgacgt tggtgcttat aactttgtct cc                         42

<210> SEQ ID NO 201
<211> LENGTH: 21
<212> TYPE: DNA
<213> ORGANISM: Homo sapiens

<400> SEQUENCE: 201
gatgtcaata agcggccctc a                                                21

<210> SEQ ID NO 202
<211> LENGTH: 30
<212> TYPE: DNA
```

<213> ORGANISM: Homo sapiens

<400> SEQUENCE: 202
agctcatata catcgaggta cacgaccgag    30

<210> SEQ ID NO 203
<211> LENGTH: 121
<212> TYPE: PRT
<213> ORGANISM: Homo sapiens

<400> SEQUENCE: 203

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120

<210> SEQ ID NO 204
<211> LENGTH: 111
<212> TYPE: PRT
<213> ORGANISM: Homo sapiens

<400> SEQUENCE: 204

Gln Ala Val Leu Thr Gln Pro Ser Ser Val Ser Gly Ser Pro Gly Gln
1               5                   10                  15

Ser Ile Thr Ile Ser Cys Thr Gly Ala Ser Gly Asp Val Gly Ala Tyr
                20                  25                  30

Asn Phe Val Ser Trp Tyr Gln Gln His Pro Gly Lys Thr Pro Lys Leu
            35                  40                  45

Ile Ile Tyr Asp Val Asn Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Tyr Cys Ala Ser Leu Val Ser Asp
                85                  90                  95

Phe Ser Val Val Phe Gly Gly Gly Thr Lys Val Thr Val Leu Gly
            100                 105                 110

<210> SEQ ID NO 205
<211> LENGTH: 266
<212> TYPE: PRT
<213> ORGANISM: Homo sapiens

<400> SEQUENCE: 205

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

```
Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
 50                  55                  60

Lys Gly Arg Phe Thr Ile Ser Arg Asp Asn Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ala Ala Trp Asn Met Gly Tyr Trp Gly
                100                 105                 110

Arg Gly Thr Leu Val Thr Val Ser Ser Gly Gly Gly Ser Gly Gly
            115                 120                 125

Gly Gly Ser Gly Gly Ser Gly Gly Ser Gly Gly Gly Gly Gly
        130                 135                 140

Ser Gly Gly Gly Ser Ala Gln Ala Val Leu Thr Gln Pro Ser Ser
145                 150                 155                 160

Val Ser Gly Ser Pro Gly Gln Ser Ile Thr Ile Ser Cys Thr Gly Ala
                165                 170                 175

Ser Gly Asp Val Gly Ala Tyr Asn Phe Val Ser Trp Tyr Gln Gln His
                180                 185                 190

Pro Gly Lys Thr Pro Lys Leu Ile Ile Tyr Asp Val Asn Lys Arg Pro
                195                 200                 205

Ser Gly Val Ser Asn Arg Phe Ser Gly Ser Lys Ser Gly Asn Thr Ala
                210                 215                 220

Ser Leu Thr Ile Ser Gly Leu Gln Ala Glu Asp Glu Ser Asp Tyr Tyr
225                 230                 235                 240

Cys Ala Ser Leu Val Ser Asp Phe Ser Val Val Phe Gly Gly Gly Thr
                245                 250                 255

Lys Val Thr Val Leu Gly Ala Ala Ala His
            260                 265

<210> SEQ ID NO 206
<211> LENGTH: 5
<212> TYPE: PRT
<213> ORGANISM: Homo sapiens

<400> SEQUENCE: 206

Asp Tyr Gly Met Asn
1               5

<210> SEQ ID NO 207
<211> LENGTH: 17
<212> TYPE: PRT
<213> ORGANISM: Homo sapiens

<400> SEQUENCE: 207

Gly Val Asn Trp Asn Gly Gly Thr Arg Asp Tyr Ala Ala Ser Val Lys
1               5                   10                  15

Gly

<210> SEQ ID NO 208
<211> LENGTH: 12
<212> TYPE: PRT
<213> ORGANISM: Homo sapiens

<400> SEQUENCE: 208

Gly Trp Tyr Ser Gly Ala Ala Trp Asn Met Gly Tyr
1               5                   10
```

<210> SEQ ID NO 209
<211> LENGTH: 14
<212> TYPE: PRT
<213> ORGANISM: Homo sapiens

<400> SEQUENCE: 209

Thr Gly Ala Ser Gly Asp Val Gly Ala Tyr Asn Phe Val Ser
1               5                   10

<210> SEQ ID NO 210
<211> LENGTH: 7
<212> TYPE: PRT
<213> ORGANISM: Homo sapiens

<400> SEQUENCE: 210

Asp Val Asn Lys Arg Pro Ser
1               5

<210> SEQ ID NO 211
<211> LENGTH: 10
<212> TYPE: PRT
<213> ORGANISM: Homo sapiens

<400> SEQUENCE: 211

Ala Ser Leu Val Ser Asp Phe Ser Val Val
1               5                   10

<210> SEQ ID NO 212
<211> LENGTH: 363
<212> TYPE: DNA
<213> ORGANISM: Homo sapiens

<400> SEQUENCE: 212

```
gaggtgcagc tggtggagtc cggggagggt gtggtacggc ctgggggtc cctgagactc      60 tcctgtgcag cctctggatt cacctttgac gattatggca tgaactgggt ccgccaagct    120
ccagggaagg gctggagtg gtctctggt gttaattgga atggtggtac cagagattat     180
gcagcctccg tgaagggccg attcaccatc tccagagaca cgccaagaa ctccctgtat    240 ctgcaaatga acagtctgag agccgaggac acggccttgt attactgtgc gagaggatgg    300
tatagtgggg ccgcgtggaa catgggctac tggggccgag aaccctggt caccgtctcc    360 tca                                                                  363
```

<210> SEQ ID NO 213
<211> LENGTH: 333
<212> TYPE: DNA
<213> ORGANISM: Homo sapiens

<400> SEQUENCE: 213

```
caggctgtgc tgactcagcc gtcctccgtg tctgggtccc ctggacagtc gatcaccatc      60
tcctgcactg gagccagcgg tgacgttggt gcttataact ttgtctcctg gtaccaacaa    120
cacccaggca aaccccccaa actcataatt tatgatgtca ataagcggcc ctcagggtt     180 tctaatcgct tctctggctc caagtctggc aacacggcct ccctgaccat ctctgggctc    240
caggccgagg acgagtctga ttattactgc gcctccctcg tctccgactt ctctgtggta    300
tttggcggag ggaccaaggt caccgtccta ggt                                 333
```

<210> SEQ ID NO 214
<211> LENGTH: 798
<212> TYPE: DNA

-continued

<213> ORGANISM: Homo sapiens

<400> SEQUENCE: 214

```
gaggtgcagc tggtggagtc cggggggaggt gtggtacggc ctgggggggtc cctgagactc      60
tcctgtgcag cctctggatt caccttttgac gattatggca tgaactgggt ccgccaagct     120
ccagggaagg gctggagtg gtctctggt gttaattgga atggtggtac cagagattat        180
gcagcctccg tgaagggccg attcaccatc tccagagaca acgccaagaa ctccctgtat      240
ctgcaaatga acagtctgag agccgaggac acggccttgt attactgtgc gagaggatgg      300
tatagtgggg ccgcgtggaa catgggctac tggggccgag aaccctggt caccgtctcg       360
agtggaggcg gcggttcagg cggaggtggc tctggtggta gcggaggtgg ctctggcggt      420
ggcgaggtg gctctggcgg tggcggaagt gcacaggctg tgctgactca gccgtcctcc       480
gtgtctgggt cccctggaca gtcgatcacc atctcctgca ctggagccag cggtgacgtt      540
ggtgcttata actttgtctc ctggtaccaa caacacccag gcaaaacccc caaactcata      600
atttatgatg tcaataagcg gccctcaggg gtttctaatc gcttctctgg ctccaagtct      660
ggcaacacgg cctccctgac catctctggg ctccaggccg aggacgagtc tgattattac      720
tgcgcctccc tcgtctccga cttctctgtg gtatttggcg agggaccaa ggtcaccgtc      780
ctaggtgcgg ccgcacat                                                   798
```

<210> SEQ ID NO 215
<211> LENGTH: 15
<212> TYPE: DNA
<213> ORGANISM: Homo sapiens

<400> SEQUENCE: 215

```
gattatggca tgaac                                                      15
```

<210> SEQ ID NO 216
<211> LENGTH: 51
<212> TYPE: DNA
<213> ORGANISM: Homo sapiens

<400> SEQUENCE: 216

```
ggtgttaatt ggaatggtgg taccagagat tatgcagcct ccgtgaaggg c               51
```

<210> SEQ ID NO 217
<211> LENGTH: 36
<212> TYPE: DNA
<213> ORGANISM: Homo sapiens

<400> SEQUENCE: 217

```
ggatggtata gtggggccgc gtggaacatg ggctac                               36
```

<210> SEQ ID NO 218
<211> LENGTH: 42
<212> TYPE: DNA
<213> ORGANISM: Homo sapiens

<400> SEQUENCE: 218

```
actggagcca gcggtgacgt tggtgcttat aactttgtct cc                         42
```

<210> SEQ ID NO 219
<211> LENGTH: 21
<212> TYPE: DNA
<213> ORGANISM: Homo sapiens

<400> SEQUENCE: 219

```
gatgtcaata agcggccctc a                                           21
```

<210> SEQ ID NO 220
<211> LENGTH: 30
<212> TYPE: DNA
<213> ORGANISM: Homo sapiens

<400> SEQUENCE: 220

```
gcctccctcg tctccgactt ctctgtggta                                  30
```

<210> SEQ ID NO 221
<211> LENGTH: 119
<212> TYPE: PRT
<213> ORGANISM: Homo sapiens

<400> SEQUENCE: 221

```
Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
                20                  25                  30

Tyr Ile His Trp Val Arg Gln Thr Pro Gly Gln Gly Phe Glu Trp Met
            35                  40                  45

Gly Trp Val Asn Pro Asp Thr Gly Gly Thr Arg Tyr Ala Gln Lys Phe
        50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115
```

<210> SEQ ID NO 222
<211> LENGTH: 109
<212> TYPE: PRT
<213> ORGANISM: Homo sapiens

<400> SEQUENCE: 222

```
Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
                20                  25                  30

His Trp Tyr Gln Gln Arg Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Leu Phe Asn Asp Asn
                85                  90                  95

Gly Val Phe Gly Gly Gly Thr Lys Leu Thr Val Leu Gly
            100                 105
```

<210> SEQ ID NO 223
<211> LENGTH: 248
<212> TYPE: PRT
<213> ORGANISM: Homo sapiens

<400> SEQUENCE: 223

```
Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
50                  55                  60

Gln Gly Trp Val Thr Met Thr Arg Asp Met Ser Asn Thr Thr Ala Tyr
65              70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Gln Ser Val Leu Thr Gln Pro Pro Ser
        130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Phe Tyr Cys Gln Val
    210                 215                 220

Trp Asp Leu Phe Asn Asp Asn Gly Val Phe Gly Gly Gly Thr Lys Leu
225                 230                 235                 240

Thr Val Leu Gly Ala Ala Ala His
                245

<210> SEQ ID NO 224
<211> LENGTH: 5
<212> TYPE: PRT
<213> ORGANISM: Homo sapiens

<400> SEQUENCE: 224

Asp Tyr Tyr Ile His
1               5

<210> SEQ ID NO 225
<211> LENGTH: 17
<212> TYPE: PRT
<213> ORGANISM: Homo sapiens

<400> SEQUENCE: 225

Trp Val Asn Pro Asp Thr Gly Gly Thr Arg Tyr Ala Gln Lys Phe Gln
1               5                   10                  15

Gly

<210> SEQ ID NO 226
<211> LENGTH: 10
<212> TYPE: PRT
<213> ORGANISM: Homo sapiens

<400> SEQUENCE: 226
```

```
Asp Leu Thr Gly Phe Asp Pro Phe Asp Ile
1               5                   10

<210> SEQ ID NO 227
<211> LENGTH: 11
<212> TYPE: PRT
<213> ORGANISM: Homo sapiens

<400> SEQUENCE: 227

Gly Gly Asn Asn Phe Arg Asn Lys Arg Val His
1               5                   10

<210> SEQ ID NO 228
<211> LENGTH: 7
<212> TYPE: PRT
<213> ORGANISM: Homo sapiens

<400> SEQUENCE: 228

Tyr Asp Ser Asp Arg Pro Ser
1               5

<210> SEQ ID NO 229
<211> LENGTH: 11
<212> TYPE: PRT
<213> ORGANISM: Homo sapiens

<400> SEQUENCE: 229

Gln Val Trp Asp Leu Phe Asn Asp Asn Gly Val
1               5                   10

<210> SEQ ID NO 230
<211> LENGTH: 357
<212> TYPE: DNA
<213> ORGANISM: Homo sapiens

<400> SEQUENCE: 230
gaggtgcagc tggtgcagtc tggggctgag gtgaagaagc ctggggcctc agtgaaggtc      60
tcctgtcagg cttctggata caccttcagc gattactata ttcactgggt gcgacagacc     120
cctggacaag ggtttgagtg gatgggatgg gtcaaccctg acactggtgg cacaagatac     180
gcgcagaagt ttcagggctg gtcacaatg accaggaca tgtccaacac cacagcctac      240
atggagctgc ccaggctgag agacgacgac acggccgtat attactgtgc gagagatcta     300
actggatttg atccttttga tatctggggc cagggaaccc tggtcaccgt ctcctca        357

<210> SEQ ID NO 231
<211> LENGTH: 327
<212> TYPE: DNA
<213> ORGANISM: Homo sapiens

<400> SEQUENCE: 231
cagtctgtgc tgactcagcc accctcagtg tcagtggccc caggaaagac ggccacgatt      60
acctgtgggg gaaacaactt tcgaaataaa agagtacact ggtatcagca gaggccaggc     120
caggcccctg tcctggtcat ctattatgac tcagaccggc cctcagggat ccctgagcga     180
ttctctggct cccgctctgg gaacacggcc accctgacca tcagcagggt cgaggccggg     240
gatgaggccg acttttactg tcaggtgtgg gatctcttca acgacaacgg cgtgttcggc     300
ggagggacca agctgaccgt cctaggt                                        327

<210> SEQ ID NO 232
<211> LENGTH: 744
```

-continued

```
<212> TYPE: DNA
<213> ORGANISM: Homo sapiens

<400> SEQUENCE: 232
gaagtgcagc tggtgcagtc tggggctgag gtgaagaagc ctggggcctc agtgaaggtc      60
tcctgtcagg cttctggata caccttcagc gattactata ttcactgggt gcgacagacc     120
cctggacaag ggtttgagtg gatgggatgg gtcaaccctg acactggtgg cacaagatac     180
gcgcagaagt ttcagggctg ggtcacaatg accagggaca tgtccaacac cacagcctac     240
atggagctgc ccaggctgag agacgacgac acgccgtat attactgtgc gagagatcta      300
actggatttg atccttttga tatctggggc caggaaccc tggtcaccgt ctcgagtgga      360
ggcggcagtt caggtggagg tggctctggc ggtggcggaa gtgcacagtc tgtgctgact     420
cagccaccct cagtgtcagt ggccccagga aagacggcca cgattacctg tgggggaaac     480
aactttcgaa ataaaagagt acactggtat cagcagaggc caggccaggc ccctgtcctg     540
gtcatctatt atgattcaga ccggcccctca gggatccctg agcgattctc tggctcccgc     600
tctgggaaca cggccaccct gaccatcagc agggtcgagg ccggggatga ggccgacttt     660
tactgtcagg tgtgggatct cttcaacgac aacggcgtgt tcggcggagg gaccaagctg     720
accgtcctag gtgcggccgc acat                                             744

<210> SEQ ID NO 233
<211> LENGTH: 15
<212> TYPE: DNA
<213> ORGANISM: Homo sapiens

<400> SEQUENCE: 233
gattactata ttcac                                                       15

<210> SEQ ID NO 234
<211> LENGTH: 51
<212> TYPE: DNA
<213> ORGANISM: Homo sapiens

<400> SEQUENCE: 234
tgggtcaacc ctgacactgg tggcacaaga tacgcgcaga gtttcaggg c                51

<210> SEQ ID NO 235
<211> LENGTH: 30
<212> TYPE: DNA
<213> ORGANISM: Homo sapiens

<400> SEQUENCE: 235
gatctaactg gatttgatcc ttttgatatc                                       30

<210> SEQ ID NO 236
<211> LENGTH: 33
<212> TYPE: DNA
<213> ORGANISM: Homo sapiens

<400> SEQUENCE: 236
gggggaaaca actttcgaaa taaaagagta cac                                   33

<210> SEQ ID NO 237
<211> LENGTH: 21
<212> TYPE: DNA
<213> ORGANISM: Homo sapiens

<400> SEQUENCE: 237
tatgactcag accggcccctc a                                               21
```

<210> SEQ ID NO 238
<211> LENGTH: 33
<212> TYPE: DNA
<213> ORGANISM: Homo sapiens

<400> SEQUENCE: 238
caggtgtggg atctcttcaa cgacaacggc gtg    33

<210> SEQ ID NO 239
<211> LENGTH: 119
<212> TYPE: PRT
<213> ORGANISM: Homo sapiens

<400> SEQUENCE: 239

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 240
<211> LENGTH: 109
<212> TYPE: PRT
<213> ORGANISM: Homo sapiens

<400> SEQUENCE: 240

Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Phe Leu Thr Asp Ser
                85                  90                  95

Gly Ser Phe Gly Gly Gly Thr Lys Leu Thr Val Leu Gly
            100                 105

<210> SEQ ID NO 241
<211> LENGTH: 248
<212> TYPE: PRT
<213> ORGANISM: Homo sapiens

<400> SEQUENCE: 241

-continued

```
Glu Val Gln Leu Val Gln Ser Gly Ala Glu Val Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
            35                  40                  45

Gly Trp Val Asn Pro Asp Thr Gly Thr Arg Tyr Ala Gln Lys Phe
50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
            85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Ser Gly Gly Gly
            115                 120                 125

Ser Gly Gly Gly Ser Ala Gln Ser Val Leu Thr Gln Pro Pro Ser
    130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
                180                 185                 190

Pro Glu Arg Phe Ser Gly Ser Arg Ser Gly Asn Thr Ala Thr Leu Thr
                195                 200                 205

Ile Ser Arg Val Glu Ala Gly Asp Glu Ala Asp Phe Tyr Cys Gln Val
        210                 215                 220

Trp Asp Phe Leu Thr Asp Ser Gly Ser Phe Gly Gly Thr Lys Leu
225                 230                 235                 240

Thr Val Leu Gly Ala Ala Ala His
            245
```

```
<210> SEQ ID NO 242
<211> LENGTH: 5
<212> TYPE: PRT
<213> ORGANISM: Homo sapiens

<400> SEQUENCE: 242

Asp Tyr Tyr Ile His
1               5

<210> SEQ ID NO 243
<211> LENGTH: 17
<212> TYPE: PRT
<213> ORGANISM: Homo sapiens

<400> SEQUENCE: 243

Trp Val Asn Pro Asp Thr Gly Gly Thr Arg Tyr Ala Gln Lys Phe Gln
1               5                   10                  15

Gly

<210> SEQ ID NO 244
<211> LENGTH: 10
<212> TYPE: PRT
<213> ORGANISM: Homo sapiens

<400> SEQUENCE: 244
```

```
Asp Leu Thr Gly Phe Asp Pro Phe Asp Ile
1               5                   10

<210> SEQ ID NO 245
<211> LENGTH: 11
<212> TYPE: PRT
<213> ORGANISM: Homo sapiens

<400> SEQUENCE: 245

Gly Gly Asn Asn Phe Arg Asn Lys Arg Val His
1               5                   10

<210> SEQ ID NO 246
<211> LENGTH: 7
<212> TYPE: PRT
<213> ORGANISM: Homo sapiens

<400> SEQUENCE: 246

Tyr Asp Ser Asp Arg Pro Ser
1               5

<210> SEQ ID NO 247
<211> LENGTH: 11
<212> TYPE: PRT
<213> ORGANISM: Homo sapiens

<400> SEQUENCE: 247

Gln Val Trp Asp Phe Leu Thr Asp Ser Gly Ser
1               5                   10

<210> SEQ ID NO 248
<211> LENGTH: 357
<212> TYPE: DNA
<213> ORGANISM: Homo sapiens

<400> SEQUENCE: 248
gaggtgcagc tggtgcagtc tggggctgag gtgaagaagc ctggggcctc agtgaaggtc      60
tcctgtcagg cttctggata caccttcagc gattactata ttcactgggt gcgacagacc     120
cctggacaag ggtttgagtg gatgggatgg gtcaaccctg acactggtgg cacaagatac     180
gcgcagaagt tcagggctg gtcacaatg accagggaca tgtccaacac cacagcctac      240
atggagctgc caggctgag agacgacgac acggccgtat attactgtgc gagagatcta     300
actggatttg atccttttga tatctggggc cagggaaccc tggtcaccgt ctcctca      357

<210> SEQ ID NO 249
<211> LENGTH: 327
<212> TYPE: DNA
<213> ORGANISM: Homo sapiens

<400> SEQUENCE: 249
cagtctgtgc tgactcagcc accctcagtg tcagtggccc caggaaagac ggccacaatt      60
acctgtgggg gaaacaactt tcgaaataaa agagtacact ggtatcagca gaggccaggc     120
caggcgcctg tcctggtcat ctattatgat tcagaccggc cctcaggat ccctgagcga      180 ttctctggct cccgctctgg gaacacggcc accctgacca tcagcagggt cgaggccggg     240
gatgaggccg actttactg tcaggtgtgg gatttcctca ccgactcggg gtcgttcggc      300
ggagggacca gctgaccgt cctaggt                                         327

<210> SEQ ID NO 250
<211> LENGTH: 744
<212> TYPE: DNA
```

-continued

<213> ORGANISM: Homo sapiens

<400> SEQUENCE: 250
gaagtgcagc tggtgcagtc tggggctgag gtgaagaagc ctggggcctc agtgaaggtc      60
tcctgtcagg cttctggata caccttcagc gattactata ttcactgggt gcgacagacc     120
cctggacaag ggtttgagtg gatgggatgg gtcaaccctg acactggtgg cacaagatac     180
gcgcagaagt tcagggctg gtcacaatg accagggaca tgtccaacac acagcctac       240
atggagctgc ccaggctgag agacgacgac acggccgtat attactgtgc gagagatcta     300
actggatttg atccttttga tatctggggc caggaacccc tggtcaccgt ctcgagtgga     360
ggcggcggtt caggcggagg tggctctggc ggtggcggaa gtgcacagtc tgtgctgact     420
cagccaccct cagtgtcagt ggccccagga aagacggcca caattacctg tgggggaaac     480
aactttcgaa ataaaagagt acactggtat cagcagaggc caggccaggc gcctgtcctg     540
gtcatctatt atgattcaga ccggccctca gggatccctg agcgattctc tggctcccgc     600
tctgggaaca cggccaccct gaccatcagc agggtcgagg ccggggatga ggccgacttt     660
tactgtcagg tgtgggattt cctcaccgac tcggggtcgt tcggcggagg gaccaagctg     720
accgtcctag gtgcggccgc acat                                            744

<210> SEQ ID NO 251
<211> LENGTH: 15
<212> TYPE: DNA
<213> ORGANISM: Homo sapiens

<400> SEQUENCE: 251
gattactata ttcac                                                      15

<210> SEQ ID NO 252
<211> LENGTH: 51
<212> TYPE: DNA
<213> ORGANISM: Homo sapiens

<400> SEQUENCE: 252
tgggtcaacc ctgacactgg tggcacaaga tacgcgcaga gtttcaggg c                51

<210> SEQ ID NO 253
<211> LENGTH: 30
<212> TYPE: DNA
<213> ORGANISM: Homo sapiens

<400> SEQUENCE: 253
gatctaactg gatttgatcc ttttgatatc                                      30

<210> SEQ ID NO 254
<211> LENGTH: 33
<212> TYPE: DNA
<213> ORGANISM: Homo sapiens

<400> SEQUENCE: 254
gggggaaaca actttcgaaa taaaagagta cac                                  33

<210> SEQ ID NO 255
<211> LENGTH: 21
<212> TYPE: DNA
<213> ORGANISM: Homo sapiens

<400> SEQUENCE: 255
tatgattcag accggccctc a                                               21

<210> SEQ ID NO 256
<211> LENGTH: 33
<212> TYPE: DNA
<213> ORGANISM: Homo sapiens

<400> SEQUENCE: 256
caggtgtggg atttcctcac cgactcgggg tcg                             33

<210> SEQ ID NO 257
<211> LENGTH: 119
<212> TYPE: PRT
<213> ORGANISM: Homo sapiens

<400> SEQUENCE: 257

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Tyr Asp Tyr Tyr Asp Arg Trp Gly Gln Gly
            100                 105                 110

Thr Leu Val Thr Val Ser Ser
        115

<210> SEQ ID NO 258
<211> LENGTH: 108
<212> TYPE: PRT
<213> ORGANISM: Homo sapiens

<400> SEQUENCE: 258

Gln Ser Val Leu Thr Gln Pro Pro Ser Met Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Phe Leu Ala Asp Glu
                85                  90                  95

Ala Met Phe Gly Gly Gly Thr Lys Leu Thr Val Leu
            100                 105

<210> SEQ ID NO 259
<211> LENGTH: 262
<212> TYPE: PRT
<213> ORGANISM: Homo sapiens

<400> SEQUENCE: 259

Glu Val Gln Leu Val Gln Ser Gly Ala Glu Val Lys Lys Pro Gly Ala

```
  1               5                  10                 15
Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
            35                  40                  45

Gly Trp Val Asn Pro Asp Thr Gly Thr Arg Tyr Ala Gln Lys Phe
 50                  55                  60

Gln Gly Trp Val Thr Met Thr Arg Asp Met Ser Asn Thr Thr Ala Tyr
 65                  70                  75                  80

Met Glu Leu Pro Arg Leu Arg Asp Asp Thr Ala Val Tyr Tyr Cys
                85                  90                  95

Ala Arg Asp Leu Thr Gly Tyr Asp Tyr Asp Arg Trp Gly Gln Gly
                100                 105                 110

Thr Leu Val Thr Val Ser Ser Gly Gly Gly Ser Gly Gly Gly
            115                 120                 125

Ser Gly Gly Gly Gly Ser Gly Gly Gly Gly Gly Ser Gly
            130                 135                 140

Gly Gly Ser Ala Gln Ser Val Leu Thr Gln Pro Ser Met Ser
145                 150                 155                 160

Val Ala Pro Gly Lys Thr Ala Thr Ile Thr Cys Gly Asn Asn Phe
                165                 170                 175

Arg Asn Lys Arg Val His Trp Tyr Gln Gln Arg Pro Gly Gln Ala Pro
            180                 185                 190

Val Leu Val Ile Tyr Tyr Asp Ser Asp Arg Pro Ser Gly Ile Pro Glu
            195                 200                 205

Arg Phe Ser Gly Ser Arg Ser Gly Asn Thr Ala Thr Leu Thr Ile Ser
210                 215                 220

Arg Val Glu Ala Gly Asp Glu Ala Asp Phe Tyr Cys Gln Val Trp Asp
225                 230                 235                 240

Phe Leu Ala Asp Glu Ala Met Phe Gly Gly Thr Lys Leu Thr Val
                245                 250                 255

Leu Gly Ala Ala Ala His
            260
```

<210> SEQ ID NO 260
<211> LENGTH: 5
<212> TYPE: PRT
<213> ORGANISM: Homo sapiens

<400> SEQUENCE: 260

```
Asp Tyr Tyr Ile His
 1               5
```

<210> SEQ ID NO 261
<211> LENGTH: 17
<212> TYPE: PRT
<213> ORGANISM: Homo sapiens

<400> SEQUENCE: 261

```
Trp Val Asn Pro Asp Thr Gly Gly Thr Arg Tyr Ala Gln Lys Phe Gln
 1               5                  10                  15
Gly
```

<210> SEQ ID NO 262
<211> LENGTH: 10
<212> TYPE: PRT
<213> ORGANISM: Homo sapiens -continued

<400> SEQUENCE: 262

Asp Leu Thr Gly Tyr Asp Tyr Tyr Asp Arg
1               5                   10

<210> SEQ ID NO 263
<211> LENGTH: 11
<212> TYPE: PRT
<213> ORGANISM: Homo sapiens

<400> SEQUENCE: 263

Gly Gly Asn Asn Phe Arg Asn Lys Arg Val His
1               5                   10

<210> SEQ ID NO 264
<211> LENGTH: 7
<212> TYPE: PRT
<213> ORGANISM: Homo sapiens

<400> SEQUENCE: 264

Tyr Asp Ser Asp Arg Pro Ser
1               5

<210> SEQ ID NO 265
<211> LENGTH: 11
<212> TYPE: PRT
<213> ORGANISM: Homo sapiens

<400> SEQUENCE: 265

Gln Val Trp Asp Phe Leu Ala Asp Glu Ala Met
1               5                   10

<210> SEQ ID NO 266
<211> LENGTH: 357
<212> TYPE: DNA
<213> ORGANISM: Homo sapiens

<400> SEQUENCE: 266
gaggtgcagc tggtgcagtc tggggctgag gtgaagaagc ctggggcctc agtgaaggtc    60
tcctgtcagg cttctggata caccttcagc gattactata ttcactgggt gcgacagacc   120
cctggacaag ggtttgagtg gatgggatgg gtcaaccctg acactggtgg cacaagatac   180
gcgcagaagt ttcagggctg ggtcacaatg accagggaca tgtccaacac cacagcctac   240
atggagctgc ccaggctgag agacgacgac acggccgtat attactgtgc gagagatcta   300
actggatacg actactacga ccggtggggc cagggaaccc tggtcaccgt ctcctca      357

<210> SEQ ID NO 267
<211> LENGTH: 327
<212> TYPE: DNA
<213> ORGANISM: Homo sapiens

<400> SEQUENCE: 267
cagtctgtgc tgactcagcc gccctcaatg tcagtggccc caggaaagac ggccacgatt    60
acctgtgggg gaaacaactt tcgaaataaa agagtacact ggtatcagca gaggccaggc   120
caggcccctg tcctggtcat ctattatgat tcagaccggc cctcagggat ccctgagcga   180
ttctctggct cccgctctgg gaacacggcc accctgacca tcagcagggt cgaggccggg   240
gatgaggccg acttttactg tcaggtgtgg gatttcctcg ccgacgaggc gatgttcggc   300
ggagggacca agctgaccgt cctaggt                                        327

<210> SEQ ID NO 268

<211> LENGTH: 786
<212> TYPE: DNA
<213> ORGANISM: Homo sapiens

<400> SEQUENCE: 268

| | | | | | |
|---|---|---|---|---|---|
| gaagtgcagc | tggtgcagtc | tggggctgag | gtgaagaagc | ctggggcctc | agtgaaggtc | 60 |
| tcctgtcagg | cttctggata | caccttcagc | gattactata | ttcactgggt | gcgacagacc | 120 |
| cctggacaag | ggtttgagtg | gatgggatgg | gtcaaccctg | acactggtgg | cacaagatac | 180 |
| gcgcagaagt | ttcagggctg | gtcacaatg | accagggaca | tgtccaacac | cacagcctac | 240 |
| atggagctgc | ccaggctgag | agacgacgac | acggccgtat | attactgtgc | gagagatcta | 300 |
| actggatacg | actactacga | ccggtggggc | cagggaaccc | tggtcaccgt | ctcgagtgga | 360 |
| ggcggcggtt | caggcggagg | tggctctggc | ggtggtggag | gtggctctgg | cggtggcgga | 420 |
| ggtggctctg | gcggtggcgg | aagtgcacag | tctgtgctga | ctcagccgcc | ctcaatgtca | 480 |
| gtggccccag | gaaagacggc | cacgattacc | tgtgggggaa | caactttcg | aaataaaaga | 540 |
| gtacactggt | atcagcagag | gccaggccag | gcccctgtcc | tggtcatcta | ttatgattca | 600 |
| gaccggccct | cagggatccc | tgagcgattc | tctggctccc | gctctgggaa | cacgccacc | 660 |
| ctgaccatca | gcagggtcga | ggccggggat | gaggccgact | tttactgtca | ggtgtgggat | 720 |
| ttcctcgccg | acgaggcgat | gttcggcgga | gggaccaagc | tgaccgtcct | aggtgcggcc | 780 |
| gcacat | | | | | | 786 |

<210> SEQ ID NO 269
<211> LENGTH: 15
<212> TYPE: DNA
<213> ORGANISM: Homo sapiens

<400> SEQUENCE: 269
gattactata ttcac   15

<210> SEQ ID NO 270
<211> LENGTH: 51
<212> TYPE: DNA
<213> ORGANISM: Homo sapiens

<400> SEQUENCE: 270
tgggtcaacc ctgacactgg tggcacaaga tacgcgcaga gtttcaggg c   51

<210> SEQ ID NO 271
<211> LENGTH: 30
<212> TYPE: DNA
<213> ORGANISM: Homo sapiens

<400> SEQUENCE: 271
gatctaactg gatacgacta ctacgaccgg   30

<210> SEQ ID NO 272
<211> LENGTH: 33
<212> TYPE: DNA
<213> ORGANISM: Homo sapiens

<400> SEQUENCE: 272
gggggaaaca actttcgaaa taaaagagta cac   33

<210> SEQ ID NO 273
<211> LENGTH: 21
<212> TYPE: DNA
<213> ORGANISM: Homo sapiens

<400> SEQUENCE: 273
tatgattcag accggccctc a         21

<210> SEQ ID NO 274
<211> LENGTH: 33
<212> TYPE: DNA
<213> ORGANISM: Homo sapiens

<400> SEQUENCE: 274
caggtgtggg atttcctcgc cgacgaggcg atg         33

<210> SEQ ID NO 275
<211> LENGTH: 119
<212> TYPE: PRT
<213> ORGANISM: Homo sapiens

<400> SEQUENCE: 275

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Gly Leu Arg Asp Asp Thr Ala Val Tyr Tyr Cys
                85                  90                  95

Ala Arg Asp Leu Thr Gly Tyr Asp Gln Tyr Thr Ala Trp Gly Gln Gly
            100                 105                 110

Thr Leu Val Thr Val Ser Ser
        115

<210> SEQ ID NO 276
<211> LENGTH: 109
<212> TYPE: PRT
<213> ORGANISM: Homo sapiens

<400> SEQUENCE: 276

Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Ser Thr Phe Pro Thr Asp Arg
                85                  90                  95

Pro Leu Phe Gly Gly Gly Thr Lys Leu Thr Val Leu Gly
            100                 105

<210> SEQ ID NO 277
<211> LENGTH: 248
<212> TYPE: PRT
<213> ORGANISM: Homo sapiens

<400> SEQUENCE: 277

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Gly Leu Arg Asp Asp Thr Ala Val Tyr Tyr Cys
                85                  90                  95

Ala Arg Asp Leu Thr Gly Tyr Asp Gln Tyr Thr Ala Trp Gly Gln Gly
            100                 105                 110

Thr Leu Val Thr Val Ser Ser Gly Gly Gly Ser Gly Gly Gly
        115                 120                 125

Ser Gly Gly Gly Ser Ala Gln Ser Val Leu Thr Gln Pro Pro Ser
130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Phe Tyr Cys Ser Thr
210                 215                 220

Phe Asp Pro Phe Thr Asp Arg Pro Leu Phe Gly Gly Thr Lys Leu
225                 230                 235                 240

Thr Val Leu Gly Ala Ala Ala His
                245

<210> SEQ ID NO 278
<211> LENGTH: 5
<212> TYPE: PRT
<213> ORGANISM: Homo sapiens

<400> SEQUENCE: 278

Asp Tyr Tyr Ile His
1               5

<210> SEQ ID NO 279
<211> LENGTH: 17
<212> TYPE: PRT
<213> ORGANISM: Homo sapiens

<400> SEQUENCE: 279

Trp Val Asn Pro Asp Thr Gly Gly Thr Arg Tyr Ala Gln Lys Phe Gln
1               5                   10                  15

Gly

<210> SEQ ID NO 280
<211> LENGTH: 10
<212> TYPE: PRT
<213> ORGANISM: Homo sapiens

<400> SEQUENCE: 280

Asp Leu Thr Gly Tyr Asp Gln Tyr Thr Ala
1               5                   10

<210> SEQ ID NO 281
<211> LENGTH: 11
<212> TYPE: PRT
<213> ORGANISM: Homo sapiens

<400> SEQUENCE: 281

Gly Gly Asn Asn Phe Arg Asn Lys Arg Val His
1               5                   10

<210> SEQ ID NO 282
<211> LENGTH: 7
<212> TYPE: PRT
<213> ORGANISM: Homo sapiens

<400> SEQUENCE: 282

Tyr Asp Ser Asp Arg Pro Ser
1               5

<210> SEQ ID NO 283
<211> LENGTH: 11
<212> TYPE: PRT
<213> ORGANISM: Homo sapiens

<400> SEQUENCE: 283

Ser Thr Phe Asp Pro Phe Thr Asp Arg Pro Leu
1               5                   10

<210> SEQ ID NO 284
<211> LENGTH: 357
<212> TYPE: DNA
<213> ORGANISM: Homo sapiens

<400> SEQUENCE: 284
gaggtgcagc tggtgcagtc tggggctgag gtgaagaagc ctggggcctc agtgaaggtc      60
tcctgtcagg cttctggata caccttcagc gattactata ttcactgggt gcgacagacc     120
ccaggacaag ggtttgagtg gatgggatgg gtcaaccctg acactggtgg cacgagatac     180
gcgcagaagt ttcagggctg gtcacaatg accagggaca tgtccaacac cacagcctac     240
atggagctgc ccgggctgag agacgacgac acggccgtat attactgtgc gagagatcta     300
actgggtacg accagtacac ggcctggggc cagggaaccc tggtcaccgt ctcctca        357

<210> SEQ ID NO 285
<211> LENGTH: 327
<212> TYPE: DNA
<213> ORGANISM: Homo sapiens

<400> SEQUENCE: 285
cagtctgtgc tgactcagcc accctcagtg tcagtggccc caggaaagac ggccacgatt      60
acctgtgggg gaaacaactt tcgaaataaa agagtacact ggtatcagca gaggccaggc     120
caggcccctg tcctggtcat ctattatgat tcagaccggc cctcagggat ccctgagcga     180
ttctctggct cccgctctgg gaacacggcc accctgacca tcagcagggt cgaggccggg     240
gatgaggccg actttactg tagcacctc gacccettca ctgatcgtcc gctgttcggc       300
ggagggacca agctgaccgt cctaggt                                         327

```
<210> SEQ ID NO 286
<211> LENGTH: 744
<212> TYPE: DNA
<213> ORGANISM: Homo sapiens

<400> SEQUENCE: 286
gaagtgcagc tggtgcagtc tggggctgag gtgaagaagc tggggcctc  agtgaaggtc      60 tcctgtcagg cttctggata caccttcagc gattactata ttcactgggt gcgacagacc     120
ccaggacaag ggtttgagtg gatgggatgg gtcaaccctg acactggtgg cacgagatac     180
gcgcagaagt ttcagggctg ggtcacaatg accagggaca tgtccaacac cacagcctac     240
atggagctgc ccgggctgag agacgacgac acggccgtat attactgtgc gagagatcta     300
actgggtacg accagtacac ggcctggggc cagggaaccc tggtcaccgt ctcgagtgga     360
ggcggcggtt caggcggagg tggctctggc ggtggcggaa gtgcacagtc tgtgctgact     420
cagccaccct cagtgtcagt ggccccagga agacggcca cgattacctg tgggggaaac     480
aactttcgaa ataaaagagt acactggtat cagcagaggc caggccaggc ccctgtcctg     540
gtcatctatt atgattcaga ccggccctca gggatccctg agcgattctc tggctcccgc     600
tctgggaaca cggccaccct gaccatcagc agggtcgagg ccggggatga ggccgacttt     660
tactgtagca ccttcgaccc cttcactgat cgtccgctgt tcggcggagg gaccaagctg     720
accgtcctag gtgcggccgc acat                                              744

<210> SEQ ID NO 287
<211> LENGTH: 15
<212> TYPE: DNA
<213> ORGANISM: Homo sapiens

<400> SEQUENCE: 287
gattactata ttcac                                                        15

<210> SEQ ID NO 288
<211> LENGTH: 51
<212> TYPE: DNA
<213> ORGANISM: Homo sapiens

<400> SEQUENCE: 288
tgggtcaacc ctgacactgg tggcacgaga tacgcgcaga gtttcagggg c                51

<210> SEQ ID NO 289
<211> LENGTH: 30
<212> TYPE: DNA
<213> ORGANISM: Homo sapiens

<400> SEQUENCE: 289
gatctaactg ggtacgacca gtacacggcc                                        30

<210> SEQ ID NO 290
<211> LENGTH: 33
<212> TYPE: DNA
<213> ORGANISM: Homo sapiens

<400> SEQUENCE: 290
gggggaaaca actttcgaaa taaaagagta cac                                    33

<210> SEQ ID NO 291
<211> LENGTH: 21
<212> TYPE: DNA
<213> ORGANISM: Homo sapiens

<400> SEQUENCE: 291
```

```
tatgattcag accggccctc a                                               21
```

<210> SEQ ID NO 292
<211> LENGTH: 33
<212> TYPE: DNA
<213> ORGANISM: Homo sapiens

<400> SEQUENCE: 292

```
agcaccttcg accccttcac tgatcgtccg ctg                                   33
```

<210> SEQ ID NO 293
<211> LENGTH: 120
<212> TYPE: PRT
<213> ORGANISM: Homo sapiens

<400> SEQUENCE: 293

```
Gln Val Gln Leu Val Gln Ser Gly Ala Glu Lys Lys Pro Gly Ala Ser
1               5                   10                  15

Val Lys Val Ser Cys Lys Ala Ser Gly Tyr Thr Phe Thr Asp Tyr Tyr
            20                  25                  30

Met His Trp Val Arg Gln Ala Pro Gly Gln Gly Leu Glu Trp Val Gly
        35                  40                  45

Trp Ile Asn Pro Tyr Thr Gly Gly Ala Phe Tyr Ala Gln Lys Phe Arg
    50                  55                  60

Gly Arg Val Thr Met Thr Arg Asp Thr Ser Ile Asn Thr Ala Tyr Met
65                  70                  75                  80

Glu Leu Ser Arg Leu Gly Ser Asp Asp Thr Ala Val Tyr Tyr Cys Ala
                85                  90                  95

Arg Glu Pro Glu Arg Phe Gly Asp Ser Thr Gly Gln Val Trp Gly Arg
            100                 105                 110

Gly Thr Met Val Thr Val Ser Ser
        115                 120
```

<210> SEQ ID NO 294
<211> LENGTH: 113
<212> TYPE: PRT
<213> ORGANISM: Homo sapiens

<400> SEQUENCE: 294

```
Gln Ala Val Leu Thr Gln Pro Ser Ser Val Ser Gly Ala Pro Arg Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Tyr His Trp Asp Lys Glu
                85                  90                  95

Gln Ser Gly Tyr Val Phe Gly Thr Gly Thr Gln Leu Thr Val Leu Ser
            100                 105                 110

Ala
```

<210> SEQ ID NO 295
<211> LENGTH: 249
<212> TYPE: PRT

<213> ORGANISM: Homo sapiens

<400> SEQUENCE: 295

Gln Val Gln Leu Val Gln Ser Gly Ala Glu Lys Pro Gly Ala Ser
1               5                   10                  15

Val Lys Val Ser Cys Lys Ala Ser Gly Tyr Thr Phe Thr Asp Tyr Tyr
            20                  25                  30

Met His Trp Val Arg Gln Ala Pro Gly Gln Gly Leu Glu Trp Val Gly
        35                  40                  45

Trp Ile Asn Pro Tyr Thr Gly Gly Ala Phe Tyr Ala Gln Lys Phe Arg
    50                  55                  60

Gly Arg Val Thr Met Thr Arg Asp Thr Ser Ile Asn Thr Ala Tyr Met
65                  70                  75                  80

Glu Leu Ser Arg Leu Gly Ser Asp Asp Thr Ala Val Tyr Tyr Cys Ala
                85                  90                  95

Arg Glu Pro Glu Arg Phe Gly Asp Ser Thr Gly Gln Val Trp Gly Arg
            100                 105                 110

Gly Thr Met Val Thr Val Ser Ser Gly Gly Gly Ser Gly Gly Gly
        115                 120                 125

Gly Ser Gly Gly Ser Arg Ser Ala Gln Ala Val Leu Thr Gln Pro Ser
130                 135                 140

Ser Val Ser Gly Ala Pro Arg Gln Arg Val Thr Ile Ser Cys Thr Gly
145                 150                 155                 160

Ser Ser Ser Asn Ile Gly Ala Gly Tyr Gly Val His Trp Tyr Gln Gln
                165                 170                 175

Leu Pro Gly Thr Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
    210                 215                 220

Tyr Cys Tyr His Trp Asp Lys Glu Gln Ser Gly Tyr Val Phe Gly Thr
225                 230                 235                 240

Gly Thr Gln Leu Thr Val Leu Ser Ala
                245

<210> SEQ ID NO 296
<211> LENGTH: 5
<212> TYPE: PRT
<213> ORGANISM: Homo sapiens

<400> SEQUENCE: 296

Asp Tyr Tyr Met His
1               5

<210> SEQ ID NO 297
<211> LENGTH: 17
<212> TYPE: PRT
<213> ORGANISM: Homo sapiens

<400> SEQUENCE: 297

Trp Ile Asn Pro Tyr Thr Gly Gly Ala Phe Tyr Ala Gln Lys Phe Arg
1               5                   10                  15

Gly

<210> SEQ ID NO 298
<211> LENGTH: 12
<212> TYPE: PRT

<213> ORGANISM: Homo sapiens

<400> SEQUENCE: 298

Glu Pro Glu Arg Phe Gly Asp Ser Thr Gly Gln Val
1               5                   10

<210> SEQ ID NO 299
<211> LENGTH: 14
<212> TYPE: PRT
<213> ORGANISM: Homo sapiens

<400> SEQUENCE: 299

Thr Gly Ser Ser Ser Asn Ile Gly Ala Gly Tyr Gly Val His
1               5                   10

<210> SEQ ID NO 300
<211> LENGTH: 7
<212> TYPE: PRT
<213> ORGANISM: Homo sapiens

<400> SEQUENCE: 300

Gly Asn Ser Asn Arg Pro Ser
1               5

<210> SEQ ID NO 301
<211> LENGTH: 11
<212> TYPE: PRT
<213> ORGANISM: Homo sapiens

<400> SEQUENCE: 301

Tyr His Trp Asp Lys Glu Gln Ser Gly Tyr Val
1               5                   10

<210> SEQ ID NO 302
<211> LENGTH: 363
<212> TYPE: DNA
<213> ORGANISM: Homo sapiens

<400> SEQUENCE: 302
caggtccagt tggtgcagtc tggggctgag gtgaagaagc ctggggcctc agtgaaggtc      60
tcctgcaagg cttctggata caccttcacc gactactata tgcactgggt gcgacaggcc     120
cctggacaag ggcttgagtg gatgggatgg atcaacccct tatactggtg gcgcattcta    180
gcacagaagt tcgggggcag ggtcacaatg accagggaca cgtccatcaa cacagcctac     240
atggagctaa gcagactggg atctgacgac acggccgtgt attattgtgc gagagaacct     300
gaaagattcg gcgactccac ggggcaggtc tggggccggg gacaatggt caccgtctcg     360 agt                                                                    363

<210> SEQ ID NO 303
<211> LENGTH: 339
<212> TYPE: DNA
<213> ORGANISM: Homo sapiens

<400> SEQUENCE: 303
caggctgtgc tgactcagcc gtcctcagtg tctggggccc caaggcagag ggtcaccatc      60
tcctgcactg ggagcagctc caacatcggg gcaggttatg gtgtacactg gtaccaacag     120
cttccaggaa cagcccccaa actcctcatc tatggtaaca gcaatcggcc ctcagggtc     180 cctgaccgat tctctggctc caagtctggc acctcagcct ccctggccat cactgggctc     240
caggctgagg atgaggctga ttattactgc taccactggg acaaggagca gagtggttat     300

```
gtcttcggaa ctgggaccca gctcaccgtt ttaagtgcg                         339
```

```
<210> SEQ ID NO 304
<211> LENGTH: 750
<212> TYPE: DNA
<213> ORGANISM: Homo sapiens

<400> SEQUENCE: 304
caggtccagt tggtgcagtc tggggctgag gtgaagaagc ctggggcctc agtgaaggtc    60
tcctgcaagg cttctggata caccttcacc gactactata tgcactgggt gcgacaggcc   120
cctggacaag gcttgagtg gtgggatgg atcaacccctt atactggtgg cgcattctat    180
gcacagaagt ttcggggcag ggtcacaatg accagggaca cgtccatcaa cacagcctac   240
atggagctaa gcagactggg atctgacgac acggccgtgt attattgtgc gagagaacct   300
gaaagattcg gcgactccac ggggcaggtc tggggccggg ggacaatggt caccgtctcg   360 agtggggcg gcggttcagg cggaggtggc tctggcggta gcagaagtgc acaggctgtg    420
ctgactcagc cgtcctcagt gtctggggcc ccaaggcaga gggtcaccat ctcctgcact   480
gggagcagct ccaacatcgg gcaggttat ggtgtacact ggtaccaaca gcttccagga    540
acagccccca aactcctcat ctatggtaac agcaatcggc cctcaggggt ccctgaccga   600
ttctctggct ccaagtctgg cacctcagcc tccctggcca tcactgggct ccaggctgag   660
gatgaggctg attattactg ctaccactgg gacaaggagc agagtggtta tgtcttcgga   720
actgggaccc agctcaccgt tttaagtgcg                                    750
```

```
<210> SEQ ID NO 305
<211> LENGTH: 15
<212> TYPE: DNA
<213> ORGANISM: Homo sapiens

<400> SEQUENCE: 305
gactactata tgcac                                                     15
```

```
<210> SEQ ID NO 306
<211> LENGTH: 51
<212> TYPE: DNA
<213> ORGANISM: Homo sapiens

<400> SEQUENCE: 306
tggatcaacc cttatactgg tggcgcattc tatgcacaga gtttcgggg c              51
```

```
<210> SEQ ID NO 307
<211> LENGTH: 36
<212> TYPE: DNA
<213> ORGANISM: Homo sapiens

<400> SEQUENCE: 307
gaacctgaaa gattcggcga ctccacgggg caggtc                              36
```

```
<210> SEQ ID NO 308
<211> LENGTH: 42
<212> TYPE: DNA
<213> ORGANISM: Homo sapiens

<400> SEQUENCE: 308
actgggagca gctccaacat cggggcaggt tatggtgtac ac                       42
```

```
<210> SEQ ID NO 309
<211> LENGTH: 21
<212> TYPE: DNA
```

<213> ORGANISM: Homo sapiens

<400> SEQUENCE: 309
ggtaacagca atcggccctc a	21

<210> SEQ ID NO 310
<211> LENGTH: 33
<212> TYPE: DNA
<213> ORGANISM: Homo sapiens

<400> SEQUENCE: 310
taccactggg acaaggagca gagtggttat gtc	33

<210> SEQ ID NO 311
<211> LENGTH: 121
<212> TYPE: PRT
<213> ORGANISM: Homo sapiens

<400> SEQUENCE: 311

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asp Tyr
                20                  25                  30

Tyr Met His Trp Val Arg Gln Ala Pro Gly Gln Gly Leu Glu Trp Val
            35                  40                  45

Gly Trp Ile Asn Pro Tyr Thr Gly Ser Ala Phe Tyr Ala Gln Lys Phe
        50                  55                  60

Arg Gly Arg Ala Thr Met Thr Arg Asn Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Gly Glu Ser Ser Gly Gln Leu Trp Gly
            100                 105                 110

Arg Gly Thr Met Val Thr Ile Ser Ser
        115                 120

<210> SEQ ID NO 312
<211> LENGTH: 113
<212> TYPE: PRT
<213> ORGANISM: Homo sapiens

<400> SEQUENCE: 312

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Pro Gly
                20                  25                  30

Tyr Gly Val His Trp Tyr Gln Gln Leu Pro Gly Thr Ala Pro Lys Leu
            35                  40                  45

Leu Ile Tyr Gly Asp Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

Leu Ser Gly Tyr Val Phe Gly Thr Gly Thr Gln Leu Thr Val Leu Ser
            100                 105                 110

Ala

```
<210> SEQ ID NO 313
<211> LENGTH: 250
<212> TYPE: PRT
<213> ORGANISM: Homo sapiens

<400> SEQUENCE: 313

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Ala Thr Met Thr Arg Asn Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Gly Glu Ser Ser Gly Gln Leu Trp Gly
            100                 105                 110

Arg Gly Thr Met Val Thr Ile Ser Gly Gly Gly Gly Ser Gly Gly
        115                 120                 125

Gly Gly Ser Gly Gly Ser Gly Ala Gln Ala Val Leu Thr Gln Pro
    130                 135                 140

Ser Ser Val Ser Gly Ala Pro Gly Gln Arg Val Thr Ile Ser Cys Thr
145                 150                 155                 160

Gly Ser Ser Ser Asn Ile Gly Pro Gly Tyr Gly Val His Trp Tyr Gln
                165                 170                 175

Gln Leu Pro Gly Thr Ala Pro Lys Leu Leu Ile Tyr Gly Asp Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Gly Leu Ser Gly Tyr Val Phe Gly
225                 230                 235                 240

Thr Gly Thr Gln Leu Thr Val Leu Ser Ala
                245                 250

<210> SEQ ID NO 314
<211> LENGTH: 5
<212> TYPE: PRT
<213> ORGANISM: Homo sapiens

<400> SEQUENCE: 314

Asp Tyr Tyr Met His
1               5

<210> SEQ ID NO 315
<211> LENGTH: 17
<212> TYPE: PRT
<213> ORGANISM: Homo sapiens

<400> SEQUENCE: 315

Trp Ile Asn Pro Tyr Thr Gly Ser Ala Phe Tyr Ala Gln Lys Phe Arg
1               5                   10                  15

Gly
```

```
<210> SEQ ID NO 316
<211> LENGTH: 12
<212> TYPE: PRT
<213> ORGANISM: Homo sapiens

<400> SEQUENCE: 316

Glu Pro Glu Lys Phe Gly Glu Ser Ser Gly Gln Leu
1               5                   10

<210> SEQ ID NO 317
<211> LENGTH: 14
<212> TYPE: PRT
<213> ORGANISM: Homo sapiens

<400> SEQUENCE: 317

Thr Gly Ser Ser Ser Asn Ile Gly Pro Gly Tyr Gly Val His
1               5                   10

<210> SEQ ID NO 318
<211> LENGTH: 7
<212> TYPE: PRT
<213> ORGANISM: Homo sapiens

<400> SEQUENCE: 318

Gly Asp Ser Asn Arg Pro Ser
1               5

<210> SEQ ID NO 319
<211> LENGTH: 11
<212> TYPE: PRT
<213> ORGANISM: Homo sapiens

<400> SEQUENCE: 319

Gln Ser Tyr Asp Ser Gly Leu Ser Gly Tyr Val
1               5                   10

<210> SEQ ID NO 320
<211> LENGTH: 363
<212> TYPE: DNA
<213> ORGANISM: Homo sapiens

<400> SEQUENCE: 320
gaagtgcagc tggtgcagtc tggggctgag gtgaagaagc ctggggcctc agtgaaggtc      60
tcctgtcagg cttctggata caccttcacc gactactata tgcactgggt gcgacaggcc    120
cctggacaag gcttgagtg gtgggtgg atcaaccctt atactggtag cgcattctat       180
gcacagaagt ttcggggcag ggccacaatg accaggaaca cgtccatcaa cacagcctac    240
atggagctga gcagactggg atctgacgac acggccgtgt attattgtgc gagagaacct    300
gaaaaattcg gcgagtccag cggccagttg tggggccggg ggacaatggt caccatctcg    360
agt                                                                  363

<210> SEQ ID NO 321
<211> LENGTH: 339
<212> TYPE: DNA
<213> ORGANISM: Homo sapiens

<400> SEQUENCE: 321
caggctgtgc tgactcagcc gtcctcagtg tctggggccc cagggcagag ggtcaccatc      60
tcctgcactg ggagcagctc caacatcggg gcaggttatg gtgtacactg gtaccaacag    120
cttccaggaa cagcccccaa actcctcatc tatggtgaca gcaatcggcc ctcagggtc     180 cctgaccgat tctctggctc caagtctggc acctcagcct ccctggccat cactgggctc    240
```

```
caggccgagg atgaggctga ttattactgc cagtcctatg acagcggcct gagtggttat    300
gtcttcggaa ctgggaccca gctcaccgtt ttaagtgcg                           339

<210> SEQ ID NO 322
<211> LENGTH: 750
<212> TYPE: DNA
<213> ORGANISM: Homo sapiens

<400> SEQUENCE: 322
gaagtgcagc tggtgcagtc tggggctgag gtgaagaagc ctggggcctc agtgaaggtc     60
tcctgtcagg cttctggata caccttcacc gactactata tgcactgggt gcgacaggcc    120
cctggacaag gcttgagtg gatgggatgg atcaaccctt atactggtag cgcattctat     180
gcacagaagt tcgggcag gccacaatg accaggaaca cgtccatcaa cacagcctac      240
atggagctga gcagactggg atctgacgac acggccgtgt attattgtgc gagagaacct    300
gaaaaattcg gcgagtccag cggccagttg tggggccggg gacaatggt caccatctcg     360 agtggaggcg gcggttcagg cggaggtggc tctggcggta gcggaagtgc acaggctgtg    420
ctgactcagc cgtcctcagt gtctggggcc ccagggcaga gggtcaccat ctcctgcact    480
gggagcagct ccaacatcgg ggcaggttat ggtgtacact ggtaccaaca gcttccagga    540
acagccccca aactcctcat ctatggtgac agcaatcggc cctcagggt ccctgaccga     600 ttctctggct ccaagtctgg cacctcagcc tccctggcca tcactgggct ccaggccgag    660
gatgaggctg attattactg ccagtcctat gacagcggcc tgagtggtta tgtcttcgga    720
actgggaccc agctcaccgt tttaagtgcg                                     750

<210> SEQ ID NO 323
<211> LENGTH: 15
<212> TYPE: DNA
<213> ORGANISM: Homo sapiens

<400> SEQUENCE: 323
gactactata tgcac                                                      15

<210> SEQ ID NO 324
<211> LENGTH: 51
<212> TYPE: DNA
<213> ORGANISM: Homo sapiens

<400> SEQUENCE: 324
tggatcaacc cttatactgg tagcgcattc tatgcacaga gtttcggggc                51

<210> SEQ ID NO 325
<211> LENGTH: 36
<212> TYPE: DNA
<213> ORGANISM: Homo sapiens

<400> SEQUENCE: 325
gaacctgaaa aattcggcga gtccagcggc cagttg                               36

<210> SEQ ID NO 326
<211> LENGTH: 42
<212> TYPE: DNA
<213> ORGANISM: Homo sapiens

<400> SEQUENCE: 326
actgggagca gctccaacat cggggcaggt tatggtgtac ac                        42
```

<210> SEQ ID NO 327
<211> LENGTH: 21
<212> TYPE: DNA
<213> ORGANISM: Homo sapiens

<400> SEQUENCE: 327
ggtgacagca atcggccctc a                                              21

<210> SEQ ID NO 328
<211> LENGTH: 33
<212> TYPE: DNA
<213> ORGANISM: Homo sapiens

<400> SEQUENCE: 328
cagtcctatg acagcggcct gagtggttat gtc                                 33

<210> SEQ ID NO 329
<211> LENGTH: 121
<212> TYPE: PRT
<213> ORGANISM: Homo sapiens

<400> SEQUENCE: 329

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Asp Ser Pro Asn Ala Glu Ile Trp Gly
            100                 105                 110

Arg Gly Thr Met Val Thr Ile Ser Ser
        115                 120

<210> SEQ ID NO 330
<211> LENGTH: 113
<212> TYPE: PRT
<213> ORGANISM: Homo sapiens

<400> SEQUENCE: 330

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Gln Leu Thr Val Leu Ser
            100                 105                 110

Ala

<210> SEQ ID NO 331
<211> LENGTH: 250
<212> TYPE: PRT
<213> ORGANISM: Homo sapiens

<400> SEQUENCE: 331

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Gly Ser Asp Thr Ala Val Tyr Tyr Cys
                85                  90                  95

Ala Arg Glu Pro Glu Lys Phe Asp Ser Pro Asn Ala Gly Ile Trp Gly
            100                 105                 110

Arg Gly Thr Met Val Thr Ile Ser Ser Glu Gly Gly Ser Gly Gly
        115                 120                 125

Gly Gly Ser Gly Gly Ser Gly Ser Ala Gln Ala Val Leu Thr Gln Pro
    130                 135                 140

Ser Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Gly Tyr Val Phe Gly
225                 230                 235                 240

Thr Gly Thr Gln Leu Thr Val Leu Ser Ala
                245                 250
```

<210> SEQ ID NO 332
<211> LENGTH: 5
<212> TYPE: PRT
<213> ORGANISM: Homo sapiens

<400> SEQUENCE: 332

```
His Tyr Tyr Met His
1               5
```

<210> SEQ ID NO 333
<211> LENGTH: 17
<212> TYPE: PRT
<213> ORGANISM: Homo sapiens

<400> SEQUENCE: 333

```
Trp Ile Asn Pro Tyr Thr Gly Gly Ala Phe Tyr Ala Gln Lys Phe Gln
1               5                   10                  15
```

Gly

<210> SEQ ID NO 334
<211> LENGTH: 12
<212> TYPE: PRT
<213> ORGANISM: Homo sapiens

<400> SEQUENCE: 334

Glu Pro Glu Lys Phe Asp Ser Pro Asn Ala Glu Ile
1               5                   10

<210> SEQ ID NO 335
<211> LENGTH: 14
<212> TYPE: PRT
<213> ORGANISM: Homo sapiens

<400> SEQUENCE: 335

Thr Gly Ser Ser Ser Asn Ile Gly Ala Gly Tyr Gly Val His
1               5                   10

<210> SEQ ID NO 336
<211> LENGTH: 7
<212> TYPE: PRT
<213> ORGANISM: Homo sapiens

<400> SEQUENCE: 336

Gly Asn Ser Asn Arg Pro Ser
1               5

<210> SEQ ID NO 337
<211> LENGTH: 11
<212> TYPE: PRT
<213> ORGANISM: Homo sapiens

<400> SEQUENCE: 337

Gln Ser Tyr Asp Ser Ser Leu Ser Gly Tyr Val
1               5                   10

<210> SEQ ID NO 338
<211> LENGTH: 363
<212> TYPE: DNA
<213> ORGANISM: Homo sapiens

<400> SEQUENCE: 338
caggtccagc tggtgcagtc tggggctgag gtgaaaaagc ctggggcctc agtgaaggtc      60
tcctgcaagg cttctggata caccttcacc cactactata tgcactgggt gcgacaggcc     120
cctggacaag gcttgagtg gtgggatgg atcaacccctt atactggtgg cgcattctat     180
gcacagaagt ttcagggcag ggtcacaatg accagggaca cgtccatcaa cacagcctac     240
atggagctga gcagactggg atctgacgac acggccgtgt attattgtgc gagagaacct     300
gaaaaattcg actcgccgaa cgccgagatc tggggccggg gacaatggtg caccatctcg     360
agt                                                                    363

<210> SEQ ID NO 339
<211> LENGTH: 339
<212> TYPE: DNA
<213> ORGANISM: Homo sapiens

<400> SEQUENCE: 339
caggctgtgc tgactcagcc gtcctcagtg tctggggccc cagggcagag ggtcaccatc      60
tcctgcactg ggagcagctc caacatcggg gcaggttatg gtgtacactg gtaccaacag    120

```
cttccaggaa cagcccccaa actcctcatc tatggtaaca gcaatcggcc ctcaggggtc      180
cctgaccgat tctctggctc caagtctggc acctcagcct ccctggccat cactgggctc      240
caggctgagg atgaggctga ttattactgc cagtcctatg acagcagcct gagtggttat      300
gtcttcggaa ccgggaccca gctcaccgtt ttaagtgcg                             339
```

<210> SEQ ID NO 340
<211> LENGTH: 750
<212> TYPE: DNA
<213> ORGANISM: Homo sapiens

<400> SEQUENCE: 340

```
caggtccagc tggtgcagtc tggggctgag gtgaaaaagc ctggggcctc agtgaaggtc      60
tcctgcaagg cttctggata caccttcacc cactactata tgcactgggt gcgacaggcc      120
cctggacaag ggcttgagtg ggtgggatgg atcaaccctt atactggtgg cgcattctat      180
gcacagaagt tcagggcag  gtcacaatg accaggaca cgtccatcaa cacagcctac       240
atggagctga gcagactggg atctgacgac acggccgtgt attattgtgc gagagaacct      300
gaaaaattcg actcgccgaa cgccgagatc tggggccggg gacaatggt caccatctcg       360 agtgaaggcg gcggttcagg cggaggtggc tctggcggta gcggaagtgc acaggctgtg      420
ctgactcagc cgtcctcagt gtctggggcc caggggcaga gggtcaccat ctcctgcact      480
gggagcagct ccaacatcgg ggcaggttat ggtgtacact ggtaccaaca gcttccagga     540
acagccccca aactcctcat ctatggtaac agcaatcggc cctcagggt ccctgaccga      600 ttctctggct ccaagtctgg cacctcagcc tccctggcca tcactgggct ccaggctgag      660
gatgaggctg attattactg ccagtcctat gacagcagcc tgagtggtta tgtcttcgga      720
accgggaccc agctcaccgt tttaagtgcg                                       750
```

<210> SEQ ID NO 341
<211> LENGTH: 15
<212> TYPE: DNA
<213> ORGANISM: Homo sapiens

<400> SEQUENCE: 341

```
cactactata tgcac                                                       15
```

<210> SEQ ID NO 342
<211> LENGTH: 51
<212> TYPE: DNA
<213> ORGANISM: Homo sapiens

<400> SEQUENCE: 342

```
tggatcaacc cttatactgg tggcgcattc tatgcacaga gtttcaggg c                51
```

<210> SEQ ID NO 343
<211> LENGTH: 36
<212> TYPE: DNA
<213> ORGANISM: Homo sapiens

<400> SEQUENCE: 343

```
gaacctgaaa aattcgactc gccgaacgcc gagatc                                36
```

<210> SEQ ID NO 344
<211> LENGTH: 42
<212> TYPE: DNA
<213> ORGANISM: Homo sapiens

<400> SEQUENCE: 344

```
actgggagca gctccaacat cggggcaggt tatggtgtac ac                          42
```

<210> SEQ ID NO 345
<211> LENGTH: 21
<212> TYPE: DNA
<213> ORGANISM: Homo sapiens

<400> SEQUENCE: 345

```
ggtaacagca atcggccctc a                                                 21
```

<210> SEQ ID NO 346
<211> LENGTH: 33
<212> TYPE: DNA
<213> ORGANISM: Homo sapiens

<400> SEQUENCE: 346

```
cagtcctatg acagcagcct gagtggttat gtc                                    33
```

<210> SEQ ID NO 347
<211> LENGTH: 121
<212> TYPE: PRT
<213> ORGANISM: Homo sapiens

<400> SEQUENCE: 347

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asn | Tyr |
|---|---|---|---|---|---|---|---|---|---|---|---|---|---|---|---|
| | | | 20 | | | | | 25 | | | | | 30 | | |

| Tyr | Met | His | Trp | Val | Arg | Gln | Ala | Pro | Gly | Gln | Gly | Leu | Glu | Trp | Val |
|---|---|---|---|---|---|---|---|---|---|---|---|---|---|---|---|
| | 35 | | | | | 40 | | | | | 45 | | | | |

| Gly | Trp | Ile | Asn | Pro | Tyr | Thr | Gly | Ser | Ala | Phe | Tyr | Ala | Gln | Lys | Phe |
|---|---|---|---|---|---|---|---|---|---|---|---|---|---|---|---|
| 50 | | | | | 55 | | | | | 60 | | | | | |

| Arg | Gly | Arg | Val | Thr | Met | Thr | Arg | Asp | Thr | Ser | Ile | Asn | Thr | Ala | Tyr |
|---|---|---|---|---|---|---|---|---|---|---|---|---|---|---|---|
| 65 | | | | 70 | | | | | 75 | | | | | 80 | |

| Met | Glu | Leu | Ser | Arg | Leu | Gly | Ser | Asp | Asp | Thr | Ala | Val | Tyr | Tyr | Cys |
|---|---|---|---|---|---|---|---|---|---|---|---|---|---|---|---|
| | | | 85 | | | | | 90 | | | | | 95 | | |

| Ala | Arg | Glu | Pro | Glu | Lys | Phe | Asp | Ser | Asp | Ser | Asp | Ser | Val | Trp | Gly |
|---|---|---|---|---|---|---|---|---|---|---|---|---|---|---|---|
| | | | 100 | | | | | 105 | | | | | 110 | | |

| Arg | Gly | Thr | Met | Val | Thr | Val | Ser | Gly |
|---|---|---|---|---|---|---|---|---|
| | | 115 | | | | | 120 | |

<210> SEQ ID NO 348
<211> LENGTH: 112
<212> TYPE: PRT
<213> ORGANISM: Homo sapiens

<400> SEQUENCE: 348

| Gln | Ala | Val | Leu | Thr | Pro | Pro | Ser | Val | Ser | Gly | Ala | Pro | Gly | Gln | Arg |
|---|---|---|---|---|---|---|---|---|---|---|---|---|---|---|---|
| 1 | | | | 5 | | | | | 10 | | | | | 15 | |

| Val | Thr | Ile | Ser | Cys | Thr | Gly | Ser | Ser | Asn | Ile | Gly | Ala | Gly | Tyr |
|---|---|---|---|---|---|---|---|---|---|---|---|---|---|---|
| | | | 20 | | | | | 25 | | | | | 30 | |

| Gly | Val | His | Trp | Tyr | Gln | Gln | Leu | Pro | Gly | Thr | Ala | Pro | Lys | Leu | Ile |
|---|---|---|---|---|---|---|---|---|---|---|---|---|---|---|---|
| | | 35 | | | | | 40 | | | | | 45 | | | |

| Ile | Tyr | Gly | Asp | Ser | Ser | Arg | Pro | Ser | Gly | Val | Pro | Asp | Arg | Phe | Ser |
|---|---|---|---|---|---|---|---|---|---|---|---|---|---|---|---|
| | 50 | | | | | 55 | | | | | 60 | | | | |

| Gly | Ser | Lys | Ser | Gly | Thr | Ser | Ala | Ser | Leu | Ala | Ile | Thr | Gly | Leu | Gln |
|---|---|---|---|---|---|---|---|---|---|---|---|---|---|---|---|
| 65 | | | | 70 | | | | | 75 | | | | | 80 | |

| Ala | Glu | Asp | Glu | Ala | Asp | Tyr | Tyr | Cys | Gln | Ser | Tyr | Asp | Ser | Asn | Leu |
|---|---|---|---|---|---|---|---|---|---|---|---|---|---|---|---|
| | | | 85 | | | | | 90 | | | | | 95 | | |

```
Ser Gly Tyr Val Phe Gly Thr Gly Thr Gln Leu Thr Val Leu Ser Ala
            100                 105                 110
```

<210> SEQ ID NO 349
<211> LENGTH: 249
<212> TYPE: PRT
<213> ORGANISM: Homo sapiens

<400> SEQUENCE: 349

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Asp Ser Asp Ser Asp Val Trp Gly
            100                 105                 110

Arg Gly Thr Met Val Thr Val Ser Gly Gly Gly Ser Ser Gly Gly
            115                 120                 125

Gly Gly Ser Gly Gly Ser Gly Ser Ala Gln Ala Val Leu Thr Pro Pro
        130                 135                 140

Ser Val Ser Gly Ala Pro Gly Gln Arg Val Thr Ile Ser Cys Thr Gly
145                 150                 155                 160

Ser Ser Ser Asn Ile Gly Ala Gly Tyr Gly Val His Trp Tyr Gln Gln
                165                 170                 175

Leu Pro Gly Thr Ala Pro Lys Leu Ile Ile Tyr Gly Asp Ser Ser Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
    210                 215                 220

Tyr Cys Gln Ser Tyr Asp Asn Ser Leu Ser Gly Tyr Val Phe Gly Thr
225                 230                 235                 240

Gly Thr Gln Leu Thr Val Leu Ser Ala
            245
```

<210> SEQ ID NO 350
<211> LENGTH: 5
<212> TYPE: PRT
<213> ORGANISM: Homo sapiens

<400> SEQUENCE: 350

```
Asn Tyr Tyr Met His
1               5
```

<210> SEQ ID NO 351
<211> LENGTH: 17
<212> TYPE: PRT
<213> ORGANISM: Homo sapiens

<400> SEQUENCE: 351

```
Trp Ile Asn Pro Tyr Thr Gly Ser Ala Phe Tyr Ala Gln Lys Phe Arg
1               5                   10                  15
```

Gly

<210> SEQ ID NO 352
<211> LENGTH: 12
<212> TYPE: PRT
<213> ORGANISM: Homo sapiens

<400> SEQUENCE: 352

Glu Pro Glu Lys Phe Asp Ser Asp Asp Ser Asp Val
1               5                   10

<210> SEQ ID NO 353
<211> LENGTH: 14
<212> TYPE: PRT
<213> ORGANISM: Homo sapiens

<400> SEQUENCE: 353

Thr Gly Ser Ser Ser Asn Ile Gly Ala Gly Tyr Gly Val His
1               5                   10

<210> SEQ ID NO 354
<211> LENGTH: 8
<212> TYPE: PRT
<213> ORGANISM: Homo sapiens

<400> SEQUENCE: 354

Gly Asp Ser Ser Arg Pro Ser Gly
1               5

<210> SEQ ID NO 355
<211> LENGTH: 11
<212> TYPE: PRT
<213> ORGANISM: Homo sapiens

<400> SEQUENCE: 355

Gln Ser Tyr Asp Asn Ser Leu Ser Gly Tyr Val
1               5                   10

<210> SEQ ID NO 356
<211> LENGTH: 363
<212> TYPE: DNA
<213> ORGANISM: Homo sapiens

<400> SEQUENCE: 356
caggttcagc tggtgcagtc tggggctgag gtgaagaagc ctggggcctc agtgaaggtc      60
tcctgcaagg cttctggata caccttcacc aactactata tgcactgggt gcgacaggcc     120
cctggacagg gcttgagtg gtgggatgg atcaaccctt atactggtag cgcattctat       180
gcacagaagt tcgggcag ggttacaatg accaggaca cgtccatcaa cacagcctac        240
atggagctga gcagactggg atctgacgac acggccgtgt attattgtgc gagagaacct    300
gaaaaattcg actccgacga ctccgacgtc tggggccgcg gacaatggt caccgtctcg     360
ggt                                                                   363

<210> SEQ ID NO 357
<211> LENGTH: 339
<212> TYPE: DNA
<213> ORGANISM: Homo sapiens

<400> SEQUENCE: 357
caggctgtgc tgactcagcc gccctcagtg tctggggccc cagggcagag ggtcaccatc      60
tcctgcactg ggagcagctc caacatcggg gcaggttatg gtgtacactg gtaccaacag    120

-continued

| | |
|---|---|
| cttccaggaa cagcccccaa actcatcatc tatggtgaca gcagtcggcc ctcagggtc | 180 |
| cctgaccgat tctctggctc caagtctggc acctcagcct ccctggccat cactgggctc | 240 |
| caggctgagg atgaggctga ttattactgc cagtcctatg acaacagcct gagcggttat | 300 |
| gtcttcggaa ctgggaccca gctcaccgtt ttaagtgcg | 339 |

<210> SEQ ID NO 358
<211> LENGTH: 750
<212> TYPE: DNA
<213> ORGANISM: Homo sapiens

<400> SEQUENCE: 358

| | |
|---|---|
| caggttcagc tggtgcagtc tggggctgag gtgaagaagc ctggggcctc agtgaaggtc | 60 |
| tcctgcaagg cttctggata caccttcacc aactactata tgcactgggt gcgacaggcc | 120 |
| cctggacagg ggcttgagtg ggtgggatgg atcaacccct tatactggta gcgcattctat | 180 |
| gcacagaagt tcggggcag ggttacaatg accaggaca cgtccatcaa cacagcctac | 240 |
| atggagctga gcagactggg atctgacgac acggccgtgt attattgtgc gagagaacct | 300 |
| gaaaaattcg actccgacga ctccgacgtc tggggccgcg gacaatggt caccgtctcg | 360 |
| ggtggaggcg gcagttcagg cggaggtggc tctggcggta gcggaagtgc acaggctgtg | 420 |
| ctgactcagc cgccctcagt gtctgggcc ccagggcaga gggtcaccat ctcctgcact | 480 |
| gggagcagct ccaacatcgg ggcaggttat ggtgtacact ggtaccaaca gcttccagga | 540 |
| acagccccca aactcatcat ctatggtgac agcagtcggc cctcagggt ccctgaccga | 600 |
| ttctctggct ccaagtctgg cacctcagcc tccctggcca tcactgggct ccaggctgag | 660 |
| gatgaggctg attattactg ccagtcctat gacaacagcc tgagcggtta tgtcttcgga | 720 |
| actgggaccc agctcaccgt tttaagtgcg | 750 |

<210> SEQ ID NO 359
<211> LENGTH: 15
<212> TYPE: DNA
<213> ORGANISM: Homo sapiens

<400> SEQUENCE: 359

| | |
|---|---|
| aactactata tgcac | 15 |

<210> SEQ ID NO 360
<211> LENGTH: 51
<212> TYPE: DNA
<213> ORGANISM: Homo sapiens

<400> SEQUENCE: 360

| | |
|---|---|
| tggatcaacc cttatactgg tagcgcattc tatgcacaga gtttcggggc | 51 |

<210> SEQ ID NO 361
<211> LENGTH: 36
<212> TYPE: DNA
<213> ORGANISM: Homo sapiens

<400> SEQUENCE: 361

| | |
|---|---|
| gaacctgaaa aattcgactc cgacgactcc gacgtc | 36 |

<210> SEQ ID NO 362
<211> LENGTH: 42
<212> TYPE: DNA
<213> ORGANISM: Homo sapiens

<400> SEQUENCE: 362

```
actgggagca gctccaacat cggggcaggt tatggtgtac ac                          42
```

<210> SEQ ID NO 363
<211> LENGTH: 24
<212> TYPE: DNA
<213> ORGANISM: Homo sapiens

<400> SEQUENCE: 363

```
ggtgacagca gtcggccctc aggg                                             24
```

<210> SEQ ID NO 364
<211> LENGTH: 33
<212> TYPE: DNA
<213> ORGANISM: Homo sapiens

<400> SEQUENCE: 364

```
cagtcctatg acaacagcct gagcggttat gtc                                   33
```

<210> SEQ ID NO 365
<211> LENGTH: 119
<212> TYPE: PRT
<213> ORGANISM: Homo sapiens

<400> SEQUENCE: 365

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Val Trp Asp Pro Leu Asp Tyr Trp Gly Arg Gly
            100                 105                 110

Thr Leu Val Thr Val Ser Ser
        115

<210> SEQ ID NO 366
<211> LENGTH: 108
<212> TYPE: PRT
<213> ORGANISM: Homo sapiens

<400> SEQUENCE: 366

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

```
Thr Phe Gly Gly Gly Thr Lys Val Glu Ile Lys Arg
            100                 105
```

<210> SEQ ID NO 367
<211> LENGTH: 243
<212> TYPE: PRT
<213> ORGANISM: Homo sapiens

<400> SEQUENCE: 367

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Val Trp Asp Pro Leu Asp Tyr Trp Gly Arg Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Asp Asp Phe Ala Thr Tyr Tyr Cys Gln Gln
    210                 215                 220

Tyr Ser Asn Tyr Pro Leu Thr Phe Gly Gly Gly Thr Lys Val Glu Ile
225                 230                 235                 240

Lys Arg Ala
```

<210> SEQ ID NO 368
<211> LENGTH: 5
<212> TYPE: PRT
<213> ORGANISM: Homo sapiens

<400> SEQUENCE: 368

```
Asp Tyr Tyr Met Ser
1               5
```

<210> SEQ ID NO 369
<211> LENGTH: 17
<212> TYPE: PRT
<213> ORGANISM: Homo sapiens

<400> SEQUENCE: 369

```
Ala Ile Ser Gly Ser Gly Gly Ser Thr Tyr Tyr Ala Asp Ser Val Lys
1               5                   10                  15
```

Gly

<210> SEQ ID NO 370
<211> LENGTH: 10
<212> TYPE: PRT
<213> ORGANISM: Homo sapiens

<400> SEQUENCE: 370

Gly Leu Trp Val Trp Asp Pro Leu Asp Tyr
1               5                   10

<210> SEQ ID NO 371
<211> LENGTH: 11
<212> TYPE: PRT
<213> ORGANISM: Homo sapiens

<400> SEQUENCE: 371

Arg Ala Ser Glu Gly Ile Tyr His Trp Leu Ala
1               5                   10

<210> SEQ ID NO 372
<211> LENGTH: 7
<212> TYPE: PRT
<213> ORGANISM: Homo sapiens

<400> SEQUENCE: 372

Lys Ala Ser Ser Leu Ala Ser
1               5

<210> SEQ ID NO 373
<211> LENGTH: 9
<212> TYPE: PRT
<213> ORGANISM: Homo sapiens

<400> SEQUENCE: 373

Gln Gln Tyr Ser Asn Tyr Pro Leu Thr
1               5

<210> SEQ ID NO 374
<211> LENGTH: 357
<212> TYPE: DNA
<213> ORGANISM: Homo sapiens

<400> SEQUENCE: 374
caagtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtctcagct attagtggta gtggtggtag cacatactac       180
gcagactccg tgaagggccg gatcaccatc tccagagaca acgccaagaa ctcactgtat     240
ctgcaaatga acagcctgag agctgaggac acggccgtgt attactgtgc gagagggctt     300
tgggtttggg atcctcttga ctactgggc agaggaaccc tggtcaccgt ctcttca         357

<210> SEQ ID NO 375
<211> LENGTH: 324
<212> TYPE: DNA
<213> ORGANISM: Homo sapiens

<400> SEQUENCE: 375
gacatccaga tgacccagtc tccttccacc ctgtctgcat ctgttggaga cagagtcacc      60
atcacctgcc gggccagtga gggtatttat cactggttgg cctggtatca gcagaagcca    120
gggaaagccc ctaaactcct gatctataag gcctctagtt tagccagtgg ggtcccatca    180

```
aggttcagcg gcagtggatc tgggacagag ttcactctca ccatcagcag cctgcagcct    240
gatgattttg caacttatta ctgccaacaa tatagtaatt atccgctcac tttcggcgga    300
gggaccaagg tggagatcaa acgt                                          324

<210> SEQ ID NO 376
<211> LENGTH: 729
<212> TYPE: DNA
<213> ORGANISM: Homo sapiens

<400> SEQUENCE: 376
caagtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg ggctggagtg ggtctcagct attagtggta gtggtggtag cacatactac    180
gcagactccg tgaagggccg gatcaccatc tccagagaca acgccaagaa ctcactgtat    240
ctgcaaatga acagcctgag agctgaggac acggccgtgt attactgtgc gagagggctt    300
tgggttgggg atcctcttga ctactggggc agaggaaccc tggtcaccgt ctcttcaggt    360
ggaggcggtt caggcggagg tggcagcggc ggtggcggat cggacatcca gatgacccag    420
tctccttcca ccctgtctgc atctgttgga cacagagtca ccatcacctg ccgggccagt    480
gagggtattt atcactggtt ggcctggtat cagcagaagc cagggaaagc ccctaaactc    540
ctgatctata aggcctctag tttagccagt ggggtcccat caaggttcag cggcagtgga    600
tctgggacag atttcactct caccatcagc agcctgcagc ctgatgattt tgcaacttat    660
tactgccaac aatatagtaa ttatccgctc actttcggcg agggaccaa ggtggagatc    720 aaacgtgcg                                                           729

<210> SEQ ID NO 377
<211> LENGTH: 15
<212> TYPE: DNA
<213> ORGANISM: Homo sapiens

<400> SEQUENCE: 377
gactactaca tgagc                                                     15

<210> SEQ ID NO 378
<211> LENGTH: 51
<212> TYPE: DNA
<213> ORGANISM: Homo sapiens

<400> SEQUENCE: 378
gctattagtg gtagtggtgg tagcacatac tacgcagact ccgtgaaggg c              51

<210> SEQ ID NO 379
<211> LENGTH: 30
<212> TYPE: DNA
<213> ORGANISM: Homo sapiens

<400> SEQUENCE: 379
gggctttggg tttgggatcc tcttgactac                                     30

<210> SEQ ID NO 380
<211> LENGTH: 33
<212> TYPE: DNA
<213> ORGANISM: Homo sapiens

<400> SEQUENCE: 380
cgggccagtg agggtattta tcactggttg gcc                                 33
```

<210> SEQ ID NO 381
<211> LENGTH: 21
<212> TYPE: DNA
<213> ORGANISM: Homo sapiens

<400> SEQUENCE: 381
aaggcctcta gtttagccag t        21

<210> SEQ ID NO 382
<211> LENGTH: 27
<212> TYPE: DNA
<213> ORGANISM: Homo sapiens

<400> SEQUENCE: 382
caacaatata gtaattatcc gctcact        27

<210> SEQ ID NO 383
<211> LENGTH: 119
<212> TYPE: PRT
<213> ORGANISM: Homo sapiens

<400> SEQUENCE: 383

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser
        115

<210> SEQ ID NO 384
<211> LENGTH: 108
<212> TYPE: PRT
<213> ORGANISM: Homo sapiens

<400> SEQUENCE: 384

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Val Glu Ile Lys Arg

<210> SEQ ID NO 385
<211> LENGTH: 243
<212> TYPE: PRT
<213> ORGANISM: Homo sapiens

<400> SEQUENCE: 385

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Asp Ile Gln Met Thr Gln Ser Pro Ser Thr
        130                 135                 140

Leu Ser Ala Ser Val Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Val
                180                 185                 190

Pro Ser Arg Phe Ser Gly Ser Gly Ser Gly Thr Glu Phe Thr Leu Thr
            195                 200                 205

Ile Ser Ser Leu Gln Pro Asp Asp Phe Ala Thr Tyr Tyr Cys Gln Gln
        210                 215                 220

Tyr Ser Asn Tyr Pro Leu Thr Phe Gly Gly Gly Thr Lys Val Glu Ile
225                 230                 235                 240

Lys Arg Ala

<210> SEQ ID NO 386
<211> LENGTH: 5
<212> TYPE: PRT
<213> ORGANISM: Homo sapiens

<400> SEQUENCE: 386

Ser Tyr Gly Ile Ser
1               5

<210> SEQ ID NO 387
<211> LENGTH: 17
<212> TYPE: PRT
<213> ORGANISM: Homo sapiens

<400> SEQUENCE: 387

Trp Ile Ser Ala Tyr Thr Gly Asn Thr Asn Tyr Ala Gln Lys Phe Gln
1               5                   10                  15

Gly

<210> SEQ ID NO 388
<211> LENGTH: 10
<212> TYPE: PRT
<213> ORGANISM: Homo sapiens

<400> SEQUENCE: 388

Asp Arg Gly Tyr Tyr Asp Ala Phe Asp Ile
1               5                   10

<210> SEQ ID NO 389
<211> LENGTH: 11
<212> TYPE: PRT
<213> ORGANISM: Homo sapiens

<400> SEQUENCE: 389

Arg Ala Ser Glu Gly Ile Tyr His Trp Leu Ala
1               5                   10

<210> SEQ ID NO 390
<211> LENGTH: 7
<212> TYPE: PRT
<213> ORGANISM: Homo sapiens

<400> SEQUENCE: 390

Lys Ala Ser Ser Leu Ala Ser
1               5

<210> SEQ ID NO 391
<211> LENGTH: 9
<212> TYPE: PRT
<213> ORGANISM: Homo sapiens

<400> SEQUENCE: 391

Gln Gln Tyr Ser Asn Tyr Pro Leu Thr
1               5

<210> SEQ ID NO 392
<211> LENGTH: 357
<212> TYPE: DNA
<213> ORGANISM: Homo sapiens

<400> SEQUENCE: 392
caggtgcagc tggtgcagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg atcagcgctt acactggtaa cacaaactat     180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgcttttga tatctggggc caaggcaccc tggtcaccgt ctcctca       357

<210> SEQ ID NO 393
<211> LENGTH: 324
<212> TYPE: DNA
<213> ORGANISM: Homo sapiens

<400> SEQUENCE: 393
gacatccaga tgacccagtc tccttccacc ctgtctgcat ctgttggaga cagagtcacc      60
atcacctgcc gggccagtga gggtatttat cactggttgg cctggtatca gcagaagcca     120
gggaaagccc ctaaactcct gatctataag gcctctagtt tagccagtgg ggtcccatca     180
aggttcagcg gcagtggatc tgggacagag ttcactctca ccatcagcag cctgcagcct     240

```
gatgattttg caacttatta ctgccaacaa tatagtaatt atccgctcac tttcggcgga    300
gggaccaagg tggagatcaa acgt                                          324

<210> SEQ ID NO 394
<211> LENGTH: 729
<212> TYPE: DNA
<213> ORGANISM: Homo sapiens

<400> SEQUENCE: 394
caggtgcagc tggtgcagtc tggagctgag gtgaagaagc ctggggcctc agtgaaggtc     60
tcctgcaagg cttctggtta cacctttacc agttatggta tcagctgggt gcgacaggcc    120
cctggacaag gcttgagtg gatgggatgg atcagcgctt acactggtaa cacaaactat     180
gcacagaagt tccagggcag agtcaccatg accacagaca catccacgag cacagcctac    240
atggaactga ggagcctgag atctgacgac acggccgtgt attactgtgc gagagatcgt    300
ggatactatg atgcttttga tatctggggc caaggcaccc tggtcaccgt ctcctcaggt    360
ggaggcggtt caggcggagg tggcagcggc ggtggcggat cggacatcca gatgacccag    420
tctccttcca ccctgtctgc atctgttgga gacagagtca ccatcacctg ccgggccagt    480
gagggtattt atcactggtt ggcctggtat cagcagaagc cagggaaagc ccctaaactc    540
ctgatctata aggcctctag tttagccagt ggggtcccat caaggttcag cggcagtgga    600
tctgggacag agttcactct caccatcagc agcctgcagc tgatgatttt gcaacttat    660 tactgccaac aatatagtaa ttatccgctc actttcggcg gagggaccaa ggtggagatc    720
aaacgtgcg                                                           729

<210> SEQ ID NO 395
<211> LENGTH: 15
<212> TYPE: DNA
<213> ORGANISM: Homo sapiens

<400> SEQUENCE: 395
agttatggta tcagc                                                     15

<210> SEQ ID NO 396
<211> LENGTH: 51
<212> TYPE: DNA
<213> ORGANISM: Homo sapiens

<400> SEQUENCE: 396
tggatcagcg cttacactgg taacacaaac tatgcacaga gttccaggg c              51

<210> SEQ ID NO 397
<211> LENGTH: 30
<212> TYPE: DNA
<213> ORGANISM: Homo sapiens

<400> SEQUENCE: 397
gatcgtggat actatgatgc ttttgatatc                                     30

<210> SEQ ID NO 398
<211> LENGTH: 33
<212> TYPE: DNA
<213> ORGANISM: Homo sapiens

<400> SEQUENCE: 398
cgggccagtg agggtattta tcactggttg gcc                                 33
```

```
<210> SEQ ID NO 399
<211> LENGTH: 21
<212> TYPE: DNA
<213> ORGANISM: Homo sapiens

<400> SEQUENCE: 399
aaggcctcta gtttagccag t                                           21

<210> SEQ ID NO 400
<211> LENGTH: 27
<212> TYPE: DNA
<213> ORGANISM: Homo sapiens

<400> SEQUENCE: 400
caacaatata gtaattatcc gctcact                                     27

<210> SEQ ID NO 401
<211> LENGTH: 119
<212> TYPE: PRT
<213> ORGANISM: Homo sapiens

<400> SEQUENCE: 401
```

Gln Met Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala His Ile Trp Tyr Asp Gly Ser Asn Glu Lys Tyr Ala Asp Ser Val
    50                  55                  60

Lys Gly Arg Met Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gln His Trp Ile Thr Ala Phe Asp Ile Trp Gly Lys Gly
            100                 105                 110

Thr Leu Val Thr Val Ser Ser
        115

```
<210> SEQ ID NO 402
<211> LENGTH: 111
<212> TYPE: PRT
<213> ORGANISM: Homo sapiens

<400> SEQUENCE: 402
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu Gly
            100                 105                 110

```
<210> SEQ ID NO 403
<211> LENGTH: 246
<212> TYPE: PRT
<213> ORGANISM: Homo sapiens

<400> SEQUENCE: 403

Gln Met Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Asn Tyr
                20                  25                  30

Gly Met Tyr Trp Val Arg Gln Ala Pro Gly Lys Gly Leu Glu Trp Val
            35                  40                  45

Ala His Ile Trp Tyr Asp Gly Ser Asn Glu Lys Tyr Ala Asp Ser Val
        50                  55                  60

Lys Gly Arg Met Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Thr Glu Gln His Trp Ile Thr Ala Phe Asp Ile Trp Gly Lys Gly
            100                 105                 110

Thr Leu Val Thr Val Ser Ser Gly Gly Gly Ser Gly Ala Gly Gly
        115                 120                 125

Ser Gly Gly Gly Gly Ser Gln Ser Ala Leu Thr Gln Pro Ala Ser Val
        130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Glu Gly Ser Lys Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Gln Ala Glu Asp Glu Ala Asp Tyr Tyr Cys
    210                 215                 220

Ser Ser Tyr Thr Thr Arg Ser Thr Arg Val Phe Gly Gly Thr Lys
225                 230                 235                 240

Leu Thr Val Leu Gly Ala
                245

<210> SEQ ID NO 404
<211> LENGTH: 5
<212> TYPE: PRT
<213> ORGANISM: Homo sapiens

<400> SEQUENCE: 404

Asn Tyr Gly Met Tyr
 1               5

<210> SEQ ID NO 405
<211> LENGTH: 17
<212> TYPE: PRT
<213> ORGANISM: Homo sapiens

<400> SEQUENCE: 405

His Ile Trp Tyr Asp Gly Ser Asn Glu Lys Tyr Ala Asp Ser Val Lys
 1               5                  10                  15

Gly
```

```
<210> SEQ ID NO 406
<211> LENGTH: 10
<212> TYPE: PRT
<213> ORGANISM: Homo sapiens

<400> SEQUENCE: 406

Glu Gln His Trp Ile Thr Ala Phe Asp Ile
1               5                   10

<210> SEQ ID NO 407
<211> LENGTH: 14
<212> TYPE: PRT
<213> ORGANISM: Homo sapiens

<400> SEQUENCE: 407

Thr Gly Thr Ser Ser Asp Val Gly Gly Tyr Asn Tyr Val Ser
1               5                   10

<210> SEQ ID NO 408
<211> LENGTH: 7
<212> TYPE: PRT
<213> ORGANISM: Homo sapiens

<400> SEQUENCE: 408

Glu Gly Ser Lys Arg Pro Ser
1               5

<210> SEQ ID NO 409
<211> LENGTH: 10
<212> TYPE: PRT
<213> ORGANISM: Homo sapiens

<400> SEQUENCE: 409

Ser Ser Tyr Thr Thr Arg Ser Thr Arg Val
1               5                   10

<210> SEQ ID NO 410
<211> LENGTH: 357
<212> TYPE: DNA
<213> ORGANISM: Homo sapiens

<400> SEQUENCE: 410
cagatgcagc tggtggagtc tgggggaggc gtggtccagc ctggggaggtc cctgagactc      60 tcctgtgcag cctctggatt caccttcagt aactatggca tgtactgggt ccgccaggct     120
ccaggcaagg gctggagtg gtggcacat atttggtatg atggaagtaa tgaaaagtat       180
gcagactccg tgaagggccg aatgaccgtc tccagagaca attccaagaa cacgttgtat    240
ttgcaaatga acagcctgag agccgaggac acggctgtgt attactgtgc gacagagcaa    300
cactggatta ctgcttttga tatctggggc aaaggaaccc tggtcaccgt ctcctca       357

<210> SEQ ID NO 411
<211> LENGTH: 333
<212> TYPE: DNA
<213> ORGANISM: Homo sapiens

<400> SEQUENCE: 411
cagtctgccc tgactcagcc tgcctccgtg tctgggtctc ctggacagtc gatcaccatc      60
tcctgcactg gaaccagcag tgacgttggt ggttataact atgtctcctg gtaccaacaa    120
cacccaggca aagcccccaa actcatgatt tatgagggca gtaagcggcc ctcagggtt     180 tctaatcgct tctctggctc caagtctggc aacacggcct ccctgacaat ctctgggctc    240
```

```
caggctgagg acgaggctga ttactactgc agctcatata caaccaggag cactcgagtt      300
ttcggcggag ggaccaagct gaccgtccta ggt                                   333

<210> SEQ ID NO 412
<211> LENGTH: 738
<212> TYPE: DNA
<213> ORGANISM: Homo sapiens

<400> SEQUENCE: 412
cagatgcagc tggtggagtc tgggggaggc gtggtccagc ctggagggtc cctgagactc       60
tcctgtgcag cctctggatt caccttcagt aactatggca tgtactgggt ccgccaggct      120
ccaggcaagg ggctggagtg ggtggcacat atttggtatg atggaagtaa tgaaaagtat      180
gcagactccg tgaagggccg aatgaccgtc tccagagaca attccaagaa cacgttgtat      240
ttgcaaatga acagcctgag agccgaggac acggctgtgt attactgtgc gacagagcaa      300
cactggatta ctgcttttga tatctggggc aaaggcaccc tggtcaccgt ctcctcaggt      360
ggaggcggtt caggcgcagg tggcagcggc ggtggcggat cacagtctgc gctgactcag      420
cctgcctccg tgtctgggtc tcctggacag tcgatcacca tctcctgcac tggaaccagc      480
agtgacgttg gtggttataa ctatgtctcc tggtaccaac aacacccagg caaagccccc      540
aaactcatga tttatgaggg cagtaagcgg ccctcagggg tttctaatcg cttctctggc      600
tccaagtctg gcaacacggc ctccctgaca atctctgggc tccaggctga ggacgaggct      660
gattattact gcagctcata tacaaccagg agcactcgag ttttcggcgg agggaccaag      720
ctgaccgtcc taggtgcg                                                    738

<210> SEQ ID NO 413
<211> LENGTH: 15
<212> TYPE: DNA
<213> ORGANISM: Homo sapiens

<400> SEQUENCE: 413
aactatggca tgtac                                                        15

<210> SEQ ID NO 414
<211> LENGTH: 51
<212> TYPE: DNA
<213> ORGANISM: Homo sapiens

<400> SEQUENCE: 414
catatttggt atgatggaag taatgaaaag tatgcagact ccgtgaaggg c                51

<210> SEQ ID NO 415
<211> LENGTH: 30
<212> TYPE: DNA
<213> ORGANISM: Homo sapiens

<400> SEQUENCE: 415
gagcaacact ggattactgc ttttgatatc                                        30

<210> SEQ ID NO 416
<211> LENGTH: 42
<212> TYPE: DNA
<213> ORGANISM: Homo sapiens

<400> SEQUENCE: 416
actggaacca gcagtgacgt tggtggttat aactatgtct cc                          42

<210> SEQ ID NO 417
```

```
<211> LENGTH: 21
<212> TYPE: DNA
<213> ORGANISM: Homo sapiens

<400> SEQUENCE: 417
gagggcagta agcggccctc a                                            21

<210> SEQ ID NO 418
<211> LENGTH: 30
<212> TYPE: DNA
<213> ORGANISM: Homo sapiens

<400> SEQUENCE: 418
agctcatata caaccaggag cactcgagtt                                   30

<210> SEQ ID NO 419
<211> LENGTH: 121
<212> TYPE: PRT
<213> ORGANISM: Homo sapiens

<400> SEQUENCE: 419
```

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ser Phe Tyr Tyr Phe Gly Tyr Trp Gly
            100                 105                 110

Arg Gly Thr Leu Val Thr Val Ser Ser
        115                 120

```
<210> SEQ ID NO 420
<211> LENGTH: 111
<212> TYPE: PRT
<213> ORGANISM: Homo sapiens

<400> SEQUENCE: 420
```

Gln Ala Ala Leu Thr Gln Pro Ala Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Phe Ser Val Val Phe Gly Gly Gly Thr Lys Leu Thr Val Leu Gly
            100                 105                 110

```
<210> SEQ ID NO 421
<211> LENGTH: 249
<212> TYPE: PRT
<213> ORGANISM: Homo sapiens

<400> SEQUENCE: 421

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ser Phe Tyr Tyr Phe Gly Tyr Trp Gly
            100                 105                 110

Arg Gly Thr Leu Val Thr Val Ser Gly Gly Gly Ser Gly Gly
        115                 120                 125

Gly Gly Ser Gly Gly Gly Ser Ala Gln Ala Ala Leu Thr Gln Pro
    130                 135                 140

Ala Ser Val Ser Gly Ser Pro Gly Gln Ser Ile Thr Ile Ser Cys Thr
145                 150                 155                 160

Gly Ala Ser Gly Asp Val Gly Ala Tyr Asn Phe Val Ser Trp Tyr Gln
                165                 170                 175

Gln His Pro Gly Lys Ala Pro Lys Leu Ile Ile Tyr Asp Val Asn Lys
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ala Asp
    210                 215                 220

Tyr Tyr Cys Ser Ser Tyr Thr Ser Thr Phe Ser Val Val Phe Gly Gly
225                 230                 235                 240

Gly Thr Lys Leu Thr Val Leu Gly Ala
                245

<210> SEQ ID NO 422
<211> LENGTH: 5
<212> TYPE: PRT
<213> ORGANISM: Homo sapiens

<400> SEQUENCE: 422

Asp Tyr Gly Met Asn
1               5

<210> SEQ ID NO 423
<211> LENGTH: 17
<212> TYPE: PRT
<213> ORGANISM: Homo sapiens

<400> SEQUENCE: 423

Gly Val Asn Trp Asn Gly Gly Thr Arg Asp Tyr Ala Ala Ser Val Lys
1               5                   10                  15

Gly
```

```
<210> SEQ ID NO 424
<211> LENGTH: 12
<212> TYPE: PRT
<213> ORGANISM: Homo sapiens

<400> SEQUENCE: 424

Gly Trp Tyr Ser Gly Ser Phe Tyr Tyr Phe Gly Tyr
1               5                   10

<210> SEQ ID NO 425
<211> LENGTH: 14
<212> TYPE: PRT
<213> ORGANISM: Homo sapiens

<400> SEQUENCE: 425

Thr Gly Ala Ser Gly Asp Val Gly Ala Tyr Asn Phe Val Ser
1               5                   10

<210> SEQ ID NO 426
<211> LENGTH: 7
<212> TYPE: PRT
<213> ORGANISM: Homo sapiens

<400> SEQUENCE: 426

Asp Val Asn Lys Arg Pro Ser
1               5

<210> SEQ ID NO 427
<211> LENGTH: 10
<212> TYPE: PRT
<213> ORGANISM: Homo sapiens

<400> SEQUENCE: 427

Ser Ser Tyr Thr Ser Thr Phe Ser Val Val
1               5                   10

<210> SEQ ID NO 428
<211> LENGTH: 363
<212> TYPE: DNA
<213> ORGANISM: Homo sapiens

<400> SEQUENCE: 428
gaggtgcagc tggtggagag cgggggaggt gtggtacggc ctgggggtc cctgagactc      60 tcctgtgcag cctctggatt cacctttgac gattatggca tgaactgggt ccgccaagct    120
ccagggaagg ggctggagtg gtctctggt gttaattgga atggtggtac cagagattat     180
gcagcctccg tgaagggccg attcaccatc tccagagaca cgccaagaa ctccctgtat     240 ctgcaaatga acagtctgag agccgaggac acggccttgt atcactgtgc gagaggatgg    300
tatagtggga gcttctacta ctttggctac tggggccgag aaccctggt caccgtctcc     360 tca                                                                  363

<210> SEQ ID NO 429
<211> LENGTH: 333
<212> TYPE: DNA
<213> ORGANISM: Homo sapiens

<400> SEQUENCE: 429
caggctgcgc tgactcagcc ggcctccgtg tctgggtctc ctggacagtc gatcaccatc    60
tcctgcactg gagccagcgg tgacgttggt gcttataact tgtctcctg gtaccaacaa    120 cacccaggca agcccccaa actcataatt tatgatgtca ataagcggcc ctcagggggtt   180 tctaatcgct tctctggctc caagtctggc aacacggcct ccctgaccat ctctgggctc   240
```

```
caggccgagg acgaggctga ttattactgc agctcatata caagcacctt ctctgtggta      300
tttggcggag ggaccaagct gaccgtccta ggt                                   333

<210> SEQ ID NO 430
<211> LENGTH: 747
<212> TYPE: DNA
<213> ORGANISM: Homo sapiens

<400> SEQUENCE: 430
gaggtgcagc tggtggagtc cggggagggt gtggtacggc ctgggggggtc cctgagactc      60 tcctgtgcag cctctggatt cacctttgac gattatggca tgaactgggt ccgccaagct     120
ccagggaagg gctggagtg gtctctggt gttaattgga atggtggtac cagagattat        180
gcagcctccg tgaagggccg attcaccatc tccagagaca acgccaagaa ctccctgtat     240
ctgcaaatga acagtctgag agccgaggac acggccttgt atcactgtgc gagaggatgg     300
tatagtggga gcttctacta ctttggctac tggggccgag aaccctggt caccgtctcg       360 agtggaggcg gcggttcagg cggaggtggc tctggcggtg gcggaagtgc acaggctgcg     420
ctgactcagc cggcctccgt gtctgggtct cctggacagt cgatcaccat ctcctgcact     480
ggagccagcg gtgacgttgg tgcttataac tttgtctcct ggtaccaaca acacccaggc     540
aaagccccca aactcataat ttatgatgtc aataagcggc cctcagggt ttctaatcgc      600 ttctctggct ccaagtctgg caacacggcc tccctgacca tctctgggct ccaggccgag     660
gacgaggctg attattactg cagctcatat acaagcacct tctctgtggt atttggcgga     720
gggaccaagc tcaccgtcct aggtgcg                                        747

<210> SEQ ID NO 431
<211> LENGTH: 15
<212> TYPE: DNA
<213> ORGANISM: Homo sapiens

<400> SEQUENCE: 431
gattatggca tgaac                                                       15

<210> SEQ ID NO 432
<211> LENGTH: 51
<212> TYPE: DNA
<213> ORGANISM: Homo sapiens

<400> SEQUENCE: 432
ggtgttaatt ggaatggtgg taccagagat tatgcagcct ccgtgaaggg c                51

<210> SEQ ID NO 433
<211> LENGTH: 36
<212> TYPE: DNA
<213> ORGANISM: Homo sapiens

<400> SEQUENCE: 433
ggatggtata gtgggagctt ctactacttt ggctac                                36

<210> SEQ ID NO 434
<211> LENGTH: 42
<212> TYPE: DNA
<213> ORGANISM: Homo sapiens

<400> SEQUENCE: 434
actggagcca gcggtgacgt tggtgcttat aactttgtct cc                         42
```

```
<210> SEQ ID NO 435
<211> LENGTH: 21
<212> TYPE: DNA
<213> ORGANISM: Homo sapiens

<400> SEQUENCE: 435
gatgtcaata agcggccctc a                                              21

<210> SEQ ID NO 436
<211> LENGTH: 30
<212> TYPE: DNA
<213> ORGANISM: Homo sapiens

<400> SEQUENCE: 436
agctcatata caagcacctt ctctgtggta                                     30

<210> SEQ ID NO 437
<211> LENGTH: 119
<212> TYPE: PRT
<213> ORGANISM: Homo sapiens

<400> SEQUENCE: 437
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

```
<210> SEQ ID NO 438
<211> LENGTH: 109
<212> TYPE: PRT
<213> ORGANISM: Homo sapiens

<400> SEQUENCE: 438
```

Ser Ser Val Leu Thr Gln Pro Pro Ser Val Ser Val Ala Pro Gly Lys
1               5                   10                  15

Thr Ala Arg Ile Thr Cys Gly Gly Asn Asn Phe Arg Asn Lys Arg Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Asp Arg
                85                  90                  95

Pro Leu Phe Gly Gly Gly Thr Lys Leu Thr Val Leu Gly
            100                 105

```
<210> SEQ ID NO 439
<211> LENGTH: 245
<212> TYPE: PRT
<213> ORGANISM: Homo sapiens

<400> SEQUENCE: 439

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Ser Val Leu Thr Gln Pro Pro Ser
    130                 135                 140

Val Ser Val Ala Pro Gly Lys Thr Ala Arg Ile Thr Cys Gly Gly Asn
145                 150                 155                 160

Asn Phe Arg Asn Lys Arg Val His Trp Tyr Gln Gln Lys Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Ser Gly Asn Thr Ala Thr Leu Thr
        195                 200                 205

Ile Ser Arg Val Glu Ala Gly Asp Glu Ala Asp Tyr Tyr Cys Gln Val
    210                 215                 220

Trp Asp Ser Ser Thr Asp Arg Pro Leu Phe Gly Gly Thr Lys Leu
225                 230                 235                 240

Thr Val Leu Gly Ala
                245

<210> SEQ ID NO 440
<211> LENGTH: 5
<212> TYPE: PRT
<213> ORGANISM: Homo sapiens

<400> SEQUENCE: 440

Asp Tyr Tyr Ile His
1               5

<210> SEQ ID NO 441
<211> LENGTH: 17
<212> TYPE: PRT
<213> ORGANISM: Homo sapiens

<400> SEQUENCE: 441

Trp Val Asn Pro Asp Thr Gly Gly Thr Arg Tyr Ala Gln Lys Phe Gln
1               5                   10                  15

Gly
```

<210> SEQ ID NO 442
<211> LENGTH: 10
<212> TYPE: PRT
<213> ORGANISM: Homo sapiens

<400> SEQUENCE: 442

Asp Leu Thr Gly Phe Asp Pro Phe Asp Ile
1               5                   10

<210> SEQ ID NO 443
<211> LENGTH: 11
<212> TYPE: PRT
<213> ORGANISM: Homo sapiens

<400> SEQUENCE: 443

Gly Gly Asn Asn Phe Arg Asn Lys Arg Val His
1               5                   10

<210> SEQ ID NO 444
<211> LENGTH: 7
<212> TYPE: PRT
<213> ORGANISM: Homo sapiens

<400> SEQUENCE: 444

Tyr Asp Ser Asp Arg Pro Ser
1               5

<210> SEQ ID NO 445
<211> LENGTH: 11
<212> TYPE: PRT
<213> ORGANISM: Homo sapiens

<400> SEQUENCE: 445

Gln Val Trp Asp Ser Ser Thr Asp Arg Pro Leu
1               5                   10

<210> SEQ ID NO 446
<211> LENGTH: 357
<212> TYPE: DNA
<213> ORGANISM: Homo sapiens

<400> SEQUENCE: 446
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt tcagggccg ggtcacaatg accagggaca tgtccatctc cacagcctac     240
atggagctgt ccaggctgag aagcgacgac acggccgtat attactgtgc gagagatcta     300
actggatttg atccttttga tatctggggc cagggaaccc tggtcaccgt ctcctca        357

<210> SEQ ID NO 447
<211> LENGTH: 327
<212> TYPE: DNA
<213> ORGANISM: Homo sapiens

<400> SEQUENCE: 447
tcgtctgtgc tgactcagcc accctcagtg tcagtggccc caggaaagac ggcccgcatt      60
acctgtgggg gaaacaactt tcgaaataaa agagtacact ggtatcagca gaagccaggc     120
caggcccctg tcctggtcat ctattatgat tcagaccggc cctcaggat ccctgagcga     180 ttctctggct cccgctctgg gaacacggcc accctgacca tcagcagggt cgaggccggg     240

```
gatgaggccg actattactg tcaggtgtgg gatagtagta ctgatcgtcc gctgttcggc    300
ggagggacca agctgaccgt cctaggt                                        327

<210> SEQ ID NO 448
<211> LENGTH: 735
<212> TYPE: DNA
<213> ORGANISM: Homo sapiens

<400> SEQUENCE: 448
caagtgcagc tggtgcagtc tggggctgag gtgaagaagc ctggggcctc agtgaaggtc     60
tcctgtaagg cttctggata cacctccagc gattactata ttcactgggt gcgacaggcc   120
cctggacaag ggttggagtg gatgggatgg gtcaaccctg acactggtgg cacaagatac   180
gcgcagaagt tcagggcccg ggtcacaatg accagggaca tgtccatctc cacagcctac   240
atggagctgt ccaggctgag aagcgacgac acggccgtat attactgtgc gagagatcta   300
actggatttg atccttttga tatctgggggc caggaacccc tggtcaccgt ctcgagtgga   360
ggcggcggtt caggcggagg tggctctggc ggtggcggaa gtgcatcgtc tgtgctgact   420
cagccaccct cagtgtcagt ggccccagga aagacggccc gcattacctg tgggggaaac   480
aactttcgaa ataaaagagt acactggtat cagcagaagc caggccaggc ccctgtcctg   540
gtcatctatt atgattcaga ccggccctca gggatccctg agcgattctc tggctcccgc   600
tctgggaaca cggccaccct gaccatcagc agggtcgagg ccggggatga ggccgactat   660
tactgtcagg tgtgggatag tagtactgat cgtccgctgt tcggcggagg gaccaagctg   720
accgtcctag gtgcg                                                    735

<210> SEQ ID NO 449
<211> LENGTH: 15
<212> TYPE: DNA
<213> ORGANISM: Homo sapiens

<400> SEQUENCE: 449
gattactata ttcac                                                     15

<210> SEQ ID NO 450
<211> LENGTH: 51
<212> TYPE: DNA
<213> ORGANISM: Homo sapiens

<400> SEQUENCE: 450
tgggtcaacc ctgacactgg tggcacaaga tacgcgcaga agtttcaggg c              51

<210> SEQ ID NO 451
<211> LENGTH: 30
<212> TYPE: DNA
<213> ORGANISM: Homo sapiens

<400> SEQUENCE: 451
gatctaactg gatttgatcc ttttgatatc                                     30

<210> SEQ ID NO 452
<211> LENGTH: 33
<212> TYPE: DNA
<213> ORGANISM: Homo sapiens

<400> SEQUENCE: 452
gggggaaaca actttcgaaa taaaagagta cac                                 33

<210> SEQ ID NO 453
```

```
<211> LENGTH: 21
<212> TYPE: DNA
<213> ORGANISM: Homo sapiens

<400> SEQUENCE: 453
tatgattcag accggccctc a                                                    21

<210> SEQ ID NO 454
<211> LENGTH: 33
<212> TYPE: DNA
<213> ORGANISM: Homo sapiens

<400> SEQUENCE: 454
caggtgtggg atagtagtac tgatcgtccg ctg                                       33

<210> SEQ ID NO 455
<211> LENGTH: 121
<212> TYPE: PRT
<213> ORGANISM: Homo sapiens

<400> SEQUENCE: 455
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Phe Trp Gly Gly Asp Asn Trp Gly
            100                 105                 110

Arg Gly Thr Leu Val Thr Val Ser Ser
        115                 120

```
<210> SEQ ID NO 456
<211> LENGTH: 112
<212> TYPE: PRT
<213> ORGANISM: Homo sapiens

<400> SEQUENCE: 456
```

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gly Ser Tyr Asp Ser Ser
                85                  90                  95

Leu Ser Gly Tyr Val Phe Gly Gly Gly Thr Gln Leu Thr Val Leu Gly
            100                 105                 110

```
<210> SEQ ID NO 457
<211> LENGTH: 250
<212> TYPE: PRT
<213> ORGANISM: Homo sapiens

<400> SEQUENCE: 457

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Phe Trp Gly Gly Asp Asn Trp Gly
            100                 105                 110

Arg Gly Thr Leu Val Thr Val Ser Gly Gly Gly Ser Gly Gly
        115                 120                 125

Gly Gly Ser Gly Gly Gly Gly Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Gly Tyr Val Phe Gly
225                 230                 235                 240

Gly Gly Thr Gln Leu Thr Val Leu Ser Ala
                245                 250

<210> SEQ ID NO 458
<211> LENGTH: 5
<212> TYPE: PRT
<213> ORGANISM: Homo sapiens

<400> SEQUENCE: 458

Asp Tyr Tyr Met His
1               5

<210> SEQ ID NO 459
<211> LENGTH: 17
<212> TYPE: PRT
<213> ORGANISM: Homo sapiens

<400> SEQUENCE: 459

Trp Ile Asn Pro Tyr Thr Gly Gly Ala Phe Tyr Ala Gln Lys Phe Arg
1               5                   10                  15

Gly
```

```
<210> SEQ ID NO 460
<211> LENGTH: 12
<212> TYPE: PRT
<213> ORGANISM: Homo sapiens

<400> SEQUENCE: 460

Glu Pro Glu Lys Phe Asp Phe Trp Gly Gly Asp Asn
1               5                   10

<210> SEQ ID NO 461
<211> LENGTH: 14
<212> TYPE: PRT
<213> ORGANISM: Homo sapiens

<400> SEQUENCE: 461

Thr Gly Ser Ser Ser Asn Ile Gly Ala Gly Tyr Gly Val His
1               5                   10

<210> SEQ ID NO 462
<211> LENGTH: 7
<212> TYPE: PRT
<213> ORGANISM: Homo sapiens

<400> SEQUENCE: 462

Gly Asn Ser Asn Arg Pro Ser
1               5

<210> SEQ ID NO 463
<211> LENGTH: 11
<212> TYPE: PRT
<213> ORGANISM: Homo sapiens

<400> SEQUENCE: 463

Gln Ser Tyr Asp Ser Ser Leu Ser Gly Tyr Val
1               5                   10

<210> SEQ ID NO 464
<211> LENGTH: 363
<212> TYPE: DNA
<213> ORGANISM: Homo sapiens

<400> SEQUENCE: 464
caggtgcagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gtgggatgg atcaaccctt atactggtgg cgcattctat       180
gcacagaagt ttcggggcag ggtcacaatg accagggaca cgtccatcag cacagcctac     240
atggagctga gcagactgag atctgacgac acggccgtgt attattgtgc gagagaacct     300
gaaaaattcg attttggggg ggtgacaac tgggggccggg gacattggt caccgtctcc      360 tca                                                                   363

<210> SEQ ID NO 465
<211> LENGTH: 336
<212> TYPE: DNA
<213> ORGANISM: Homo sapiens

<400> SEQUENCE: 465
caggctgtgc tgactcagcc gccgtcagtg tctggggccc cagggcagag ggtcaccatc      60
tcctgcactg ggagcagctc caacatcggg gcaggttatg gtgtacactg gtaccaacag     120
cttccaggaa cagcccccaa actcctcatc tatggtaaca gcaatcggcc ctcagggtc      180 cctgaccgat tctctggctc caagtctggc acctcagcct ccctggccat cactgggctc     240
```

```
caggctgagg atgaggctga ttattactgc cagtcctatg acagcagcct gagtggttat    300
gtcttcggag gtgggaccca gctcaccgtc ctaggt                              336

<210> SEQ ID NO 466
<211> LENGTH: 750
<212> TYPE: DNA
<213> ORGANISM: Homo sapiens

<400> SEQUENCE: 466
caggtccagc tggtgcagtc tggggctgag gtgaagaagc ctggggcctc agtgaaggtc     60
tcctgcaagg cttctggata caccttcacc gactactata tgcactgggt gcgacaggcc    120
cctggacaag gcttgagtg gtgggatgg atcaacccttt atactggtgg cgcattctat    180
gcacagaagt ttcggggcag ggtcacaatg accaggggaca cgtccatcag cacagcctac    240
atggagctga gcagactgag atctgacgac acggccgtgt attattgtgc gagagaacct    300
gaaaaattcg attttggggg gggtgacaac tggggccggg ggacattggt caccgtctcg    360
agtggaggcg gcggttcagg cggaggtggc tctggcggtg gcggaagtgc acaggctgtg    420
ctgactcagc cgccgtcagt gtctggggcc ccagggcaga gggtcaccat ctcctgcact    480
gggagcagct ccaacatcgg ggcaggttat ggtgtacact ggtaccaaca gcttccagga    540
acagccccca aactcctcat ctatggtaac agcaatcggc cctcaggggt ccctgaccga    600
ttctctggct ccaagtctgg cacctcagcc tccctggcca tcactgggct ccaggctgag    660
gatgaggctg attattactg ccagtcctat gacagcagcc tgagtggtta tgtcttcgga    720
ggtgggaccc agctcaccgt tttaagtgcg                                    750

<210> SEQ ID NO 467
<211> LENGTH: 15
<212> TYPE: DNA
<213> ORGANISM: Homo sapiens

<400> SEQUENCE: 467
gactactata tgcac                                                     15

<210> SEQ ID NO 468
<211> LENGTH: 51
<212> TYPE: DNA
<213> ORGANISM: Homo sapiens

<400> SEQUENCE: 468
tggatcaacc cttatactgg tggcgcattc tatgcacaga agtttcgggg c              51

<210> SEQ ID NO 469
<211> LENGTH: 36
<212> TYPE: DNA
<213> ORGANISM: Homo sapiens

<400> SEQUENCE: 469
gaacctgaaa aattcgattt tggggggggt gacaac                               36

<210> SEQ ID NO 470
<211> LENGTH: 42
<212> TYPE: DNA
<213> ORGANISM: Homo sapiens

<400> SEQUENCE: 470
actgggagca gctccaacat cggggcaggt tatggtgtac ac                        42
```

```
<210> SEQ ID NO 471
<211> LENGTH: 21
<212> TYPE: DNA
<213> ORGANISM: Homo sapiens

<400> SEQUENCE: 471
ggtaacagca atcggccctc a                                              21

<210> SEQ ID NO 472
<211> LENGTH: 33
<212> TYPE: DNA
<213> ORGANISM: Homo sapiens

<400> SEQUENCE: 472
cagtcctatg acagcagcct gagtggttat gtc                                 33

<210> SEQ ID NO 473
<211> LENGTH: 119
<212> TYPE: PRT
<213> ORGANISM: Homo sapiens

<400> SEQUENCE: 473
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser
        115

```
<210> SEQ ID NO 474
<211> LENGTH: 108
<212> TYPE: PRT
<213> ORGANISM: Homo sapiens

<400> SEQUENCE: 474
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Met Gly Glu Tyr Asn Ala
                85                  90                  95

Thr Phe Gly Gly Gly Thr Lys Val Glu Ile Lys Arg
            100                 105

```
<210> SEQ ID NO 475
<211> LENGTH: 242
<212> TYPE: PRT
<213> ORGANISM: Homo sapiens

<400> SEQUENCE: 475

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Thr Tyr Tyr Cys Gln Gln
    210                 215                 220

Met Gly Glu Tyr Asn Ala Thr Phe Gly Gly Gly Thr Lys Val Glu Ile
225                 230                 235                 240

Lys Arg

<210> SEQ ID NO 476
<211> LENGTH: 5
<212> TYPE: PRT
<213> ORGANISM: Homo sapiens

<400> SEQUENCE: 476

Ser Tyr Gly Ile Ser
1               5

<210> SEQ ID NO 477
<211> LENGTH: 17
<212> TYPE: PRT
<213> ORGANISM: Homo sapiens

<400> SEQUENCE: 477

Trp Val Ser Ala Tyr Thr Gly Asn Thr Asn Tyr Ala Gln Lys Phe Gln
1               5                   10                  15

Gly
```

```
<210> SEQ ID NO 478
<211> LENGTH: 10
<212> TYPE: PRT
<213> ORGANISM: Homo sapiens

<400> SEQUENCE: 478

Asp Arg Gly Tyr Tyr Asp Ala Phe Asp Ile
1               5                   10

<210> SEQ ID NO 479
<211> LENGTH: 11
<212> TYPE: PRT
<213> ORGANISM: Homo sapiens

<400> SEQUENCE: 479

Arg Ala Ser Glu Gly Ile Tyr His Trp Leu Ala
1               5                   10

<210> SEQ ID NO 480
<211> LENGTH: 7
<212> TYPE: PRT
<213> ORGANISM: Homo sapiens

<400> SEQUENCE: 480

Lys Ala Ser Ser Leu Ala Ser
1               5

<210> SEQ ID NO 481
<211> LENGTH: 9
<212> TYPE: PRT
<213> ORGANISM: Homo sapiens

<400> SEQUENCE: 481

Gln Gln Met Gly Glu Tyr Asn Ala Thr
1               5

<210> SEQ ID NO 482
<211> LENGTH: 357
<212> TYPE: DNA
<213> ORGANISM: Homo sapiens

<400> SEQUENCE: 482
caggtgcagc tggtgcagtc tggagctgag gtgaagaagc ctggggcctc agtgaaggtc     60
tcctgcaagg cttctggtta cacctttacc agttatggta tcagctgggt gcgacaggcc    120
cctggacaag gcttgagtg gatgggatgg gtcagcgctt acactggtaa cacaaactat    180
gcacagaagt tccagggcag agtcaccatg accacagaca tccacgag cacagcctac    240 atggaactga ggagcctgag atctgacgac acggccgtgt attactgtgc gagagatcgt    300
ggatactatg atgcttttga tatctggggc caaggcaccc tggtcaccgt ctcctca      357

<210> SEQ ID NO 483
<211> LENGTH: 324
<212> TYPE: DNA
<213> ORGANISM: Homo sapiens

<400> SEQUENCE: 483
gacatccaga tgacccagtc tccttccacc ctgtctgcat ctgttggaga cagagtcacc     60
atcacctgcc gggccagtga gggtatttat cactggttgg cctggtatca gcagaagcca    120
gggaaagccc ctaaactcct gatctataag gcctctagtt tagccagtgg ggtcccatca    180
aggttcagcg gcagtggatc tgggacagag ttcactctca ccatcagcag cctgcagcct    240
gatgattttg caacttatta ctgccaacaa atgggcgagt acaacgccac cttcggcgga    300
```

```
gggaccaagg tggagatcaa acgt                                          324

<210> SEQ ID NO 484
<211> LENGTH: 726
<212> TYPE: DNA
<213> ORGANISM: Homo sapiens

<400> SEQUENCE: 484
caggtgcagc tggtgcagtc tggagctgag gtgaagaagc ctggggcctc agtgaaggtc    60
tcctgcaagg cttctggtta cacctttacc agttatggta tcagctgggt gcgacaggcc   120
cctggacaag gcttgagtg gatgggatgg gtcagcgctt acactggtaa cacaaactat    180
gcacagaagt tccagggcag agtcaccatg accacagaca catccacgag cacagcctac   240
atggaactga ggagcctgag atctgacgac acggccgtgt attactgtgc gagagatcgt   300
ggatactatg atgcttttga tatctggggc caaggcaccc tggtcaccgt ctcctcaggt   360
ggaggcggtt caggcggagg tggcagcggc ggtggcggat cggacatcca gatgacccag   420
tctccttcca ccctgtctgc atctgttgga cacagagtca ccatcacctg ccgggccagt   480
gagggtattt atcactggtt ggcctggtat cagcagaagc cagggaaagc ccctaaactc   540
ctgatctata aggcctctag tttagccagt ggggtcccat caaggttcag cggcagtgga   600
tctgggacag agttcactct caccatcagc agcctgcagc ctgatgattt tgcaacttat   660
tactgccaac aaatgggcga gtacaacgcc accttcggcg agggaccaa ggtggagatc    720 aaacgt                                                              726

<210> SEQ ID NO 485
<211> LENGTH: 15
<212> TYPE: DNA
<213> ORGANISM: Homo sapiens

<400> SEQUENCE: 485
agttatggta tcagc                                                     15

<210> SEQ ID NO 486
<211> LENGTH: 51
<212> TYPE: DNA
<213> ORGANISM: Homo sapiens

<400> SEQUENCE: 486
tgggtcagcg cttacactgg taacacaaac tatgcacaga gttccagggc                51

<210> SEQ ID NO 487
<211> LENGTH: 30
<212> TYPE: DNA
<213> ORGANISM: Homo sapiens

<400> SEQUENCE: 487
gatcgtggat actatgatgc ttttgatatc                                     30

<210> SEQ ID NO 488
<211> LENGTH: 33
<212> TYPE: DNA
<213> ORGANISM: Homo sapiens

<400> SEQUENCE: 488
cgggccagtg agggtattta tcactggttg gcc                                 33

<210> SEQ ID NO 489
<211> LENGTH: 21
```

<212> TYPE: DNA
<213> ORGANISM: Homo sapiens

<400> SEQUENCE: 489
aaggcctcta gtttagccag t     21

<210> SEQ ID NO 490
<211> LENGTH: 27
<212> TYPE: DNA
<213> ORGANISM: Homo sapiens

<400> SEQUENCE: 490
caacaaatgg gcgagtacaa cgccacc     27

<210> SEQ ID NO 491
<211> LENGTH: 121
<212> TYPE: PRT
<213> ORGANISM: Homo sapiens

<400> SEQUENCE: 491

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120

<210> SEQ ID NO 492
<211> LENGTH: 111
<212> TYPE: PRT
<213> ORGANISM: Homo sapiens

<400> SEQUENCE: 492

Gln Ala Ala Leu Thr Gln Pro Ala Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Phe Ser Val Val Phe Gly Gly Gly Thr Lys Leu Thr Val Leu Gly
            100                 105                 110

<210> SEQ ID NO 493

```
<211> LENGTH: 248
<212> TYPE: PRT
<213> ORGANISM: Homo sapiens

<400> SEQUENCE: 493

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser Gly Gly Gly Gly Ser Gly Gly
        115                 120                 125

Gly Gly Ser Gly Gly Gly Ser Ala Gln Ala Ala Leu Thr Gln Pro
    130                 135                 140

Ala Ser Val Ser Gly Ser Pro Gly Gln Ser Ile Thr Ile Ser Cys Thr
145                 150                 155                 160

Gly Ala Ser Gly Asp Val Gly Ala Tyr Asn Phe Val Ser Trp Tyr Gln
                165                 170                 175

Gln His Pro Gly Lys Ala Pro Lys Leu Ile Ile Tyr Asp Val Asn Lys
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ala Asp
    210                 215                 220

Tyr Tyr Cys Ser Ser Tyr Thr Ser Thr Phe Ser Val Val Phe Gly Gly
225                 230                 235                 240

Gly Thr Lys Leu Thr Val Leu Gly
                245

<210> SEQ ID NO 494
<211> LENGTH: 5
<212> TYPE: PRT
<213> ORGANISM: Homo sapiens

<400> SEQUENCE: 494

Asp Tyr Gly Met Asn
1               5

<210> SEQ ID NO 495
<211> LENGTH: 17
<212> TYPE: PRT
<213> ORGANISM: Homo sapiens

<400> SEQUENCE: 495

Gly Val Asn Trp Asn Gly Gly Thr Arg Asp Tyr Ala Ala Ser Val Lys
1               5                   10                  15

Gly

<210> SEQ ID NO 496
```

```
<211> LENGTH: 12
<212> TYPE: PRT
<213> ORGANISM: Homo sapiens

<400> SEQUENCE: 496

Gly Trp Tyr Ser Gly Ala Ala Trp Asn Met Gly Tyr
1               5                   10

<210> SEQ ID NO 497
<211> LENGTH: 14
<212> TYPE: PRT
<213> ORGANISM: Homo sapiens

<400> SEQUENCE: 497

Thr Gly Ala Ser Gly Asp Val Gly Ala Tyr Asn Phe Val Ser
1               5                   10

<210> SEQ ID NO 498
<211> LENGTH: 7
<212> TYPE: PRT
<213> ORGANISM: Homo sapiens

<400> SEQUENCE: 498

Asp Val Asn Lys Arg Pro Ser
1               5

<210> SEQ ID NO 499
<211> LENGTH: 10
<212> TYPE: PRT
<213> ORGANISM: Homo sapiens

<400> SEQUENCE: 499

Ser Ser Tyr Thr Ser Thr Phe Ser Val Val
1               5                   10

<210> SEQ ID NO 500
<211> LENGTH: 363
<212> TYPE: DNA
<213> ORGANISM: Homo sapiens

<400> SEQUENCE: 500
```

| | | | | | |
|---|---|---|---|---|---|
| gaggtgcagc | tggtggagag | cgggggaggt | gtggtacggc | ctgggggtc | cctgagactc | 60 |
| tcctgtgcag | cctctggatt | cacctttgac | gattatggca | tgaactgggt | ccgccaagct | 120 |
| ccagggaagg | gctggagtg | gtctctggt | gttaattgga | atggtggtac | cagagattat | 180 |
| gcagcctccg | tgaagggccg | attcaccatc | tccagagaca | acgccaagaa | ctccctgtat | 240 |
| ctgcaaatga | acagtctgag | agccgaggac | acggccttgt | atcactgtgc | gagaggatgg | 300 |
| tatagtgggg | ccgcgtggaa | catgggctac | tggggccgag | aaccctggt | caccgtctcc | 360 |
| tca | | | | | | 363 |

```
<210> SEQ ID NO 501
<211> LENGTH: 333
<212> TYPE: DNA
<213> ORGANISM: Homo sapiens

<400> SEQUENCE: 501
```

| | | | | | |
|---|---|---|---|---|---|
| caggctgcgc | tgactcagcc | ggcctccgtg | tctgggtctc | ctggacagtc | gatcaccatc | 60 |
| tcctgcactg | gagccagcgg | tgacgttggt | gcttataact | ttgtctcctg | gtaccaacaa | 120 |
| cacccaggca | aagcccccaa | actcataatt | tatgatgtca | ataagcggcc | ctcaggggtt | 180 |
| tctaatcgct | tctctggctc | caagtctggc | aacacggcct | ccctgaccat | ctctgggctc | 240 |

| | |
|---|---|
| caggccgagg acgaggctga ttattactgc agctcatata caagcacctt ctctgtggta | 300 |
| tttggcggag ggaccaagct gaccgtccta ggt | 333 |

<210> SEQ ID NO 502
<211> LENGTH: 744
<212> TYPE: DNA
<213> ORGANISM: Homo sapiens

<400> SEQUENCE: 502

| | |
|---|---|
| gaggtgcagc tggtggagag cgggggaggt gtggtacggc ctgggggggtc cctgagactc | 60 |
| tcctgtgcag cctctggatt cacctttgac gattatggca tgaactgggt ccgccaagct | 120 |
| ccagggaagg ggctggagtg ggtctctggt gttaattgga atggtggtac cagagattat | 180 |
| gcagcctccg tgaagggccg attcaccatc tccagagaca cgccaagaa ctccctgtat | 240 |
| ctgcaaatga acagtctgag agccgaggac acggccttgt atcactgtgc gagaggatgg | 300 |
| tatagtgggg ccgcgtggaa catgggctac tggggccgag gaaccctggt caccgtctcc | 360 |
| tcaggaggcg gcggttcagg cggaggtggc tctggcggtg gcggaagtgc acaggctgcg | 420 |
| ctgactcagc cggcctccgt gtctgggtct cctggacagt cgatcaccat ctcctgcact | 480 |
| ggagccagcg gtgacgttgg tgcttataac tttgtctcct ggtaccaaca cacccaggc | 540 |
| aaagccccca aactcataat ttatgatgtc aataagcggc cctcagggggt ttctaatcgc | 600 |
| ttctctggct ccaagtctgg caacacggcc tccctgacca tctctgggct ccaggccgag | 660 |
| gacgaggctg attattactg cagctcatat acaagcacct tctctgtggt atttggcgga | 720 |
| gggaccaagc tgaccgtcct aggt | 744 |

<210> SEQ ID NO 503
<211> LENGTH: 15
<212> TYPE: DNA
<213> ORGANISM: Homo sapiens

<400> SEQUENCE: 503

| | |
|---|---|
| gattatggca tgaac | 15 |

<210> SEQ ID NO 504
<211> LENGTH: 51
<212> TYPE: DNA
<213> ORGANISM: Homo sapiens

<400> SEQUENCE: 504

| | |
|---|---|
| ggtgttaatt ggaatggtgg taccagagat tatgcagcct ccgtgaaggg c | 51 |

<210> SEQ ID NO 505
<211> LENGTH: 36
<212> TYPE: DNA
<213> ORGANISM: Homo sapiens

<400> SEQUENCE: 505

| | |
|---|---|
| ggatggtata gtggggccgc gtggaacatg ggctac | 36 |

<210> SEQ ID NO 506
<211> LENGTH: 42
<212> TYPE: DNA
<213> ORGANISM: Homo sapiens

<400> SEQUENCE: 506

| | |
|---|---|
| actggagcca gcggtgacgt tggtgcttat aactttgtct cc | 42 |

<210> SEQ ID NO 507

```
<211> LENGTH: 21
<212> TYPE: DNA
<213> ORGANISM: Homo sapiens

<400> SEQUENCE: 507
gatgtcaata agcggccctc a                                              21

<210> SEQ ID NO 508
<211> LENGTH: 30
<212> TYPE: DNA
<213> ORGANISM: Homo sapiens

<400> SEQUENCE: 508
agctcatata caagcacctt ctctgtggta                                     30

<210> SEQ ID NO 509
<211> LENGTH: 119
<212> TYPE: PRT
<213> ORGANISM: Homo sapiens

<400> SEQUENCE: 509

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Pro Phe Asp Ile Trp Gly Gln Gly
            100                 105                 110

Thr Leu Val Thr Val Ser Ser
        115

<210> SEQ ID NO 510
<211> LENGTH: 109
<212> TYPE: PRT
<213> ORGANISM: Homo sapiens

<400> SEQUENCE: 510

Ser Ser Val Leu Thr Gln Pro Pro Ser Val Ser Val Ala Pro Gly Lys
1               5                   10                  15

Thr Ala Arg Ile Thr Cys Gly Gly Asn Asn Phe Arg Asn Lys Arg Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Leu Phe Asn Asp Asn
                85                  90                  95

Gly Val Phe Gly Gly Gly Thr Lys Leu Thr Val Leu Gly
            100                 105
```

```
<210> SEQ ID NO 511
<211> LENGTH: 244
<212> TYPE: PRT
<213> ORGANISM: Homo sapiens

<400> SEQUENCE: 511

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Tyr Ile His Trp Val Arg Gln Ala Pro Gly Gln Gly Leu Glu Trp Met
            35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Ser Ser Gly Gly Gly
        115                 120                 125

Ser Gly Gly Gly Ser Ala Ser Ser Val Leu Thr Gln Pro Pro Ser
130                 135                 140

Val Ser Val Ala Pro Gly Lys Thr Ala Arg Ile Thr Cys Gly Gly Asn
145                 150                 155                 160

Asn Phe Arg Asn Lys Arg Val His Trp Tyr Gln Gln Lys Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Tyr Tyr Cys Gln Val
    210                 215                 220

Trp Asp Leu Phe Asn Asp Asn Gly Val Phe Gly Gly Gly Thr Lys Leu
225                 230                 235                 240

Thr Val Leu Gly

<210> SEQ ID NO 512
<211> LENGTH: 5
<212> TYPE: PRT
<213> ORGANISM: Homo sapiens

<400> SEQUENCE: 512

Asp Tyr Tyr Ile His
1               5

<210> SEQ ID NO 513
<211> LENGTH: 17
<212> TYPE: PRT
<213> ORGANISM: Homo sapiens

<400> SEQUENCE: 513

Trp Val Asn Pro Asp Thr Gly Gly Thr Arg Tyr Ala Gln Lys Phe Gln
1               5                   10                  15

Gly

<210> SEQ ID NO 514
```

```
<211> LENGTH: 10
<212> TYPE: PRT
<213> ORGANISM: Homo sapiens

<400> SEQUENCE: 514

Asp Leu Thr Gly Phe Asp Pro Phe Asp Ile
1               5                   10

<210> SEQ ID NO 515
<211> LENGTH: 11
<212> TYPE: PRT
<213> ORGANISM: Homo sapiens

<400> SEQUENCE: 515

Gly Gly Asn Asn Phe Arg Asn Lys Arg Val His
1               5                   10

<210> SEQ ID NO 516
<211> LENGTH: 7
<212> TYPE: PRT
<213> ORGANISM: Homo sapiens

<400> SEQUENCE: 516

Tyr Asp Ser Asp Arg Pro Ser
1               5

<210> SEQ ID NO 517
<211> LENGTH: 11
<212> TYPE: PRT
<213> ORGANISM: Homo sapiens

<400> SEQUENCE: 517

Gln Val Trp Asp Leu Phe Asn Asp Asn Gly Val
1               5                   10

<210> SEQ ID NO 518
<211> LENGTH: 357
<212> TYPE: DNA
<213> ORGANISM: Homo sapiens

<400> SEQUENCE: 518
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt tcagggccga ggtcacaatg accaggggaca tgtccatctc cacagcctac     240
atggagctgt ccaggctgag aagcgacgac acggccgtat attactgtgc gagagatcta     300
actggatttg atccttttga tatctggggc cagggaaccc tggtcaccgt ctcctca        357

<210> SEQ ID NO 519
<211> LENGTH: 327
<212> TYPE: DNA
<213> ORGANISM: Homo sapiens

<400> SEQUENCE: 519
tcgtctgtgc tgactcagcc accctcagtg tcagtggccc caggaaagac ggcccgcatt      60
acctgtgggg gaaacaactt cgaaataaa agagtacact ggtatcagca aaagccaggc     120
caggcccctg tcctggtcat ctattatgat tcagaccggc cctcagggat ccctgagcga     180
ttctctggct cccgctctgg gaacacggcc accctgacca tcagcagggt cgaggccggg     240
gatgaggccg actattactg tcaggtgtgg gatctcttca acgacaacgg cgtgttcggc     300
```

```
ggagggacca agctgaccgt cctaggt                                              327
```

<210> SEQ ID NO 520
<211> LENGTH: 732
<212> TYPE: DNA
<213> ORGANISM: Homo sapiens

<400> SEQUENCE: 520

```
caggtccagc tggtgcagtc tggggctgag gtgaagaagc ctggggcctc agtgaaggtc           60
tcctgtaagg cttctggata cccttcagc gattactata ttcactgggt gcgacaggcc          120
cctggacaag ggttggagtg gatgggatgg gtcaaccctg acactggtgg cacaagatac         180
gcgcagaagt tcagggccg gtcacaatg accagggaca tgtccatctc cacagcctac          240
atggagctgt ccaggctgag aagcgacgac acggccgtat attactgtgc gagagatcta         300
actggatttg atccttttga tatctggggc cagggaaccc tggtcaccgt ctcctcagga         360
ggcggcagtt caggtggagg tggctctggc ggtggcggaa gtgcatcgtc tgtgctgact         420
cagccaccct cagtgtcagt ggccccagga agacggccc gcattacctg tgggggaaac         480
aactttcgaa ataaaagagt acactggtat cagcagaagc caggccaggc ccctgtcctg         540
gtcatctatt atgattcaga ccggcctca gggatccctg agcgattctc tggctcccgc         600
tctgggaaca cggccaccct gaccatcagc agggtcgagg ccggggatga ggccgactat         660
tactgtcagg tgtgggatct cttcaacgac aacggcgtgt tcggcggagg gaccaagctg         720
accgtcctag gt                                                              732
```

<210> SEQ ID NO 521
<211> LENGTH: 15
<212> TYPE: DNA
<213> ORGANISM: Homo sapiens

<400> SEQUENCE: 521

```
gattactata ttcac                                                           15
```

<210> SEQ ID NO 522
<211> LENGTH: 51
<212> TYPE: DNA
<213> ORGANISM: Homo sapiens

<400> SEQUENCE: 522

```
tgggtcaacc ctgacactgg tggcacaaga tacgcgcaga gtttcagggc                     51
```

<210> SEQ ID NO 523
<211> LENGTH: 30
<212> TYPE: DNA
<213> ORGANISM: Homo sapiens

<400> SEQUENCE: 523

```
gatctaactg gatttgatcc ttttgatatc                                           30
```

<210> SEQ ID NO 524
<211> LENGTH: 33
<212> TYPE: DNA
<213> ORGANISM: Homo sapiens

<400> SEQUENCE: 524

```
gggggaaaca actttcgaaa taaaagagta cac                                       33
```

<210> SEQ ID NO 525
<211> LENGTH: 21
<212> TYPE: DNA

<213> ORGANISM: Homo sapiens

<400> SEQUENCE: 525
tatgattcag accggccctc a                                        21

<210> SEQ ID NO 526
<211> LENGTH: 33
<212> TYPE: DNA
<213> ORGANISM: Homo sapiens

<400> SEQUENCE: 526
caggtgtggg atctcttcaa cgacaacggc gtg                            33

<210> SEQ ID NO 527
<211> LENGTH: 119
<212> TYPE: PRT
<213> ORGANISM: Homo sapiens

<400> SEQUENCE: 527

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 528
<211> LENGTH: 109
<212> TYPE: PRT
<213> ORGANISM: Homo sapiens

<400> SEQUENCE: 528

Ser Ser Val Leu Thr Gln Pro Pro Ser Val Ser Val Ala Pro Gly Lys
1               5                   10                  15

Thr Ala Arg Ile Thr Cys Gly Gly Asn Asn Phe Arg Asn Lys Arg Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Phe Leu Thr Asp Ser
                85                  90                  95

Gly Ser Phe Gly Gly Gly Thr Lys Leu Thr Val Leu Gly
            100                 105

<210> SEQ ID NO 529
<211> LENGTH: 244

```
<212> TYPE: PRT
<213> ORGANISM: Homo sapiens

<400> SEQUENCE: 529

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Ser Ser Val Leu Thr Gln Pro Pro Ser
130                 135                 140

Val Ser Val Ala Pro Gly Lys Thr Ala Arg Ile Thr Cys Gly Gly Asn
145                 150                 155                 160

Asn Phe Arg Asn Lys Arg Val His Trp Tyr Gln Gln Lys Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Tyr Tyr Cys Gln Val
210                 215                 220

Trp Asp Phe Leu Thr Asp Ser Gly Ser Phe Gly Gly Gly Thr Lys Leu
225                 230                 235                 240

Thr Val Leu Gly

<210> SEQ ID NO 530
<211> LENGTH: 5
<212> TYPE: PRT
<213> ORGANISM: Homo sapiens

<400> SEQUENCE: 530

Asp Tyr Tyr Ile His
1               5

<210> SEQ ID NO 531
<211> LENGTH: 17
<212> TYPE: PRT
<213> ORGANISM: Homo sapiens

<400> SEQUENCE: 531

Trp Val Asn Pro Asp Thr Gly Gly Thr Arg Tyr Ala Gln Lys Phe Gln
1               5                   10                  15

Gly

<210> SEQ ID NO 532
<211> LENGTH: 10
<212> TYPE: PRT
```

<213> ORGANISM: Homo sapiens

<400> SEQUENCE: 532

Asp Leu Thr Gly Phe Asp Pro Phe Asp Ile
1               5                   10

<210> SEQ ID NO 533
<211> LENGTH: 11
<212> TYPE: PRT
<213> ORGANISM: Homo sapiens

<400> SEQUENCE: 533

Gly Gly Asn Asn Phe Arg Asn Lys Arg Val His
1               5                   10

<210> SEQ ID NO 534
<211> LENGTH: 7
<212> TYPE: PRT
<213> ORGANISM: Homo sapiens

<400> SEQUENCE: 534

Tyr Asp Ser Asp Arg Pro Ser
1               5

<210> SEQ ID NO 535
<211> LENGTH: 11
<212> TYPE: PRT
<213> ORGANISM: Homo sapiens

<400> SEQUENCE: 535

Gln Val Trp Asp Phe Leu Thr Asp Ser Gly Ser
1               5                   10

<210> SEQ ID NO 536
<211> LENGTH: 357
<212> TYPE: DNA
<213> ORGANISM: Homo sapiens

<400> SEQUENCE: 536

```
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accagggaca tgtccatctc cacagcctac     240
atggagctgt ccaggctgag aagcgacgac acggccgtat attactgtgc gagagatcta     300
actggatttg atccttttga tatctggggc caggaaccc tggtcaccgt ctcctca        357
```

<210> SEQ ID NO 537
<211> LENGTH: 327
<212> TYPE: DNA
<213> ORGANISM: Homo sapiens

<400> SEQUENCE: 537

```
tcgtctgtgc tgactcagcc acccctcagtg tcagtggccc caggaaagac ggcccgcatt      60
acctgtgggg gaaacaactt tcgaaataaa agagtacact ggtatcagca gaagccaggc     120
caggcccctg tcctggtcat ctattatgat tcagaccggc cctcagggat ccctgagcga     180
ttctctggct cccgctctgg gaacacggcc accctgacca tcagcagggt cgaggccggg     240
gatgaggccg actattactg tcaggtgtgg gatttcctca ccgactcggg gtcgttcggc     300
ggagggacca agctgaccgt cctaggt                                         327
```

```
<210> SEQ ID NO 538
<211> LENGTH: 732
<212> TYPE: DNA
<213> ORGANISM: Homo sapiens

<400> SEQUENCE: 538
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accaggggaca tgtccatctc cacagcctac     240
atggagctgt ccaggctgag aagcgacgac acggccgtat attactgtgc gagagatcta     300
actggatttg atccttttga tatctggggc caggaacccc tggtcaccgt ctcctcagga     360
ggcggcggtt caggcggagg tggctctggc ggtggcggaa gtgcatcgtc tgtgctgact     420
cagccaccct cagtgtcagt ggccccagga aagacggccc gcattacctg tgggggaaac     480
aactttcgaa ataaaagagt acactggtat cagcagaagc caggccaggc ccctgtcctg     540
gtcatctatt atgattcaga ccggccctca gggatccctg agcgattctc tggctcccgc     600
tctgggaaca cggccaccct gaccatcagc agggtcgagg ccggggatga ggccgactat     660
tactgtcagg tgtgggattt cctcaccgac tcggggtcgt tcggcggagg gaccaagctg     720
accgtcctag gt                                                        732

<210> SEQ ID NO 539
<211> LENGTH: 15
<212> TYPE: DNA
<213> ORGANISM: Homo sapiens

<400> SEQUENCE: 539
gattactata ttcac                                                      15

<210> SEQ ID NO 540
<211> LENGTH: 51
<212> TYPE: DNA
<213> ORGANISM: Homo sapiens

<400> SEQUENCE: 540
tgggtcaacc ctgacactgg tggcacaaga tacgcgcaga gtttcaggg c                51

<210> SEQ ID NO 541
<211> LENGTH: 30
<212> TYPE: DNA
<213> ORGANISM: Homo sapiens

<400> SEQUENCE: 541
gatctaactg gatttgatcc ttttgatatc                                       30

<210> SEQ ID NO 542
<211> LENGTH: 33
<212> TYPE: DNA
<213> ORGANISM: Homo sapiens

<400> SEQUENCE: 542
gggggaaaca actttcgaaa taaaagagta cac                                   33

<210> SEQ ID NO 543
<211> LENGTH: 21
<212> TYPE: DNA
<213> ORGANISM: Homo sapiens
```

<400> SEQUENCE: 543
tatgattcag accggccctc a                    21

<210> SEQ ID NO 544
<211> LENGTH: 33
<212> TYPE: DNA
<213> ORGANISM: Homo sapiens

<400> SEQUENCE: 544
caggtgtggg atttcctcac cgactcgggg tcg                    33

<210> SEQ ID NO 545
<211> LENGTH: 121
<212> TYPE: PRT
<213> ORGANISM: Homo sapiens

<400> SEQUENCE: 545

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Arg Phe Gly Asp Ser Thr Gly Val Trp Gly
            100                 105                 110

Arg Gly Thr Leu Val Thr Val Ser Ser
        115                 120

<210> SEQ ID NO 546
<211> LENGTH: 112
<212> TYPE: PRT
<213> ORGANISM: Homo sapiens

<400> SEQUENCE: 546

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Tyr His Trp Asp Lys Glu
                85                  90                  95

Gln Ser Gly Tyr Val Phe Gly Gly Gly Thr Gln Leu Thr Val Leu Gly
            100                 105                 110

<210> SEQ ID NO 547
<211> LENGTH: 249
<212> TYPE: PRT
<213> ORGANISM: Homo sapiens

<400> SEQUENCE: 547

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Pro Glu Arg Phe Gly Asp Ser Thr Gly Gln Val Trp Gly
            100                 105                 110

Arg Gly Thr Leu Val Thr Val Ser Ser Gly Gly Gly Ser Gly Gly
        115                 120                 125

Gly Gly Ser Gly Gly Ser Arg Ser Ala Gln Ala Val Leu Thr Gln Pro
130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
210                 215                 220

Tyr Tyr Cys Tyr His Trp Asp Lys Glu Gln Ser Gly Tyr Val Phe Gly
225                 230                 235                 240

Gly Gly Thr Gln Leu Thr Val Leu Gly
                245

<210> SEQ ID NO 548
<211> LENGTH: 5
<212> TYPE: PRT
<213> ORGANISM: Homo sapiens

<400> SEQUENCE: 548

Asp Tyr Tyr Met His
1               5

<210> SEQ ID NO 549
<211> LENGTH: 17
<212> TYPE: PRT
<213> ORGANISM: Homo sapiens

<400> SEQUENCE: 549

Trp Ile Asn Pro Tyr Thr Gly Ala Phe Tyr Ala Gln Lys Phe Arg
1               5                   10                  15

Gly

<210> SEQ ID NO 550
<211> LENGTH: 12
<212> TYPE: PRT
<213> ORGANISM: Homo sapiens

<400> SEQUENCE: 550

Glu Pro Glu Arg Phe Gly Asp Ser Thr Gly Gln Val
1               5                   10

<210> SEQ ID NO 551
<211> LENGTH: 14
<212> TYPE: PRT
<213> ORGANISM: Homo sapiens

<400> SEQUENCE: 551

Thr Gly Ser Ser Ser Asn Ile Gly Ala Gly Tyr Gly Val His
1               5                   10

<210> SEQ ID NO 552
<211> LENGTH: 7
<212> TYPE: PRT
<213> ORGANISM: Homo sapiens

<400> SEQUENCE: 552

Gly Asn Ser Asn Arg Pro Ser
1               5

<210> SEQ ID NO 553
<211> LENGTH: 11
<212> TYPE: PRT
<213> ORGANISM: Homo sapiens

<400> SEQUENCE: 553

Tyr His Trp Asp Lys Glu Gln Ser Gly Tyr Val
1               5                   10

<210> SEQ ID NO 554
<211> LENGTH: 363
<212> TYPE: DNA
<213> ORGANISM: Homo sapiens

<400> SEQUENCE: 554
caggtgcagc tggtgcagtc tgggggctgag gtgaagaagc ctggggcctc agtgaaggtc        60
tcctgcaagg cttctggata caccttcacc gactactata tgcactgggt gcgacaggcc       120
cctggacaag gcttgagtg gtgggatgg atcaaccctt atactggtgg cgcattctat         180
gcacagaagt ttcggggcag ggtcacaatg accagggaca cgtccatcag cacagcctac       240
atggagctga gcagactgag atctgacgac acggccgtgt attattgtgc gagagaacct       300
gaaagattcg gcgactccac ggggcaggtc tggggccggg gacattggt caccgtctcc        360 tca                                                                    363

<210> SEQ ID NO 555
<211> LENGTH: 336
<212> TYPE: DNA
<213> ORGANISM: Homo sapiens

<400> SEQUENCE: 555
caggctgtgc tgactcagcc gccgtcagtg tctggggccc cagggcagag ggtcaccatc        60
tcctgcactg ggagcagctc caacatcggg gcaggttatg gtgtacactg gtaccaacag       120
cttccaggaa cagccccaa actcctcatc tatggtaaca gcaatcggcc ctcagggtc         180 cctgaccgat tctctggctc caagtctggc acctcagcct ccctggccat cactgggctc       240
caggctgagg atgaggctga ttattactgc taccactggg acaaggagca gagtggttat       300
gtcttcggag gtgggaccca gctcaccgtc ctaggt                                 336

<210> SEQ ID NO 556
<211> LENGTH: 747
<212> TYPE: DNA
<213> ORGANISM: Homo sapiens

<400> SEQUENCE: 556

```
caggtgcagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gatgggatgg atcaaccctt atactggtgg cgcattctat     180
gcacagaagt ttcggggcag ggtcacaatg accagggaca cgtccatcag cacagcctac     240
atggagctga gcagactgag atctgacgac acggccgtgt attattgtgc gagagaacct     300
gaaagattcg gcgactccac ggggcaggtc tggggccggg ggacattggt caccgtctcc     360
tcagggggcg gcggttcagg cggaggtggc tctggcggta gcagaagtgc acaggctgtg     420
ctgactcagc cgccgtcagt gtctgggccc ccagggcaga gggtcaccat ctcctgcact     480
gggagcagct ccaacatcgg ggcaggttat ggtgtacact ggtaccaaca gcttccagga     540
acagccccca aactcctcat ctatggtaac agcaatcggc cctcagggt ccctgaccga      600
ttctctggct ccaagtctgg cacctcagcc tccctggcca tcactgggct ccaggctgag     660
gatgaggctg attattactg ctaccactgg gacaaggagc agagtggtta tgtcttcgga     720
ggtgggaccc agctcaccgt cctaggt                                          747
```

<210> SEQ ID NO 557
<211> LENGTH: 15
<212> TYPE: DNA
<213> ORGANISM: Homo sapiens

<400> SEQUENCE: 557

```
gactactata tgcac                                                        15
```

<210> SEQ ID NO 558
<211> LENGTH: 51
<212> TYPE: DNA
<213> ORGANISM: Homo sapiens

<400> SEQUENCE: 558

```
tggatcaacc cttatactgg tggcgcattc tatgcacaga gtttcgggg c                 51
```

<210> SEQ ID NO 559
<211> LENGTH: 36
<212> TYPE: DNA
<213> ORGANISM: Homo sapiens

<400> SEQUENCE: 559

```
gaacctgaaa gattcggcga ctccacgggg caggtc                                 36
```

<210> SEQ ID NO 560
<211> LENGTH: 42
<212> TYPE: DNA
<213> ORGANISM: Homo sapiens

<400> SEQUENCE: 560

```
actgggagca gctccaacat cggggcaggt tatggtgtac ac                          42
```

<210> SEQ ID NO 561
<211> LENGTH: 21
<212> TYPE: DNA
<213> ORGANISM: Homo sapiens

<400> SEQUENCE: 561
ggtaacagca atcggccctc a                                        21

<210> SEQ ID NO 562
<211> LENGTH: 33
<212> TYPE: DNA
<213> ORGANISM: Homo sapiens

<400> SEQUENCE: 562
taccactggg acaaggagca gagtggttat gtc                           33

<210> SEQ ID NO 563
<211> LENGTH: 121
<212> TYPE: PRT
<213> ORGANISM: Homo sapiens

<400> SEQUENCE: 563

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Gly Glu Ser Ser Gly Gln Leu Trp Gly
            100                 105                 110

Arg Gly Thr Leu Val Thr Val Ser Ser
        115                 120

<210> SEQ ID NO 564
<211> LENGTH: 112
<212> TYPE: PRT
<213> ORGANISM: Homo sapiens

<400> SEQUENCE: 564

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

Leu Ser Gly Tyr Val Phe Gly Gly Gly Thr Gln Leu Thr Val Leu Gly
            100                 105                 110

<210> SEQ ID NO 565
<211> LENGTH: 249
<212> TYPE: PRT

<213> ORGANISM: Homo sapiens

<400> SEQUENCE: 565

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Gly Glu Ser Gly Gln Leu Trp Gly
            100                 105                 110

Arg Gly Thr Leu Val Thr Val Ser Gly Gly Gly Ser Gly Gly
            115                 120                 125

Gly Gly Ser Gly Gly Ser Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asp Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Gly Leu Ser Gly Tyr Val Phe Gly
225                 230                 235                 240

Gly Gly Thr Gln Leu Thr Val Leu Gly
                245

<210> SEQ ID NO 566
<211> LENGTH: 5
<212> TYPE: PRT
<213> ORGANISM: Homo sapiens

<400> SEQUENCE: 566

Asp Tyr Tyr Met His
1               5

<210> SEQ ID NO 567
<211> LENGTH: 17
<212> TYPE: PRT
<213> ORGANISM: Homo sapiens

<400> SEQUENCE: 567

Trp Ile Asn Pro Tyr Thr Gly Ser Ala Phe Tyr Ala Gln Lys Phe Arg
1               5                   10                  15

Gly

<210> SEQ ID NO 568
<211> LENGTH: 12
<212> TYPE: PRT

<210> SEQ ID NO 568
<211> LENGTH: 11
<212> TYPE: PRT
<213> ORGANISM: Homo sapiens

<400> SEQUENCE: 568

Glu Pro Glu Lys Phe Gly Glu Ser Ser Gly Gln Leu
1               5                   10

<210> SEQ ID NO 569
<211> LENGTH: 14
<212> TYPE: PRT
<213> ORGANISM: Homo sapiens

<400> SEQUENCE: 569

Thr Gly Ser Ser Ser Asn Ile Gly Ala Gly Tyr Gly Val His
1               5                   10

<210> SEQ ID NO 570
<211> LENGTH: 7
<212> TYPE: PRT
<213> ORGANISM: Homo sapiens

<400> SEQUENCE: 570

Gly Asp Ser Asn Arg Pro Ser
1               5

<210> SEQ ID NO 571
<211> LENGTH: 11
<212> TYPE: PRT
<213> ORGANISM: Homo sapiens

<400> SEQUENCE: 571

Gln Ser Tyr Asp Ser Gly Leu Ser Gly Tyr Val
1               5                   10

<210> SEQ ID NO 572
<211> LENGTH: 363
<212> TYPE: DNA
<213> ORGANISM: Homo sapiens

<400> SEQUENCE: 572

```
caggtgcagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gtgggatgg atcaacccctt atactggtag cgcttttctat     180
gcacagaagt ttcggggcag ggtcacaatg accagggaca cgtccatcag cacagcctac     240
atggagctga gcagactgag atctgacgac acggccgtgt attattgtgc gagagaacct     300
gaaaaattcg gcgagtccag cggccagttg tggggccggg ggacattggt caccgtctcc     360
tca                                                                  363
```

<210> SEQ ID NO 573
<211> LENGTH: 336
<212> TYPE: DNA
<213> ORGANISM: Homo sapiens

<400> SEQUENCE: 573

```
caggctgtgc tgactcagcc gccgtcagtg tctggggccc cagggcagag ggtcaccatc      60
tcctgcactg ggagcagctc caacatcggg gcaggttatg gtgtacactg gtaccaacag     120
cttccaggaa cagcccccaa actcctcatc tatggtgaca gcaatcggcc ctcagggtc      180
cctgaccgat tctctggctc caagtctggc acctcagcct ccctggccat cactgggctc     240
caggctgagg atgaggctga ttattactgc cagtcctatg acagcggcct gagtggttat     300
```

```
gtcttcggag gtgggaccca gctcaccgtc ctaggt                                 336
```

```
<210> SEQ ID NO 574
<211> LENGTH: 747
<212> TYPE: DNA
<213> ORGANISM: Homo sapiens

<400> SEQUENCE: 574
caggtgcagc tggtgcagtc tggggctgag gtgaagaagc ctggggcctc agtgaaggtc         60
tcctgcaagg cttctggata caccttcacc gactactata tgcactgggt gcgacaggcc        120
cctggacaag gcttgagtg gtgggatgg atcaaccctt atactggtag cgctttctat         180
gcacagaagt ttcggggcag ggtcacaatg accagggaca cgtccatcag cacagcctac        240
atggagctga gcagactgag atctgacgac acggccgtgt attattgtgc gagagaacct        300
gaaaaattcg gcgagtccag cggccagttg tggggccggg ggacattggt caccgtctcc        360
tcaggaggcg gcggttcagg cggaggtggc tctggcggta gcggaagtgc acaggctgtg        420
ctgactcagc cgccgtcagt gtctggggcc ccagggcaga gggtcaccat ctcctgcact        480
gggagcagct ccaacatcgg ggcaggttat ggtgtacact ggtaccaaca gcttccagga        540
acagccccca aactcctcat ctatggtgac agcaatcggc cctcagggt ccctgaccga         600 ttctctggct ccaagtctgg cacctcagcc tccctggcca tcactgggct ccaggctgag        660
gatgaggctg attattactg ccagtcctat gacagcggcc tgagtggtta tgtcttcgga        720
ggtgggaccc agctcaccgt cctaggt                                           747
```

```
<210> SEQ ID NO 575
<211> LENGTH: 15
<212> TYPE: DNA
<213> ORGANISM: Homo sapiens

<400> SEQUENCE: 575
gactactata tgcac                                                         15
```

```
<210> SEQ ID NO 576
<211> LENGTH: 51
<212> TYPE: DNA
<213> ORGANISM: Homo sapiens

<400> SEQUENCE: 576
tggatcaacc cttatactgg tagcgctttc tatgcacaga gtttcggggg c                 51
```

```
<210> SEQ ID NO 577
<211> LENGTH: 36
<212> TYPE: DNA
<213> ORGANISM: Homo sapiens

<400> SEQUENCE: 577
gaacctgaaa aattcggcga gtccagcggc cagttg                                  36
```

```
<210> SEQ ID NO 578
<211> LENGTH: 42
<212> TYPE: DNA
<213> ORGANISM: Homo sapiens

<400> SEQUENCE: 578
actgggagca gctccaacat cggggcaggt tatggtgtac ac                           42
```

```
<210> SEQ ID NO 579
<211> LENGTH: 21
<212> TYPE: DNA
```

<213> ORGANISM: Homo sapiens

<400> SEQUENCE: 579
ggtgacagca atcggccctc a                                          21

<210> SEQ ID NO 580
<211> LENGTH: 33
<212> TYPE: DNA
<213> ORGANISM: Homo sapiens

<400> SEQUENCE: 580
cagtcctatg acagcggcct gagtggttat gtc                             33

<210> SEQ ID NO 581
<211> LENGTH: 121
<212> TYPE: PRT
<213> ORGANISM: Homo sapiens

<400> SEQUENCE: 581

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Pro Asn Ala Glu Ile Trp Gly
            100                 105                 110

Arg Gly Thr Leu Val Thr Val Ser Ser
        115                 120

<210> SEQ ID NO 582
<211> LENGTH: 112
<212> TYPE: PRT
<213> ORGANISM: Homo sapiens

<400> SEQUENCE: 582

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Gly Gly Thr Gln Leu Thr Val Leu Gly
            100                 105                 110

<210> SEQ ID NO 583
<211> LENGTH: 249

```
<212> TYPE: PRT
<213> ORGANISM: Homo sapiens

<400> SEQUENCE: 583

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Pro Asn Ala Glu Ile Trp Gly
            100                 105                 110

Arg Gly Thr Leu Val Thr Val Ser Ser Glu Gly Gly Ser Gly Gly
        115                 120                 125

Gly Gly Ser Gly Gly Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Gly Tyr Val Phe Gly
225                 230                 235                 240

Gly Gly Thr Gln Leu Thr Val Leu Gly
                245

<210> SEQ ID NO 584
<211> LENGTH: 5
<212> TYPE: PRT
<213> ORGANISM: Homo sapiens

<400> SEQUENCE: 584

His Tyr Tyr Met His
1               5

<210> SEQ ID NO 585
<211> LENGTH: 17
<212> TYPE: PRT
<213> ORGANISM: Homo sapiens

<400> SEQUENCE: 585

Trp Ile Asn Pro Tyr Thr Gly Gly Ala Phe Tyr Ala Gln Lys Phe Gln
1               5                   10                  15

Gly

<210> SEQ ID NO 586
<211> LENGTH: 12
```

```
<212> TYPE: PRT
<213> ORGANISM: Homo sapiens

<400> SEQUENCE: 586

Glu Pro Glu Lys Phe Asp Ser Pro Asn Ala Glu Ile
1               5                   10

<210> SEQ ID NO 587
<211> LENGTH: 14
<212> TYPE: PRT
<213> ORGANISM: Homo sapiens

<400> SEQUENCE: 587

Thr Gly Ser Ser Ser Asn Ile Gly Ala Gly Tyr Gly Val His
1               5                   10

<210> SEQ ID NO 588
<211> LENGTH: 7
<212> TYPE: PRT
<213> ORGANISM: Homo sapiens

<400> SEQUENCE: 588

Gly Asn Ser Asn Arg Pro Ser
1               5

<210> SEQ ID NO 589
<211> LENGTH: 11
<212> TYPE: PRT
<213> ORGANISM: Homo sapiens

<400> SEQUENCE: 589

Gln Ser Tyr Asp Ser Ser Leu Ser Gly Tyr Val
1               5                   10

<210> SEQ ID NO 590
<211> LENGTH: 363
<212> TYPE: DNA
<213> ORGANISM: Homo sapiens

<400> SEQUENCE: 590
caggtgcagc tggtgcagtc tggggctgag gtgaagaagc ctggggcctc agtgaaggtc      60
tcctgcaagg cttctggata caccttcacc cactactata tgcactgggt gcgacaggcc     120
cctggacaag ggcttgagtg ggtgggatgg atcaacccct tatactggtgg cgcattctat    180 gcacagaagt tcagggcag ggtcacaatg accaggaca cgtccatcag cacagcctac       240
atggagctga gcagactgag atctgacgac acggccgtgt attattgtgc gagagaacct     300
gaaaaattcg actcgccgaa cgccgagatc tggggccggg gacattggt caccgtctcc      360 tca                                                                   363

<210> SEQ ID NO 591
<211> LENGTH: 336
<212> TYPE: DNA
<213> ORGANISM: Homo sapiens

<400> SEQUENCE: 591
caggctgtgc tgactcagcc gccgtcagtg tctggggccc cagggcagag ggtcaccatc      60
tcctgcactg ggagcagctc caacatcggg gcaggttatg gtgtacactg gtaccaacag     120
cttccaggaa cagccccccaa actcctcatc tatggtaaca gcaatcgccc ctcaggggtc    180
cctgaccgat tctctggctc caagtctggc acctcagcct ccctggccat cactgggctc     240
caggctgagg atgaggctga ttattactgc cagtcctatg acagcagcct gagtggttat     300
```

```
gtcttcggag gtgggaccca gctcaccgtc ctaggt                                      336

<210> SEQ ID NO 592
<211> LENGTH: 747
<212> TYPE: DNA
<213> ORGANISM: Homo sapiens

<400> SEQUENCE: 592
caggtgcagc tggtgcagtc tggggctgag gtgaagaagc ctggggcctc agtgaaggtc            60
tcctgcaagg cttctggata caccttcacc cactactata tgcactgggt gcgacaggcc          120
cctggacaag gcttgagtg gtgggatgg atcaacccctt atactggtgg cgcattctat           180
gcacagaagt ttcagggcag gtcacaatg accaggaca cgtccatcag cacagcctac            240
atggagctga gcagactgag atctgacgac acggccgtgt attattgtgc gagagaacct          300
gaaaaattcg actcgccgaa cgccgagatc tggggccggg gacattggt caccgtctcc           360 tcagaaggcg gcggttcagg cggaggtggc tctggcggta gcggaagtgc acaggctgtg          420
ctgactcagc cgccgtcagt gtctgggcc ccagggcaga gggtcaccat ctcctgcact           480
gggagcagct ccaacatcgg ggcaggttat ggtgtacact ggtaccaaca gcttccagga          540
acagccccca aactcctcat ctatggtaac agcaatcggc cctcaggggt ccctgaccga          600
ttctctggct ccaagtctgg cacctcagcc tccctggcca tcactgggct ccaggctgag          660
gatgaggctg attattactg ccagtcctat gacagcagcc tgagtggtta tgtcttcgga          720
ggtgggaccc agctcaccgt cctaggt                                              747

<210> SEQ ID NO 593
<211> LENGTH: 15
<212> TYPE: DNA
<213> ORGANISM: Homo sapiens

<400> SEQUENCE: 593
cactactata tgcac                                                            15

<210> SEQ ID NO 594
<211> LENGTH: 51
<212> TYPE: DNA
<213> ORGANISM: Homo sapiens

<400> SEQUENCE: 594
tggatcaacc cttatactgg tggcgcattc tatgcacaga agtttcaggg c                    51

<210> SEQ ID NO 595
<211> LENGTH: 36
<212> TYPE: DNA
<213> ORGANISM: Homo sapiens

<400> SEQUENCE: 595
gaacctgaaa aattcgactc gccgaacgcc gagatc                                     36

<210> SEQ ID NO 596
<211> LENGTH: 42
<212> TYPE: DNA
<213> ORGANISM: Homo sapiens

<400> SEQUENCE: 596
actgggagca gctccaacat cggggcaggt tatggtgtac ac                              42

<210> SEQ ID NO 597
<211> LENGTH: 21
```

```
<212> TYPE: DNA
<213> ORGANISM: Homo sapiens

<400> SEQUENCE: 597
ggtaacagca atcggccctc a                                              21

<210> SEQ ID NO 598
<211> LENGTH: 33
<212> TYPE: DNA
<213> ORGANISM: Homo sapiens

<400> SEQUENCE: 598
cagtcctatg acagcagcct gagtggttat gtc                                 33

<210> SEQ ID NO 599
<211> LENGTH: 121
<212> TYPE: PRT
<213> ORGANISM: Homo sapiens

<400> SEQUENCE: 599
```

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Asp Ser Asp Val Trp Gly
            100                 105                 110

Arg Gly Thr Leu Val Thr Val Ser Ser
        115                 120

```
<210> SEQ ID NO 600
<211> LENGTH: 112
<212> TYPE: PRT
<213> ORGANISM: Homo sapiens

<400> SEQUENCE: 600
```

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Phe Gly Gly Gly Thr Gln Leu Thr Val Leu Gly
            100                 105                 110

```
<210> SEQ ID NO 601
```

```
<211> LENGTH: 249
<212> TYPE: PRT
<213> ORGANISM: Homo sapiens

<400> SEQUENCE: 601

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Asp Ser Asp Val Trp Gly
            100                 105                 110

Arg Gly Thr Leu Val Thr Val Ser Ser Gly Gly Ser Ser Gly Gly
            115                 120                 125

Gly Gly Ser Gly Gly Ser Gly Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Val His Trp Tyr Gln
                165                 170                 175

Gln Leu Pro Gly Thr Ala Pro Lys Leu Leu Ile Tyr Gly Asp Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Asn Ser Leu Ser Gly Tyr Val Phe Gly
225                 230                 235                 240

Gly Gly Thr Gln Leu Thr Val Leu Gly
                245

<210> SEQ ID NO 602
<211> LENGTH: 5
<212> TYPE: PRT
<213> ORGANISM: Homo sapiens

<400> SEQUENCE: 602

Asn Tyr Tyr Met His
1               5

<210> SEQ ID NO 603
<211> LENGTH: 17
<212> TYPE: PRT
<213> ORGANISM: Homo sapiens

<400> SEQUENCE: 603

Trp Ile Asn Pro Tyr Thr Gly Ser Ala Phe Tyr Ala Gln Lys Phe Arg
1               5                   10                  15

Gly

<210> SEQ ID NO 604
```

```
<211> LENGTH: 12
<212> TYPE: PRT
<213> ORGANISM: Homo sapiens

<400> SEQUENCE: 604

Glu Pro Glu Lys Phe Asp Ser Asp Asp Ser Asp Val
1               5                   10

<210> SEQ ID NO 605
<211> LENGTH: 14
<212> TYPE: PRT
<213> ORGANISM: Homo sapiens

<400> SEQUENCE: 605

Thr Gly Ser Ser Ser Asn Ile Gly Ala Gly Tyr Gly Val His
1               5                   10

<210> SEQ ID NO 606
<211> LENGTH: 7
<212> TYPE: PRT
<213> ORGANISM: Homo sapiens

<400> SEQUENCE: 606

Gly Asp Ser Asn Arg Pro Ser
1               5

<210> SEQ ID NO 607
<211> LENGTH: 11
<212> TYPE: PRT
<213> ORGANISM: Homo sapiens

<400> SEQUENCE: 607

Gln Ser Tyr Asp Asn Ser Leu Ser Gly Tyr Val
1               5                   10

<210> SEQ ID NO 608
<211> LENGTH: 363
<212> TYPE: DNA
<213> ORGANISM: Homo sapiens

<400> SEQUENCE: 608
caggtgcagc tggtgcagtc tggggctgag gtgaagaagc ctggggcctc agtgaaggtc      60
tcctgcaagg cttctggata caccttcacc aactactata tgcactgggt gcgacaggcc     120
cctggacaag ggcttgagtg ggtgggatgg atcaaccctt atactggtag cgcattctat     180
gcacagaagt tcgggggcag ggtcacaatg accagggaca cgtccatcag cacagcctac     240
atggagctga gcagactgag atctgacgac acggccgtgt attattgtgc gagagaacct     300
gaaaaattcg actccgacga ctccgacgtc tggggccgcg ggacattggt caccgtctcc     360
tca                                                                   363

<210> SEQ ID NO 609
<211> LENGTH: 336
<212> TYPE: DNA
<213> ORGANISM: Homo sapiens

<400> SEQUENCE: 609
caggctgtgc tgactcagcc gccgtcagtg tctggggccc agggcagag ggtcaccatc       60 tcctgcactg ggagcagctc caacatcggg gcaggttatg gtgtacactg gtaccaacag     120
cttccaggaa cagccccaa actcctcatc tatggtgaca gcaatcggcc ctcaggggtc      180
cctgaccgat tctctggctc caagtctggc acctcagcct ccctggccat cactgggctc     240
```
caggctgagg atgaggctga ttattactgc cagtcctatg acaacagcct gagcggttat    300
gtcttcggag gtgggaccca gctcaccgtc ctaggt                              336

<210> SEQ ID NO 610
<211> LENGTH: 747
<212> TYPE: DNA
<213> ORGANISM: Homo sapiens

<400> SEQUENCE: 610
caggtgcagc tggtgcagtc tggggctgag gtgaagaagc ctggggcctc agtgaaggtc     60
tcctgcaagg cttctggata caccttcacc aactactata tgcactgggt gcgacaggcc   120
cctggacaag gcttgagtg gtgggatgg atcaaccctt atactggtag cgcattctat     180
gcacagaagt tcggggcag gtcacaatg accaggaca cgtccatcag cacagcctac     240
atggagctga gcagactgag atctgacgac acggccgtgt attattgtgc gagagaacct   300
gaaaaattcg actccgacga ctccgacgtc tgggccgcg ggacattggt caccgtctcc   360
tcaggaggcg gcagttcagg cggaggtggc tctggcggta gcggaagtgc acaggctgtg   420
ctgactcagc cgccgtcagt gtctgggcc ccagggcaga gggtcaccat ctcctgcact    480
gggagcagct ccaacatcgg ggcaggttat ggtgtacact ggtaccaaca gcttccagga   540
acagccccca aactcctcat ctatggtgac agcaatcggc cctcaggggt ccctgaccga   600
ttctctggct ccaagtctgg cacctcagcc tccctggcca tcactgggct ccaggctgag   660
gatgaggctg attattactg ccagtcctat gacaacagcc tgagcggtta tgtcttcgga   720
ggtgggaccc agctcaccgt cctaggt                                       747

<210> SEQ ID NO 611
<211> LENGTH: 15
<212> TYPE: DNA
<213> ORGANISM: Homo sapiens

<400> SEQUENCE: 611
aactactata tgcac                                                     15

<210> SEQ ID NO 612
<211> LENGTH: 51
<212> TYPE: DNA
<213> ORGANISM: Homo sapiens

<400> SEQUENCE: 612
tggatcaacc cttatactgg tagcgcattc tatgcacaga agtttcgggg c              51

<210> SEQ ID NO 613
<211> LENGTH: 36
<212> TYPE: DNA
<213> ORGANISM: Homo sapiens

<400> SEQUENCE: 613
gaacctgaaa aattcgactc cgacgactcc gacgtc                              36

<210> SEQ ID NO 614
<211> LENGTH: 42
<212> TYPE: DNA
<213> ORGANISM: Homo sapiens

<400> SEQUENCE: 614
actgggagca gctccaacat cggggcaggt tatggtgtac ac                       42

<210> SEQ ID NO 615

```
<211> LENGTH: 21
<212> TYPE: DNA
<213> ORGANISM: Homo sapiens

<400> SEQUENCE: 615
ggtgacagca atcggccctc a                                              21

<210> SEQ ID NO 616
<211> LENGTH: 33
<212> TYPE: DNA
<213> ORGANISM: Homo sapiens

<400> SEQUENCE: 616
cagtcctatg acaacagcct gagcggttat gtc                                 33

<210> SEQ ID NO 617
<211> LENGTH: 121
<212> TYPE: PRT
<213> ORGANISM: Homo sapiens

<400> SEQUENCE: 617
```

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120

```
<210> SEQ ID NO 618
<211> LENGTH: 110
<212> TYPE: PRT
<213> ORGANISM: Homo sapiens

<400> SEQUENCE: 618
```

Gln Ala Ala Leu Thr Gln Pro Ala Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Leu Val Ser Asp
                85                  90                  95

Phe Ser Val Val Phe Gly Gly Gly Thr Lys Leu Thr Val Leu
            100                 105                 110

```
<210> SEQ ID NO 619
<211> LENGTH: 261
<212> TYPE: PRT
<213> ORGANISM: Homo sapiens

<400> SEQUENCE: 619

Glu Val Gln Leu Val Glu Ser Gly Gly Gly Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Gly Gly Gly Gly Ser Gly Gly
        115                 120                 125

Gly Gly Ser Gly Gly Ser Gly Gly Ser Gly Gly Gly Gly Gly
    130                 135                 140

Ser Gly Gly Gly Ser Ala Gln Ala Ala Leu Thr Gln Pro Ala Ser
145                 150                 155                 160

Val Ser Gly Ser Pro Gly Gln Ser Ile Thr Ile Ser Cys Thr Gly Ala
                165                 170                 175

Ser Gly Asp Val Gly Ala Tyr Asn Phe Val Ser Trp Tyr Gln Gln His
            180                 185                 190

Pro Gly Lys Ala Pro Lys Leu Ile Ile Tyr Asp Val Asn Lys Arg Pro
        195                 200                 205

Ser Gly Val Ser Asn Arg Phe Ser Gly Ser Lys Ser Gly Asn Thr Ala
    210                 215                 220

Ser Leu Thr Ile Ser Gly Leu Gln Ala Glu Asp Glu Ala Asp Tyr Tyr
225                 230                 235                 240

Cys Ala Ser Leu Val Ser Asp Phe Ser Val Phe Gly Gly Gly Thr
                245                 250                 255

Lys Leu Thr Val Leu
        260

<210> SEQ ID NO 620
<211> LENGTH: 5
<212> TYPE: PRT
<213> ORGANISM: Homo sapiens

<400> SEQUENCE: 620

Asp Tyr Gly Met Asn
1               5

<210> SEQ ID NO 621
<211> LENGTH: 17
<212> TYPE: PRT
<213> ORGANISM: Homo sapiens

<400> SEQUENCE: 621

Gly Val Asn Trp Asn Gly Gly Thr Arg Asp Tyr Ala Ala Ser Val Lys
1               5                   10                  15
```

-continued

Gly

<210> SEQ ID NO 622
<211> LENGTH: 12
<212> TYPE: PRT
<213> ORGANISM: Homo sapiens

<400> SEQUENCE: 622

Gly Trp Tyr Ser Gly Ala Ala Trp Asn Met Gly Tyr
1               5                   10

<210> SEQ ID NO 623
<211> LENGTH: 16
<212> TYPE: PRT
<213> ORGANISM: Homo sapiens

<400> SEQUENCE: 623

Ser Cys Thr Gly Ala Ser Gly Asp Val Gly Ala Tyr Asn Phe Val Ser
1               5                   10                  15

<210> SEQ ID NO 624
<211> LENGTH: 7
<212> TYPE: PRT
<213> ORGANISM: Homo sapiens

<400> SEQUENCE: 624

Asp Val Asn Lys Arg Pro Ser
1               5

<210> SEQ ID NO 625
<211> LENGTH: 10
<212> TYPE: PRT
<213> ORGANISM: Homo sapiens

<400> SEQUENCE: 625

Ala Ser Leu Val Ser Asp Phe Ser Val Val
1               5                   10

<210> SEQ ID NO 626
<211> LENGTH: 363
<212> TYPE: DNA
<213> ORGANISM: Homo sapiens

<400> SEQUENCE: 626
gaggtgcagc tggtggagag cggcggaggc gtggtgagac caggcggcag cctgagactg      60
agctgcgccg ccagcggctt caccttcgac gactacggca tgaactgggt gaggcaggcc     120
ccaggcaagg gcctggagtg ggtgtccggc gtgaactgga acggcggcac cagagactac     180
gccgcctctg tgaagggcag attcaccatc agccgggaca cgccaagaa cagcctgtac      240 ctgcagatga acagcctgag agccgaggac accgccctgt accactgcgc cagaggctgg     300
tacagcggag ccgcctggaa catgggctac tggggcagag gcaccctggt gaccgtgtcc     360
agc                                                                   363

<210> SEQ ID NO 627
<211> LENGTH: 330
<212> TYPE: DNA
<213> ORGANISM: Homo sapiens -continued

<400> SEQUENCE: 627

```
caggccgccc tgacccagcc cgccagcgtg tctggcagcc caggccagag catcaccatc    60
agctgcaccg gcgccagcgg cgatgtgggc gcctacaact tcgtgtcctg gtatcagcag   120
cacccoggca aggcccccaa gctgatcatc tacgacgtga acaagagacc cagcggcgtg   180
tccaacagat tcagcggcag caagagcggc aacaccgcca gcctgaccat cagcggactg   240
caggccgagg acgaggccga ctactactgc gccagcctgg tgtccgactt cagcgtggtg   300
ttcggcggag gcaccaagct gaccgtgctg                                    330
```

<210> SEQ ID NO 628
<211> LENGTH: 783
<212> TYPE: DNA
<213> ORGANISM: Homo sapiens

<400> SEQUENCE: 628

```
gaggtgcagc tggtggagag cggcggaggc gtggtgagac caggcggcag cctgagactg    60
agctgcgccg ccagcggctt caccttcgac gactacggca tgaactgggt gaggcaggcc   120
ccaggcaagg gcctggagtg ggtgtccggc gtgaactgga acggcggcac cagagactac   180
gccgcctctg tgaagggcag attcaccatc agccgggaca cgccaagaa cagcctgtac   240
ctgcagatga acagcctgag agccgaggac accgccctgt accactgcgc cagaggctgg   300
tacagcggag ccgcctggaa catgggctac tggggcagag gcaccctggt gaccgtgtcc   360
agcggaggcg gcggttcagg cggaggtggc tctggtggta gcggaggtgg ctctggcggt   420
ggcggaggtg gctctggcgg tggcggaagt gcacaggccg ccctgaccca gccgccagc   480
gtgtctggca gcccaggcca gagcatcacc atcagctgca ccggcgccag cggcgatgtg   540
ggcgcctaca acttcgtgtc ctggtatcag cagcaccccg gcaaggcccc caagctgatc   600
atctacgacg tgaacaagag acccagcggc gtgtccaaca gattcagcgg cagcaagagc   660
ggcaacaccg ccagcctgac catcagcgga ctgcaggccg aggacgaggc cgactactac   720
tgcgccagcc tggtgtccga cttcagcgtg gtgttcggcg gaggcaccaa gctgaccgtg   780
ctg                                                                 783
```

<210> SEQ ID NO 629
<211> LENGTH: 15
<212> TYPE: DNA
<213> ORGANISM: Homo sapiens

<400> SEQUENCE: 629

```
gactacggca tgaac                                                     15
```

<210> SEQ ID NO 630
<211> LENGTH: 51
<212> TYPE: DNA
<213> ORGANISM: Homo sapiens

<400> SEQUENCE: 630

```
ggcgtgaact ggaacggcgg caccagagac tacgccgcct ctgtgaaggg c             51
```

<210> SEQ ID NO 631
<211> LENGTH: 36
<212> TYPE: DNA
<213> ORGANISM: Homo sapiens

<400> SEQUENCE: 631

```
ggctggtaca gcggagccgc ctggaacatg ggctac                              36
```

```
<210> SEQ ID NO 632
<211> LENGTH: 42
<212> TYPE: DNA
<213> ORGANISM: Homo sapiens

<400> SEQUENCE: 632
accggcgcca gcggcgatgt gggcgcctac aacttcgtgt cc                    42

<210> SEQ ID NO 633
<211> LENGTH: 21
<212> TYPE: DNA
<213> ORGANISM: Homo sapiens

<400> SEQUENCE: 633
gacgtgaaca agagacccag c                                           21

<210> SEQ ID NO 634
<211> LENGTH: 30
<212> TYPE: DNA
<213> ORGANISM: Homo sapiens

<400> SEQUENCE: 634
gccagcctgg tgtccgactt cagcgtggtg                                  30
```